(12) United States Patent
Hwang et al.

(10) Patent No.: US 11,046,974 B2
(45) Date of Patent: Jun. 29, 2021

(54) INSECTICIDAL PROTEIN DISCOVERY PLATFORM AND INSECTICIDAL PROTEINS DISCOVERED THEREFROM

(71) Applicant: Zymergen Inc., Emeryville, CA (US)

(72) Inventors: William W. Hwang, Emeryville, CA (US); Jeffrey Kim, Berkeley, CA (US); Oliver Liu, San Francisco, CA (US); Jennifer Shock, San Francisco, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 17/009,438

(22) Filed: Sep. 1, 2020

(65) Prior Publication Data

US 2020/0399654 A1 Dec. 24, 2020

Related U.S. Application Data

(63) Continuation of application No. PCT/US2019/020218, filed on Mar. 1, 2019.

(60) Provisional application No. 62/637,515, filed on Mar. 2, 2018.

(51) Int. Cl.
| | | |
|---|---|---|
| *C12N 15/82* | (2006.01) | |
| *C07K 14/21* | (2006.01) | |
| *A01N 63/50* | (2020.01) | |
| *C12N 15/10* | (2006.01) | |

(52) U.S. Cl.
CPC ......... *C12N 15/8286* (2013.01); *A01N 63/50* (2020.01); *C07K 14/21* (2013.01); *C12N 15/1093* (2013.01); *C12N 2800/22* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,188,960 A | 2/1993 | Payne et al. |
| 5,880,275 A | 3/1999 | Fischhoff et al. |
| 6,033,874 A | 3/2000 | Baum et al. |
| 6,083,499 A | 7/2000 | Narva et al. |
| 6,127,180 A | 10/2000 | Narva et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,399,330 B1 | 6/2002 | Donovan et al. |
| 6,548,291 B1 | 4/2003 | Narva et al. |
| 6,624,145 B1 | 9/2003 | Narva et al. |
| 6,713,063 B1 | 3/2004 | Malvar et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,105,332 B2 | 9/2006 | Abad et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,476,781 B2 | 1/2009 | Abad et al. |
| 7,491,869 B2 | 2/2009 | Abad et al. |
| 7,504,229 B2 | 3/2009 | Donovan et al. |
| 7,803,943 B2 | 9/2010 | Mao et al. |
| 7,858,849 B2 | 12/2010 | Cerf et al. |
| 7,923,602 B2 | 4/2011 | Carozzi et al. |
| 8,084,416 B2 | 12/2011 | Sampson et al. |
| 8,236,757 B2 | 8/2012 | Carozzi et al. |
| 8,304,604 B2 | 11/2012 | Lira et al. |
| 8,304,605 B2 | 11/2012 | Lira et al. |
| 8,318,900 B2 | 11/2012 | Sampson et al. |
| 8,319,019 B2 | 11/2012 | Abad et al. |
| 8,334,431 B2 | 12/2012 | Sampson et al. |

(Continued)

FOREIGN PATENT DOCUMENTS

| | | |
|---|---|---|
| WO | WO 2004/074462 A2 | 9/2004 |
| WO | WO 2005/021585 A2 | 3/2005 |

(Continued)

OTHER PUBLICATIONS

US 8,476,226 B2, 07/2013, Lira et al. (withdrawn)
Opota et al. (2011) PLoS Pathog 7(9):e1002259.*
Kupferschmied et al. (2013) Front Plant Sci 4:287.*
Raaijmakers & Mazzola (2012) Annu Rev Phytopathol 50:403-24.*
Altschul, et al., "Basic local alignment search tool". J Mol Biol. (Oct. 5, 1990); 15(3): 403-410.
Altschul, et al., "Gapped BLAST and PSI-BLAST: a new generation of protein database search programs." Nucleic Acids Res. (Sep. 1, 1997); 25(17): 3389-3402.
Barton, G.J., "Protein multiple sequence alignment and flexible pattern matching". Methods Enzymol. (1990); 183: 403-428.

(Continued)

*Primary Examiner* — Russell T Boggs
(74) *Attorney, Agent, or Firm* — Cooley LLP

(57) ABSTRACT

The disclosure presents a platform for discovering novel insecticidal proteins from highly heterogeneous environmental sources. The methodology utilizes metagenomic enrichment procedures and unique genetic amplification techniques, which enables access to a broad class of unknown microbial diversity and their resultant proteome. The disclosed insecticidal protein discovery platform (IPDP) can be computationally driven and is able to integrate molecular biology, automation, and advanced machine learning protocols. The platform will enable researchers to rapidly and accurately access the vast repertoire of untapped insecticidal proteins produced by uncharacterized and complex microbial environmental samples. Also presented herein are a group of newly discovered pore-forming toxins (PFT) from a rare class of insecticidal proteins, which were discovered utilizing the insecticidal protein discovery platform.

47 Claims, 10 Drawing Sheets

Specification includes a Sequence Listing.

(56) References Cited

U.S. PATENT DOCUMENTS

| | | |
|---|---|---|
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,802,933 B2 | 8/2014 | Abad et al. |
| 8,802,934 B2 | 8/2014 | Abad et al. |
| 9,688,730 B2 | 6/2017 | Cerf et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0250311 A1 | 12/2004 | Carozzi et al. |
| 2006/0112447 A1 | 5/2006 | Bogdanova et al. |
| 2006/0191034 A1 | 8/2006 | Baum et al. |
| 2008/0295207 A1 | 11/2008 | Baum et al. |
| 2009/0144852 A1 | 6/2009 | Tomso et al. |
| 2010/0005543 A1 | 1/2010 | Sampson et al. |
| 2010/0017914 A1 | 1/2010 | Hart et al. |
| 2010/0197592 A1 | 8/2010 | Heinrichs et al. |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0263488 A1 | 10/2011 | Carozzi et al. |
| 2012/0278954 A1 | 11/2012 | Bowen et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0167268 A1 | 6/2013 | Narva et al. |
| 2013/0167269 A1 | 6/2013 | Narva et al. |
| 2014/0007292 A1* | 1/2014 | Cerf et al. ............. C07K 14/21 800/279 |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2016/0186204 A1 | 6/2016 | Liu et al. |
| 2016/0366891 A1 | 12/2016 | Diehn et al. |
| 2017/0367349 A1 | 12/2017 | Gruver et al. |
| 2021/0015109 A1 | 1/2021 | Hwang et al. |

FOREIGN PATENT DOCUMENTS

| | | | |
|---|---|---|---|
| WO | WO 2005/038032 A1 | 4/2005 | |
| WO | WO 2006/034363 A1 | 3/2006 | |
| WO | WO 2006/083891 A2 | 8/2006 | |
| WO | WO 2006/119457 A1 | 11/2006 | |
| WO | WO 2007/027776 A2 | 3/2007 | |
| WO | WO 2011/103247 A2 | 8/2011 | |
| WO | WO 2011/103248 A2 | 8/2011 | |
| WO | WO 2012/139004 A2 | 10/2012 | |
| WO | WO 2014/008054 A2 | 1/2014 | |
| WO | WO 2019/094213 | * | 5/2019 |
| WO | WO 2019/169227 A1 | 9/2019 | |

OTHER PUBLICATIONS

Bashford, et al., "Determinants of a protein fold. Unique features of the globin amino acid sequences". J Mol Biol. (Jul. 5, 1987); 196(1): 199-216.

Bravo, et al., "Mode of action of Bacillus thuringiensis Cry and Cyt toxins and their potential for insect control". Toxicon (Mar. 15, 2007); 49(4): 423-435. Epub Nov. 30, 2006.

Churchill, G.A., "Stochastic models for heterogeneous DNA sequences". Bull Math Biol. (1989); 51(1): 79-94.

Crickmore, et al., "A structure-based nomenclature for Bacillus thuringiensis and other bacteria-derived pesticidal proteins". Journal of Invertebrate Pathology (2020); Available online Jul. 9, 2020, 107438, 5 pages.

Crickmore, et al., "Revision of the nomenclature for the Bacillus thuringiensis pesticidal crystal proteins". Microbiol Mol Biol Rev. (Sep. 1998); 62(3): 807-813.

Durbin, et al., "Profile HMMs for sequence families". Biological Sequence Analysis: Probabilistic Models of Proteins and Nucleic Acids. Cambridge University Press: Cambridge, UK (1998); Ch. 5, pp. 100-132, 40 pages.

Eddy, S.R., "Profile hidden Markov models". Bioinformatics (1998); 14(9): 755-763.

Finn, et al., "The Pfam protein families database". Nucleic Acids Res. (Jan. 2008); 36(Database issue): D281-288. Epub Nov. 26, 2007.

GenBank: KT795291.1, "Pseudomonas chlororaphis IPD072Aa gene, complete cds". Update Sep. 23, 2016, 1 page.

Gribskov, et al., "Profile analysis". Methods Enzymol (1990); 183: 146-159.

Gribskov, et al., "Profile analysis: detection of distantly related proteins." Proc Natl Acad Sci U S A. (Jul. 1987); 84(13): 4355-4358.

Krogh, et al., "Hidden Markov models in computational biology. Applications to protein modeling". J Mol Biol. (Feb. 4, 1994); 235(5): 1501-1531.

Mulder, et al., "The InterPro Database, 2003 brings increased coverage and new features". Nucleic Acids Res. (Jan. 1, 2003); 31(1): 315-318.

Naimov, et al., "Solubilization, Activation, and Insecticidal Activity of Bacillus thuringiensis Serovar thompsoni HD542 Crystal Proteins". Applied and Environmental Microbiology (Dec. 2008); 74(23): 7145-7151.

Parker and Feil, "Pore-forming protein toxins: from structure to function". Prog Biophys Mol Biol. (May 2005); 88(1): 91-142.

PCT/US2019/020218, International Preliminary Report on Patentability dated Sep. 8, 2020, 8 pages.

PCT/US2019/020218, International Search Report and Written Opinion dated Jun. 11, 2019, 13 pages.

PCT/US2019/020218, Invitation to Pay Additional Search Fees dated Apr. 18, 2019, 8 pages.

Pearson and Lipman, "Improved tools for biological sequence comparison". Proc Natl Acad Sci U S A (Apr. 1988); 85(8): 2444-2448.

Purcell, et al., "Cholesterol oxidase: a potent insecticidal protein active against boll weevil larvae". Biochem Biophys Res Commun. (Nov. 15, 1993); 196(3):1406-1413.

Qaim and Zilberman, "Yield Effects of Genetically Modified Crops in Developing Countries", Science (Feb. 7, 2003); 299(5608): 900-902.

Sanahuja, et al., "Bacillus thuringiensis: a century of research, development and commercial applications". Plant Biotechnol J. (Apr. 2011); 9(3): 283-300. Epub Feb. 2, 2011.

Schellenberger, et al., "A selective insecticidal protein from Pseudomonas for controlling corn rootworms". Science (Nov. 4, 2016); 354 (6312): 634-637.

Schuler, et al., "Insect-resistant transgenic plants". Trends Biotechnol. (Apr. 1, 1998); 16(4): 168-175.

Smith and Waterman, "Identification of common molecular subsequences". Journal of Molecular Biology (Mar. 25, 1981); 147(1): 195-197.

Sonnhammer, et al., "Pfam: A comprehensive database of protein domain families based on seed alignments". Proteins (1997); 28(3): 405-420.

Wei, Jun-Zhi, et al., "A selective insecticidal protein from Pseudomonas mosselii for corn rootworm control". Plant Biotechnol J. (Feb. 2018); 16(2): 649-659. Epub Oct. 1, 2017.

* cited by examiner

FIGURE 1

```
┌─────────────────────────────┐
│     Collect Soil Sample     │
└─────────────────────────────┘

┌─────────────────────────────┐
│ Resuspend in Buffered Solution │
└─────────────────────────────┘

┌─────────────────────────────┐
│  Dilution and Plating on Solid  │
│  Nutrient Limiting Agar Media   │
└─────────────────────────────┘

┌─────────────────────────────┐
│ Collect Bacterial Growth from │
│            Plates             │
└─────────────────────────────┘

┌─────────────────────────────┐
│  Isolate All Genomic DNA from   │
│  Enriched Sample as a Mixture   │
│    via Lysis and Precipitation  │
└─────────────────────────────┘

┌─────────────────────────────┐
│  Genes Encoding Proteins From   │
│  the Monalysin Class are Further│
│  Enriched Using Degenerate PCR  │
│ and Cloned into Plasmid Vectors │
│   for Recovery and Sequencing   │
└─────────────────────────────┘

┌─────────────────────────────┐
│    Identification of Novel      │
│ Insecticidal Proteins Utilizing │
│   Homology and Profile/HMM      │
│            Methods              │
└─────────────────────────────┘
```

FIGURE 3

```
                    10         20         30         40
1. ZIP1   MTIKEELS PQSHSVELDQLQVGEVSAREALTSNFAGSFDQFPTKSG  (SEQ ID NO:2)
2. ZIP2   MTIKEELS PQSHSVELDQLQVGEVSAREALTSNFAGSFDQFPTKSG  (SEQ ID NO:4)
3. ZIP6   MTIKEEL  PQSHSVELDQLQVGEVSAREALTSNFAGSFDQFPTKSG  (SEQ ID NO:12)
4. ZIP8   MTIKEELS PQSHSVELDQLQVGEVSAREALTSNFAGSFDQFPTKSG  (SEQ ID NO:14)
5. ZIP9   MTIKEELS PQSHSVELDQLQVGEVSAREALTSNFAGSFDQFPTKSG  (SEQ ID NO:16)
6. ZIP10  MTIKEELS PQSHSVELDQLQVGEVSAREALTSNFAGSFDQFPTKSG  (SEQ ID NO:18)
7. ZIP11  MTIKEELS PQSHSVELDQLQVGEVSAREALTANFAGSFDQFPTKSG  (SEQ ID NO:20)
8. ZIP12  MTIKEEL  PQSHSVELDQLQVGEVSAREALTSNFAGSFDQFPTKSG  (SEQ ID NO:22)

50         60         70         80         90
1. ZIP1   FEIDKYLLNYADPKKGC LDGVTVYGDIYIGKQNWGTYTRPV AY   (SEQ ID NO:2)
2. ZIP2   FEIDKYLLNYADPKKGC LDGVTVYGDIYIGKQNWGTYTRPV AY   (SEQ ID NO:4)
3. ZIP6   FEIDKYLLNYADPKKGC LDGVTVYGDIYIGKQNWGTYTRPV AY   (SEQ ID NO:12)
4. ZIP8   FEIDKYLLNYADPKKGC LDGVTVYGDIYIGKQNWGTYTRPV AY   (SEQ ID NO:14)
5. ZIP9  GFEIDKYLLNYADPKKGC LDGVTVYGDIYIGKQNWGTYTRPV AY   (SEQ ID NO:16)
6. ZIP10  FEIDKYLLNYADPKKGC LDGVTVYGDIYIGKQNWGTYTRPV AY   (SEQ ID NO:18)
7. ZIP11  FEIDKYLLNYADPKKGC LDGVTVYGDIYIGKQNWGTYTRPV AY   (SEQ ID NO:20)
8. ZIP12  FEIDKYLLNYADPKKGC LDGVTVYGDIYIGKQNWGTYTRPV AY   (SEQ ID NO:22)

100        110        120        130        140
1. ZIP1   QHTDTI IPQQVTQTKSYQLSKGHTQ FTKSVSAKYSVGGSIDIVN   (SEQ ID NO:2)
2. ZIP2   QHTDTI IPQQVTQTKSYQLSKGHTQ FTKSVSAKYSVGGSIDIVN   (SEQ ID NO:4)
3. ZIP6   QHTDTI IPQQVTQTKSYQLSKGHTQ FTKSVSAKYSVGGSIDIVN   (SEQ ID NO:12)
4. ZIP8   QHTDTI IPQQVTQTKSYQLSKGHTQ FTKSVSAKYSVGGSIDIVN   (SEQ ID NO:14)
5. ZIP9   QHTDTI IPQQVTQTKSYQLSKGHTQ FTKSVSAKYSVGGSIDIVN   (SEQ ID NO:16)
6. ZIP10  QHTDTI IPQQVTQTKSYQLSKGHTQ FTKSVSAKYSVGGSIDIVNV  (SEQ ID NO:18)
7. ZIP11  QHTDTI IPQQVTQTKSYQLSKGHTQ FTKSVSAKYSVGGSIDIVN   (SEQ ID NO:20)
8. ZIP12  QHTDTI IPQQVTQTRSYQLSKGHTQ FTKSVSAKYSVGGSIDIVN   (SEQ ID NO:22)

150        160        170        180
1. ZIP1   SSDITVGFSSTEAWST QTFTQSTELAGPGTFFVYQVVFVYAHNATS  (SEQ ID NO:2)
2. ZIP2   SSDITVGFSSTEAWST QTFTQSTELAGPGTFFVYQVVFVYAHNATS  (SEQ ID NO:4)
3. ZIP6   SSDITVGFSSTEAWST QTFTQSTELAGPGTFFVYQVVFVYAHNATS  (SEQ ID NO:12)
4. ZIP8   SSDITVGFSSTEAWST QTFTQSTELAGPGTFFVYQVVFVYAHNATS  (SEQ ID NO:14)
5. ZIP9   SSDITVGFSSTEAWST QTFTQSTELAGPGTFFVYQVVFVYAHNATS  (SEQ ID NO:16)
6. ZIP10  SSDITVGFSSTEAWST QTFTQSTELAGPGTFFVYQVVFVYAHNATS  (SEQ ID NO:18)
7. ZIP11  SSDITVGFSSTEAWST QTFTQSTELAGPGTFFVYQVVFVYAHNATS  (SEQ ID NO:20)
8. ZIP12  SSDITVGFSSTEAWST QTFTQSTELAGPGTFFVYQVVFVYAHNATS  (SEQ ID NO:22)

190        200        210        220        230
1. ZIP1   AGGQNGNAFAYSKTQQVNSRLDLYYLSAIT DRTVIVESS AI PLD  (SEQ ID NO:2)
2. ZIP2   AGGQNGNAFAYSKTQQVNSRLDLYYLSAIT DRTVIVESS AI PLD  (SEQ ID NO:4)
3. ZIP6   AGGQNGNAFAYSKTQQVNSRLDLYYLSAIT DRTVIVESS AI PLD  (SEQ ID NO:12)
4. ZIP8   AGGQNGNAFAYSKTQQVNSRLDLYYLSAIT DRTVIVESS AI PLD  (SEQ ID NO:14)
5. ZIP9   AGGQNGNAFAYSKTQQVNSRLDLYYLSAIT DRTVIVESS AI PLD  (SEQ ID NO:16)
6. ZIP10  AGGQNGNAFAYSKTQQVNSRLDLYYLSAIT DRTVIVESS AI PLD  (SEQ ID NO:18)
7. ZIP11  AGGQNGNAFAYSKTQQVNSRLDLYYLSAIT DRTVIVESS AI PLD  (SEQ ID NO:20)
8. ZIP12  AGGQNGNAFAYSKTQQVNSRLDLYYLSAIT DRTVIVESS AI PLD  (SEQ ID NO:22)

240        250        260        270      278
1. ZIP1    DTVQRNVLIQNYN ASNSGHFSFDW AY DP RRY *           (SEQ ID NO:2)
2. ZIP2    DTVQRNVLIQNYN ASNSGHFSFDW AYTILIAVXE LRSGC *    (SEQ ID NO:4)
3. ZIP6    DTVQRNVLMENYN SSNSGHFSFDW AY DP RRY *           (SEQ ID NO:12)
4. ZIP8    DTVQRNVLIQNYN ASNSGHFSFDW AY DP RRY *           (SEQ ID NO:14)
5. ZIP9    DTVQRNVLIQNYN ASNSGHFSFDW AY DP RRY *           (SEQ ID NO:16)
6. ZIP10   DTVQRNVLIQNYN ASNSGHFSFDW AYTILIAVIE LRSGC *    (SEQ ID NO:18)
7. ZIP11   DTVQRNVLIQNYN ASNSGHFSFDW AY DP RRY *           (SEQ ID NO:20)
8. ZIP12   DTVQRNVLIQNYN ASNSGHFSFDW AY DP RRY *           (SEQ ID NO:22)
```

FIGURE 4

```
                    1         10        20        30        40
1. ZIP1          MTIKEEL  PQSHSVELDQL     SR ALTSN AG FDQFPTK G  (SEQ ID NO:2)
2. ZIP2          MTIKEEL  PQSHSVELDQL     SR ALTSN AG FDQFPTK G  (SEQ ID NO:4)
3. ZIP6          MTIKEEL  PQSHSVELDQL     SR ALTSN AG FDQFPTK G  (SEQ ID NO:12)
4. ZIP8          MTIKEEL  PQSHSVELDQL     SR ALTSN AG FDQFPTK G  (SEQ ID NO:14)
5. ZIP9          MTIKEEL  PQSHSVELDQL     SR ALTSN AG FDQFPTK G  (SEQ ID NO:16)
6. ZIP10         MTIKEEL  PQSHSVELDQL     SR ALTSN AG FDQFPTK G  (SEQ ID NO:18)
7. ZIP11         MTIKEEL  PQSHSVELDQL     SR ALTAN AG FDQFPT  G  (SEQ ID NO:20)
8. ZIP12         MTIKEEL  PQSHSVELDQL     SR ALTSN AG FDQFPT  G  (SEQ ID NO:22)
9. Monalysin-WT  MTIKEEL  PQSHS ELDV SKEAA SR ALTSN SG FDDYPTK G  (SEQ ID NO:87)

50        60        70        80        90
1. ZIP1           F ID YLLNYA PKKGC LDGVTVYGD IYIGKQNWGTYTRPV AYL  (SEQ ID NO:2)
2. ZIP2           F ID YLLNYA PKKGC LDGVTVYGD IYIGKQNWGTYTRPV AYL  (SEQ ID NO:4)
3. ZIP6           F ID YLLNYA PKKGC LDGVTVYGD IYIGKQNWGTYTRPV AYL  (SEQ ID NO:12)
4. ZIP8           F ID YLLNYA PKKGC LDGVTVYGD IYIGKQNWGTYTRPV AYL  (SEQ ID NO:14)
5. ZIP9           F ID YLLNYA PKKGC LDGVTVYGD IYIGKQNWGTYTRPV AYL  (SEQ ID NO:16)
6. ZIP10          F ID YLLNYA PKKGC LDGVTVYGD IYIGKQNWGTYTRPV AYL  (SEQ ID NO:18)
7. ZIP11          F ID YLLNYA PKKGC LDGVTVYGD IYIGKQNWGTYTRPV AYL  (SEQ ID NO:20)
8. ZIP12          F ID YLLNYA PKKGC LDGVTVYGD IYIGKQNWGTYTRPV AYL  (SEQ ID NO:22)
9. Monalysin-WT   F ID YLLDYS PKQGC VDGITVYGD IYIGKQNWGTYTRPV AYL  (SEQ ID NO:87)

100       110       120       130       140
1. ZIP1          QH DT I PC VT T SYQLSKGHTQ F  SVSAKYSVC SIDIVNI  (SEQ ID NO:2)
2. ZIP2          QH DT I PC VT T SYQLSKGHTQ F  SVSAKYSVC SIDIVNI  (SEQ ID NO:4)
3. ZIP6          QH DT I PC VT T SYQLSKGHTQ F  SVSAKYSVC SIDIVNI  (SEQ ID NO:12)
4. ZIP8          QH DT I PC VT T SYQLSKGHTQ F  SVSAKYSVC SIDIVNI  (SEQ ID NO:14)
5. ZIP9          QH DT I PC VT T SYQLSKGHTQ F  SVSAKYSVC SIDIVNI  (SEQ ID NO:16)
6. ZIP10         QH DT I PC VT T SYQLSKGHTQ F  SVSAKYSVC SIDIVNI  (SEQ ID NO:18)
7. ZIP11         QH DT I PC VT T SYQLSKGHTQ F  SVSAKYSVC SIDIVNI  (SEQ ID NO:20)
8. ZIP12         QH DT I PC VT T SYQLSKGHTQ F  SVSAKYSVC SIDIVNI  (SEQ ID NO:22)
9. Monalysin-WT  QY ETI IPC VT T SYQLTKGHTR F  SVNAKYSYC NIDIVNY  (SEQ ID NO:87)

150       160       170       180
1. ZIP1           SDIT GFS TEAWST QTFT STEL GPGTF VYQVV VYAHNATS  (SEQ ID NO:2)
2. ZIP2           SDIT GFS TEAWST QTFT STEL GPGTF VYQVV VYAHNATS  (SEQ ID NO:4)
3. ZIP6           SDIT GFS TEAWST QTFT STEL GPGTF VYQVV VYAHNATS  (SEQ ID NO:12)
4. ZIP8           SDIT GFS TEAWST QTFT STEL GPGTF VYQVV VYAHNATS  (SEQ ID NO:14)
5. ZIP9           SDIT GFS TEAWST QTFT STEL GPGTF VYQVV VYAHNATS  (SEQ ID NO:16)
6. ZIP10          SDIT GFS TEAWST QTFT STEL GPGTF VYQVV VYAHNATS  (SEQ ID NO:18)
7. ZIP11          SDIT GFS TEAWST QTFT STEL GPGTF VYQVV VYAHNATS  (SEQ ID NO:20)
8. ZIP12          SDIT GFS TEAWST QTFT STEL GPGTF VYQVV VYAHNATS  (SEQ ID NO:22)
9. Monalysin-WT   SEIS GFT SESWST QSFT TTEM GPGTF IYQVV VYAHNATS  (SEQ ID NO:87)

190       200       210       220       230
1. ZIP1          AG QN NAFAYSKTC V SRLDLYYLSA IT R VIV SS AIDPLD  (SEQ ID NO:2)
2. ZIP2          AG QN NAFAYSKTC V SRLDLYYLSA IT R VIV SS AIDPLD  (SEQ ID NO:4)
3. ZIP6          AG QN NAFAYSKTC V SRLDLYYLSA IT R VIV SS AI PLD  (SEQ ID NO:12)
4. ZIP8          AG QN NAFAYSKTC V SRLDLYYLSA IT R VIV SS AIDPLD  (SEQ ID NO:14)
5. ZIP9          AG QN NAFAYSKTC V SRLDLYYLSA IT R VIV SS AIDPLD  (SEQ ID NO:16)
6. ZIP10         AG QN NAFAYSKTC V SRLDLYYLSA IT R VIV SS AIDPLD  (SEQ ID NO:18)
7. ZIP11         AG QN NAFAYSKTC V SRLDLYYLSA IT R VIV SS AIDPLD  (SEQ ID NO:20)
8. ZIP12         AG QN NAFAYSKTC V SRLDLYYLSA IT R VIV SS AIDPLD  (SEQ ID NO:22)
9. Monalysin-WT  AG QN NAFAYSKTC V SRVDLYYLSA IT R VIV SS AVDPLD  (SEQ ID NO:87)

240       250       260       270       278
1. ZIP1          DTVQRNVL IQNYN  SNSGHFSFDW AYNP HRY *                   (SEQ ID NO:2)
2. ZIP2          DTVQRNVL IQNYN  SNSGHFSFDW AYTILAVXELRSGC*              (SEQ ID NO:4)
3. ZIP6          DTVQRNVL MENYN  SNSGHFSFDW AYNP HRY *                   (SEQ ID NO:12)
4. ZIP8          DTVQRNVL IQNYN  SNSGHFSFDW AYNP HRY *                   (SEQ ID NO:14)
5. ZIP9          DTVQRNVL IQNYN  SNSGHFSFDW AYNP HRY *                   (SEQ ID NO:16)
6. ZIP10         DTVQRNVL IQNYN  SNSGHFSFDW AYTILAVIELRSGC*              (SEQ ID NO:18)
7. ZIP11         DTVQRNVL IQNYN  SNSGHFSFDW AYNP HRY *                   (SEQ ID NO:20)
8. ZIP12         DTVQRNVL IQNYN  SNSGHFSFDW AYNP HRY *                   (SEQ ID NO:22)
9. Monalysin-WT  DTVQRNVL MENYN  SNSGHFSFDW AYNP HRY                     (SEQ ID NO:87)
```

FIGURE 7

| Protein | Concentration (mg/ml) | Mortality (%) |
|---|---|---|
| ZIP1 | 0.357 | 100 |
| ZIP2 | 0.320 | 100 |
| ZIP4 | 0.189 | 88 |
| ZIP6 | 0.422 | 38 |
| ZIP8 | 0.285 | 50 |
| ZIP9 | 0.254 | 63 |
| ZIP10 | 0.061 | 50 |
| ZIP11 | 0.250 | 44 |
| ZIP12 | 0.049 | 19 |
| ZIP16 | 0.207 | 100 |

FIGURE 8

| N | Protein | LC50 (mg/ml) | Lower 95% | Upper 95% |
|---|---|---|---|---|
| 448 | ZIP1 | 0.256 | 0.229 | 0.289 |
| 384 | ZIP2 | 0.196 | 0.157 | 0.236 |
| 160 | ZIP4 | 0.073 | 0.055 | 0.092 |

FIGURE 9A

| Protein | Concentration (mg/ml) | Mean Weight Compared to Control (%) |
|---------|----------------------|-------------------------------------|
| ZIP1    | 0.455                | 42                                  |
| ZIP2    | 0.736                | 36                                  |
| ZIP4    | 0.310                | 54                                  |

FIGURE 9B

| Protein | Concentration (mg/ml) | Mean Weight Compared to Control (%) |
|---------|----------------------|-------------------------------------|
| ZIP1    | 0.250                | 40                                  |
| ZIP2    | 0.250                | 49                                  |
| ZIP4    | 0.250                | 36                                  |

Lanes 1 and 11 — Negative Control (untransformed soybean leaves)
Lanes 2 and 3 — ZIP1 Transformed soybean leaves
Lanes 4 through 10 — ZIP2 Transformed soybean leaves
Lanes 12 and 13 — ZIP4 Transformed soybean leaves

Lane 14 — Negative Control (untransformed maize leaves)
Lanes 15 and 16 — ZIP2 Transformed maize leaves

SEQUENCE LISTING

<160> NUMBER OF SEQ ID NOS: 87

<210> SEQ ID NO 1
<211> LENGTH: 813
<212> TYPE: DNA
<213> ORGANISM: Unknown
<220> FEATURE:
<223> OTHER INFORMATION: undefined Pseudomonas species

<400> SEQUENCE: 1

```
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gtcggtcag cgccaaatac agcgttggcg gcagtatcga catcgtcaac      420
atcagctcgg atatcaccgt tggtttcagc agcaccgagg cctggtcgac gaaccagacc     480
ttcacccaaa gcaccgagct ggccggccct ggcaccttct tgtctatca ggtggtgttt      540
gtctatgcgc acaacgccac ttcggccggt gggcagaatg caatgccttt gcctatagc      600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
tggagcgcct acaacgatcc tcatcgccgt tat                                  813
```

<210> SEQ ID NO 2
<211> LENGTH: 271
<212> TYPE: PRT
<213> ORGANISM: Unknown
<220> FEATURE:
<223> OTHER INFORMATION: undefined Pseudomonas species

<400> SEQUENCE: 2

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160
```

Phe Thr Gln Ser Thr Glu Leu Ala Gly Pro Gly Thr Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 3
<211> LENGTH: 831
<212> TYPE: DNA
<213> ORGANISM: Unknown
<220> FEATURE:
<223> OTHER INFORMATION: undefined Pseudomonas species

<400> SEQUENCE: 3

```
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gtcggtcag cgccaaatac agcgttggcg cagtatcga catcgtcaac       420
atcagctcgg atatcaccgt tggtttcagc agcaccgagg cctggtcgac gaaccagacc     480
ttcacccaaa gcaccgagct ggccggccct ggcaccttct tgtctatca ggtggtgttt      540
gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg ccagcaaca gcgggcactt ctcgttcgac      780
tggagcgcct acacgatcct catcgccgtt attgaactga gatccggctg c              831
```

<210> SEQ ID NO 4
<211> LENGTH: 277
<212> TYPE: PRT
<213> ORGANISM: Unknown
<220> FEATURE:
<223> OTHER INFORMATION: undefined Pseudomonas species

<400> SEQUENCE: 4

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

```
Phe Glu Ile Asp Lys Tyr Leu Leu Asn Tyr Ala Asp Pro Lys Lys Gly
     50                  55                  60
Cys Trp Leu Asp Gly Val Thr Val Tyr Gly Asp Ile Tyr Ile Gly Lys
 65                  70                  75                  80
Gln Asn Trp Gly Thr Tyr Thr Arg Pro Val Phe Ala Tyr Leu Gln His
                 85                  90                  95
Thr Asp Thr Ile Ser Ile Pro Gln Gln Val Thr Gln Thr Lys Ser Tyr
            100                 105                 110
Gln Leu Ser Lys Gly His Thr Gln Ser Phe Thr Lys Ser Val Ser Ala
        115                 120                 125
Lys Tyr Ser Val Gly Gly Ser Ile Asp Ile Val Asn Ile Ser Ser Asp
130                 135                 140
Ile Thr Val Gly Phe Ser Ser Thr Glu Ala Trp Ser Thr Asn Gln Thr
145                 150                 155                 160
Phe Thr Gln Ser Thr Glu Leu Ala Gly Pro Gly Thr Phe Phe Val Tyr
                165                 170                 175
Gln Val Val Phe Val Tyr Ala His Asn Ala Thr Ser Ala Gly Gly Gln
            180                 185                 190
Asn Gly Asn Ala Phe Ala Tyr Ser Lys Thr Gln Gln Val Asn Ser Arg
        195                 200                 205
Leu Asp Leu Tyr Tyr Leu Ser Ala Ile Thr Gln Asp Arg Thr Val Ile
    210                 215                 220
Val Glu Ser Ser Asn Ala Ile Asp Pro Leu Asp Trp Asp Thr Val Gln
225                 230                 235                 240
Arg Asn Val Leu Ile Gln Asn Tyr Asn Pro Ala Ser Asn Ser Gly His
                245                 250                 255
Phe Ser Phe Asp Trp Ser Ala Tyr Thr Ile Leu Ile Ala Val Ile Glu
            260                 265                 270
Leu Arg Ser Gly Cys
        275

<210> SEQ ID NO 5
<211> LENGTH: 813
<212> TYPE: DNA
<213> ORGANISM: Unknown
<220> FEATURE:
<223> OTHER INFORMATION: undefined Pseudomonas species

<400> SEQUENCE: 5
atgacgatca aggaagagct gagccaaccc caaagccatt cggtcgagct cgaccagttg      60
caagtcgggg aagtccctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag ctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggagac gcagaccaag agctaccagt gagcaaagg ccacacccag     360
tcgttcacca gtcggtcag cgccaaatac ggcgttggcg gcagtatcga catcgtcaac     420
atcagctcgg atatcaccgt tggtttcagc agcaccgagg cctggtcgac gaaccagacc     480
ttcacccaaa gcaccgagct ggccggccct ggcaccttct tgtctatca ggttgttctt     540
gtttatgcgc acaacgccac ttcggcgggc aggcagaatg gtaatgcctt cgcctataac     600
aagacccagc aggtgggctc cgcgcctgac ctgtactacc tgtcggccat cactcagaac     660
agaacggtca ttgtcgagtc cagcaaggcc atcgacccgc tggattggga tacggtgcaa     720
```

```
cgcaacgtgc tgatggaaaa ctacaaccca gccagtaaca gcggacactt cagcttcgac    780
tggagtgcct acaacgatcc tcatcgccgt tat                                 813
```

<210> SEQ ID NO 6
<211> LENGTH: 271
<212> TYPE: PRT
<213> ORGANISM: Unknown
<220> FEATURE:
<223> OTHER INFORMATION: undefined Pseudomonas species

<400> SEQUENCE: 6

```
Met Thr Ile Lys Glu Glu Leu Ser Gln Pro Gln Ser His Ser Val Glu
1               5                   10                  15

Leu Asp Gln Leu Gln Val Gly Glu Val Pro Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Glu Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Gly Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Leu Val Tyr Ala His Asn Ala Thr Ser Ala Gly Arg Gln
            180                 185                 190

Asn Gly Asn Ala Phe Ala Tyr Asn Lys Thr Gln Gln Val Gly Ser Arg
        195                 200                 205

Leu Asp Leu Tyr Tyr Leu Ser Ala Ile Thr Gln Asn Arg Thr Val Ile
    210                 215                 220

Val Glu Ser Ser Lys Ala Ile Asp Pro Leu Asp Trp Asp Thr Val Gln
225                 230                 235                 240

Arg Asn Val Leu Met Glu Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 7
<211> LENGTH: 813
<212> TYPE: DNA
<213> ORGANISM: Unknown
<220> FEATURE:
<223> OTHER INFORMATION: undefined Pseudomonas species

<400> SEQUENCE: 7

```
atgacgatca aggaagaact gagcaatcct caaagccatt cggtcgagct cgaccagttg    60
caagtcgggg aagtctctgc acgcgaagcg ttgaccgcca acttcgccgg cagtttcgat   120
```

-continued

```
cagttcccga ccaaaagcgg cagcttcgag atcgacaaat acctgctcaa ctacgcagac    180
ccgaaacaag gctgctggct ggacggcgtc accgtctacg gtgacatcta catcggcaag    240
cagaactggg gcacctacac gcgcccggtg ttcgcctacc tgcagcacac ggacaccatc    300
tcgattccgc agcaggtgac gcagaccaag agctaccagt tgagcaaagg ccacacccag    360
tcgttcacca gtcggtcag cgccaagtac agcgttggcg gcagtatcga catcgtcaac     420
gtcagctcgg atatcaccgt tggtttcagc agcaccgagg cctggtcgac gacccagacc    480
ttcacccaga gcaccgagct ggccggccct ggcaccttct ttgtctatca ggtggtgttt    540
gtctacgcgc acaacgccac ctcggcgggc cggcagaatg gcaatgcctt tgcctatagc    600
aagacccagc aggtggattc gcggctcgat ctctactatc tgtcggcgat cacccaggac    660
cgtacggtca tcgtcgagtc cagcaaggca atcaacccgc tggactggga taccgtgcag    720
cgcaacgtgc tgatcgagaa ctacaacccg gcctccaaca gtgggcactt ccgcttcgac    780
tggagcgcct acaacgatcc tcatcgtcgt tac                                 813
```

<210> SEQ ID NO 8
<211> LENGTH: 271
<212> TYPE: PRT
<213> ORGANISM: Unknown
<220> FEATURE:
<223> OTHER INFORMATION: undefined Pseudomonas species
<220> FEATURE:
<221> NAME/KEY: misc_feature
<222> LOCATION: (251)..(251)
<223> OTHER INFORMATION: Xaa can be any naturally occurring amino acid

<400> SEQUENCE: 8

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220
```

Val Pro Ser Ser Asn Ala Val Thr Pro Leu Asp Trp Asp Thr Val Gln
225                 230                 235                 240

Arg Asn Val Leu Met Glu Asn Tyr Asn Pro Xaa Ser Asn Ser Gly His
            245                 250                 255

Phe Ser Phe Asp Trp Ser Ala Tyr Asn Asp Pro His Arg Arg Tyr
        260                 265                 270

<210> SEQ ID NO 9
<211> LENGTH: 813
<212> TYPE: DNA
<213> ORGANISM: Unknown
<220> FEATURE:
<223> OTHER INFORMATION: undefined Pseudomonas species

<400> SEQUENCE: 9

```
atgacgatca aggaagagct gagcaatcct caaagccatt cggtcgagct cgaccagttg      60
caagtcgggg aagtctctgc acgcgaagcg ttgaccgcca acttcgccgg cagtttcgat     120
cagttcccga ccaaaagcgg cagcttcgag atcgacaaat acctgctcaa ctacgcagac     180
ccgaaacaag gctgctggct ggacggcgtc accgtctacg gtgacatcta catcggcaag     240
cagaactggg gcacctacac gcgcccggtg ttcgcctacc tgcaacacac ggacaccatc     300
tcgattccgc agcaggtgac gcagaccaag agctaccagt tgagcaaagg ccacacccag     360
tcgttcacca gtcggtcag cgccaagtac aacgttggcg cagtatcga catcgtcaac      420
gtcagctcgg atatcactgt cggtttcagc agcaccgagg cctggtcgac gacccagacc     480
ttcacccaga gcaccgagct ggccggccct ggcaccttct tgtctatca ggtggtgttt      540
gtctacgcgc acaacgccac ctcggcgggc cggcagaatg caatgccctt gcctatagc      600
aagacccagc aggtggattc gcggctcgat ctctactacc tgtcggccat cacccaggac     660
cgtacggtca tcgtcgagtc cagcaaggca atcaacccgc tggaccggga taccgtgcag     720
cgcaacgtgc tgatcgagaa ctacaacccg gcctccaaca gtgggcactt ccgcttcgac     780
tggagcgcct acaacgatcc tcatcgccgt tat                                  813
```

<210> SEQ ID NO 10
<211> LENGTH: 271
<212> TYPE: PRT
<213> ORGANISM: Unknown
<220> FEATURE:
<223> OTHER INFORMATION: undefined Pseudomonas species

<400> SEQUENCE: 10

Met Thr Ile Lys Glu Glu Leu Ser Asn Pro Gln Ser His Ser Val Glu
1               5                   10                  15

Leu Asp Gln Leu Gln Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
            115                 120                 125

Lys Tyr Asn Val Gly Gly Ser Ile Asp Ile Val Asn Val Ser Ser Asp
        130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Arg Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 11
<211> LENGTH: 813
<212> TYPE: DNA
<213> ORGANISM: Unknown
<220> FEATURE:
<223> OTHER INFORMATION: undefined Pseudomonas species

<400> SEQUENCE: 11

```
atgacgatca aggaagagct gggccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg tccgcctacc tgcagcacac cgacaccatc     300
tcgattccgc agcaggtgac gcagaccaag agctaccagt tgagcaaagg ccacacccag     360
tcgttcacca gtcggtcagc gccaaatac agcgttggcg cagtatcga tcgtcaac       420
atcagctcgg atatcaccgt tggtttcagc agcaccgagg cctggtcgac gaaccagacc     480
ttcacccaaa gcaccgagct ggccggcccct ggcaccttct tgtctatca ggtggtgttt     540
gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaaggcc atcgcgccgc tggattggga tactgtccag     720
cgcaatgtac tgatggagaa ctacaaccag agcagcaata gcgggcactt cagtttcgac     780
tggagcgcct acaacgatcc tcatcgccgt tat                                  813
```

<210> SEQ ID NO 12
<211> LENGTH: 271
<212> TYPE: PRT
<213> ORGANISM: Unknown
<220> FEATURE:
<223> OTHER INFORMATION: undefined Pseudomonas species

<400> SEQUENCE: 12

Met Thr Ile Lys Glu Glu Leu Gly Gln Pro Gln Ser His Ser Val Glu

```
1               5                    10                    15
Leu Asp Gln Leu Gln Val Gly Glu Val Ser Ala Arg Glu Ala Leu Thr
              20                    25                    30

Ser Asn Phe Ala Gly Ser Phe Asp Gln Phe Pro Thr Lys Ser Gly Ser
              35                    40                    45

Phe Glu Ile Asp Lys Tyr Leu Leu Asn Tyr Ala Asp Pro Lys Lys Gly
              50                    55                    60

Cys Trp Leu Asp Gly Val Thr Val Tyr Gly Asp Ile Tyr Ile Gly Lys
 65               70                    75                    80

Gln Asn Trp Gly Thr Tyr Thr Arg Pro Val Ser Ala Tyr Leu Gln His
                  85                    90                    95

Thr Asp Thr Ile Ser Ile Pro Gln Gln Val Thr Gln Thr Lys Ser Tyr
              100                   105                   110

Gln Leu Ser Lys Gly His Thr Gln Ser Phe Thr Lys Ser Val Ser Ala
              115                   120                   125

Lys Tyr Ser Val Gly Gly Ser Ile Asp Ile Val Asn Ile Ser Ser Asp
              130                   135                   140

Ile Thr Val Gly Phe Ser Ser Thr Glu Ala Trp Ser Thr Asn Gln Thr
145               150                   155                   160

Phe Thr Gln Ser Thr Glu Leu Ala Gly Pro Gly Thr Phe Phe Val Tyr
                  165                   170                   175

Gln Val Val Phe Val Tyr Ala His Asn Ala Thr Ser Ala Gly Gly Gln
              180                   185                   190

Asn Gly Asn Ala Phe Ala Tyr Ser Lys Thr Gln Gln Val Asn Ser Arg
              195                   200                   205

Leu Asp Leu Tyr Tyr Leu Ser Ala Ile Thr Gln Asp Arg Thr Val Ile
              210                   215                   220

Val Glu Ser Ser Lys Ala Ile Ala Pro Leu Asp Trp Asp Thr Val Gln
225               230                   235                   240

Arg Asn Val Leu Met Glu Asn Tyr Asn Gln Ser Ser Asn Ser Gly His
                  245                   250                   255

Phe Ser Phe Asp Trp Ser Ala Tyr Asn Asp Pro His Arg Arg Tyr
              260                   265                   270

<210> SEQ ID NO 13
<211> LENGTH: 813
<212> TYPE: DNA
<213> ORGANISM: Unknown
<220> FEATURE:
<223> OTHER INFORMATION: undefined Pseudomonas species

<400> SEQUENCE: 13
atgacgatca aggaagagct gagccaaccc caaagccatt cggtcgagct cgaccagttg     60
caagtcgggg aagtctctgc acgcgaagcg ttgacctcca acttcgccgg cagtttcgat    120
cagttcccga ccaaaagcgg cagcttcgag atcgacaaat acctgctcaa ctacgcggat    180
ccgaaaaaag gctgctggct ggacggcgtc accgtctacg gtgacatcta catcggcaag    240
cagaactggg gcacctacac gcgcccggtg ttcgcctacc tgcagcacac cgacaccatc    300
ttgattccgc agcaggtgac gcagaccaag agctaccagt gagcaaagg ccacacccag    360 tcgttcacca agtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggcccc ggcaccttct tgtctatca ggtggtgttt    540 gtctatgcgc acaacgccac ttcggccggt gggcagaatg gcaatgcctt tgcctatagc    600
```

```
aagacccagc aggtgaactc gcggctcgac ctttactacc tgtcggccat cacccaggac      660
cgtacggtca tcgtcgagtc cagcaatgca atcgacccgc tggactggga taccgtgcag      720
cgcaacgtgc tgatccagaa ctacaacccg gccagcaaca gcgggcactt ctcgttcgac      780
tggagcgcct acaacgatcc tcatcgccgt tat                                   813
```

<210> SEQ ID NO 14
<211> LENGTH: 271
<212> TYPE: PRT
<213> ORGANISM: Unknown
<220> FEATURE:
<223> OTHER INFORMATION: undefined Pseudomonas species

<400> SEQUENCE: 14

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Leu Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 15
<211> LENGTH: 813
<212> TYPE: DNA
<213> ORGANISM: Unknown
<220> FEATURE:
<223> OTHER INFORMATION: undefined Pseudomonas species

<400> SEQUENCE: 15

```
atgacgatca aggaagagct gagccaaccc caaagccatt cggtcgagct cgaccagttg    60
caagtcgggg aagtctctgc acgcgaagcg ttgacctcca acttcgccgg cagtttcgat   120
cagttcccga ccaaaagcgg cggcttcgag atcgacaaat acctgctcaa ctacgcggat   180
ccgaaaaaag ctgctggct  ggacggcgtc accgtctacg gtgacatcta catcggcaag   240
cagaactggg gcacctacac gcgcccggtg ttcgcctacc tgcagcacac cgacaccatc   300
tcgattccgc agcaggtgac gcagaccaag agctaccagt tgagcaaagg ccacacccag   360
ccgttcacca gtcggtcag  cgccaaatac agcgttggcg gcagtatcga catcgtcaac   420
atcagctcgg atatcaccgt tggtttcagc agcaccgagg cctggtcgac gaaccagacc   480
ttcacccaaa gcaccgagct ggccggccct ggcaccttct tgtctatca  ggtggtgttt   540
gtctatgcgc acaacgccac ttcggccggt gggcagaatg gcaatgcctt tgcctatagc   600
aagacccagc aggtgaactc gcggctcgac ctttactacc tgtcggccat cacccaggac   660
cgtacggtca tcgtcgagtc cagcaatgca atcgacccgc tggactggga taccgtgcag   720
cgcaacgtgc tgatccagaa ctacaacccg gccagcaaca gcgggcactt ctcgttcgac   780
tggagcgcct acaacgatcc tcatcgccgt tat                                 813
```

<210> SEQ ID NO 16
<211> LENGTH: 271
<212> TYPE: PRT
<213> ORGANISM: Unknown
<220> FEATURE:
<223> OTHER INFORMATION: undefined Pseudomonas species

<400> SEQUENCE: 16

```
Met Thr Ile Lys Glu Glu Leu Ser Gln Pro Gln Ser His Ser Val Glu
1               5                  10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Gly
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Pro Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
```

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
            245                 250                 255

Phe Ser Phe Asp Trp Ser Ala Tyr Asn Asp Pro His Arg Arg Tyr
        260                 265                 270

<210> SEQ ID NO 17
<211> LENGTH: 831
<212> TYPE: DNA
<213> ORGANISM: Unknown
<220> FEATURE:
<223> OTHER INFORMATION: undefined Pseudomonas species
<220> FEATURE:
<221> NAME/KEY: misc_feature
<222> LOCATION: (657)..(657)
<223> OTHER INFORMATION: n is a, c, g, or t

<400> SEQUENCE: 17
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac ggacaccatc     300
tcgattccgc agcaggtgac gcagaccaag agctaccagt tgagcaaagg ccacacccag     360
tcgttcacca gtcggtcag cgccaagtac agcgttggcg gcagtatcga catcgtcaac      420
gtcagctcgg atatcactgt cggtttcagc agcaccgagg cctggtcgac gacccagacc     480
ttcacccaaa gcaccgagct ggccggtccg ggcaccttct tgtctatca ggtggtgttt      540 gtctatgcgc acaacgccac ttcggccggt gggcagaatg gcaatgcctt tgcctatagc     600
aagacccagc aggtgaactc gcggctcgac ctttactacc tgtcggccat cacccangac     660
cgtacggtca tcgtcgagtc cagcaatgca atcgacccgc tggaccggga taccgtgcag     720
cgcaacgtgc tgatccagaa ctacaacccg gccagcaaca gcgggcactt ctcgttcgac     780
tggagcgcct acacgatcct catcgccgtt attgaactga gatccggctg c             831

<210> SEQ ID NO 18
<211> LENGTH: 277
<212> TYPE: PRT
<213> ORGANISM: Unknown
<220> FEATURE:
<223> OTHER INFORMATION: undefined Pseudomonas species
<220> FEATURE:
<221> NAME/KEY: misc_feature
<222> LOCATION: (219)..(219)
<223> OTHER INFORMATION: Xaa can be any naturally occurring amino acid

<400> SEQUENCE: 18

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

```
Cys Trp Leu Asp Gly Val Thr Val Tyr Gly Asp Ile Tyr Ile Gly Lys
 65                  70                  75                  80

Gln Asn Trp Gly Thr Tyr Thr Arg Pro Val Phe Ala Tyr Leu Gln His
             85                  90                  95

Thr Asp Thr Ile Ser Ile Pro Gln Gln Val Thr Gln Thr Lys Ser Tyr
        100                 105                 110

Gln Leu Ser Lys Gly His Thr Gln Ser Phe Thr Lys Ser Val Ser Ala
    115                 120                 125

Lys Tyr Ser Val Gly Gly Ser Ile Asp Ile Val Asn Val Ser Ser Asp
130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Val Asn Ser Arg
        195                 200                 205

Leu Asp Leu Tyr Tyr Leu Ser Ala Ile Thr Xaa Asp Arg Thr Val Ile
210                 215                 220

Val Glu Ser Ser Asn Ala Ile Asp Pro Leu Asp Arg Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Thr Ile Leu Ile Ala Val Ile Glu
            260                 265                 270

Leu Arg Ser Gly Cys
        275

<210> SEQ ID NO 19
<211> LENGTH: 813
<212> TYPE: DNA
<213> ORGANISM: Unknown
<220> FEATURE:
<223> OTHER INFORMATION: undefined Pseudomonas species

<400> SEQUENCE: 19
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
ttgattccgc agcaggtgac gcagaccaag agctaccagt tgagcaaagg ccacacccag     360
tcgttcacca gtcggtcag cgccaaatac agcgttggcg gcagtatcga catcgtcaac      420
atcagctcgg atatcaccgt tggtttcagc agcaccgagg cctggtcgac gaaccagacc     480
ttcacccaaa gcaccgagct ggccggcccc ggcaccttct tgtctatca ggtggtgttt      540 gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
tggagcgcct acaacgatcc tcatcgccgt tat                                   813
```

<210> SEQ ID NO 20
<211> LENGTH: 271
<212> TYPE: PRT
<213> ORGANISM: Unknown
<220> FEATURE:
<223> OTHER INFORMATION: undefined Pseudomonas species

<400> SEQUENCE: 20

```
Met Thr Ile Lys Glu Glu Leu Ser Asn Pro Gln Ser His Ser Val Glu
1               5                   10                  15

Leu Asp Gln Leu Gln Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 21
<211> LENGTH: 813
<212> TYPE: DNA
<213> ORGANISM: Unknown
<220> FEATURE:
<223> OTHER INFORMATION: undefined Pseudomonas species

<400> SEQUENCE: 21

```
atgacgatca aggaagagct gggccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgccggct ggacggcgtc accgtctacg gtgacatcta catcggcaag     240
```

-continued

```
cagaactggg gcacctacac gcgcccggtg ttcgcctacc tgcagcacac cgacaccatc    300
tcgattccgc agcaggtgac acagactcgc agctaccagt gagcaaagg ccacacccag     360 tcgttcacca gtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggccct ggcaccttct tgtctatca ggtggtgttt     540 gtctatgcgc acaacgccac ttcggccggt gggcagaatg caatgccttt gcctatagc    600 aagacccagc aggtgaactc gcggctcgac ctttactacc tgtcggccat cacccaggac    660
cgtacggtca tcgtcgagtc cagcaatgca atcgacccgc tggactggga taccgtgcag    720
cgcaacgtgc tgatccagaa ctacaacccg ccagcaaca gcgggcactt ctcgttcgac    780
tggagcgcct acaacgatcc tcatcgccgt tat                                 813
```

<210> SEQ ID NO 22
<211> LENGTH: 271
<212> TYPE: PRT
<213> ORGANISM: Unknown
<220> FEATURE:
<223> OTHER INFORMATION: undefined Pseudomonas species

<400> SEQUENCE: 22

```
Met Thr Ile Lys Glu Glu Leu Gly Gln Pro Gln Ser His Ser Val Glu
1               5                   10                  15

Leu Asp Gln Leu Gln Val Gly Glu Val Ser Ala Arg Glu Ala Leu Thr
                20                  25                  30

Ser Asn Phe Ala Gly Ser Phe Asp Gln Phe Pro Thr Lys Ser Gly Ser
            35                  40                  45

Phe Glu Ile Asp Lys Tyr Leu Leu Asn Tyr Ala Asp Pro Lys Lys Gly
        50                  55                  60

Cys Arg Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Arg Ser Tyr
                100                 105                 110

Gln Leu Ser Lys Gly His Thr Gln Ser Phe Thr Lys Ser Val Ser Ala
            115                 120                 125

Lys Tyr Ser Val Gly Gly Ser Ile Asp Ile Val Asn Ile Ser Ser Asp
        130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255
```

```
Phe Ser Phe Asp Trp Ser Ala Tyr Asn Asp Pro His Arg Arg Tyr
            260                 265                 270
```

<210> SEQ ID NO 23
<211> LENGTH: 813
<212> TYPE: DNA
<213> ORGANISM: Unknown
<220> FEATURE:
<223> OTHER INFORMATION: undefined Pseudomonas species

<400> SEQUENCE: 23

```
atgacgatca aggaagagct gggccaaccc caaagccgtt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag ctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt gagcaaagg ccacacccag     360
tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggccct ggcaccttct tgtctatca ggtggtgttt     540
gtctatgcgc acaacgccac ctcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
tggagcgcct acaacgatcc tcatcgccgt tat                                  813
```

<210> SEQ ID NO 24
<211> LENGTH: 271
<212> TYPE: PRT
<213> ORGANISM: Unknown
<220> FEATURE:
<223> OTHER INFORMATION: undefined Pseudomonas species

<400> SEQUENCE: 24

```
Met Thr Ile Lys Glu Glu Leu Gly Gln Pro Gln Ser Arg Ser Val Glu
1               5                   10                  15

Leu Asp Gln Leu Gln Val Gly Glu Val Ser Ala Arg Glu Ala Leu Thr
                20                  25                  30

Ser Asn Phe Ala Gly Ser Phe Asp Gln Phe Pro Thr Lys Ser Gly Ser
            35                  40                  45

Phe Glu Ile Asp Lys Tyr Leu Leu Asn Tyr Ala Asp Pro Lys Lys Gly
        50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
```

```
                145                 150                 155                 160
Phe Thr Gln Ser Thr Glu Leu Ala Gly Pro Gly Thr Phe Val Tyr
                    165                 170                 175

Gln Val Val Phe Val Tyr Ala His Asn Ala Thr Ser Ala Gly Gly Gln
                180                 185                 190

Asn Gly Asn Ala Phe Ala Tyr Ser Lys Thr Gln Gln Val Asn Ser Arg
            195                 200                 205

Leu Asp Leu Tyr Tyr Leu Ser Ala Ile Thr Gln Asp Arg Thr Val Ile
            210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 25
<211> LENGTH: 813
<212> TYPE: DNA
<213> ORGANISM: Unknown
<220> FEATURE:
<223> OTHER INFORMATION: undefined Pseudomonas species

<400> SEQUENCE: 25
atgacgatca aggaagagct gggccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgatggtt atttgctgga ctacagctca     180
cccaagcaag gttgctgggt ggacggtatc actgtctatg cgatatctac atcggcaag     240 cagaactggg gcacttatac ccgcccggtg tttgcctacc tacagtatgt ggaaaccatc     300
tccattccac agaatgtgac gaccaccctc agctatcagc tgaccaaggg catacccgt     360 tccttcgaga ccagtgtcaa cgccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaaggggcca gggacgttcg tcatttacca ggtcgtgctg     540
gtgtatgcgc acaacgccac ctcggcaggg cggcagaatg ccaatgcctt cgcctacagc     600
aaaacccagg cagtgggctc gcgggtggac ttgtactact gtcggccat tacccagcgc     660 aagcgggtca tcgttccgtc gagcaatgcc gtcacgccgc tggactggga tacggtgcaa     720
cgcaacgtgc tgatggaaaa ctacaacccca ggcagtaaca gcggacactt cggcttcgac     780
tggagtgcct acaacgatcc tcatcgccgt tat                                   813

<210> SEQ ID NO 26
<211> LENGTH: 271
<212> TYPE: PRT
<213> ORGANISM: Unknown
<220> FEATURE:
<223> OTHER INFORMATION: undefined Pseudomonas species

<400> SEQUENCE: 26

Met Thr Ile Lys Glu Glu Leu Gly Gln Pro Gln Ser His Ser Ile Glu
1               5                   10                  15

Leu Asp Glu Val Ser Lys Glu Ala Ala Ser Thr Arg Ala Ala Leu Thr
                20                  25                  30

Ser Asn Leu Ser Gly Arg Phe Asp Gln Tyr Pro Thr Lys Lys Gly Asp
            35                  40                  45
```

```
Phe Ala Ile Asp Gly Tyr Leu Leu Asp Tyr Ser Ser Pro Lys Gln Gly
            50                  55                  60

Cys Trp Val Asp Gly Ile Thr Val Tyr Gly Asp Ile Tyr Ile Gly Lys
 65                  70                  75                  80

Gln Asn Trp Gly Thr Tyr Thr Arg Pro Val Phe Ala Tyr Leu Gln Tyr
                 85                  90                  95

Val Glu Thr Ile Ser Ile Pro Gln Asn Val Thr Thr Leu Ser Tyr
                100                 105                 110

Gln Leu Thr Lys Gly His Thr Arg Ser Phe Glu Thr Ser Val Asn Ala
            115                 120                 125

Lys Tyr Ser Val Gly Ala Asn Ile Asp Ile Val Asn Val Gly Ser Glu
130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
            195                 200                 205

Val Asp Leu Tyr Tyr Leu Ser Ala Ile Thr Gln Arg Lys Arg Val Ile
            210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Gly Phe Asp Trp Ser Ala Tyr Asn Asp Pro His Arg Arg Tyr
            260                 265                 270

<210> SEQ ID NO 27
<211> LENGTH: 813
<212> TYPE: DNA
<213> ORGANISM: Unknown
<220> FEATURE:
<223> OTHER INFORMATION: undefined Pseudomonas species

<400> SEQUENCE: 27
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaggcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gccggtcag cgccaaatac agcgttggcg cagtatcga catcgtcaac     420 atcagctcgg atatcaccgt tggtttcagc agcaccgagg cctggtcgac gaaccagacc     480
ttcacccaaa gcaccgagct ggccggcccct ggcaccttct tgtctatca ggtggtgttt     540 gtctatgcgc acaacgccac ttcggccggt gggcagaatg caatgccttt gcctatagc     600 aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
```
tggagcgcct acaacgatcc tcatcgccgt tat                                    813

<210> SEQ ID NO 28
<211> LENGTH: 271
<212> TYPE: PRT
<213> ORGANISM: Unknown
<220> FEATURE:
<223> OTHER INFORMATION: undefined Pseudomonas species

<400> SEQUENCE: 28

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Gly Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Pro Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 29
<211> LENGTH: 813
<212> TYPE: DNA
<213> ORGANISM: Unknown
<220> FEATURE:
<223> OTHER INFORMATION: undefined Pseudomonas species

<400> SEQUENCE: 29
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180

-continued

```
ccgaaaaaag gctgctggct ggacggcgtc accgtctacg gtgacatcta catcggcaag      240
cagaactggg gcacctacac gcgcccggtg ttcgcctacc tgcagcacac cgacaccatc      300
tcgattccgc agcaggtgac gcagaccaag agctaccagt tgagcaaagg ccacacccag      360
tcgttcacca gtcggtcag cgccaaatac agcgttggcg gcagtatcga catcgtcaac       420
atcagctcgg atatcaccgt tggtttcagc agcaccgagg cctggtcgac gaaccagacc      480
ttcacccaaa gcaccgagct ggccggcccect ggcaccttct tgtctatca ggtggtgtct    540 gtctatgcgc acaacgccac ttcggccggt gggcagaatg gcaatgcctt tgcctatagc      600
aagacccagc aggtgaactc gcggctcgac ctttactacc tgtcggccat cacccaggac      660
cgtacggtca tcgtcgagtc cagcaatgca atcgacccgc tggactggga taccgtgcag      720
cgcaacgtgc tgatccagaa ctacaacccg gccagcaaca gcgggcactt ctcgttcgac      780
tggagcgcct acaacgatcc tcatcgccgt tat                                   813
```

<210> SEQ ID NO 30
<211> LENGTH: 271
<212> TYPE: PRT
<213> ORGANISM: Unknown
<220> FEATURE:
<223> OTHER INFORMATION: undefined Pseudomonas species

<400> SEQUENCE: 30

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Ser Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255
```

```
Phe Ser Phe Asp Trp Ser Ala Tyr Asn Asp Pro His Arg Arg Tyr
            260                 265                 270

<210> SEQ ID NO 31
<211> LENGTH: 813
<212> TYPE: DNA
<213> ORGANISM: Unknown
<220> FEATURE:
<223> OTHER INFORMATION: undefined Pseudomonas species

<400> SEQUENCE: 31
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttgag atcgacaaat acctgctcaa ctacgcggat      180
ccgaaaaaag gctgctggct ggacggcgtc accgtctacg gtgacatcta tcggcaag      240 cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca agtcggtcag cgccaaatac agcgttggcg gcggtatcga catcgtcaac     420
atcagctcgg atatcaccgt tggtttcagc agcaccgagg cctggtcgac gaaccagacc     480
ttcacccaaa gcaccgagct ggccggccct ggcaccttct tgtctatca ggtggtgttt      540 gtctatgcgc acaacgccac ttcggccggt gggcagaatg caatgccttt gcctatagc      600 aagacccagc aggtgaactc gcggctcgac ctttactgcc tgtcggccat cacccaggac     660
cgtacggtca tcgtcgagtc cagcaatgca atcgacccgc tggactggga taccgtgcag     720
cgcaacgtgc tgatccagaa ctacaacccg ccagcaaca gcgggcactt ctcgttcgac      780
tggagcgcct acaacgatcc tcatcgccgt tat                                  813

<210> SEQ ID NO 32
<211> LENGTH: 271
<212> TYPE: PRT
<213> ORGANISM: Unknown
<220> FEATURE:
<223> OTHER INFORMATION: undefined Pseudomonas species

<400> SEQUENCE: 32

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Gly Ile Asp Ile Val Asn Ile Ser Ser Asp
    130                 135                 140
```

```
Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Cys Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 33
<211> LENGTH: 813
<212> TYPE: DNA
<213> ORGANISM: Unknown
<220> FEATURE:
<223> OTHER INFORMATION: undefined Pseudomonas species

<400> SEQUENCE: 33
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gtcggtcag cgccaaatac agcgttggcg gcagtatcga catcgtcaac      420
atcagctcgg atatcaccgt tggtttcagc agcaccgagg cctggtcgac gaaccagacc     480
ttcacccaaa gcaccgagct ggccggccct ggcaccttct tgtctatca ggtggtgttt      540
gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc cggactggga taccgtgcag     720
cgcaacgtgc tgatccagaa ctacaacccg gccagcaaca gcgggcactt ctcgttcgac     780
tggagcgcct acaacgatcc tcatcgccgt tat                                  813

<210> SEQ ID NO 34
<211> LENGTH: 271
<212> TYPE: PRT
<213> ORGANISM: Unknown
<220> FEATURE:
<223> OTHER INFORMATION: undefined Pseudomonas species

<400> SEQUENCE: 34

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
```

```
              35                  40                  45
Phe Glu Ile Asp Lys Tyr Leu Leu Asn Tyr Ala Asp Pro Lys Lys Gly
        50                  55                  60

Cys Trp Leu Asp Gly Val Thr Val Tyr Gly Asp Ile Tyr Ile Gly Lys
 65                  70                  75                  80

Gln Asn Trp Gly Thr Tyr Thr Arg Pro Val Phe Ala Tyr Leu Gln His
                 85                  90                  95

Thr Asp Thr Ile Ser Ile Pro Gln Gln Val Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
210                 215                 220

Val Glu Ser Ser Asn Ala Ile Asp Pro Pro Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 35
<211> LENGTH: 813
<212> TYPE: DNA
<213> ORGANISM: Unknown
<220> FEATURE:
<223> OTHER INFORMATION: undefined Pseudomonas species

<400> SEQUENCE: 35
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt gagcaaagg ccacacccag     360 tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggcccct ggcaccttct tgtctatca ggtggtgttt     540 gtctatgcgc acaacgccac ttcggccggt gggcagaatg gcaatgcctt tgcctatggc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
```
tggagcgcct acaacgatcc tcatcgccgt tat                                    813

<210> SEQ ID NO 36
<211> LENGTH: 271
<212> TYPE: PRT
<213> ORGANISM: Unknown
<220> FEATURE:
<223> OTHER INFORMATION: undefined Pseudomonas species

<400> SEQUENCE: 36

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Val Thr Gln Thr Lys Ser Tyr
            100                 105                 110

Gln Leu Ser Lys Gly His Thr Gln Ser Phe Thr Lys Ser Val Ser Ala
            115                 120                 125

Lys Tyr Ser Val Gly Gly Ser Ile Asp Ile Val Asn Ile Ser Ser Asp
        130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Gly Lys Thr Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 37
<211> LENGTH: 813
<212> TYPE: DNA
<213> ORGANISM: Unknown
<220> FEATURE:
<223> OTHER INFORMATION: undefined Pseudomonas species

<400> SEQUENCE: 37
atgacgatca aggaagagct gggccaaccc caaagccatt cggtcgagct cgaccagttg     60
caagtcgggg aagtctctgc acgcgaagcg ttgacctcca acttcgccgg cagtttcgat    120
cagttcccga ccaaaagcgg cagcttcgag atcgacaaat acctgctcaa ctacgcggat    180

-continued

```
ccgaaaaaag gctgctggct ggacggcgtc accgtctacg gtgacatcta catcggcaag    240
cagaactggg gcacctacac gcgcccggtg ttcgcctacc tgcagcacac cgacaccatc    300
tcgattccgc agcaggtgac gcagaccaag agctaccagt tgagcaaagg ccacacccag    360
tcgttcacca gtcggtcag cgccaaatac agcgttggcg gcagtatcga catcgtcaac     420
atcagctcgg atatcaccgt tggtttcagc agcaccgagg cctggtcgac gaaccagacc    480
ttcacccaaa gcaccgagct ggccggccct ggcaccttct tgtctatca ggtggtgttt     540
gtctatgcgc acaacgccac ttcggccggt gggcagaatg gcaatgcctt tgcctatagc    600
aagacccagc aggtgaactc gcggctcgac ctttactacc tgtcggccat cacccaggac    660
cgtacggtca tcgtcgagtc cagcaatgca atcgacccgc tggactggga taccgtgcag    720
cgcaacgtgc tgatccagaa ctacaacccg gccagcaaca gcgggcactt ctcgttcgac    780
tggagcgcct acaacgatcc tcatcgccgt tat                                 813
```

<210> SEQ ID NO 38
<211> LENGTH: 271
<212> TYPE: PRT
<213> ORGANISM: Unknown
<220> FEATURE:
<223> OTHER INFORMATION: undefined Pseudomonas species

<400> SEQUENCE: 38

```
Met Thr Ile Lys Glu Glu Leu Gly Gln Pro Gln Ser His Ser Val Glu
1               5                   10                  15
Leu Asp Gln Leu Gln Val Gly Glu Val Ser Ala Arg Glu Ala Leu Thr
            20                  25                  30
Ser Asn Phe Ala Gly Ser Phe Asp Gln Phe Pro Thr Lys Ser Gly Ser
        35                  40                  45
Phe Glu Ile Asp Lys Tyr Leu Leu Asn Tyr Ala Asp Pro Lys Lys Gly
    50                  55                  60
Cys Trp Leu Asp Gly Val Thr Val Tyr Gly Asp Ile Tyr Ile Gly Lys
65                  70                  75                  80
Gln Asn Trp Gly Thr Tyr Thr Arg Pro Val Phe Ala Tyr Leu Gln His
                85                  90                  95
Thr Asp Thr Ile Ser Ile Pro Gln Gln Val Thr Gln Thr Lys Ser Tyr
            100                 105                 110
Gln Leu Ser Lys Gly His Thr Gln Ser Phe Thr Lys Ser Val Ser Ala
        115                 120                 125
Lys Tyr Ser Val Gly Gly Ser Ile Asp Ile Val Asn Ile Ser Ser Asp
    130                 135                 140
Ile Thr Val Gly Phe Ser Ser Thr Glu Ala Trp Ser Thr Asn Gln Thr
145                 150                 155                 160
Phe Thr Gln Ser Thr Glu Leu Ala Gly Pro Gly Thr Phe Phe Val Tyr
                165                 170                 175
Gln Val Val Phe Val Tyr Ala His Asn Ala Thr Ser Ala Gly Gly Gln
            180                 185                 190
Asn Gly Asn Ala Phe Ala Tyr Ser Lys Thr Gln Gln Val Asn Ser Arg
        195                 200                 205
Leu Asp Leu Tyr Tyr Leu Ser Ala Ile Thr Gln Asp Arg Thr Val Ile
    210                 215                 220
Val Glu Ser Ser Asn Ala Ile Asp Pro Leu Asp Trp Asp Thr Val Gln
225                 230                 235                 240
Arg Asn Val Leu Ile Gln Asn Tyr Asn Pro Ala Ser Asn Ser Gly His
```

```
                      245                 250                 255
Phe Ser Phe Asp Trp Ser Ala Tyr Asn Asp Pro His Arg Arg Tyr
        260                 265                 270

<210> SEQ ID NO 39
<211> LENGTH: 813
<212> TYPE: DNA
<213> ORGANISM: Unknown
<220> FEATURE:
<223> OTHER INFORMATION: undefined Pseudomonas species

<400> SEQUENCE: 39
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag ctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt cgagcaaagg ccacacccag     360
tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggcccct ggcaccttct tgtctatca ggtggtgttt     540 gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg ccagcaaca gcgggcactt ctcgttcgac     780
tggagcgcct acaacgatcc tcatcgccgt tat                                  813

<210> SEQ ID NO 40
<211> LENGTH: 271
<212> TYPE: PRT
<213> ORGANISM: Unknown
<220> FEATURE:
<223> OTHER INFORMATION: undefined Pseudomonas species

<400> SEQUENCE: 40

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Ser Ser Lys Gly His Thr Gln Ser Phe Lys Ser Val Ser Ala
        115                 120                 125

Lys Tyr Ser Val Gly Gly Ser Ile Asp Ile Val Asn Ile Ser Ser Asp
    130                 135                 140
```

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
            165                 170                 175

Gln Val Val Phe Val Tyr Ala His Asn Ala Thr Ser Ala Gly Gly Gln
        180                 185                 190

Asn Gly Asn Ala Phe Ala Tyr Ser Lys Thr Gln Gln Val Asn Ser Arg
    195                 200                 205

Leu Asp Leu Tyr Tyr Leu Ser Ala Ile Thr Gln Asp Arg Thr Val Ile
210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 41
<211> LENGTH: 813
<212> TYPE: DNA
<213> ORGANISM: Unknown
<220> FEATURE:
<223> OTHER INFORMATION: undefined Pseudomonas species

<400> SEQUENCE: 41
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggcccct ggcaccttct tgtctatca ggtggtgttt     540 gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagcc cagcaatgca atcgacccgc tggactggga taccgtgcag     720
cgcaacgtgc tgatccagaa ctacaacccg ccagcaaca gcgggcactt ctcgttcgac     780
tggagcgcct acaacgatcc tcatcgccgt tat                                  813

<210> SEQ ID NO 42
<211> LENGTH: 271
<212> TYPE: PRT
<213> ORGANISM: Unknown
<220> FEATURE:
<223> OTHER INFORMATION: undefined Pseudomonas species

<400> SEQUENCE: 42

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

| | | | | | | | | | | | |
|---|---|---|---|---|---|---|---|---|---|---|---|
|Ser|Asn|Phe|Ala|Gly|Ser|Phe|Asp|Gln|Phe|Pro|Thr|Lys|Ser|Gly|Ser|
| | |35| | | |40| | | |45| |

Ser Asn Phe Ala Gly Ser Phe Asp Gln Phe Pro Thr Lys Ser Gly Ser
                35                  40                  45

Phe Glu Ile Asp Lys Tyr Leu Leu Asn Tyr Ala Asp Pro Lys Lys Gly
 50                  55                  60

Cys Trp Leu Asp Gly Val Thr Val Tyr Gly Asp Ile Tyr Ile Gly Lys
65                   70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Lys Ser Tyr
                100                 105                 110

Gln Leu Ser Lys Gly His Thr Gln Ser Phe Thr Lys Ser Val Ser Ala
                115                 120                 125

Lys Tyr Ser Val Gly Gly Ser Ile Asp Ile Val Asn Ile Ser Ser Asp
130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
                180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
        210                 215                 220

Val Glu Pro Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 43
<211> LENGTH: 813
<212> TYPE: DNA
<213> ORGANISM: Unknown
<220> FEATURE:
<223> OTHER INFORMATION: undefined Pseudomonas species

<400> SEQUENCE: 43

```
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag ctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agccaccagt gagcaaagg ccacacccag     360
tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggccct ggcaccttct tgtctatca ggtggtgttt     540
gtctatgcgc acaacgccac ttcggccggt gggcagaatg gcaatgcctt tgcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
```

```
cgcaacgtgc tgatccagaa ctacaacccg ccagcaaca gcgggcactt ctcgttcgac      780
tggagcgcct acaacgatcc tcatcgccgt tat                                 813
```

<210> SEQ ID NO 44
<211> LENGTH: 271
<212> TYPE: PRT
<213> ORGANISM: Unknown
<220> FEATURE:
<223> OTHER INFORMATION: undefined Pseudomonas species

<400> SEQUENCE: 44

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
 50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser His
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 45
<211> LENGTH: 813
<212> TYPE: DNA
<213> ORGANISM: Unknown
<220> FEATURE:
<223> OTHER INFORMATION: undefined Pseudomonas species

<400> SEQUENCE: 45

```
atgacgatca aggaagagct gaaccaaccc caaagccatt cggtcgagct cgaccagttg      60
caagtcgggg aagtctctgc acgcgaagcg ttgacctcca acttcgccgg cagtttcgat     120
```

```
cagttcccga ccaaaagcgg cagcttcgag atcgacaaat acctgctcaa ctacgcggat    180
ccgaaaaaag gctgctggct ggacggcgtc accgtctacg gtgacatcta catcggcaag    240
cagaactggg gcacctacac gcgcccggtg ttcgcctacc tgcagcacac cgacaccatc    300
tcgattccgc agcaggtgac gcagaccaag agctaccagt tgagcaaagg ccacacccag    360
tcgttcacca agtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggccct ggcaccttct ttgtctatca ggtggtgttt    540
gtctatgcgc acaacgccac ttcggccggt gggcagaatg gcaatgcctt tgcctatagc    600
aagacccagc aggtgaactc gcggctcgac ctttactacc tgtcggccat cacccaggac    660
cgtacggtca tcgtcgagtc cagcaatgca atcgacccgc tggactggga taccgtgcag    720
cgcaacgtgc tgatccagaa ctacaacccg gccagcaaca gcgggcactt ctcgttcgac    780
tggagcgcct acaacgatcc tcatcgccgt tat                                 813
```

<210> SEQ ID NO 46
<211> LENGTH: 271
<212> TYPE: PRT
<213> ORGANISM: Unknown
<220> FEATURE:
<223> OTHER INFORMATION: undefined Pseudomonas species

<400> SEQUENCE: 46

```
Met Thr Ile Lys Glu Glu Leu Asn Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240
```

Arg Asn Val Leu Ile Gln Asn Tyr Asn Pro Ala Ser Asn Ser Gly His
                245                 250                 255
Phe Ser Phe Asp Trp Ser Ala Tyr Asn Asp Pro His Arg Arg Tyr
        260                 265                 270

<210> SEQ ID NO 47
<211> LENGTH: 813
<212> TYPE: DNA
<213> ORGANISM: Unknown
<220> FEATURE:
<223> OTHER INFORMATION: undefined Pseudomonas species

<400> SEQUENCE: 47

```
atgacgatca aggaagagct gagccaaccc caaagccatt tggtcgagct cgaccagttg       60
caagtcgggg aagtctctgc acgcgaagcg ttgacctcca acttcgccgg cagtttcgat      120
cagttcccga ccaaaagcgg cagcttcgag atcgacaaat acctgctcaa ctacgcggat      180
ccgaaaaaag gctgctggct ggacggcgtc accgtctacg gtgacatcta catcggcaag      240
cagaactggg gcacctacac gcgcccggtg ttcgcctacc tgcagcacac cgacaccatc      300
tcgattccgc agcaggtgac gcagaccaag agctaccagt tgagcaaagg ccacacccag      360
tcgttcacca gtcggtcag cgccaaatac agcgttggcg gcagtatcga catcgtcaac      420
atcagctcgg atatcaccgt tggtttcagc agcaccgagg cctggtcgac gaaccagacc      480
ttcacccaaa gcaccgagct ggccggccct ggcaccttct tgtctatca ggtggtgttt      540
gtctatgcgc acaacgccac ttcggccggt gggcagaatg caatgccttt gcctatagc      600
aagacccagc aggtgaactc gcggctcgac ctttactacc tgtcggccat cacccaggac      660
cgtacggtca tcgtcgagtc cagcaatgca atcgacccgc tggactggga taccgtgcag      720
cgcaacgtgc tgatccagaa ctacaacccg gccagcaaca gcgggcactt ctcgttcgac      780
tggagcgcct acaacgatcc tcatcgccgt tat                                   813
```

<210> SEQ ID NO 48
<211> LENGTH: 271
<212> TYPE: PRT
<213> ORGANISM: Unknown
<220> FEATURE:
<223> OTHER INFORMATION: undefined Pseudomonas species

<400> SEQUENCE: 48

Met Thr Ile Lys Glu Glu Leu Ser Gln Pro Gln Ser His Leu Val Glu
1               5                   10                  15
Leu Asp Gln Leu Gln Val Gly Glu Val Ser Ala Arg Glu Ala Leu Thr
            20                  25                  30
Ser Asn Phe Ala Gly Ser Phe Asp Gln Phe Pro Thr Lys Ser Gly Ser
        35                  40                  45
Phe Glu Ile Asp Lys Tyr Leu Leu Asn Tyr Ala Asp Pro Lys Lys Gly
    50                  55                  60
Cys Trp Leu Asp Gly Val Thr Val Tyr Gly Asp Ile Tyr Ile Gly Lys
65                  70                  75                  80
Gln Asn Trp Gly Thr Tyr Thr Arg Pro Val Phe Ala Tyr Leu Gln His
                85                  90                  95
Thr Asp Thr Ile Ser Ile Pro Gln Gln Val Thr Gln Thr Lys Ser Tyr
            100                 105                 110
Gln Leu Ser Lys Gly His Thr Gln Ser Phe Thr Lys Ser Val Ser Ala
        115                 120                 125
Lys Tyr Ser Val Gly Gly Ser Ile Asp Ile Val Asn Ile Ser Ser Asp

```
                  130                 135                 140
Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
                260                 265                 270

<210> SEQ ID NO 49
<211> LENGTH: 813
<212> TYPE: DNA
<213> ORGANISM: Unknown
<220> FEATURE:
<223> OTHER INFORMATION: undefined Pseudomonas species

<400> SEQUENCE: 49
atgacgatca aggaagagct gagccaaccc caaagccatt cggtcgagct cgaccagttg    60
caagtcgggg aagtctctgc acgcgaagcg ttgacctcca acttcgccgg cagtttcgat   120
cagttcccga ccaaaagcgg cagcttcaag atcgacaaat acctgctcaa ctacgcggat   180
ccgaaaaaag gctgctggct ggacggcgtc accgtctacg gtgacatcta catcggcaag   240
cagaactggg gcacctacac gcgcccggtg ttcgcctacc tgcagcacac cgacaccatc   300
tcgattccgc agcaggtgac gcagaccaag agctaccagt tgagcaaagg ccacacccag   360
tcgttcacca gtcggtcag cgccaaatac agcgttggcg cagtatcga catcgtcaac   420 atcagctcgg atatcaccgt tggtttcagc agcaccgagg cctggtcgac gaaccagacc   480
ttcacccaaa gcaccgagct ggccggccct ggcaccttct tgtctatca ggtggtgttt   540 gtctatgcgc acaacgccac ttcggccggt gggcagaatg gcaatgcctt tgcctatagc   600
aagacccagc aggtgaactc gcggctcgac ctttactacc tgtcggccat cacccaggac   660
cgtacggtca tcgtcgagtc cagcaatgca atcgacccgc tggactggga taccgtgcag   720
cgcaacgtgc tgatccagaa ctacaacccg gccagcaaca gcgggcactt ctcgttcgac   780
tggagcgcct acaacgatcc tcatcgccgt tat                                 813

<210> SEQ ID NO 50
<211> LENGTH: 271
<212> TYPE: PRT
<213> ORGANISM: Unknown
<220> FEATURE:
<223> OTHER INFORMATION: undefined Pseudomonas species

<400> SEQUENCE: 50

Met Thr Ile Lys Glu Glu Leu Ser Gln Pro Gln Ser His Ser Val Glu
1               5                  10                  15

Leu Asp Gln Leu Gln Val Gly Glu Val Ser Ala Arg Glu Ala Leu Thr
            20                  25                  30
```

```
Ser Asn Phe Ala Gly Ser Phe Asp Gln Phe Pro Thr Lys Ser Gly Ser
        35                  40                  45

Phe Lys Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 51
<211> LENGTH: 813
<212> TYPE: DNA
<213> ORGANISM: Unknown
<220> FEATURE:
<223> OTHER INFORMATION: undefined Pseudomonas species

<400> SEQUENCE: 51
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca gtcggtcag cgccaaatac agcgttggcg gcagtatcga catcgtcaac     420
atcagctcgg atatcaccgt tggtttcagc agcaccgagg cctggtcgac gaaccagacc     480
ttcacccgaa gcaccgagct ggccggccct ggcaccttct tgtctatca ggtggtgttt     540 gtctatgcgc acaacgccac ttcggccggt gggcagaatg caatgccttt gcctatagc     600 aagacccagc aggtgaactc gcggctcgac ctttactacc tgtcggccat cacccaggac     660
cgtacggtca tcgtcgagtc cagcaatgca atcgacccgc tggactggga taccgtgcag     720
```
cgcaacgtgc tgatccagaa ctacaacccg gccagcaaca gcgggcactt ctcgttcgac    780
tggagcgcct acaacgatcc tcatcgccgt tat                                 813

<210> SEQ ID NO 52
<211> LENGTH: 271
<212> TYPE: PRT
<213> ORGANISM: Unknown
<220> FEATURE:
<223> OTHER INFORMATION: undefined Pseudomonas species

<400> SEQUENCE: 52

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Arg Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 53
<211> LENGTH: 813
<212> TYPE: DNA
<213> ORGANISM: Unknown
<220> FEATURE:
<223> OTHER INFORMATION: undefined Pseudomonas species

<400> SEQUENCE: 53
atgacgatca aggaagagct gagccaaccc caaagccatt cggtcgagct cgaccagttg    60
caagtcgggg aagtctctgc acgcgaagcg ttgacctcca acttcgccgg cagtttcgat   120

```
cagttcccga ccaaaagcgg cagcttcgag atcgacaaat acctgctcag ctacgcggat    180
ccgaaaaaag gctgctggct ggacggcgtc accgtctacg gtgacatcta catcggcaag    240
cagaactggg gcacctacac gcgcccggtg ttcgcctacc tgcagcacac cgacaccatc    300
tcgattccgc agcaggtgac gcagaccaag agctaccagt tgagcaaagg ccacacccag    360
tcgttcacca gtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggccct ggcaccttct tgtctatca ggtggtgttt    540 gtctatgcgc acaacgccac ttcggccggt gggcagaatg caatgccctt tgcctatagc    600
aagacccagc aggtgagctc gcggctcgac ctttactacc tgtcggccat cacccaggac    660
cgtacggtca tcgtcgagtc cagcagtgca atcgacccgc tggactggga taccgtgcag    720
cgcaacgtgc tgatccagaa ctacaacccg gccagcaaca gcgggcactt ctcgttcgac    780
tggagcgcct acaacgatcc tcatcgccgt tat                                 813
```

<210> SEQ ID NO 54
<211> LENGTH: 271
<212> TYPE: PRT
<213> ORGANISM: Unknown
<220> FEATURE:
<223> OTHER INFORMATION: undefined Pseudomonas species

<400> SEQUENCE: 54

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Ser Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Val Ser Ser Arg
        195                 200                 205

Leu Asp Leu Tyr Tyr Leu Ser Ala Ile Thr Gln Asp Arg Thr Val Ile
    210                 215                 220

Val Glu Ser Ser Ser Ala Ile Asp Pro Leu Asp Trp Asp Thr Val Gln
225                 230                 235                 240
```

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 55
<211> LENGTH: 813
<212> TYPE: DNA
<213> ORGANISM: Unknown
<220> FEATURE:
<223> OTHER INFORMATION: undefined Pseudomonas species

<400> SEQUENCE: 55

```
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag ctgctggct  ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacacccag     360
tcgttcacca agtcggtcag cgccaaatac agcgttggcg gcagtatcga catcgtcaac     420
atcagctcgg atatcaccgt tggtttcagc agcaccgagg cctggtcgac gaaccagacc     480
ttcacccaaa gcaccgagct ggccggccct ggcaccttct tgtctatca  ggtggtgttt     540
gtctatgcgc acaacgccac ttcggccggt gggcagaatg caatgccctt gcctatagc      600
aagacccagc gggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
tggagcgcct acaacgatcc tcatcgccgt tat                                  813
```

<210> SEQ ID NO 56
<211> LENGTH: 271
<212> TYPE: PRT
<213> ORGANISM: Unknown
<220> FEATURE:
<223> OTHER INFORMATION: undefined Pseudomonas species

<400> SEQUENCE: 56

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Arg Val Asn Ser Arg
        195                 200                 205

Leu Asp Leu Tyr Tyr Leu Ser Ala Ile Thr Gln Asp Arg Thr Val Ile
210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 57
<211> LENGTH: 813
<212> TYPE: DNA
<213> ORGANISM: Unknown
<220> FEATURE:
<223> OTHER INFORMATION: undefined Pseudomonas species

<400> SEQUENCE: 57
atgacgatca aggaagagct gagccaaccc caaagccatt cggtcgagct cgaccagttg      60
caagtcgggg aagtctctgc acgcgaagcg ttgacctcca acttcgccgg cagtttcgat     120
cagttcccga ccaaaagcgg cagcttcgag atcgacaaat acctgctcaa ctacgcggat     180
ccgaaaaaag gctgctggct ggacggcgtc accgtctacg gtgacatcta catcggcaag     240
cagaactggg gcacctacac gcgcccggtg ttcgcctacc tgcagcacac cgacaccatc     300
tcgattccgc agcaggtgac gcagaccaag agctaccagt tgagcaaagg ccacgcccag     360
tcgttcacca gtcggtcag cgccaaatac agcgttggcg cagtatcga catcgtcaac      420
atcagctcgg atatcaccgt tggtttcagc agcaccgagg cctggtcgac gaaccagacc     480
ttcacccaaa gcaccgagct ggccggccct ggcaccttct tgtctatca ggtggtgttt     540
gtctatgcgc acaacgccac ttcggccggt gggcagaatg gcaatgcctt gcctatagc     600
aagacccagc aggtgaactc gcggctcgac ctttactacc tgtcggccat cacccaggac     660
cgtacggtca tcgtcgagtc cagcaatgca atcgacccgc tggactggga taccgtgcag     720
cgcaacgtgc tgatccagaa ctacaacccg gccagcaaca gcgggcactt ctcgttcgac     780
tggagcgcct acaacgatcc tcatcgccgt tat                                   813

<210> SEQ ID NO 58
<211> LENGTH: 271
<212> TYPE: PRT
<213> ORGANISM: Unknown
<220> FEATURE:
<223> OTHER INFORMATION: undefined Pseudomonas species

<400> SEQUENCE: 58

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr

|  |  |  |  |  | 20 |  |  |  |  | 25 |  |  |  |  | 30 |  |  |
|---|---|---|---|---|---|---|---|---|---|---|---|---|---|---|---|---|---|

Ser Asn Phe Ala Gly Ser Phe Asp Gln Phe Pro Thr Lys Ser Gly Ser
            35                  40                  45

Phe Glu Ile Asp Lys Tyr Leu Leu Asn Tyr Ala Asp Pro Lys Lys Gly
        50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Ala Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 59
<211> LENGTH: 813
<212> TYPE: DNA
<213> ORGANISM: Unknown
<220> FEATURE:
<223> OTHER INFORMATION: undefined Pseudomonas species

<400> SEQUENCE: 59

| atgacgatca | aggaagagct | gagccaaccc | caaagccatt | cggtcgagct | cgaccagttg | 60 |
|---|---|---|---|---|---|---|
| caagtcgggg | aagtctctgc | acgcgaagcg | ttgacctcca | acttcgccgg | cagtttcgat | 120 |
| cagttcccga | ccaaaagcgg | caacttcgag | atcgacaaat | acctgctcaa | ctacgcggat | 180 |
| ccgaaaaaag | gctgctggct | ggacggcgtc | accgtctacg | gtgacatcta | catcggcaag | 240 |
| cagaactggg | gcacctacac | gcgcccggtg | ttcgcctacc | tgcagcacac | cgacaccatc | 300 |
| tcgattccgc | agcaggtgac | gcagaccaag | agctaccagt | tgagcaaagg | ccacacccag | 360 |
| tcgttcacca | agtcggtcag | cgccaaatac | agcgttggcg | gcagtatcga | catcgtcaac | 420 |
| atcagctcgg | atatcaccgt | tggtttcagc | agcaccgagg | cctggtcgac | gaaccagacc | 480 |
| ttcacccaaa | gcaccgagct | ggccggccct | ggcaccttct | tgtctatca | ggtggtgttt | 540 |
| gtctatgcgc | acaacgccac | ttcggccggt | gggcagaatg | gcaatgcctt | gcctatagc | 600 |
| aagacccagc | aggtgaactc | gcggctcgac | ctttactacc | tgtcggccat | cacccaggac | 660 |

```
cgtacggtca tcgtcgagtc cagcaatgca atcgacccgc tggactggga taccgtgcag    720
cgcaacgtgc tgatccagaa ctacaacccg gccagcaaca gcgggcactt ctcgttcgac    780
tggagcgcct acaacgatcc tcatcgccgt tat                                 813
```

<210> SEQ ID NO 60
<211> LENGTH: 271
<212> TYPE: PRT
<213> ORGANISM: Unknown
<220> FEATURE:
<223> OTHER INFORMATION: undefined Pseudomonas species

<400> SEQUENCE: 60

```
Met Thr Ile Lys Glu Glu Leu Ser Gln Pro Gln Ser His Ser Val Glu
1               5                  10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Asn
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 61
<211> LENGTH: 813
<212> TYPE: DNA
<213> ORGANISM: Unknown
<220> FEATURE:
<223> OTHER INFORMATION: undefined Pseudomonas species

<400> SEQUENCE: 61

```
atgacgatca aggaagagct gagccaaccc caaagccatt cggtcgagct cgaccagttg    60
```

-continued

```
caagtcgggg aagtctctgc acgcgaagcg ttgacctcca acttcgccgg cagtttcgat    120
cagttcccga ccaaaagcgg cagcttcgag atcgacaaat acctgatcaa ctacgcggat    180
ccgaaaaaag gctgctggct ggacggcgtc accgtctacg gtgacatcta catcggcaag    240
cagaactggg gcacctacac gcgcccggtg ttcgcctacc tgcagcacac cgacaccatc    300
tcgattccgc agcaggtgac gcagaccaag agctaccagt tgagcaaagg ccacacccag    360
tcgttcacca gtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggcccct ggcaccttct tgtctatca ggtggtgttt    540 gtctatgcgc acaacgccac ttcggccggt gggcagaatg gcaatgcctt tgcctatagc    600
aagacccagc aggtgaactc gcggctcgac ctttactacc tgtcggccat cacccaggac    660
cgtacggtca tcgtcgagtc cagcaatgca atcgacccgc tggactggga taccgtgcag    720
cgcaacgtgc tgatccagaa ctacaacccg ccagcaaca gcgggcactt ctcgttcgac    780
tggagcgcct acaacgatcc tcatcgccgt tat                                 813
```

```
<210> SEQ ID NO 62
<211> LENGTH: 271
<212> TYPE: PRT
<213> ORGANISM: Unknown
<220> FEATURE:
<223> OTHER INFORMATION: undefined Pseudomonas species

<400> SEQUENCE: 62
```

| Met | Thr | Ile | Lys | Glu | Glu | Leu | Ser | Gln | Pro | Gln | Ser | His | Ser | Val | Glu |
|---|---|---|---|---|---|---|---|---|---|---|---|---|---|---|---|
| 1 | | | | 5 | | | | | 10 | | | | | 15 | |

| Leu | Asp | Gln | Leu | Gln | Val | Gly | Glu | Val | Ser | Ala | Arg | Glu | Ala | Leu | Thr |
| | | | 20 | | | | | 25 | | | | | 30 | | |

| Ser | Asn | Phe | Ala | Gly | Ser | Phe | Asp | Gln | Phe | Pro | Thr | Lys | Ser | Gly | Ser |
| | | | | 35 | | | | | 40 | | | | | 45 | |

| Phe | Glu | Ile | Asp | Lys | Tyr | Leu | Ile | Asn | Tyr | Ala | Asp | Pro | Lys | Lys | Gly |
| | | 50 | | | | | 55 | | | | | 60 | | | |

| Cys | Trp | Leu | Asp | Gly | Val | Thr | Val | Tyr | Gly | Asp | Ile | Tyr | Ile | Gly | Lys |
| 65 | | | | | 70 | | | | | 75 | | | | | 80 |

| Gln | Asn | Trp | Gly | Thr | Tyr | Thr | Arg | Pro | Val | Phe | Ala | Tyr | Leu | Gln | His |
| | | | | 85 | | | | | 90 | | | | | 95 | |

| Thr | Asp | Thr | Ile | Ser | Ile | Pro | Gln | Gln | Val | Thr | Gln | Thr | Lys | Ser | Tyr |
| | | | 100 | | | | | 105 | | | | | 110 | | |

| Gln | Leu | Ser | Lys | Gly | His | Thr | Gln | Ser | Phe | Thr | Lys | Ser | Val | Ser | Ala |
| | | | | 115 | | | | | 120 | | | | | 125 | |

| Lys | Tyr | Ser | Val | Gly | Gly | Ser | Ile | Asp | Ile | Val | Asn | Ile | Ser | Ser | Asp |
| | | 130 | | | | | 135 | | | | | 140 | | | |

| Ile | Thr | Val | Gly | Phe | Ser | Ser | Thr | Glu | Ala | Trp | Ser | Thr | Asn | Gln | Thr |
| 145 | | | | | 150 | | | | | 155 | | | | | 160 |

| Phe | Thr | Gln | Ser | Thr | Glu | Leu | Ala | Gly | Pro | Gly | Thr | Phe | Phe | Val | Tyr |
| | | | | 165 | | | | | 170 | | | | | 175 | |

| Gln | Val | Val | Phe | Val | Tyr | Ala | His | Asn | Ala | Thr | Ser | Ala | Gly | Gly | Gln |
| | | | 180 | | | | | 185 | | | | | 190 | | |

| Asn | Gly | Asn | Ala | Phe | Ala | Tyr | Ser | Lys | Thr | Gln | Gln | Val | Asn | Ser | Arg |
| | | | | 195 | | | | | 200 | | | | | 205 | |

| Leu | Asp | Leu | Tyr | Tyr | Leu | Ser | Ala | Ile | Thr | Gln | Asp | Arg | Thr | Val | Ile |
| | | 210 | | | | | 215 | | | | | 220 | | | |

| Val | Glu | Ser | Ser | Asn | Ala | Ile | Asp | Pro | Leu | Asp | Trp | Asp | Thr | Val | Gln |

```
                225                 230                 235                 240
Arg Asn Val Leu Ile Gln Asn Tyr Asn Pro Ala Ser Asn Ser Gly His
                    245                 250                 255

Phe Ser Phe Asp Trp Ser Ala Tyr Asn Asp Pro His Arg Arg Tyr
                260                 265                 270

<210> SEQ ID NO 63
<211> LENGTH: 813
<212> TYPE: DNA
<213> ORGANISM: Unknown
<220> FEATURE:
<223> OTHER INFORMATION: undefined Pseudomonas species

<400> SEQUENCE: 63
atgacgatca aggaagagct gagccaaccc caaagccatt cggtcgagct cgaccagttg     60
caagtcgggg aagtctctgc acgcgaagcg ttgacctcca acttcgccgg cagtttcgat    120
cagttcccga ccaaaagcgg cagcttcgag atcgacaaat acctgctcaa ctacgcggat    180
ccgaaaaaag ctgctggct ggacggcgtc accgtctacg gtgacatcta catcggcaag    240
cagaactggg gcacctacac gcgcccggtg ttcgcctacc tgcagcacac cgacaccatc    300
tcgattccgc agcaggtgac gcagaccaag agctaccagt tgagcaaagg ccacacccag    360
tcgttcacca agtcggtcag cgccaaatac agcgttggcg gcagtatcga catcgtcaac    420
atcagctcgg atatcaccgt ggtttcagc agcaccgagg cctggtcgac gaaccagacc    480
ttcacccaaa gcaccgagct ggccggcccct ggcaccttct tgtctatca ggtggtgttt    540 gtctatgcgc acaacgccac ttcggccggt gggcagaatg caatgccctt tgcctatagc    600
aagacccagc aggtgaactc gcggctcgac ctttactacc tgtcggccat caccaggac    660 cgtacggtca tcgtcgagtc cagcaatgca atcgacccgc tggactggga taccgtgcag    720
cgcaacgtgc tgatccagaa ctacaaccg ccagcaaca gcgggcactt ctcgttcgac    780
tggggcgcct acaacgatcc tcatcgccgt tat                                  813

<210> SEQ ID NO 64
<211> LENGTH: 271
<212> TYPE: PRT
<213> ORGANISM: Unknown
<220> FEATURE:
<223> OTHER INFORMATION: undefined Pseudomonas species

<400> SEQUENCE: 64

Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125
```

```
Lys Tyr Ser Val Gly Gly Ser Ile Asp Ile Val Asn Ile Ser Ser Asp
        130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
                180                 185                 190

Asn Gly Asn Ala Phe Ala Tyr Ser Lys Thr Gln Gln Val Asn Ser Arg
            195                 200                 205

Leu Asp Leu Tyr Tyr Leu Ser Ala Ile Thr Gln Asp Arg Thr Val Ile
        210                 215                 220

Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Gly Ala Tyr Asn Asp Pro His Arg Arg Tyr
                260                 265                 270

<210> SEQ ID NO 65
<211> LENGTH: 813
<212> TYPE: DNA
<213> ORGANISM: Unknown
<220> FEATURE:
<223> OTHER INFORMATION: undefined Pseudomonas species

<400> SEQUENCE: 65
atgacgatca aggaagagct gggccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgatggtt atttgctgga ctacagctca     180
cccaagcaag gttgctgggt ggacggtatc actgtctatg cgatatcta catcggcaag      240 cagaactggg gcacttatac ccgcccggtg tttgcctacc tacagtatgt ggaaaccatc     300
tccattccac agaatgtgac gaccacccte agctatcagc tgaccaaggg cataccccgt     360
tccttcgaga ccagtgtcaa cgccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaagggggcca gggacgttcg tcatttacca ggtcgtgctg     540
gtgtatgcgc acaacgccac ctcggcaggg cggcagaatg ccaatgcctt cgcctacagc     600
aaaacccagg cagtgggctc gcgggtggac ttgtactact tgtcggccat tacccagcgc     660
aagcgggtca tcgttccgtc gagcaatgcc gtcacgccgc tggactggga tacggtgcaa     720
cgcaacgtgc tgatggaaaa ctacaaccca ggcagtaaca gcggacactt cagcttcgac     780
tggagtgcct acaacgatcc tcatcgccgt tat                                  813

<210> SEQ ID NO 66
<211> LENGTH: 271
<212> TYPE: PRT
<213> ORGANISM: Unknown
<220> FEATURE:
<223> OTHER INFORMATION: undefined Pseudomonas species

<400> SEQUENCE: 66

Met Thr Ile Lys Glu Glu Leu Gly Gln Pro Gln Ser His Ser Ile Glu
1               5                   10                  15
```

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Ser Phe Asp Trp Ser Ala Tyr Asn Asp Pro His Arg Arg Tyr
            260                 265                 270

<210> SEQ ID NO 67
<211> LENGTH: 813
<212> TYPE: DNA
<213> ORGANISM: Unknown
<220> FEATURE:
<223> OTHER INFORMATION: undefined Pseudomonas species

<400> SEQUENCE: 67
atgacgatca aggaagagct gggccagcct caaagccatt cgatcgaact ggacgaggtg      60
agcaaggagg ccgcaagtac gcgggccgcg ttgacttcca acctgtctgg ccgcttcgac     120
cagtacccga ccaagaaggg cgactttgcg atcgatggtt atttgctgga ctacagctca     180
cccaagcaag gttgctgggt ggacggtatc actgtctatg gcgatatcta catcggcaag     240
cagaactggg gcacttatac ccgcccggtg tttgcctacc tacagtatgt ggaaaccatc     300
tccattccac agaatgtgac gaccaccctc agctatcagc tgaccaaggg catacccgt      360 tccttcgaga ccagtgtcaa cgccaagtac agcgttggcg ccaacataga tatcgtcaac     420
gtgggttcgg agatttccac cgggtttacc cgcagcgagt cctggtccac cacgcagtcg     480
ttcaccgata ccaccgagat gaagggggcca gggacgttcg tcatttacca ggtcgtgctg     540
gtgtatgcgc acaacgccac ctcggcaggg cggcagaatg ccaatgcctt cgcctacagc     600
aaaacccagg cagtgggctc gcgggtggac ttgtactact tgtcggccat acccagcgc      660

```
aagcgggtca tcgttccgtc gagcaatgcc gtcacgccgc tggactggga tacggtgcaa    720
cgcaacgtgc tgatggaaaa ctacaaccca ggcagtaaca gcggacactt ccgctccgac    780
tggagcgcct acaacgatcc tcatcgccgt tat                                 813
```

```
<210> SEQ ID NO 68
<211> LENGTH: 271
<212> TYPE: PRT
<213> ORGANISM: Unknown
<220> FEATURE:
<223> OTHER INFORMATION: undefined Pseudomonas species

<400> SEQUENCE: 68

Met Thr Ile Lys Glu Glu Leu Gly Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
                85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
                165                 170                 175

Gln Val Val Leu Val Tyr Ala His Asn Ala Thr Ser Ala Gly Arg Gln
            180                 185                 190

Asn Ala Asn Ala Phe Ala Tyr Ser Lys Thr Gln Ala Val Gly Ser Arg
        195                 200                 205

Val Asp Leu Tyr Tyr Leu Ser Ala Ile Thr Gln Arg Lys Arg Val Ile
    210                 215                 220

Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
                245                 250                 255

Phe Arg Ser Asp Trp Ser Ala Tyr Asn Asp Pro His Arg Arg Tyr
            260                 265                 270

<210> SEQ ID NO 69
<211> LENGTH: 813
<212> TYPE: DNA
<213> ORGANISM: Unknown
<220> FEATURE:
<223> OTHER INFORMATION: undefined Pseudomonas species

<400> SEQUENCE: 69
atgacgatca aggaagagct gagccaaccc caaagccatt cggtcgagct cgaccagttg    60
```

```
caagtcgggg aagtctctgc acgcgaagcg ttgacctcca acttcgccgg cagtttcgat    120
cagttcccga ccaaaagcgg cagcttcgag atcgacaaat acctgctcaa ctacgcggat    180
ccgaaaaaag gctgctggct ggacggcgtc accgtctacg gtgacatcta catcggcaag    240
cagaactggg gcacctacac gcgcccggtg ttcgcctacc tgcagcacac cggcaccatc    300
tcgattccgc agcaggtgac gcagaccaag agctaccagt tgagcaaagg ccacacccag    360
tcgttcacca gtcggtcag cgccaaatac agcgttggcg gcagtatcga catcgtcaac    420
atcagctcgg atatcaccgt tggtttcagc agcaccgagg cctggtcgac gaaccagacc    480
ttcacccaaa gcaccgagct ggccggccct ggcaccttct tgtctatca ggtggtgttt    540 gtctatgcgc acaacgccac ttcggccggt gggcagaatg gcaatgcctt tgcctatagc    600
aagacccagc aggtgaactc gcggctcgac ctttactacc tgtcggccat cacccaggac    660
cgtacggtca tcgtcgagtc cagcaatgca atcgaccgc tggactggga taccgtgcag    720
cgcaacgtgc tgatccagaa ctacaacccg gccagcaaca gcgggcactt ctcgttcgac    780
tggagcgcct acaacgatcc tcatcgccgt tat                                 813
```

<210> SEQ ID NO 70
<211> LENGTH: 271
<212> TYPE: PRT
<213> ORGANISM: Unknown
<220> FEATURE:
<223> OTHER INFORMATION: undefined Pseudomonas species

<400> SEQUENCE: 70

```
Met Thr Ile Lys Glu Glu Leu Ser Gln Pro Gln Ser His Ser Val Glu
1               5                   10                  15

Leu Asp Gln Leu Gln Val Gly Glu Val Ser Ala Arg Glu Ala Leu Thr
            20                  25                  30

Ser Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Lys Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Gly Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
        115                 120                 125

Lys Tyr Ser Val Gly Gly Ser Ile Asp Ile Val Asn Ile Ser Ser Asp
    130                 135                 140

Ile Thr Val Gly Phe Ser Ser Thr Glu Ala Trp Ser Thr Asn Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Gly Gln
            180                 185                 190

Asn Gly Asn Ala Phe Ala Tyr Ser Lys Thr Gln Gln Val Asn Ser Arg
        195                 200                 205

Leu Asp Leu Tyr Tyr Leu Ser Ala Ile Thr Gln Asp Arg Thr Val Ile
    210                 215                 220
```

```
Val Glu Ser Ser Asn Ala Ile Asp Pro Leu Asp Trp Asp Thr Val Gln
225                 230                 235                 240

Arg Asn Val Leu Ile Gln Asn Tyr Asn Pro Ala Ser Asn Ser Gly His
                245                 250                 255

Phe Ser Phe Asp Trp Ser Ala Tyr Asn Asp Pro His Arg Arg Tyr
            260                 265                 270
```

<210> SEQ ID NO 71
<211> LENGTH: 813
<212> TYPE: DNA
<213> ORGANISM: Unknown
<220> FEATURE:
<223> OTHER INFORMATION: undefined Pseudomonas species

<400> SEQUENCE: 71

```
atgacgatca aggaagagct gagcaatcct caaagccatt cggtcgagct cgaccagttg      60
caagtcgggg aagtctctgc acgcgaagcg ttgaccgcca acttcgccgg cagtttcgat     120
cagttcccga ccaaaagcgg cagcttcgag atcgacaaat acctgctcaa ctacgcagac     180
ccgaaacaag gctgctggct ggacggcgtc accgtctacg gtgacatcta catcggcaag     240
cagaactggg gcacctacac gcgcccggtg ttcgcctacc tgcagcacac ggacaccatc     300
tcgattccgc agcaggtgac gcagaccaag agctaccagc tgagcaaagg ccacacccag     360
tcgttcacca gtcggtcag cgccaagtac agcgttggcg cagtatcga catcgtcaac      420
gtcagctcgg atatcactgt cggtttcagc agcaccgagg cctggtcgac gacccagacc     480
ttcacccaaa gcaccgagct ggccggtccg ggcaccttct tgtctatca ggtggtgttt      540
gtctacgcgc acaacgccac ctcggcgggc cggcagaatg gcaatgcctt tgcctatagc     600
aagacccagc aggtggattc gcggctcgat ctctactacc tgtcggccat cacccaggac     660
cgtacggtca tcgtcgagtc cagcaaggca atcaacccgc tggactggga taccgtgcag     720
cgcaacgtgc tgatcgagaa ctacaacccg gcctccaaca gtgggcactt ccgcttcgac     780
tggagcgcct acaacgatcc tcatcgtcgt tac                                   813
```

<210> SEQ ID NO 72
<211> LENGTH: 271
<212> TYPE: PRT
<213> ORGANISM: Unknown
<220> FEATURE:
<223> OTHER INFORMATION: undefined Pseudomonas species

<400> SEQUENCE: 72

```
Met Thr Ile Lys Glu Glu Leu Ser Asn Pro Gln Ser His Ser Val Glu
1               5                   10                  15

Leu Asp Gln Leu Gln Val Gly Glu Val Ser Ala Arg Glu Ala Leu Thr
            20                  25                  30

Ala Asn Phe Ala Gly Ser Phe Asp Gln Phe Pro Thr Lys Ser Gly Ser
        35                  40                  45

Phe Glu Ile Asp Lys Tyr Leu Leu Asn Tyr Ala Asp Pro Lys Gln Gly
    50                  55                  60

Cys Trp Leu Asp Gly Val Thr Val Tyr Gly Asp Ile Tyr Ile Gly Lys
65                  70                  75                  80

Gln Asn Trp Gly Thr Tyr Thr Arg Pro Val Phe Ala Tyr Leu Gln His
                85                  90                  95

Thr Asp Thr Ile Ser Ile Pro Gln Gln Val Thr Gln Thr Lys Ser Tyr
            100                 105                 110

Gln Leu Ser Lys Gly His Thr Gln Ser Phe Thr Lys Ser Val Ser Ala
```

```
            115                 120                 125
Lys Tyr Ser Val Gly Gly Ser Ile Asp Ile Val Asn Val Ser Ser Asp
    130                 135                 140

Ile Thr Val Gly Phe Ser Ser Thr Glu Ala Trp Ser Thr Thr Gln Thr
145                 150                 155                 160

Phe Thr Gln Ser Thr Glu Leu Ala Gly Pro Gly Thr Phe Phe Val Tyr
                165                 170                 175

Gln Val Val Phe Val Tyr Ala His Asn Ala Thr Ser Ala Gly Arg Gln
            180                 185                 190

Asn Gly Asn Ala Phe Ala Tyr Ser Lys Thr Gln Gln Val Asp Ser Arg
        195                 200                 205

Leu Asp Leu Tyr Tyr Leu Ser Ala Ile Thr Gln Asp Arg Thr Val Ile
    210                 215                 220

Val Glu Ser Ser Lys Ala Ile Asn Pro Leu Asp Trp Asp Thr Val Gln
225                 230                 235                 240

Arg Asn Val Leu Ile Glu Asn Tyr Asn Pro Ala Ser Asn Ser Gly His
                245                 250                 255

Phe Arg Phe Asp Trp Ser Ala Tyr Asn Asp Pro His Arg Arg Tyr
            260                 265                 270

<210> SEQ ID NO 73
<211> LENGTH: 271
<212> TYPE: PRT
<213> ORGANISM: Pseudomonas chlororaphis

<400> SEQUENCE: 73

Met Pro Ile Lys Glu Glu Leu Ser Gln Pro Gln Ser His Ser Ile Glu
1               5                   10                  15

Leu Asp Asp Leu Lys Ser Glu Gln Gly Ser Leu Arg Ala Ala Leu Thr
            20                  25                  30

Ser Asn Phe Ala Gly Asn Phe Asp Gln Phe Pro Thr Lys Arg Gly Gly
        35                  40                  45

Phe Ala Ile Asp Ser Tyr Leu Leu Asp Tyr Ser Ala Pro Lys Gln Gly
    50                  55                  60

Cys Trp Val Asp Gly Ile Thr Val Tyr Gly Asp Ile Phe Ile Gly Lys
65                  70                  75                  80

Gln Asn Trp Gly Thr Tyr Thr Arg Pro Val Phe Ala Tyr Leu Gln Tyr
                85                  90                  95

Met Asp Thr Ile Ser Ile Pro Gln Gln Val Thr Gln Thr Arg Ser Tyr
            100                 105                 110

Gln Leu Thr Lys Gly His Thr Lys Thr Phe Thr Thr Asn Val Ser Ala
        115                 120                 125

Lys Tyr Ser Val Gly Gly Ser Ile Asp Ile Val Asn Val Gly Ser Asp
    130                 135                 140

Ile Ser Ile Gly Phe Ser Asn Ser Glu Ser Trp Ser Thr Thr Gln Thr
145                 150                 155                 160

Phe Ser Asn Ser Thr Gln Leu Thr Gly Pro Gly Thr Phe Ile Val Tyr
                165                 170                 175

Gln Val Val Met Val Tyr Ala His Asn Ala Thr Ser Ala Gly Arg Gln
            180                 185                 190

Asn Gly Asn Ala Phe Ala Tyr Asn Lys Thr Asn Thr Val Gly Ser Arg
        195                 200                 205

Leu Asp Leu Tyr Tyr Leu Ser Ala Ile Thr Gln Asn Ser Thr Val Ile
    210                 215                 220
```

```
Val Asp Ser Ser Lys Ala Ile Ala Pro Leu Asp Trp Asp Thr Val Gln
225                 230                 235                 240

Arg Asn Val Leu Met Glu Asn Tyr Asn Pro Gly Ser Asn Ser Gly His
            245                 250                 255

Phe Ser Phe Asp Trp Ser Ala Tyr Asn Asp Pro His Arg Arg Tyr
        260                 265                 270

<210> SEQ ID NO 74
<211> LENGTH: 578
<212> TYPE: PRT
<213> ORGANISM: Pseudomonas brenneri

<400> SEQUENCE: 74

Met Ser Thr Pro Phe Lys Gln Phe Thr Ser Pro Ala Gly Gln Ala Pro
1               5                   10                  15

Lys Asp Tyr Asn Lys Leu Gly Leu Glu Asn Gln Leu Pro Gln Phe Glu
            20                  25                  30

Thr Asp Trp Asn Asn Asp Leu Thr Gly Trp Thr Gln Ser Ala Ile Ile
        35                  40                  45

Gly Asn Pro Trp Ser Gly Leu Asn Asp Ala Pro Arg Ser Gly Tyr Tyr
50                  55                  60

Asn Pro Leu Val Glu Gly Tyr Gly Pro Thr Thr Pro Pro Ala Ile Thr
65                  70                  75                  80

Trp Ala Pro Phe Pro Asn Arg Leu Trp Thr Phe Phe Tyr Asn Asn Gly
                85                  90                  95

Thr Ala Val Ile Pro Gln Leu Gly Gly Lys Ala Met Ser Leu Gln Gln
            100                 105                 110

Val Met Glu Leu Thr Asp Asn Gly Gln Ile Thr Ile Asn Asn Thr Leu
        115                 120                 125

Tyr Met Leu Tyr Asp Pro Asn Lys Gln Gly Thr Leu Leu Gln Leu Pro
130                 135                 140

Val Thr Arg Cys Pro Thr Ile Asp Trp Gln Gly Lys Tyr Lys Asp Phe
145                 150                 155                 160

Ser Pro Ser Gly Pro Arg Gly Trp Leu Asp Glu Tyr Cys Glu Trp Ser
                165                 170                 175

Ile Val Arg Asp Ala Asp Gly Asn Met Arg Lys Ile Thr Phe Thr Cys
            180                 185                 190

Glu Asn Pro Ala Tyr Phe Leu Ala Met Trp Arg Ile Asp Pro Asn Ala
        195                 200                 205

Val Leu Gly Leu Tyr Arg Asp Tyr Ile Asp Pro Gln Val Gln Leu Glu
210                 215                 220

Asp Leu Tyr Leu Arg Tyr Thr Ala Asp Cys Pro Thr Gly Lys Ala Gly
225                 230                 235                 240

Asp Pro Val Ile Asp Pro Thr Thr Gly Gln Pro Ala Tyr Asp Thr Val
                245                 250                 255

Asn Lys Trp Asn Ala Gly Thr Ala Cys Val Pro Gly Gln Tyr Gly Gly
            260                 265                 270

Ala Met His Leu Thr Ser Gly Pro Asn Thr Leu Ser Ala Glu Val Tyr
        275                 280                 285

Leu Ala Ala Ala Thr Ile Leu Arg Pro Leu Ala Ser Ser Gln Asn
290                 295                 300

Ser Gln Ala Leu Ile Cys Cys Ala Gln Tyr Gly Gln Asn Tyr Arg Asn
305                 310                 315                 320

Ser Asp Pro His Ile Gly Phe Ser Ala Asn Ser Val Ala Val Asn Asn
                325                 330                 335
```

-continued

Arg Leu Ser Leu Thr Asn Pro Ile Gly Leu Tyr Leu Gln Gln Pro Thr
            340                 345                 350

Asp Phe Ser Ala Trp Lys Gly Pro Gln Gly Gln Asp Val Ser Gln Tyr
            355                 360                 365

Trp Lys Ile Thr Arg Gly Thr Ala Lys Ser Ala Ala Asn Gly Ser Asp
        370                 375                 380

Gln Ile Leu Gln Ala Val Phe Glu Val Pro Val Ser Ala Gly Phe Ser
385                 390                 395                 400

Ile Asn Asp Ile Thr Ile Ser Gly Gln Pro Ile Asp Tyr Val Trp Val
                405                 410                 415

Ile Ala Gln Gln Leu Leu Val Gly Leu Ser Val Thr Thr Pro Ile
            420                 425                 430

Ser Pro Thr Pro Asp Ser Cys Pro Cys Val Lys Asp Arg Val Asn Gly
            435                 440                 445

Val Gln Pro Trp Pro Val Gln Leu Leu Pro Leu Asp Leu Phe Tyr Gly
        450                 455                 460

Gln Ser Pro Thr Asp Leu Pro Ala Trp Leu Ala Pro Gly Thr Ser Gly
465                 470                 475                 480

Gln Phe Ala Leu Val Val Gln Gly Ala Asp Leu Lys Thr Thr Ala Glu
                485                 490                 495

Thr Ala Arg Val Gln Phe Ser Asn Pro Gly Val Thr Ala Gln Val Thr
            500                 505                 510

Gln Phe Leu Pro Asp Ala Ser Ala Ile Pro Gly Gln Thr Asn Ser Gly
        515                 520                 525

Gly Thr Gln Gly Tyr Leu Leu Thr Ile Thr Val Ser Pro Thr Ala Ala
530                 535                 540

Pro Gly Leu Val Thr Val Arg Ala Leu Asn Pro Gly Glu Ala Asp Asn
545                 550                 555                 560

Pro Ser Ala Thr Glu His Pro Trp Glu Ser Gly Leu Ala Leu Val Pro
                565                 570                 575

Gly Ala

<210> SEQ ID NO 75
<211> LENGTH: 535
<212> TYPE: PRT
<213> ORGANISM: Pseudomonas brenneri

<400> SEQUENCE: 75

Met Ser Arg Leu Arg Leu Ser Val Leu Ser Leu Leu Thr Ser Val Val
1               5                   10                  15

Leu Ser Leu Phe Ala Met Gln Ala Ala Tyr Ala Ser Pro Thr Ser Asp
            20                  25                  30

Ala Asp Ala Cys Val Gln Gln Leu Val Phe Asn Pro Lys Ser Gly
        35                  40                  45

Gly Phe Leu Pro Ile Asn Asn Phe Asn Ala Thr Gly Gln Ser Phe Met
    50                  55                  60

Asn Cys Phe Gly Trp Gln Leu Phe Ile Ala Leu Asn Trp Pro Val Asn
65                  70                  75                  80

Pro Gly Trp Pro Ala Thr Pro Ala Leu Ala Gly Glu Pro Asp Met Asn
                85                  90                  95

Ser Thr Leu Ala Gln Phe Gly Val Pro Thr Ala Ser Gly Gln Pro Met
            100                 105                 110

Ser Val Ala Pro Val Trp Ala Ser Tyr Lys Asp Ala Asn Asp Ile Phe
        115                 120                 125

Leu Pro Gly Ala Pro Ala Pro Thr Gly Trp Gly Val Gln Thr Leu Val
130                 135                 140

Pro Ser Asn Cys Ser Thr Gln Gly Ser Leu Arg Ala Ile Ser Val Gly
145                 150                 155                 160

Ala Arg Lys Phe Met Thr Ala Thr Ser Glu Ser Ala Ile Asn Ala Arg
            165                 170                 175

His Gly Phe His Leu Ser Ser Gly Thr Leu Ala Ser Ile Pro Asp Pro
                180                 185                 190

Ile Met Glu Ala Ser Gly Gly Trp Leu Thr Asp Gln Ser Gln Asn Leu
        195                 200                 205

Val Phe Phe Glu Arg Lys Val Gly Lys Ala Glu Phe Asp Tyr Ile Val
210                 215                 220

Ser Lys Gly Leu Tyr Asp Ala Ala Asn Gln Leu Thr Val Ala Gln Asn
225                 230                 235                 240

Leu Asp Asn Gln Asn Pro Gly Gly Leu Ser Leu Pro Ile Gly Glu Pro
                245                 250                 255

Met Arg Ser Leu Pro Pro Asn Pro Val Pro Gln Glu Gln Leu Gly Ala
            260                 265                 270

Leu Glu Val Lys Ala Ala Trp Arg Ile Leu Thr Gly Lys Pro Glu Leu
        275                 280                 285

Tyr Gly Arg Tyr Leu Thr Thr Val Ala Trp Leu Lys Asn Pro Ala Thr
290                 295                 300

Leu Gln Cys Thr Gln Gln Val Val Gly Leu Val Gly Leu His Ile Ile
305                 310                 315                 320

Asn Lys Thr Gln Ala Ser Pro Asn Phe Ile Trp Thr Thr Phe Glu Gln
                325                 330                 335

Val Asp Asn Val Pro Glu Pro Asn Gln Val Pro Pro Gln Gln Thr Pro
            340                 345                 350

Pro Asp Ser Phe Ala Phe Asn Asn Pro Asn Cys Gly Thr Gly Pro Glu
        355                 360                 365

Cys Thr Pro Asn Val Ala Arg Ile Gln Cys Lys Gln His His Pro Asp
370                 375                 380

Arg Asp Cys Thr Glu Pro Phe Pro Arg Asp Gln Pro Val Gln Thr Thr
385                 390                 395                 400

Arg Glu His Pro Leu Pro Thr Glu Leu Gln Ala Leu Asn Gly Ala Val
                405                 410                 415

Gln Ala Asn Phe Ala Gln Gln Ser Gly Lys Ser Val Phe Gln Tyr
            420                 425                 430

Tyr Lys Leu Ile Asn Val Leu Trp Thr Leu Thr Pro Asn Pro Pro Thr
        435                 440                 445

Gln Pro Glu Pro Gly Val Ser Ala Gln Val Pro Leu Ser Tyr Gly Pro
450                 455                 460

Phe Ile Ser Gln Gly Asn Val Pro Val Ala Asn Thr Thr Leu Glu Thr
465                 470                 475                 480

Tyr Val Gln Gly Asp Asn Cys Asn Ala Cys His Gln Tyr Ala Thr Ile
                485                 490                 495

Ala Gly Ser Ser Thr Leu Ala Ser Asp Phe Ser Phe Leu Phe Asn Ser
            500                 505                 510

Ala Asp Ser Ala Ser Lys Asn Ser Leu Val Lys Arg Val Lys Ala Phe
        515                 520                 525

Gln Thr Leu Lys Asp Gln Pro
530                 535

<210> SEQ ID NO 76
<211> LENGTH: 256
<212> TYPE: PRT
<213> ORGANISM: Pseudomonas brenneri

<400> SEQUENCE: 76

Met Gly Ser Ile Thr Asp His Asn Gln Leu Ala Trp Val Ala Ser
1               5                   10                  15

Leu Asp Ile Pro Glu Ala Ser Gly Val Lys Thr Arg Ser Arg Asn Val
                20                  25                  30

Val Ala Arg Ala Asn Ala Glu Asp Glu Gly Ala Ala Val Val Arg Gly
            35                  40                  45

Ser Ile Thr Ser Phe Val Thr Gly Leu Ser Gln Gln Ala Arg Asp Asp
50                  55                  60

Val Gln Asn Ser Thr Leu Leu Met Gln Leu Ala Ala Asp Lys Lys Phe
65                  70                  75                  80

Asn Pro Glu Lys Gln Arg Glu Glu Trp Phe Lys Phe Tyr Thr Asp Gly
                85                  90                  95

Leu Ala Asn Leu Gly Trp Gly Arg Val Ser Ser Tyr Tyr Gln Ser Tyr
            100                 105                 110

Gln Pro Arg Asn Thr Asn Val Thr Met Asp Gln Val Leu Glu Val
            115                 120                 125

Ile Ala Ala Val Val Gly Ala Asp Ser Ala Val Tyr Lys Val Thr Glu
130                 135                 140

Lys Thr Phe Ser Ser Leu Gln Asp Asn Pro Lys Asn Gln Ala Pro Leu
145                 150                 155                 160

Lys Leu Phe Asp Ser Ser Ser Thr Arg Asp Ser Val Gly Thr Phe Gln
                165                 170                 175

Ile Leu Pro Val Met Gln Asp Arg Asp Gly Asn Val Val Met Val Leu
            180                 185                 190

Thr Thr Val Asn Ala Ser Thr Thr Val Gln Arg Gly Ser Phe Leu Phe
            195                 200                 205

Trp Ser Trp Ser Lys Thr Thr Ala Trp Met Tyr Arg Ala Ala Gln Gln
210                 215                 220

Thr Val Leu Asn Glu Ser Val Tyr Ala Thr Val Arg Gln Ser Val Ile
225                 230                 235                 240

Lys Lys Leu Gly Lys Asn Ala Glu Glu Phe Ile Asp Asp Leu Glu Ile
                245                 250                 255

<210> SEQ ID NO 77
<211> LENGTH: 260
<212> TYPE: PRT
<213> ORGANISM: Pseudomonas brenneri

<400> SEQUENCE: 77

Met Lys Leu Ser Ala Asp Glu Val Tyr Val Ile Ser Gly Asn Leu Leu
1               5                   10                  15

Ser Ala Thr Pro Ser Leu Thr Asp Pro Thr Val Leu Glu Asp Ile Ala
                20                  25                  30

Asn Ser Asn Leu Leu Cys Gln Leu Ala Ala Asp Lys Asn Gln Gly Thr
            35                  40                  45

Arg Phe Ile Asp Pro Ala Ala Trp Leu Asp Phe Arg Ser Ser Leu
50                  55                  60

Gly Arg Leu Phe Trp Arg Ile Ser Asn Ser Gly Thr Val Ser Tyr Ala
65                  70                  75                  80

```
Ile Pro Gln Leu Val His Lys Ile Thr Val Lys Glu Val Leu Glu Lys
                85                  90                  95

Thr Phe Tyr Lys Thr Leu Asp Arg Pro Gln Arg Ile Arg Val Glu Glu
            100                 105                 110

Ser Ile Glu Leu Leu Gly Glu Gln Ser Ala Asp Ser Pro Ser Ala Thr
        115                 120                 125

Leu Tyr Ser Leu Lys Thr Gln Val Asn Phe Asn Glu Thr Thr Ser Ser
    130                 135                 140

Pro Gly Leu Leu Pro His Ser Ile Ser Ser Val Asn Leu Gln Leu Ser
145                 150                 155                 160

Val Val His Ser Glu Thr Cys Ile Ser Val Cys Ser Val Tyr Phe Lys
                165                 170                 175

Thr Ser Thr Arg Ile Gly Asp Asp Val Phe Asn Gln Lys Phe Pro Val
            180                 185                 190

Lys Glu Leu Leu Gly Asn Val Ser Val Ser Thr Phe Glu Ala Lys Leu
        195                 200                 205

Leu Glu Ser Ser Tyr Ala Gly Ile Arg Gln Ser Ile Ile Asp Lys Leu
    210                 215                 220

Gly Glu Asp Asn Ile Arg Glu Asn Ile Leu Leu Val Pro Ala Val Ser
225                 230                 235                 240

Pro Ser Leu Ser Asn Thr Arg His Ala Gly Leu Gln Phe Val Gln
                245                 250                 255

Glu Leu Asp Ile
            260
```

<210> SEQ ID NO 78
<211> LENGTH: 555
<212> TYPE: PRT
<213> ORGANISM: Pseudomonas rhodesiae

<400> SEQUENCE: 78

```
Met Ala Lys Leu Thr Gln Phe Ser Thr Pro Ala Asp Ile Gln Asp Phe
1               5                   10                  15

Ser Asp Ser Pro Ala Gln Gln Glu Arg Met Asn Ala Ala Trp Ser Gly
            20                  25                  30

Asn Ile Asn Arg Trp Val Asn Ala Ala Leu Val Gly Asp Val Trp Asp
        35                  40                  45

Leu Ile Asn Tyr Gly Pro Arg Pro Ala Phe Tyr Asn Pro Leu Asp Thr
    50                  55                  60

Asp Thr Pro Ser Thr Ser Val Asn Ala Pro Ile Thr Trp Asn Ala Phe
65                  70                  75                  80

Pro Gly Arg Ile Pro Ala Leu Phe Pro Asn Gln Ser Ala Asn Trp Leu
                85                  90                  95

Gln Trp Ala Asp Gln Gly Val Pro Ala Asn Val Thr Thr Asn Leu Cys
            100                 105                 110

Thr Gln Gln Ser Val Pro Pro Ala Pro Tyr Ser Pro Thr Gly Pro Arg
        115                 120                 125

Gly Trp Gln Asp Glu Tyr Cys Glu Trp Ser Val Thr Arg Asn Ala Ala
    130                 135                 140

Gly Gln Ile Thr Ser Val Met Phe Thr Cys Glu Asn Pro Glu Tyr Trp
145                 150                 155                 160

Met Thr Leu Trp Gln Val Asp Pro Gly Lys Val Leu Gln Arg Tyr Gln
                165                 170                 175

Gln Leu Ile Asn Pro Ala Val Gln Leu Ala Asp Leu Ser Leu Lys Asp
            180                 185                 190
```

```
Ala Gln Gly Gln Thr Val Ile Asp Pro Val Thr Gly Ala Pro Cys Tyr
        195                 200                 205

Asn Pro Leu Asn Lys Trp Asn Ser Gly Thr Gln Thr Leu Pro Gly Ser
        210                 215                 220

Gly Gly Ala Met His Leu Thr Ser Ser Pro Asn Thr Leu Gly Ala Glu
225                 230                 235                 240

Tyr Asp Leu Ala Ala Ala Thr Met Pro Arg Glu Leu Asn Asn Glu
                245                 250                 255

Pro Val Thr Ser Ala Ser Gln Leu Val Cys Tyr Ala Arg Tyr Gly Arg
                260                 265                 270

Ile Gly Arg His Ser Asp Pro Thr Ile Gly Gln Asn Val Asn Gln Tyr
        275                 280                 285

Val Asn Tyr Thr Ser Gly Leu Thr Glu Val Arg Ala Thr Leu Thr Asn
        290                 295                 300

Pro Pro Gly Leu Tyr Ile Gln Thr Pro Asp Phe Ser Gly Tyr Thr Thr
305                 310                 315                 320

Pro Asp Gly Ser Pro Ala Ala Cys Trp Thr Ile Asn Arg Gly His
                325                 330                 335

Leu Ala Gln Thr Ser Asp Asp Ile Asp Arg Ile Leu His Ala Thr Phe
        340                 345                 350

Ser Val Pro Ala Gly Lys Asn Phe Thr Val Ser Asp Ile Ser Ile Asn
        355                 360                 365

Gly Ala Lys Ile Gln Tyr Ala Ser Gln Ile Ala Gly Thr Ile Thr Met
        370                 375                 380

Gly Leu Met Ala Thr Val Phe Gly Asn Ser Val Thr Gln Gln Pro
385                 390                 395                 400

Val Ala Gly Thr Leu Asp Ser Asp Asn Pro Ser Pro Ser Val Ser Ala
                405                 410                 415

Leu Gln Pro Leu Ser Val Phe Asn Ala Tyr Arg Ala Gln Glu Leu Ala
                420                 425                 430

Ser Asn Glu Gln Ala Leu Ser Ile Pro Ile Leu Ala Leu Ala Ile Arg
        435                 440                 445

Pro Gly Gln Gln Val Asp Asn Ile Ala Leu Leu Asn Thr Ser Gln
        450                 455                 460

Thr Pro Asn Gly Ala Ser Phe Ser Val Val Glu Gly Gly Val Ser Ile
465                 470                 475                 480

Ser Ile Thr Gly Thr Gln Asp Leu Pro Gly Leu Asp Met Ser Leu Tyr
                485                 490                 495

Leu Val Ser Ile Ser Ala Asp Ala Asn Ala Ala Pro Gly Asp Arg Thr
                500                 505                 510

Val Leu Ala Ser Val Pro Gly Met Ala Ser Thr Gln Gln Ala Ala Ile
        515                 520                 525

Gly Leu Leu Thr Val Gly Gly Pro Thr Leu Val Thr Ser Gln Thr Gly
        530                 535                 540

Pro Ser Lys Pro Asn Phe Arg Arg Gly Arg Gly
545                 550                 555

<210> SEQ ID NO 79
<211> LENGTH: 451
<212> TYPE: PRT
<213> ORGANISM: Pseudomonas rhodesiae

<400> SEQUENCE: 79

Met Arg Arg Arg Pro Thr Val Leu Leu Gly Leu Ala Leu Leu Leu Gly
```

-continued

```
1               5                   10                  15
Leu Pro Ala Thr Gln Ala Met Gly Ala Pro Leu Cys Gly Ser Pro Phe
                20                  25                  30

Val Pro Ser Pro Thr Leu Gln Pro Thr Leu Ala Pro Pro Asn Phe Ser
                35                  40                  45

Ala Ser Asp Ser Ala Val Asp Cys Phe Met Trp Gln Thr Met Val Tyr
            50                  55                  60

Leu Asn Trp Pro Ala Thr Pro Gly Gln Arg Gly Val Pro Asn Ala Ala
65                      70                  75                  80

Ala Ser Leu Gly Ser Pro Gly Pro Ser Val Trp Gln Thr Tyr Lys Asp
                85                  90                  95

Tyr Asn Glu Leu Tyr Leu Pro Asn Gly Gln Gln Pro Pro Ala Trp Asn
                100                 105                 110

Asp Asn Phe Leu Ser Val Gln Arg Leu Gln Thr Arg Gly Val Ala Arg
            115                 120                 125

Ala Leu Pro Ser Ile Arg Leu Leu Asn Ser Thr Ser Lys Val Phe Arg
            130                 135                 140

Ala Ala Asn Ala Asn Glu Ser Pro Ala Leu Arg Glu Ile Glu Gln Val
145                 150                 155                 160

Gly Gly Gly Val Leu Tyr Asp Gln Ala Gly Ser Pro Val Tyr Tyr Glu
                165                 170                 175

Met Leu Val Asn Glu Val Asn Phe Asp Phe Ile Tyr Asn Asn Gln Leu
            180                 185                 190

Tyr Asn Pro Ala Gln Gln Asn Leu Tyr Ala Lys Gln Lys Gly Ile Val
            195                 200                 205

Leu Pro Asn Asn Ser Ile Glu Ile Lys Ala Ala Trp Lys Val Leu Ser
    210                 215                 220

Asp Pro Asp Asn Pro Gln Arg Phe Leu Thr Ala Gln Ala Leu Leu Pro
225                 230                 235                 240

Gly Ser Ser Thr Pro Val Thr Val Gly Leu Val Gly Leu His Val Phe
                245                 250                 255

Gln Met Pro Ser Ser Ala Phe Asn Gln Gly Phe Trp Ala Thr Phe Gln
                260                 265                 270

Gln Leu Asp Asn Ala Pro Thr Val Ala Gly Ala Thr Pro Gly Ala His
            275                 280                 285

Tyr Ser Phe Asn Asn Pro Gln Cys Ala Pro Ala Gln Cys Pro Pro Asn
            290                 295                 300

Asp Lys Thr Ser Asn Pro Thr Gln Val Val Gln Asn Phe Pro Pro Thr
305                 310                 315                 320

Pro Glu Ala Gln Asn Ile Asn His Tyr Met Gln Asn Leu Ile Ala Gln
                325                 330                 335

Gln Ala Pro Gly Ser Ala Leu Gln Tyr Tyr Gln Leu Val Asp Val Gln
            340                 345                 350

Trp Pro Thr Ser Pro Gln Ala Ile Gly Gln Pro Gly Ala Thr Ala Pro
            355                 360                 365

Ala Pro Ser Gly Thr Pro Asn His Asp Thr Leu Ile Asn Pro Val Leu
            370                 375                 380

Glu Thr Phe Leu Gln Ala Asn His Lys Ser Cys Leu Gly Cys His Val
385                 390                 395                 400

Tyr Ala Ser Val Ala Ala Asp Gly Ser Asn Pro Pro Thr His Tyr Gln
                405                 410                 415

Ala Ser Phe Ser Phe Leu Leu Gly His Ala Lys Ser Pro Ala Leu Gly
                420                 425                 430
```

-continued

```
Ser Asn Leu Lys Ser Leu Ala Gln Gln Ile Glu Asp Ala Ser Leu Ser
        435                 440                 445

Leu Gln His
    450

<210> SEQ ID NO 80
<211> LENGTH: 96
<212> TYPE: PRT
<213> ORGANISM: Pseudomonas antarctica

<400> SEQUENCE: 80

Met Lys Leu Ser Asn Val Leu Leu Ser Ile Val Phe Ala Trp Gln
1               5                   10                  15

Gly Met Ala Phe Ala Asp Thr Gln Lys Ser Asn Ala Glu Thr Leu Leu
            20                  25                  30

Ser Asn Asp Lys Pro Pro Leu Thr Gln Ala Ala Gln Glu Lys Glu Gln
        35                  40                  45

Glu Asn Val Glu Ala Asp Arg Asn Glu Cys Trp Ser Ala Lys Asn Cys
    50                  55                  60

Ser Gly Lys Ile Leu Asn Asn Lys Asp Ala His Asn Cys Lys Leu Ser
65                  70                  75                  80

Gly Gly Lys Ser Trp Arg Ser Lys Thr Thr Gly Gln Cys Thr Asn Leu
                85                  90                  95

<210> SEQ ID NO 81
<211> LENGTH: 89
<212> TYPE: PRT
<213> ORGANISM: Pseudomonas chlororaphis

<400> SEQUENCE: 81

Met Ser Ala Gln Glu Asn Phe Val Gly Gly Trp Thr Pro Tyr His Lys
1               5                   10                  15

Leu Thr Pro Lys Asp Gln Glu Val Phe Lys Glu Ala Leu Ala Gly Phe
            20                  25                  30

Val Gly Val Gln Tyr Thr Pro Glu Leu Val Ser Thr Gln Val Val Asn
        35                  40                  45

Gly Thr Asn Tyr Arg Tyr Gln Ser Lys Ala Thr Leu Pro Gly Ser Ser
    50                  55                  60

Glu Ser Trp Gln Ala Val Val Glu Ile Tyr Ala Pro Ile Lys Gly Lys
65                  70                  75                  80

Pro His Ile Thr Gln Ile His Arg Ile
                85

<210> SEQ ID NO 82
<211> LENGTH: 295
<212> TYPE: PRT
<213> ORGANISM: Pseudomonas putida

<400> SEQUENCE: 82

Met His Ala Pro Gly Ala Ile Pro Ser Glu Lys Glu Ser Ala His Ala
1               5                   10                  15

Trp Leu Thr Glu Thr Lys Ala Asn Ala Lys Ser Thr Ala Leu Arg Gly
            20                  25                  30

Asn Ile Phe Ala Gln Asp Tyr Asn Arg Gln Leu Leu Thr Ala Thr Gly
        35                  40                  45

Gln Ser Met Arg Ser Gly Ala Asp Ala Ile Asn Pro Phe Phe Ser Pro
    50                  55                  60
```

```
Ala Lys Gly Thr Ala Thr Gly Ser Tyr Ala Lys Asp Ala Asp Ala Asn
 65                  70                  75                  80

Val Ser Pro Gly Ser Ala Pro Val Ser Ile Tyr Glu Gly Leu Gln Thr
                 85                  90                  95

Ala Ile Asp Ile Ala Arg Arg Arg Ser Gly Tyr Asn Pro Leu Asp Gln
            100                 105                 110

Pro Thr Asp Gln Lys Pro Lys Ser Ala Gly Asp Arg Glu His Phe Ile
        115                 120                 125

Ala Phe Thr Gln Gln Ile Ala Glu Ile Pro Phe Leu Ser Leu Leu Ala
    130                 135                 140

Ala Gln Val Thr Gln Ile Gln Gln Lys Ser His Asp Ala Asn Ala Leu
145                 150                 155                 160

Val Asp Ser Phe Val Lys Gly Phe Ile Gly Leu Lys Asn Gln Asp Val
                165                 170                 175

Glu Gln Ile Lys Gln Ser Leu Ser Ser Leu Val Asn Ala Ala Leu Ser
            180                 185                 190

Tyr Ser Glu Gln Thr Glu Arg Gln Ser Asn Phe Asn Gln Asn Ile Leu
        195                 200                 205

Gln Thr Gly Asp Ser Gly Ser Val Asn Phe Met Leu Tyr Ala Ser Glu
    210                 215                 220

Phe Thr Ile Lys Ala Ser Ser His Lys Gly Thr Ile Thr Phe Gln Ser
225                 230                 235                 240

Ser Tyr Thr Leu Ser Gln Ala Ile Tyr Gln Leu Ser Val Glu Ser Trp
                245                 250                 255

Asn Asn Val Lys Asp Val Phe Ser Lys Gln Gln Lys Thr Asp Thr Gln
            260                 265                 270

Gln Trp Leu Gly Asp Thr Thr Thr Gln Val Arg Glu Gly Ser Lys Leu
        275                 280                 285

Arg Ala Ile Cys Leu Val Ser
    290                 295

<210> SEQ ID NO 83
<211> LENGTH: 295
<212> TYPE: PRT
<213> ORGANISM: Pseudomonas putida

<400> SEQUENCE: 83

Met Asn Ala Pro Gly Ala Ala Pro Ser Glu Lys Glu Val Ala His Ala
1               5                  10                  15

Trp Leu Glu Gly Lys Ala Arg Val Lys Ser Thr Thr Ala His Gly Asn
            20                  25                  30

Ile Phe Ala His Asp Tyr Asn His Pro His Gln Leu Thr Ser Thr Gly
        35                  40                  45

Arg Ala Met Arg Thr Gly Ala Asp Ala Ile Asn Pro Phe Phe Ser Pro
    50                  55                  60

Ala Ala Gly Ala Ala Thr Asp Ser Tyr Ala Asn Asp Ala Asn Lys Asn
 65                  70                  75                  80

Val Ser Pro Gly Lys Ala Pro Val Ser Ile Tyr Glu Gly Leu Gln Thr
                 85                  90                  95

Ala Ile Asp Ile Ala Arg Arg Arg Ser Glu Tyr Asn Pro Leu Asp Gln
            100                 105                 110

Pro Thr Asp Gln Arg Pro Lys Ala Lys Gly Asp Arg Glu His Phe Ile
        115                 120                 125

Ala Phe Thr Gln Gln Ile Ala Glu Ile Pro Phe Leu Ser Leu Leu Ala
    130                 135                 140
```

```
Ala Gln Val Thr Gln Ile Gln Gln Lys Ser His Asp Ala Asn Ala Leu
145                 150                 155                 160

Ile Asp Ser Phe Val Lys Gly Phe Ile Gly Leu Ala Ala Lys Asp Val
            165                 170                 175

Glu Gln Ile Lys Lys Ser Leu Ser Ser Leu Val Asn Ala Ala Leu Ser
        180                 185                 190

Tyr Ser Glu Gln Thr Glu Arg Gln Ser Asn Phe Asn Gln Asn Ile Leu
    195                 200                 205

Gln Thr Gly Ile Ala Gly Ser Val Asn Phe Met Leu Tyr Ala Ser Glu
210                 215                 220

Phe Thr Ile Lys Ala Thr Ser Lys Lys Gly Thr Ile Thr Phe Gln Ser
225                 230                 235                 240

Ser Tyr Thr Leu Ser Gln Ala Val Tyr Gln Leu Ser Val Glu Ser Trp
            245                 250                 255

Glu Asn Val Arg Asp Val Phe Ala Lys Gln Gln Lys Thr Asp Thr Gln
                260                 265                 270

Gln Trp Leu Gly Asp Thr Thr Pro Val Lys Pro Gly Ser Ser Leu
        275                 280                 285

Arg Ala Ile Cys Leu Val Ser
290                 295

<210> SEQ ID NO 84
<211> LENGTH: 291
<212> TYPE: PRT
<213> ORGANISM: Pseudomonas fulva

<400> SEQUENCE: 84

Met His Ala Pro Thr Val Lys Glu Leu Ala His Ala Trp Leu Thr Glu
1               5                   10                  15

Thr Thr Ala Lys Ala Asn Ser Thr Ile Val Arg Gly Asn Ile Phe Ala
            20                  25                  30

His Glu Tyr Asn His Gln Leu Leu Thr Pro Thr Gly Leu Ser Met Arg
        35                  40                  45

Ser Gly Ala Asp Ala Ile Asn Pro Phe Tyr Ser Pro Ala Ser Gly Ala
50                  55                  60

Ala Thr Asp Ser Tyr Ala Lys Asp Ala Asn Asn Val Ser Pro Gly
65                  70                  75                  80

Ser Ala Pro Val Ser Ile Tyr Glu Gly Leu Gln Thr Ser Ile Asp Ile
            85                  90                  95

Ala Arg Arg Arg Ser Gly Tyr Asn Pro Leu Asp Gln Pro Thr Asp Gln
        100                 105                 110

Lys Pro Lys Ala Ala Gly Asp Arg Glu His Phe Ile Ala Phe Thr Gln
    115                 120                 125

Gln Ile Ala Asn Ile Pro Phe Leu Ser Leu Leu Ala Ala Gln Val Thr
130                 135                 140

Gln Ile Gln Gln Lys Ser His Asp Ala Asn Ala Leu Val Asp Ser Phe
145                 150                 155                 160

Val Lys Gly Phe Ile Gly Leu Lys Asn Gln Asp Val Glu Gln Ile Lys
            165                 170                 175

Gln Ser Leu Ser Ser Leu Val Asn Ala Ala Leu Ser Tyr Ser Glu Gln
        180                 185                 190

Thr Glu Arg Gln Ser Asn Phe Asn Gln Asn Ile Leu Gln Thr Gly Asn
    195                 200                 205

Gly Gly Ser Val Asn Phe Met Leu Tyr Ala Ser Glu Phe Thr Ile Lys
```

```
            210                 215                 220
Ala Ser Ser His Lys Gly Thr Ile Thr Phe Gln Ser Ser Tyr Thr Leu
225                 230                 235                 240

Ser Gln Ala Ile Tyr Gln Leu Ser Val Glu Ser Trp Asn Asn Val Lys
                245                 250                 255

Asp Thr Phe Ser Lys Gln Gln Lys Thr Asp Thr Glu Gln Trp Leu Asp
                260                 265                 270

Asp Thr Thr Thr Pro Val Lys Glu Gly Ser Lys Leu Arg Ala Ile Cys
            275                 280                 285

Leu Val Gly
        290

<210> SEQ ID NO 85
<211> LENGTH: 295
<212> TYPE: PRT
<213> ORGANISM: Pseudomonas chlororaphis

<400> SEQUENCE: 85

Met Ser Thr Gln Asn His Lys His Ile Thr Glu Lys Thr Leu Ala Trp
1               5                   10                  15

Leu Asn Thr Thr His Glu Ser Asn Lys Leu Ser Thr Gln Thr Asn Pro
            20                  25                  30

Asn Ile Phe Val Leu Asp Arg Ser Arg Ser Ser Phe Ser Glu Ser Leu
        35                  40                  45

Leu Thr Pro Gly Ser Arg Ala Asp Ile Ala Asn Pro Phe Phe Ala Pro
    50                  55                  60

Ala Gly Ser Leu Ala Thr Ala Arg Tyr Leu Gln Ala Ala Asn Asn Asn
65                  70                  75                  80

Ala Ser Ser Gly Ser Ala Pro Thr Ser Leu Gln Asp Gly Leu Gln Thr
                85                  90                  95

Cys Val Asn Met Ala Arg Thr Arg Ser Gly Trp Asn Pro Asn Asp Pro
            100                 105                 110

Pro Thr Ala Ala Asn Pro His Thr Thr Gly Asp Tyr Glu His Phe Ile
        115                 120                 125

Ser Phe Thr Lys Glu Ile Ser Arg Ile Pro Phe Leu Thr Leu Glu Ser
    130                 135                 140

Ala Ser Ser Ser Leu Val Met Gln Gln Ser His Asn Ala Asp Asp Leu
145                 150                 155                 160

Ile Asn Ser Phe Ala Asn Gly Phe His Gly Leu Glu Thr Ala Asp Ile
                165                 170                 175

Glu Glu Thr Lys Arg Gly Leu Lys Glu Leu Val Lys Ala Ala Leu Ser
            180                 185                 190

Glu Cys Glu Lys Thr Asn Arg Glu Ser Phe Phe Asn Gln His Thr Leu
        195                 200                 205

Gln Gln Lys Asp Asp Thr Ala Ile Tyr Leu Ile Tyr Ser Ser Thr Phe
    210                 215                 220

Ser Ile Val Ala Thr Asp Gln Lys Gly Thr Ile Asn Phe Gln Ser Ser
225                 230                 235                 240

Tyr Leu Leu Thr Gln Ser Lys Tyr Thr Leu Ser Asn Ala Thr Trp Asp
                245                 250                 255

Arg Ile Lys Asp Leu Phe Tyr Asp Gln Gln Lys Thr Asp Thr Asn Thr
            260                 265                 270

Trp Leu Asn Gly Met Lys Thr Leu Pro Arg Ala Gly Ser Thr Ala Arg
        275                 280                 285
```

```
Ala Thr Cys Leu Glu Gly Gln
    290             295

<210> SEQ ID NO 86
<211> LENGTH: 86
<212> TYPE: PRT
<213> ORGANISM: Pseudomonas chlororaphis

<400> SEQUENCE: 86

Met Gly Ile Thr Val Thr Asn Asn Ser Ser Asn Pro Ile Glu Val Ala
1               5                   10                  15

Ile Asn His Trp Gly Ser Asp Gly Asp Thr Ser Phe Phe Ser Val Gly
            20                  25                  30

Asn Gly Lys Gln Glu Thr Trp Asp Arg Ser Asp Ser Arg Gly Phe Val
        35                  40                  45

Leu Ser Leu Lys Lys Asn Gly Ala Gln His Pro Tyr Tyr Val Gln Ala
    50                  55                  60

Ser Ser Lys Ile Glu Val Asp Asn Asn Ala Val Lys Asp Gln Gly Arg
65                  70                  75                  80

Leu Ile Glu Pro Leu Ser
            85

<210> SEQ ID NO 87
<211> LENGTH: 271
<212> TYPE: PRT
<213> ORGANISM: Pseudomonas entomophila

<400> SEQUENCE: 87

Met Thr Ile Lys Glu Glu Leu Gly Gln Pro Gln Ser His Ser Ile Glu
1               5                   10                  15

Leu Asp Glu Val Ser Lys Glu Ala Ala Ser Thr Arg Ala Ala Leu Thr
            20                  25                  30

Ser Asn Leu Ser Gly Arg Phe Asp Gln Tyr Pro Thr Lys Lys Gly Asp
        35                  40                  45

Phe Ala Ile Asp Gly Tyr Leu Leu Asp Tyr Ser Ser Pro Lys Gln Gly
    50                  55                  60

Cys Trp Val Asp Gly Ile Thr Val Tyr Gly Asp Ile Tyr Ile Gly Lys
65                  70                  75                  80

Gln Asn Trp Gly Thr Tyr Thr Arg Pro Val Phe Ala Tyr Leu Gln Tyr
            85                  90                  95

Val Glu Thr Ile Ser Ile Pro Gln Asn Val Thr Thr Leu Ser Tyr
            100                 105                 110

Gln Leu Thr Lys Gly His Thr Arg Ser Phe Glu Thr Ser Val Asn Ala
        115                 120                 125

Lys Tyr Ser Val Gly Ala Asn Ile Asp Ile Val Asn Val Gly Ser Glu
    130                 135                 140

Ile Ser Thr Gly Phe Thr Arg Ser Glu Ser Trp Ser Thr Thr Gln Ser
145                 150                 155                 160

Phe Thr Asp Thr Thr Glu Met Lys Gly Pro Gly Thr Phe Val Ile Tyr
            165                 170                 175

Gln Val Val Leu Val Tyr Ala His Asn Ala Thr Ser Ala Gly Arg Gln
        180                 185                 190

Asn Ala Asn Ala Phe Ala Tyr Ser Lys Thr Gln Ala Val Gly Ser Arg
    195                 200                 205

Val Asp Leu Tyr Tyr Leu Ser Ala Ile Thr Gln Arg Lys Arg Val Ile
    210                 215                 220
```

-continued

```
Val Pro Ser Ser Asn Ala Val Thr Pro Leu Asp Trp Asp Thr Val Gln
225                 230                 235                 240

Arg Asn Val Leu Met Glu Asn Tyr Asn Pro Gly Ser Asn Ser Gly His
            245                 250                 255

Phe Ser Phe Asp Trp Ser Ala Tyr Asn Asp Pro His Arg Arg Tyr
            260                 265                 270
```

INSECTICIDAL PROTEIN DISCOVERY PLATFORM AND INSECTICIDAL PROTEINS DISCOVERED THEREFROM

CROSS-REFERENCE TO RELATED APPLICATIONS

This application is a Continuation of International PCT Application No. PCT/US2019/020218, filed Mar. 1, 2019, which claims the benefit of priority to U.S. Provisional Application No. 62/637,515 filed on Mar. 2, 2018, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_022_01WO_SeqList_ST25.txt. The text file is 167 KB, was created on Feb. 27, 2019, and is being submitted electronically via EFS-Web.

FIELD

The present disclosure is directed to an approach for discovering novel insecticidal proteins from highly heterogeneous environmental sources. The methodology utilizes metagenomic enrichment procedures and unique genetic amplification techniques, which enables access to a broad class of unknown microbial diversity and their resultant proteome.

The disclosed insecticidal protein discovery platform (IPDP) can be computationally driven and is able to integrate molecular biology, automation, and advanced machine learning protocols. The platform will enable researchers to rapidly and accurately access the vast repertoire of untapped insecticidal proteins produced by uncharacterized and complex microbial environmental samples.

Also presented herein are a group of newly discovered pore-forming toxins (PFT) from a rare class of insecticidal proteins, which were discovered utilizing the insecticidal protein discovery platform.

BACKGROUND

It is estimated that by the year 2050 the world's population will have reached over 9 billion people. Estimates by agricultural experts at the United Nations project that in order to feed such a large global population, then total food production must increase by 70% to meet future demands. This challenge is exacerbated by numerous factors, including: diminishing freshwater resources, limited supplies of arable land, rising energy prices, increasing input costs, and environment concerns attached to modern row crop agriculture.

An age old problem, which will continue to be one of the most pressing concerns facing our global agricultural industry, is pesticidal pressure and the associated reduction in yields and reduced productivity stemming therefrom. Traditional synthetic chemicals have been successful in helping farmers battle problematic insects, but these chemicals face increasing scrutiny over concerns about their impact on human health and potential detrimental environmental effects. Consequently, in order to meet the needs of a growing global population, there will be an increased demand for biotechnological solutions to combat agricultural pests.

One leading biotechnological pesticide solution comes from *Bacillus thuringiensis* (Bt), a gram-positive, spore forming bacterium. Bt bacteria were identified as insect pathogens and their insecticidal activity was attributed to the parasporal crystals encoded by the Cry genes, of which there are over 100 known isoforms. This observation led to the development of bioinsecticides based on Bt bacteria for the control of certain insect species. Plants have now been genetically engineered to express the Bt insecticidal proteins, which alleviates the need for external application to the plants. However, similar to the situation where insect resistance develops due to continuous use of chemical insecticides, the continuous expression of these insecticidal Bt proteins in plants also imposes strong selection for resistance in target pest populations. Consequently, the industry has seen an alarming rate of insect populations becoming resistant to Bt crops. Furthermore, Bt proteins have a limited range of activity and are not effective against some of the currently problematic insect species.

Thus, in view of an expanding global population, environmental concerns associated with traditional chemical insecticides, and growing insect resistance to Bt traits, there is a great need in the art for the identification of novel insecticidal proteins, which can be incorporated into biotechnological products useful for modern agriculture.

SUMMARY OF THE DISCLOSURE

The present disclosure provides novel insecticidal proteins, which can be utilized in modern row crop agriculture. These insecticidal proteins can be developed into standalone products for application directly to a plant species, or can be incorporated into the genome of a host plant for expression.

Unlike traditional synthetic chemical insecticides, the taught insecticidal proteins do not pose environmental concerns. Further, the insecticidal proteins belong to a newly discovered class, which have several advantages over the current industry standard Cry protein products derived from *Bacillus thuringiensis* (Bt) encoded sequences.

Besides the novel insecticidal proteins themselves, the disclosure provides a platform for discovering additional insecticidal proteins, by accessing the vast repertoire of untapped insecticidal proteins produced by uncharacterized and complex microbial environmental samples.

The insecticidal protein discovery platform (IPDP) utilizes metagenomic enrichment procedures and unique genetic amplification techniques, enabling access to a broad class of unknown microbial diversity and their resultant proteome. Because the platform can be computationally driven and is able to integrate molecular biology, automation, and advanced machine learning protocols, researchers will now be able to rapidly and systematically develop models and search queries, to identify additional novel insecticidal proteins.

In certain embodiments, the disclosure provide a method for constructing a genomic library, enriched for DNA from *Pseudomonas* encoding insecticidal proteins, comprising: a) providing an initial sample comprising one or more microorganisms; b) exposing the initial sample to a solid nutrient limiting media that enriches for growth of species from the genus *Pseudomonas*, which results in a subsequent sample enriched for *Pseudomonas* sp.; c) isolating DNA from the subsequent enriched sample; d) extracting DNA from the isolated DNA and performing degenerate PCR with primers selected to amplify target insecticidal protein genes; e) cloning the PCR-amplified DNA into a plasmid; and f) sequencing the cloned DNA from said plasmid. In certain embodiments, the method comprises assembling the sequenced DNA into a genomic library. In certain embodiments, the method comprises identifying insecticidal protein genes within the sequenced DNA. In some embodiments, the identified insecticidal proteins are unknown. In some embodiments, a Hidden Markov model is used to identify insecticidal protein genes. In some embodiments, any gene (i.e. a nucleotide sequence) in Table 3 (e.g. SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and 71) can be found. In some embodiments, any gene encoding a protein found in Table 3 (e.g. SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72) can be found. In some embodiments, the primers are selected to amplify target insecticidal protein genes that encode a protein with at least 50% sequence identity to SEQ ID NO: 87.

In some embodiments, the disclosure provides for an isolated nucleic acid molecule encoding an insecticidal protein having at least about 80%, 81%, 82%, 83%, 84%, 85%, 86%, 87%, 88%, 89%, 90%, 91%, 92%, 93%, 94%, 95%, 96%, 97%, 98%, 99%, or greater sequence identity to a protein selected from the group consisting of: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72. In certain embodiments, the isolated nucleic acid molecule is codon optimized for expression in a host cell of interest. In certain embodiments, the isolated nucleic acid molecule is codon optimized for expression in a plant cell. In certain embodiments, the isolated nucleic acid molecule has at least about 80%, 81%, 82%, 83%, 84%, 85%, 86%, 87%, 88%, 89%, 90%, 91%, 92%, 93%, 94%, 95%, 96%, 97%, 98%, 99%, or greater sequence identity to a nucleic acid sequence selected from the group consisting of: SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and 71.

In some embodiments, the disclosure provides for a nucleotide construct, comprising: a nucleic acid molecule encoding an insecticidal protein having at least about 80% sequence identity to a protein selected from the group consisting of: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72, said nucleic acid molecule operably linked to a heterologous regulatory element. In aspects, the heterologous regulatory element is a promoter. In aspects, the heterologous regulatory element is a plant promoter. In some embodiments, the disclosure provides for transgenic plant cells that comprise said nucleotide constructs. In some embodiments, the disclosure provides for stably transformed plants that express said proteins from the nucleotide construct. In some embodiments, insects feed upon the transgenic plants and are killed.

In some embodiments, the disclosure provides for an isolated insecticidal protein, comprising: an amino acid sequence with at least about 80%, 81%, 82%, 83%, 84%, 85%, 86%, 87%, 88%, 89%, 90%, 91%, 92%, 93%, 94%, 95%, 96%, 97%, 98%, 99%, or greater sequence identity to an amino acid sequence selected from the group consisting of: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72. In some embodiments, the isolated insecticidal protein is recombinant. In some embodiments, the disclosure provides for transgenic plant cells that express said proteins. In some embodiments, insects feed upon the transgenic plants and are killed. In some embodiments, the aforementioned insecticidal proteins are contained in agricultural compositions. In some embodiments, said agricultural compositions are used to spray upon plants and/or insects, in order to provide effective insect control. In some embodiments, the insecticidal proteins are found in cell lysate and the cell lysate can be utilized to control insect pest populations. In some embodiments, the natural *Pseudomonas* host organism can be formulated into a composition and utilized to combat insect pests.

In certain embodiments, the disclosure provides novel insecticidal proteins, wherein the proteins having an amino acid sequence which score at or above a bit score of 521.5 and/or sequences which match at an E-value of less than or equal to 7.9e-161 when scored using the HMM in Table 6. These proteins can be provided in any form (e.g., as isolated or recombinant proteins) or as part of any of the compositions (e.g., plants or agricultural compositions) disclosed herein.

BRIEF DESCRIPTION OF THE FIGURES

FIG. 1 outlines a workflow of the taught insecticidal protein discovery platform (IPDP).

FIG. 3 illustrates a multiple sequence alignment of eight novel insecticidal proteins (ZIP1, ZIP2, ZIP6, ZIP8, ZIP9, ZIP10, ZIP11, ZIP12) found in Table 3, which were discovered utilizing the IPDP.

FIG. 4 illustrates a multiple sequence alignment of eight novel insecticidal proteins (ZIP1, ZIP2, ZIP6, ZIP8, ZIP9, ZIP10, ZIP11, ZIP12) found in Table 3, which were discovered utilizing the IPDP, as compared to monalysin.

FIG. 7 illustrates the results of insect bioassay experiments with ten purified insecticidal proteins found in Table 3. Insects (*Halyomorpha halys*—Brown Marmorated Stink Bug) that ingested water containing purified insecticidal proteins (ZIP1, ZIP2, ZIP4, ZIP6, ZIP8, ZIP9, ZIP10, ZIP11, and ZIP12, and ZIP16) discovered via the IPDP exhibited mortality rates of varying degrees. The concentration of purified insecticidal protein used for this experiment is also presented in FIG. 7.

FIG. 8 illustrates the results of insect bioassay experiments with three purified insecticidal proteins (ZIP1, ZIP2, and ZIP4) found in Table 3 against Brown Marmorated Stinkbugs. Purified proteins of varying concentrations were ingested by insects (N=number of insects assayed) and the mortality data was subject to Probit Analysis to generate the lethal concentration required to kill 50% of the population (LC50) with upper and lower 95% confidence intervals.

FIGS. 9A-B illustrates the results of insect bioassay experiments with three purified insecticidal proteins (ZIP1, ZIP2, and ZIP4) found in Table 3 against members of two major Orders of insects; Fall Armyworm and Southern Corn Rootworm. The percent reduction in the mean weight of insects that ingested the listed concentration of purified protein mixed with solid diet as compared to buffer only control is reported. FIG. 9A presents experiments performed on Fall Armyworm (*Spodoptera frugiperda*), while FIG. 9B illustrates experiments performed on Southern Corn Rootworm (*Diabrotica undecimpunctata*)

DETAILED DESCRIPTION

Definitions

Figure 2:
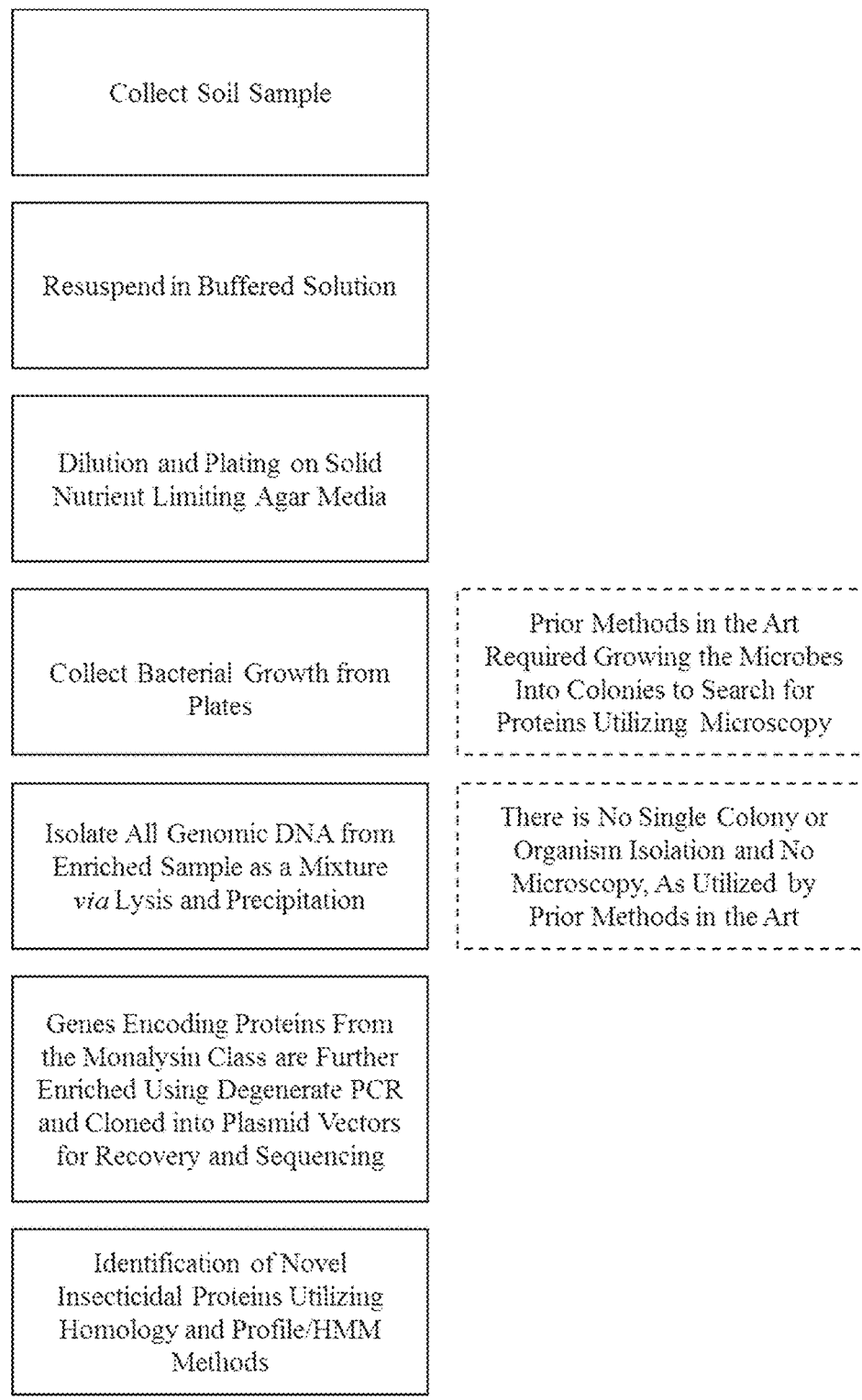
FIG. 2 outlines a workflow of the taught insecticidal protein discovery platform (IPDP) and illustrates two steps utilized by methods of the prior art, which are not required by the current IPDP.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6)*Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that rearranges one or more elements of at least one natural nucleic acid or protein sequence.

For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, a "synthetic amino acid sequence" or "synthetic peptide" or "synthetic protein" is an amino acid sequence that is not known to occur in nature or that is not naturally occurring. Generally, such a synthetic protein sequence will comprise at least one amino acid difference when compared to any other naturally occurring protein sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and can be inferred based on the degree of sequence identity.

The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different from that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g. small molecule, peptide, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process.

The term "insecticidal protein" or "pesticidal protein" or "insecticidal toxin" or "pesticidal toxin" is used to refer to a protein that has toxic activity against one or more pests. Examples of pests include various orders of insects, including: Lepidopterans, Dipterans, Hemipterans, and Coleopterans, to name a few. Pests also include non-insect organisms that are a pest to agriculture, including for example, members of the Nematoda phylum.

Insecticidal/Pesticidal Proteins

The disclosure teaches an insecticidal protein discovery platform and insecticidal proteins discovered therefrom. However, it should be understood that the term "insecticidal" is not limited to merely insects, but rather covers a broader taxonomic grouping of organisms that are commonly referred to as "pests." Consequently, the phrase "insecticidal protein" can be taken to be synonymous with "pesticidal protein" and the phrase "insecticidal protein discovery platform" can be taken to be synonymous with "pesticidal protein discovery platform." Furthermore, in some aspects, the disclosure provides for insecticidal toxins and a platform for discovering insecticidal toxins, which may not be limited to protein embodiments.

Insecticidal Proteins—Monalysins

*Pseudomonas entomophila* is an entomopathogenic bacterium that infects and kills *Drosophila*. *P. entomophila* pathogenicity is linked to its ability to cause irreversible damages to the *Drosophila* gut, preventing epithelium renewal and repair. Recently, Opota and colleagues reported the identification of a novel pore-forming toxin (PFT), which they termed "Monalysin," contributes to the virulence of *P. entomophila* against *Drosophila*. Opota, et al., "Monalysin, a Novel B-Pore-Forming Toxin from the *Drosophila* Pathogen *Pseudomonas entomophila*, Contributes to Host Intestinal Damage and Lethality," PLoS Pathogens, September 2011, Vol. 7, Issue 9. Opota demonstrated Monalysin requires N-terminal cleavage to become fully active, forms oligomers in vitro, and induces pore-formation in artificial lipid membranes. The prediction of the secondary structure of the membrane-spanning domain indicates that Monalysin is a PFT of the B-type. The expression of Monalysin is regulated by both the GacS/GacA two-component system and the Pvf regulator, two signaling systems that control *P. entomophila* pathogenicity. In addition, AprA, a metalloprotease secreted by *P. entomophila*, can induce the rapid cleavage of pro-Monalysin into its active form. Reduced cell death is observed upon infection with a mutant deficient in Monalysin production showing that Monalysin plays a role in *P. entomophila* ability to induce intestinal cell damages, which is consistent with its activity as a PFT. Opota's study, together with the well-established action of *Bacillus thuringiensis* Cry toxins, suggests that production of PFTs is a common strategy of entomopathogens to disrupt insect gut homeostasis. Id.

Opota discovered Monalysin (PSEEN3174), by characterizing the protein product of the unknown gene pseen3174. According to Opota, the Monalysin amino acid sequence does not show homology to other sequences using P Blast, except for two uncharacterized orthologs found in *Pseudomonas putida* F1 strain (Figure S1 of Opota). Neither the *P. entomophila* nor the *P. putida* gene products displayed any obvious protein domains. However, Opota utilized the HHpred software (Homology detection & structure prediction by HMM-HMM comparison) to reveal the presence of an internal region with alternating polar and hydrophobic residues flanked by a stretch of serine and threonine residues, a hallmark of the membrane-spanning region of 3-barrel pore-forming toxins. Id.

Opota's DNA sequence searches and analysis were performed using the *Pseudomonas* genome database (*pseudomonas*.com, which can be accessed on the worldwide web using the "www" prefix). The monalysin gene (ORF PSEEN3174) corresponds to the accession number YP_608728.1. Monalysin putative orthologs in *Pseudomonas putida* Pput_1063 and Pput_1064 correspond to the accessions numbers YP_001266408.1, YP_001266409.1 respectively. The ORF PSEEN0535 involved in the production of the type VI secretion system corresponds to the accession number YP_606298.1.

Insecticidal Proteins—*Pseudomonas* Insecticidal Proteins (PIPs)

There are several known families of *Pseudomonas* insecticidal proteins, including: PIP-1, 45, 47, 64, 72, 74, 75, and 77. These PIP proteins, along with identifying characteristics, are provided in the below Table 1. Further information can be found in: (1) U. Schellenberger et al., "A selective insecticidal protein from *Pseudomonas* for controlling corn rootworms," Science, 2016 Nov. 4; 354(6312):634-637 (providing IPD072Aa, an 86 AA protein, GenBank Accession No. KT795291) incorporated by reference herein; and (2) Jun-Zhi Wei et al., "A selective insecticidal protein from *Pseudomonas mosselii* for corn rootworm control," Plant Biotechnology Journal, 2018, Vol. 16, pgs. 649-659 (providing PIP-47aa) incorporated by reference herein.

TABLE 1

Pseudomonas insecticidal proteins (PIPs) and Monalysin

| Source Publication[1] | PIP Identifier | Amino Acid Sequence[2] | Source Organism |
|---|---|---|---|
| 13792861/ US9688730B2 | PIP-1 | SEQ ID NO: 2 MPIKEELSQPQSHSIELDDLKSEQGSLRAAL TSNFAGNFDQFPTKRGGFAIDSYLLDYSAPK QGCWVDGITVYGDIFIGKQNWGTYTRPVFAY LQYMDTISIPQQVTQTRSYQLTKGHTKTFTT NVSAKYSVGGSIDIVNVGSDISIGFSNSESW STTQTFSNSTQLTGPGTFIVYQVVMVYAHNA TSAGRQNGNAFAYNKTNTVGSRLDLYYLSAI TQNSTVIVDSSKAIAPLDWDTVQRNVLMENY NPGSNSGHFSFDWSAYNDPHRRY (SEQ ID NO: 73) | P. chlororaphis |
| 15543689/ US20170367349A1 | PIP-45-1 | SEQ ID NO: 1 MSTPFKQFTSPAGQAPKDYNKLGLENQLPQF ETDWNNDLTGWTQSAIIGNPWSGLNDAPRSG YYNPLVEGYGPTTPPAITWAPFPNRLWTFFY NNGTAVIPQLGGKAMSLQQVMELTDNGQITI NNTLYMLYDPNKQGTLLQLPVTRCPTIDWQG KYKDFSPSGPRGWLDEYCEWSIVRDADGNMR KITFTCENPAYFLAMWRIDPNAVLGLYRDYI DPQVQLEDLYLRYTADCPTGKAGDPVIDPTT GQPAYDTVNKWNAGTACVPGQYGGAMHLTSG PNTLSAEVYLAAAATILRPLASSQNSQALIC CAQYGQNYRNSDPHIGFSANSVAVNNRLSLT NPIGLYLQQPTDFSAWKGPQGQDVSQYWKIT RGTAKSAANGSDQILQAVFEVPVSAGFSIND ITISGQPIDYVWVIAQQLLVGLSVTTTPISP TPDSCPCVKDRVNGVQPWPVQLLPLDLFYGQ SPTDLPAWLAPGTSGQFALVVQGADLKTTAE TARVQFSNPGVTAQVTQFLPDASAIPGQTNS GGTQGYLLTITVSPTAAPGLVTVRALNPGEA DNPSATEHPWESGLALVPGA (SEQ ID NO: 74) | P. brenneri |
| 15543689/ US20170367349A1 | PIP-45-2 | SEQ ID NO: 2 MSRLRLSVLSLLTSVVLSLFAMQAAYASPTS DADACVQQQLVFNPKSGGFLPINNFNATGQS FMNCFGWQLFIALNWPVNPGWPATPALAGEP DMNSTLAQFGVPTASGQPMSVAPVWASYKDA NDIFLPGAPAPTGWGVQTLVPSNCSTQGSLR AISVGARKFMTATSESAINARHGFHLSSGTL ASIPDPIMEASGGWLTDQSQNLVFFERKVGK AEFDYIVSKGLYDAANQLTVAQNLDNQNPGG LSLPIGEPMRSLPPNPVPQEQLGALEVKAAW RILIGKPELYGRYLTIVAWLKNPATLQCTQQ VVGLVGLHIINKTQASPNFIWTTFEQVDNVP EPNQVPPQQTPPDSFAFNNPNCGTGPECTPN VARIQCKQHHPDRDCTEPFPRDQPVQTTREH PLPTELQALNGAVQANFAQQSQGKSVFQYYK LINVLWTLTPNPPTQPEPGVSAQVPLSYGPF ISQGNVPVANTTLETYVQGDNCNACHQYATI AGSSTLASDFSFLFNSADSASKNSLVKRVKA FQTLKDQP (SEQ ID NO: 75) | P. brenneri |

TABLE 1-continued

Pseudomonas insecticidal proteins (PIPs) and Monalysin

| Source Publication[1] | PIP Identifier | Amino Acid Sequence[2] | Source Organism |
|---|---|---|---|
| 15543689/ US20170367349A1 | PIP-64-1 | SEQ ID NO: 53<br>MGSITDHNQLLAWVASLDIPEASGVKTRSRN<br>VVARANAEDEGAAVVRGSITSFVTGLSQQAR<br>DDVQNSTLLMQLAADKKFNPEKQREEWFKFY<br>TDGLANLGWGRVSSYYQSYQPRNTNVTMDQV<br>VLEVIAAVVGADSAVYKVTEKTFSSLQDNPK<br>NQAPLKLFDSSSTRDSVGTFQILPVMQDRDG<br>NVVMVLTTVNASTTVQRGSFLFWSWSKTTAW<br>MYRAAQQTVLNESVYATVRQSVIKKLGKNAE<br>EFIDDLEI<br>(SEQ ID NO: 76) | P. brenneri |
| 15543689/ US20170367349A1 | PIP-64-2 | SEQ ID NO: 54<br>MKLSADEVYVISGNLLSATPSLTDPTVLEDI<br>ANSNLLCQLAADKNQGTRFIDPAAWLDFYRS<br>SLGRLFWRISNSGTVSYAIPQLVHKITVKEV<br>LEKTFYKTLDRPQRIRVEESIELLGEQSADS<br>PSATLYSLKTQVNFNETTSSPGLLPHSISSV<br>NLQLSVVHSETCISVCSVYFKTSTRIGDDVF<br>NQKFPVKELLGNVSVSTFEAKLLESSYAGIR<br>QSIIDKLGEDNIRENILLVPAVSPSLSNTRH<br>AGALQFVQELDI<br>(SEQ ID NO: 77) | P. brenneri |
| 15543689/ US20170367349A1 | PIP-74-1 | SEQ ID NO: 73<br>MAKLTQFSTPADIQDFSDSPAQQERMNAAWS<br>GNINRWVNAALVGDVWDLINYGPRPAFYNPL<br>DTDTPSTSVNAPITWNAFPGRIPALFPNQSA<br>NWLQWADQGVPANVTTNLCTQQSVPPAPYSP<br>TGPRGWQDEYCEWSVTRNAAGQITSVMFTCE<br>NPEYWMTLWQVDPGKVLQRYQQLINPAVQLA<br>DLSLKDAQGQTVIDPVTGAPCYNPLNKWNSG<br>TQTLPGSGGAMHLTSSPNTLGAEYDLAAAAT<br>MPRELNNEPVTSASQLVCYARYGRIGRHSDP<br>TIGQNVNQYVNYTSGLTEVRATLINPPGLYI<br>QTPDFSGYTTPDGSPAAACWTINRGHLAQTS<br>DDIDRILHATFSVPAGKNFTVSDISINGAKI<br>QYASQIAGTITMGLMATVFGNSGVTQQPVAG<br>TLDSDNPSPSVSALQPLSVFNAYRAQELASN<br>EQALSIPILALAIRPGQQVDNIALLLNTSQT<br>PNGASFSVVEGGVSISITGTQDLPGLDMSLY<br>LVSISADANAAPGDRTVLASVPGMASTQQAA<br>IGLLTVGGPTLVTSQTGPSKPNFRRGRG<br>(SEQ ID NO: 78) | P. rhodesiae |
| 15543689/ US20170367349A1 | PIP-74-2 | SEQ ID NO: 74<br>MRRRPTVLLGLALLLGLPATQAMGAPLCGSP<br>FVPSPTLQPTLAPPNFSASDSAVDCFMWQTM<br>VYLNWPATPGQRGVPNAAASLGSPGPSVWQT<br>YKDYNELYLPNGQQPPAWNDNFLSVQRLQTR<br>GVARALPSIRLLNSTSKVFRAANANESPALR<br>EIEQVGGGVLYDQAGSPVYYEMLVNEVNFDF<br>IYNNQLYNPAQQNLYAKQKGIVLPNNSIEIK<br>AAWKVLSDPDNPQRFLTAQALLPGSSTPVTV<br>GLVGLHVFQMPSSAFNQGFWATFQQLDNAPT<br>VAGATPGAHYSFNNPQCAPAQCPPNDKTSNP<br>TQVVQNFPPTPEAQNINHYMQNLIAQQAPGS<br>ALQYYQLVDVQWPTSPQAIGQPGATAPAPSG<br>TPNHDTLINPVLETFLQANHKSCLGCHVYAS<br>VAADGSNPPTHYQASFSFLLGHAKSPALGSN<br>LKSLAQQIEDASLSLQH<br>(SEQ ID NO: 79) | P. rhodesiae |
| 15543689/ US20170367349A1 | PIP-75 | SEQ ID NO: 79<br>MKLSNVLLLSIVFAWQGMAFADTQKSNAETL<br>LSNDKPPLTQAAQEKEQENVEADRNECWSAK<br>NCSGKILNNKDAHNCKLSGGKSMRSKTTGQC<br>TNL<br>(SEQ ID NO: 80) | P. antarctica |

TABLE 1-continued

Pseudomonas insecticidal proteins (PIPs) and Monalysin

| Source Publication[1] | PIP Identifier | Amino Acid Sequence[2] | Source Organism |
|---|---|---|---|
| 15543689/ US20170367349A1 | PIP-77 | SEQ ID NO: 88 MSAQENFVGGWTPYHKLTPKDQEVFKEALAG FVGVQYTPELVSTQVVNGTNYRYQSKATLPG SSESWQAVVEIYAPIKGKPHITQIHRI (SEQ ID NO: 81) | P. chlororaphis |
| 14912356/ US20160186204A1 | PIP-47Aa | SEQ ID NO: 2 MHAPGAIPSEKESAHAWLTETKANAKSTALR GNIFAQDYNRQLLTATGQSMRSGADAINPFF SPAKGTATGSYAKDADANVSPGSAPVSIYEG LQTAIDIARRRSGYNPLDQPTDQKPKSAGDR EHFIAFTQQIAEIPFLSLLAAQVTQIQQKSH DANALVDSFVKGFIGLKNQDVEQIKQSLSSL VNAALSYSEQTERQSNFNQNILQTGDSGSVN FMLYASEFTIKASSHKGTITFQSSYTLSQAI YQLSVESWNNVKDVFSKQQKTDTQQWLGDTT TQVREGSKLRAICLVS (SEQ ID NO: 82) | P. putida |
| 14912356/ US20160186204A1 | PIP-47Bb | SEQ ID NO: 4 MNAPGAAPSEKEVAHAWLEGKARVKSTTAHG NIFAHDYNHPQLTSTGRAMRTGADAINPFF SPAAGAATDSYANDANKNVSPGKAPVSIYEG LQTAIDIARRRSEYNPLDQPTDQRPKAKGDR EHFIAFTQQIAEIPFLSLLAAQVTQIQQKSH DANALIDSFVKGFIGLAAKDVEQIKKSLSSL VNAALSYSEQTERQSNFNQNILQTGIAGSVN FMLYASEFTIKATSKKGTITFQSSYTLSQAV YQLSVESWENVRDVFAKQQKTDTQQWLGDTT TPVKPGSSLRAICLVS (SEQ ID NO: 83) | P. putida |
| 14912356/ US20160186204A1 | PIP-47Ba | SEQ ID NO: 6 MHAPTVKELAHAWLTETTAKANSTIVRGNIF AHEYNHQLLTPTGLSMRSGADAINPFYSPAS GAATDSYAKDANNNVSPGSAPVSIYEGLQTS IDIARRRSGYNPLDQPTDQKPKAAGDREHFI AFTQQIANIPFLSLLAAQVTQIQQKSHDANA LVDSFVKGFIGLKNQDVEQIKQSLSSLVNAA LSYSEQTERQSNFNQNILQTGNGGSVNFMLY ASEFTIKASSHKGTITFQSSYTLSQAIYQLS VESWNNVKDTFSKQQKTDTEQWLDDTTTPVK EGSKLRAICLVG (SEQ ID NO: 84) | P. fulva |
| 14912356/ US20160186204A1 | PIP47Fa | SEQ ID NO: 8 MSTQNHKHITEKTLAWLNTTHESNKLSTQTN PNIFVLDRSRSSFSESLLTPGSRADIANPFF APAGSLATARYLQAANNNASSGSAPTSLQDG LQTCVNMARTRSGWNPNDPPTAANPHTTGDY EHFISFTKEISRIPPFLTLESASSSLVMQQSH VKAALSECEKTNRESFFNQHTLQQKDDTAIY LIYSSTFSIVATDQKGTINFQSSYLLTQSKY TLSNATWDRIKDLFYDQQKTDTNTWLNGMKT LPRAGSTARATCLEGQ (SEQ ID NO: 85) | P. chlororaphis |
| 15022109/ US20160366891A1 | PIP-72Aa | SEQ ID NO: 2 MGITVTNNSSNPIEVAINHWGSDGDTSFFSV GNGKQETWDRSDSRGFVLSLKKNGAQHPYYV QASSKIEVDNNAVKDQGRLIEPLS (SEQ ID NO: 86) | P. chlororaphis |
| Monalysin from Opota et al. is also derived from a Pseudomonas | Monalysin | MTIKEELGQPQSHSIELDEVSKEAASTRAAL TSNLSGRFDQYPTKKGDFAIDGYLLDYSSPK QGCWVDGITVYGDTYIGKQNWGTYTRPVFAY LQYVETISIPQNVITTLSYQLTKGHTRSFET SVNAKYSVGANIDIVNVGSEISTGETRSESW STTQSFTDTTEMKGPGTFVIYQVVLVYAHNA TSAGRQNANAFAYSKTQAVGSRVDLYYLSAI | P. entomophila |

TABLE 1-continued

Pseudomonas insecticidal proteins (PIPs) and Monalysin

| Source Publication[1] | PIP Identifier | Amino Acid Sequence[2] | Source Organism |
|---|---|---|---|
| | | TQRKRVIVPSSNAVTPLDWDTVQRNVLMENY NPGSNSGHFSFDWSAYNDPHRRY (SEQ ID NO: 87) | |

[1]All of the application publications in Table 1 are incorporated herein by reference.
[2]SEQ ID NO from original source application/publication displayed before sequence, SEQ ID NO according to current application displayed after sequence and underlined.

Insecticidal Proteins—Cry proteins

Bacillus thuringiensis (Bt) are gram-positive spore-forming bacteria with entomopathogenic properties. Bt produce insecticidal proteins during the sporulation phase as parasporal crystals. These crystals are predominantly comprised of one or more proteins (Cry and Cyt toxins), also called δ-endotoxins. Cry proteins are parasporal inclusion (Crystal) proteins from Bacillus thuringiensis that exhibit experimentally verifiable toxic effect to a target organism or have significant sequence similarity to a known Cry protein. Similarly, Cyt proteins are parasporal inclusion proteins from Bacillus thuringiensis that exhibit hemolytic (Cytolitic) activity or has obvious sequence similarity to a known Cyt protein. These toxins are highly specific to their target insect, are innocuous to humans, vertebrates and plants, and are completely biodegradable. Bravo A, Gill S S, Soberón M., "Mode of action of Bacillus thuringiensis Cry and Cyt toxins and their potential for insect control," Toxicon: Official Journal of the International Society on Toxinology. 2007; 49(4):423-435.

Bt Cry and Cyt toxins belong to a class of bacterial toxins known as pore-forming toxins (PFT) that are secreted as water-soluble proteins undergoing conformational changes in order to insert into, or to translocate across, cell membranes of their host. There are two main groups of PFT: (i) the α-helical toxins, in which α-helix regions form the trans-membrane pore, and (ii) the β-barrel toxins, that insert into the membrane by forming a β-barrel composed of β-sheet hairpins from each monomer. See, Parker M W, Feil S C, "Pore-forming protein toxins: from structure to function," Prog. Biophys. Mol. Biol. 2005 May; 88(1):91-142. The first class of PFT includes toxins such as the colicins, exotoxin A, diphtheria toxin and also the Cry three-domain toxins. On the other hand, aerolysin, α-hemolysin, anthrax protective antigen, cholesterol-dependent toxins as the perfringolysin O and the Cyt toxins belong to the β-barrel toxins. Id. In general, PFT-producing bacteria secrete their toxins and these toxins interact with specific receptors located on the host cell surface. In most cases, PFT are activated by host proteases after receptor binding inducing the formation of an oligomeric structure that is insertion competent. Finally, membrane insertion is triggered, in most cases, by a decrease in pH that induces a molten globule state of the protein. Id.

The development of transgenic crops that produce Bt Cry proteins has allowed the substitution of chemical insecticides by environmentally friendly alternatives. In transgenic plants the Cry toxin is produced continuously, protecting the toxin from degradation and making it reachable to chewing and boring insects. Cry protein production in plants has been improved by engineering cry genes with a plant biased codon usage, by removal of putative splicing signal sequences and deletion of the carboxy-terminal region of the protoxin. See, Schuler T H, et al., "Insect-resistant transgenic plants," Trends Biotechnol. 1998; 16:168-175. The use of insect resistant crops has diminished considerably the use of chemical pesticides in areas where these transgenic crops are planted. See, Qaim M, Zilberman D, "Yield effects of genetically modified crops in developing countries," Science. 2003 Feb. 7; 299(5608):900-902.

Known Cry proteins include: S-endotoxins including but not limited to: the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51, Cry52, Cry 53, Cry 54, Cry55, Cry56, Cry57, Cry58, Cry59. Cry60, Cry61, Cry62, Cry63, Cry64, Cry65, Cry66, Cry67, Cry68, Cry69, Cry70 and Cry71 classes of δ-endotoxin genes and the B. thuringiensis cytolytic cyt1 and cyt2 genes.

Members of these classes of B. thuringiensis insecticidal proteins include, but are not limited to: Cry1Aa1 (Accession #AAA22353); Cry1Aa2 (Accession #AAA22552); CryAa3 (Accession #BAA00257); Cry1Aa4 (Accession #CAA31886); Cry1Aa5 (Accession #BAA04468); Cry1Aa6 (Accession #AAA86265); Cry1 Aa7 (Accession #AAD46139); Cry1Aa8 (Accession #126149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); CryAa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #I12419); Cry1Ab12 (Accession #AAC64003); Cry1Ab13 (Accession #AAN76494); Cry1Ab14 (Accession #AAG16877); Cry1Ab1 5 (Accession #AAO13302); Cry1Ab1 6 (Accession #AAK55546); Cry1Ab1 7 (Accession #AAT46415); Cry1Ab1 8 (Accession #AAQ88259); Cry1Ab1 9 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1 Ab26 (Accession #HQ847729); Cry1Ab27 (Accession #JN135249); Cry1 Ab28 (Accession #JN135250); Cry1Ab29 (Accession #JN135251); Cry1Ab30 (Accession #JN135252);

Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AAO39719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #I76415); Cry1Da3 (Accession #HQ439784); Cry1Db1 (Accession #CAA80234); Cry1Db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AAO13756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AA013734); Cry2Aa9 (Accession #AA013750); Cry2Aa10 (Accession #AAQ04263); Cry2Aa11 (Accession #AAQ52384); Cry2Aa12 (Accession #AB183671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AA013296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab1 5 (Accession #HM037126); Cry2Ab1 6 (Accession #GQ866914); Cry2Ab1 7 (Accession #HQ439789); Cry2Ab1 8 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CA078739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #115475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac (Accession #134543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7 Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #AC144005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8Db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1

(Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX74110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9Db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #I32932); Cry21Aa2 (Accession #I66477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #I34547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30Db1 (Accession #BAE80088); Cry30Ea1 (Accession #ACC95445); Cry30Ea2 (Accession #FJ499389); Cry30Fa1 (Accession #AC122625); Cry30Ga (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BA144026); Cry31Ab (Accession #BAE79809); Cry31Ab2 (Accession #BAF32570); Cry31Ac1 (Accession #BAF34368); Cry31Ac2 (Accession #AB731600); Cry31Ad1 (Accession #BA144022); Cry32Aa (Accession #AAG36711); Cry32Aa2 (Accession #GU063849); Cry32Ab (Accession #GU063850); Cry32Ba1 (Accession #BAB78601); Cry32Ca1 (Accession #BAB78602); Cry32Cb (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47 Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542);

Cry50Aa1 (Accession #BAE86999); Cry50Ba1 (Accession #GU446675); Cry50Ba2 (Accession #GU446676); Cry51Aa1 (Accession #AB114444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EA057254); Cry60Aa3 (Accession #EEM99278); Cry60Ba1 (Accession #GU810818); Cry60Ba2 (Accession #EA057253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BA144028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569); Cyt1Aa (GenBank Accession Number X03182); Cyt1Ab (GenBank Accession Number X98793); Cyt1B (GenBank Accession Number U37196); Cyt2A (GenBank Accession Number Z14147); and Cyt2B (GenBank Accession Number U52043).

Examples of δ-endotoxins also include but are not limited to Cry1A proteins of U.S. Pat. Nos. 5,880,275, 7,858,849 8,530,411, 8,575,433, and 8,686,233; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families, including but not limited to the Cry9D protein of U.S. Pat. No. 8,802,933 and the Cry9B protein of U.S. Pat. No. 8,802,934; a Cry15 protein of Naimov, et al., (2008), "Applied and Environmental Microbiology," 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949, 626, 7,385,107 and 7,504,229; a CryET33 and CryET34 homologs of US Patent Publication Number 2006/0191034, 2012/0278954, and PCT Publication Number WO 2012/ 139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; TIC853 toxins of U.S. Pat. No. 8,513,494, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-008orf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247 and U.S. Pat. No. 8,759,619; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI1182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI12, AXMI114, AXMI16, AXMI117, AXMI118, AXMI119, AXMI120, AXMI121, AXMI122, AXMI123, AXMI124, AXMI1257, AXMI1268, AXMI127, AXMI129, AXMI64, AXMI151, AXMI161, AXMI183, AXMI132, AXMI138, AXMI137 of US Patent Application Publication Number 2010/0005543, AXMI270 of US Patent Application Publication US20140223598, AXMI279 of US Patent Application Publication US20140223599, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710.

Other Cry proteins are well known to one skilled in the art. See, N. Crickmore, et al., "Revision of the Nomenclature for the *Bacillus thuringiensis* Pesticidal Crystal Proteins,"

Microbiology and Molecular Biology Reviews," (1998) Vol 62: 807-813; see also, N. Crickmore, et al., "*Bacillus thuringiensis* toxin nomenclature" (2016), at btnomenclature.info, which can be accessed on the worldwide web using the "www" prefix The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, CryF+Cry1Ac, Cry2Ab, Cry3A, mCry3A, Cry3Bb1, Cry34Ab1, Cry35Ab1, Vip3A, mCry3A, Cry9c and CBI-Bt have received regulatory approval. See, Sanahuja et al., "*Bacillus thuringiensis*: a century of research, development and commercial applications," (2011) Plant Biotech. Journal, April 9(3):283-300 and the CERA (2010) GM Crop Database Center for Environmental Risk Assessment (CERA), ILSI Research Foundation, Washington D.C. at cera-gmc.org/index.php?action=gm_crop_database, which can be accessed on the worldwide web using the "www" prefix. More than one pesticidal proteins well known to one skilled in the art can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1Da& Cry1Be (US2012/0331590); Cry1DA & Cry1Fa (US2012/0331589); Cry1Ab & Cry1Be (US2012/0324606); Cry1Fa & Cry2Aa and Cry1I & Cry1E (US2012/0324605); Cry34Ab/35Ab and Cry6Aa (US20130167269); Cry34Ab/VCry35Ab & Cry3Aa (US20130167268); Cry1Ab & Cry1F (US20140182018); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) Biochem. Biophys. Res. Commun. 15:1406-1413).

Insecticidal Proteins—Vips

Pesticidal proteins also include Vip (vegetative insecticidal proteins) toxins.

As described in the art, "Entomopathogenic bacteria produce insecticidal proteins that accumulate in inclusion bodies or parasporal crystals (such as the aforementioned Cry and Cyt proteins), as well as insecticidal proteins that are secreted into the culture medium. Among the latter are the Vip proteins, which are divided into four families according to their amino acid identity. The Vip1 and Vip2 proteins act as binary toxins and are toxic to some members of the Coleoptera and Hemiptera. The Vip1 component is thought to bind to receptors in the membrane of the insect midgut, and the Vip2 component enters the cell, where it displays its ADP-ribosyltransferase activity against actin, preventing microfilament formation. Vip3 has no sequence similarity to Vip1 or Vip2 and is toxic to a wide variety of members of the Lepidoptera. Its mode of action has been shown to resemble that of the Cry proteins in terms of proteolytic activation, binding to the midgut epithelial membrane, and pore formation, although Vip3A proteins do not share binding sites with Cry proteins. The latter property makes them good candidates to be combined with Cry proteins in transgenic plants (*Bacillus thuringiensis*-treated crops [Bt crops]) to prevent or delay insect resistance and to broaden the insecticidal spectrum. There are commercially grown varieties of Bt cotton and Bt maize that express the Vip3Aa protein in combination with Cry proteins. For the most recently reported Vip4 family, no target insects have been found yet." See, Chakroun et al., "Bacterial Vegetative Insecticidal Proteins (Vip) from Entomopathogenic Bacteria," Microbiol. Mol. Biol. Rev. 2016 Mar. 2; 80(2):329-350.

VIPs can be found in U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html, which can be accessed on the worldwide web using the "www" prefix).

Insecticidal Proteins—Toxin Complex (TC) Family Proteins

Pesticidal proteins also include toxin complex (TC) proteins, obtainable from organisms such as *Xenorhabdus, Photorhabdus* and *Paenibacillus* (see, U.S. Pat. Nos. 7,491, 698 and 8,084,418). Some TC proteins have "stand alone" insecticidal activity and other TC proteins enhance the activity of the stand-alone toxins produced by the same given organism. The toxicity of a "stand-alone" TC proteins (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptCWi. Examples of Class C proteins are TccC, XptC1Xb and XptB1 Wi. Pesticidal proteins also include spider, snake and scorpion venom proteins. Examples of spider venom peptides include, but are not limited to lycotoxin-1 peptides and mutants thereof (U.S. Pat. No. 8,334,366).

Insecticidal Proteins—Combinations

In some embodiments, the disclosure contemplates utilizing a combination of one or more insecticidal proteins. For example, it is known that Cry proteins have limited utility against all common agricultural pests, as the proteins only target specific receptors found in susceptible insect species. Consequently, by expressing a Cry along with a novel insecticidal protein as taught herein, it is contemplated that a plant species would have expanded protection against a broader class of insects.

The disclosure therefore contemplates engineered plant species that produce a novel insecticidal protein as taught herein, in combination with said plant species also expressing one or more other insecticidal proteins, e.g. Monalysin, PIP, Cry, Cyt, VIP, TC, and any combination thereof.

Nucleic Acid Molecules Encoding Discovered Insecticidal Proteins

One aspect of the disclosure pertains to isolated or recombinant nucleic acid molecules comprising nucleic acid sequences encoding insecticidal polypeptides, proteins, or biologically active portions thereof, as well as nucleic acid molecules sufficient for use as hybridization probes to identify nucleic acid molecules encoding proteins with regions of sequence homology.

As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecule encoding an insecticidal protein of the disclosure can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments, an isolated nucleic acid molecule encoding an insecticidal protein has one or more changes in the nucleic acid sequence compared to the native or genomic nucleic acid sequence. In some embodiments, the change in the native or genomic nucleic acid sequence includes, but is not limited to: changes in the nucleic acid sequence due to the degeneracy of the genetic code; changes in the nucleic acid sequence due to the amino acid substitution, insertion, deletion, and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments, the nucleic acid molecule encoding an insecticidal protein is a non-genomic sequence.

A variety of polynucleotides that encode an insecticidal protein of the disclosure are contemplated. Such polynucleotides are useful for production of the insecticidal proteins in host cells when operably linked to suitable promoter, transcription termination and/or polyadenylation sequences. Such polynucleotides are also useful as probes for isolating homologous or substantially homologous polynucleotides that encode further insecticidal proteins.

Polynucleotides that encode an insecticidal protein of the disclosure can be synthesized de novo from a sequence disclosed herein. The sequence of the polynucleotide gene can be deduced from a disclosed protein sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide.

Furthermore, synthetic polynucleotide sequences of the disclosure can be designed so that they will be expressed in plants. U.S. Pat. No. 5,500,365 describes a method for synthesizing plant genes to improve the expression level of the protein encoded by the synthesized gene. This method relates to the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein. A similar method for obtaining enhanced expression of transgenes in monocotyledonous plants is disclosed in U.S. Pat. No. 5,689,052. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments, a nucleic acid molecule encoding an insecticidal protein of the disclosure is a non-genomic nucleic acid sequence. As used herein a "non-genomic nucleic acid sequence" or "non-genomic nucleic acid molecule" refers to a nucleic acid molecule that has one or more changes in the nucleic acid sequence compared to a native or genomic nucleic acid sequence. In some embodiments, the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous *intrans*; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a cDNA.

In some embodiments, the disclosure teaches nucleic acid molecules that encode insecticidal proteins taught herein, as well as nucleic acid molecules that encode proteins taught herein that have had an amino acid substitution, deletion, insertion, and fragments thereof and combinations thereof.

Also provided are nucleic acid molecules that encode transcription and/or translation products that are subsequently spliced to ultimately produce functional insecticidal proteins. Splicing can be accomplished in vitro or in vivo, and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an insecticidal protein encoding sequence. An example of trans-splicing would be where a polynucleotide is encrypted by separating the coding sequence into two or more fragments that can be separately transcribed and then spliced to form the full-length pesticidal protein encoding sequence. The use of a splicing enhancer sequence, which can be introduced into a construct, can facilitate splicing either in cis or trans-splicing of polypeptides (U.S. Pat. Nos. 6,365,377 and 6,531,316). Thus, in some embodiments the polynucleotides do not directly encode a full-length insecticidal protein, but rather encode a fragment or fragments of same.

Nucleic acid molecules that are fragments of the aforementioned sequences encoding insecticidal proteins are also encompassed by the embodiments. "Fragment" as used herein refers to a portion of the nucleic acid sequence encoding an insecticidal protein. A fragment of a nucleic acid sequence may encode a biologically active portion of a protein or it may be a fragment that can be used as a hybridization probe or PCR primer using methods disclosed herein. Nucleic acid molecules that are fragments of a nucleic acid sequence comprise at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, or more contiguous nucleotides, or up to the number of nucleotides present in a full-length nucleic acid sequence encoding an insecticidal protein taught herein. "Contiguous nucleotides" is used herein to refer to nucleotide residues that are immediately adjacent to one another. Fragments of the nucleic acid sequences of the embodiments will encode protein fragments that retain the biological activity of the insecticidal protein. In some embodiments, a fragment of a nucleic acid sequence will encode at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, or more contiguous amino acids, or up to the total number of amino acids present in a full-length insecticidal protein taught herein. In some embodiments, the fragment is an N-terminal and/or a C-terminal truncation of at least about 1, 2, 3, 4, 5, 6, 7, 8, 9, 10, 11, 12, 13, 14 or more amino acids from the N-terminus and/or C-terminus relative to an insecticidal protein taught herein, e.g., by proteolysis, insertion of a start codon, deletion of the codons encoding the deleted amino acids with the concomitant insertion of a stop codon or by insertion of a stop codon in the coding sequence.

In some embodiments, an insecticidal protein is encoded by a nucleic acid sequence sufficiently similar to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71. "Sufficiently similar" is used herein to refer to an amino acid or nucleic acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence similarity compared to a reference sequence using one of the alignment programs described herein, or known to one of skill in the art, using standard parameters.

In some embodiments, an insecticidal protein is encoded by a nucleic acid sequence that has sufficient sequence identity to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71. "Sufficient sequence identity" is used herein to refer to an amino acid or nucleic acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity compared to a reference sequence using one of the alignment programs described herein, or known to one of skill in the art, using standard parameters.

Percent Identity Calculations

One of skill in the art will recognize that the aforementioned values can be appropriately adjusted to determine corresponding homology or identity of proteins encoded by two nucleic acid sequences by taking into account codon degeneracy, amino acid similarity, reading frame positioning, and the like. In some embodiments the sequence homology is against the full length sequence of the polynucleotide encoding a protein. In some embodiments, the sequence identity is calculated using ClustalW algorithm in the ALIGNX® module of the Vector NTI® Program Suite (Invitrogen Corporation, Carlsbad, Calif.) with all default parameters. In some embodiments the sequence identity is across the entire length of polypeptide calculated using ClustalW algorithm in the ALIGNX module of the Vector NTI Program Suite (Invitrogen Corporation, Carlsbad, Calif.) with all default parameters.

To determine the percent identity of two amino acid sequences, or of two nucleic acid sequences, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence. The percent identity between two sequences can be determined using techniques similar to those described below, with or without allowing gaps. In calculating percent identity, typically exact matches are counted.

The determination of percent identity between two sequences (nucleic acid or amino acid) can be accomplished using a mathematical algorithm. A non-limiting example of a mathematical algorithm utilized for the comparison of two sequences is the algorithm of Karlin and Altschul, (1990) Proc. Natl. Acad. Sci. USA 87:2264, modified as in Karlin and Altschul, (1993) Proc. Natl. Acad. Sci. USA 90:5873-5877. Such an algorithm is incorporated into the BLASTN and BLASTX programs of Altschul, et al., (1990) J. Mol. Biol. 215:403. BLAST nucleotide searches can be performed with the BLASTN program, score=100, wordlength=12, to obtain nucleic acid sequences homologous to pesticidal nucleic acid molecules of the embodiments. BLAST protein searches can be performed with the BLASTX program, score=50, wordlength=3, to obtain amino acid sequences homologous to pesticidal protein molecules of the embodiments. To obtain gapped alignments for comparison purposes, Gapped BLAST (in BLAST 2.0) can be utilized as described in Altschul, et al., (1997) Nucleic Acids Res. 25:3389. Alternatively, PSI-Blast can be used to perform an iterated search that detects distant relationships between molecules. See, Altschul, et al., (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins, et al., (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX® module of the Vector NTI® Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins.

Another non-limiting example of a mathematical algorithm utilized for the comparison of sequences is the algorithm of Myers and Miller, (1988) CABIOS 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Another non-limiting example of a mathematical algorithm utilized for the comparison of sequences is the algorithm of Needleman and Wunsch, (1970) J. Mol. Biol. 48(3):443-453, used GAP Version 10 software to determine sequence identity or similarity using the following default parameters: % identity and % similarity for a nucleic acid sequence using GAP Weight of 50 and Length Weight of 3; % identity or % similarity for an amino acid sequence using GAP weight of 8 and length weight of 2, and the BLOSUM62 scoring program. Equivalent programs may also be used. Thus, any sequence comparison program that, for any two sequences in question, generates an alignment having identical nucleotide or amino acid residue matches and calculates a percent sequence identity can be used.

Nucleic Acid Molecule Variants

The disclosure provides nucleic acid molecules encoding insecticidal protein variants. "Variants" of encoding nucleic acid sequences may include those sequences that encode insecticidal proteins disclosed herein, but that differ conservatively, because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis, but which still encode the disclosed insecticidal proteins.

The present disclosure provides isolated or recombinant polynucleotides that encode any of the insecticidal proteins disclosed herein. Those having ordinary skill in the art will readily appreciate that due to the degeneracy of the genetic code, a multitude of nucleotide sequences encoding proteins of the present disclosure exist. Table A is a codon table that provides the synonymous codons for each amino acid. For example, the codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

TABLE A

Synonymous Codon Table

| Alanine | Ala | GCA, GCC, GCG, GCU |
| Cysteine | Cys | UGC, UGU |
| Aspartic Acid | Asp | GAC, GAU |
| Glutamic Acid | Glu | GAA, GAG |
| Phenylalanine | Phe | UUC, UUU |
| Glycine | Gly | GGA, GGC, GGG, GGU |
| Histidine | His | CAC, CAU |
| Isoleucine | Ile | AUA, AUC, AUU |
| Lysine | Lys | AAA, AAG |
| Leucine | Leu | UUA, UUG, CUA, CUC, CUG, CUU |

TABLE A-continued

Synonymous Codon Table

| Methionine | Met | AUG |
| Asparagine | Asn | AAC, AAU |
| Proline | Pro | CCA, CCC, CCG, CCU |
| Glutamine | Gln | CAA, CAG |
| Arginine | Arg | AGA, AGG, CGA, CGC, CGG, CGU |
| Serine | Ser | AGC, AGU, UCA, UCC, UCG, UCU |
| Threonine | Thr | ACA, ACC, ACG, ACU |
| Valine | Val | GUA, GUC, GUG, UU |
| Tryptophan | Trp | UGG |
| Tyrosine | Tyr | UAC, UAU |

The skilled artisan will further appreciate that changes can be introduced by mutation of the nucleic acid sequences thereby leading to changes in the amino acid sequence of the encoded proteins, without altering the biological activity of the proteins. Thus, variant nucleic acid molecules can be created by introducing one or more nucleotide substitutions, additions, and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal protein homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries, and any recombinant polynucleotide produced by such methods.

A variety of diversity generating protocols, including nucleic acid recursive recombination protocols are available and fully described in the art. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. pesticidal activity. This can include identifying any activity that can be detected, for example, in an automated or automatable format, by any of the assays in the art, see, e.g., discussion of screening of insecticidal activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for proteins having pesticidal activity or fragments thereof, are found in the following publications and the references cited therein: Soong, et al., (2000) Nat. Genet. 25(4):436-439; Stemmer, et al., (1999) Tumor Targeting 4: 1-4; Ness, et al., (1999) Nat. Biotechnol. 17:893-896; Chang, et al., (1999) Nat. Biotechnol. 17:793-797; Minshull and Stemmer, (1999) Curr. Opin. Chem. Biol. 3:284-290; Christians, et al., (1999) Nat. Biotechnol. 17:259-264; Crameri, et al., (1998) Nature 391:288-291; Crameri, et al., (1997) Nat. Biotechnol. 15:436-438; Zhang, et al., (1997) PNAS USA 94:4504-4509; Patten, et al., (1997) Curr. Opin. Biotechnol. 8:724-733; Crameri, et al., (1996) Nat. Med. 2:100-103; Crameri, et al., (1996) Nat. Biotechnol. 14:315-319; Gates, et al., (1996) J. Mol. Biol. 255:373-386; Stemmer, (1996) "Sexual PCR and Assembly PCR" In: The Encyclopedia of Molecular Biology. VCH Publishers, New York. pp. 447-457; Crameri and Stemmer, (1995) BioTechniques 18: 194-195; Stemmer, et al., (1995) Gene, 164:49-53; Stemmer, (1995) Science 270: 1510; Stemmer, (1995) Biotechnology 13:549-553; Stemmer, (1994) Nature 370: 389-391 and Stemmer, (1994) PNAS USA 91:10747-10751.

Mutational methods of generating diversity include, for example, site-directed mutagenesis (Ling, et al., (1997) Anal Biochem 254(2): 157-178; Dale, et al., (1996) Methods Mol. Biol. 57:369-374; Smith, (1985) Ann. Rev. Genet. 19:423-462; Botstein and Shortle, (1985) Science 229:1193-1201; Carter, (1986) Biochem. J. 237: 1-7 and Kunkel, (1987) "The efficiency of oligonucleotide directed mutagenesis" in Nucleic Acids & Molecular Biology (Eckstein and Lilley, eds., Springer Verlag, Berlin)); mutagenesis using uracil containing templates (Kunkel, (1985) PNAS USA 82:488-492; Kunkel, et al., (1987) Methods Enzymol. 154:367-382 and Bass, et al., (1988) Science 242:240-245); oligonucleotide-directed mutagenesis (Zoller and Smith, (1983) Methods Enzymol. 100:468-500; Zoller and Smith, (1987) Methods Enzymol. 154:329-350 (1987); Zoller and Smith, (1982) Nucleic Acids Res. 10:6487-6500), phosphorothioate-modified DNA mutagenesis (Taylor, et al., (1985) Nucleic Acids Res. 13:8749-8764; Taylor, et al., (1985) Nucleic Acids Res. 13:8765-8787 (1985); Nakamaye and Eckstein, (1986) Nucleic Acids Res. 14:9679-9698; Sayers, et al., (1988) Nucleic Acids Res. 16:791-802 and Sayers, et al., (1988) Nucleic Acids Res. 16:803-814); mutagenesis using gapped duplex DNA (Kramer, et al., (1984) Nucleic Acids Res. 12:9441-9456; Kramer and Fritz, (1987) Methods Enzymol. 154:350-367; Kramer, et al., (1988) Nucleic Acids Res. 16:7207 and Fritz, et al., (1988) Nucleic Acids Res. 16:6987-6999).

Additional suitable methods include point mismatch repair (Kramer, et al., (1984) Cell 38:879-887), mutagenesis using repair-deficient host strains (Carter, et al., (1985) Nucleic Acids Res. 13:4431-4443 and Carter, (1987) Methods in Enzymol. 154:382-403), deletion mutagenesis (Eghtedarzadeh and Henikoff, (1986) Nucleic Acids Res. 14: 5115), restriction-selection and restriction-purification (Wells, et al., (1986) Phil. Trans. R. Soc. Lond. A317:415-423), mutagenesis by total gene synthesis (Nambiar, et al., (1984) Science 223:1299-1301; Sakamar and Khorana, (1988) Nucleic Acids Res. 14:6361-6372; Wells, et al., (1985) Gene 34:315-323 and Grundstriim, et al., (1985) Nucleic Acids Res. 13:3305-3316), double-strand break repair (Mandecki, (1986) PNAS USA, 83:7177-7181 and Arnold, (1993) Curr. Opin. Biotech. 4:450-455). Additional details on many of the above methods can be found in Methods Enzymol Volume 154, which also describes useful controls for trouble-shooting problems with various mutagenesis methods.

Additional details regarding various diversity generating methods can be found in the following US Patents, PCT Publications, and Applications and EPO publications: U.S. Pat. Nos. 5,723,323, 5,763,192, 5,814,476, 5,817,483, 5,824,514, 5,976,862, 5,605,793, 5,811,238, 5,830,721, 5,834,252, 5,837,458, WO 1995/22625, WO 1996/33207, WO 1997/20078, WO 1997/35966, WO 1999/41402, WO 1999/41383, WO 1999/41369, WO 1999/41368, EP 752008, EP 0932670, WO 1999/23107, WO 1999/21979, WO 1998/31837, WO 1998/27230, WO 1998/27230, WO 2000/00632, WO 2000/09679, WO 1998/42832, WO 1999/29902, WO 1998/41653, WO 1998/41622, WO 1998/42727, WO 2000/18906, WO 2000/04190, WO 2000/42561, WO 2000/42559, WO 2000/42560, and WO 2001/23401.

Nucleic Acid Molecule Probes to Find Related Nucleic Acids

The nucleotide sequences of the embodiments can also be used to isolate corresponding sequences from other organisms, particularly other bacteria, particularly a *Pseudomonas* species. In this manner, methods such as PCR, hybridization, and the like can be used to identify such sequences based on their sequence homology to the sequences set forth herein.

Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook, et al., (1989) Molecular Cloning: A Laboratory Manual (2nd ed., Cold Spring Harbor Laboratory Press, Plainview, N.Y.), hereinafter "Sambrook". See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector specific primers, partially-mismatched primers, and the like.

To identify insecticidal proteins of the disclosure from bacterial collections, the bacterial cell lysates can be screened with antibodies generated against a taught protein using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

Alternatively, mass spectrometry based protein identification methods can be used to identify homologs of the taught proteins using protocols in the literature (Scott Patterson, (1998), 10.22, 1-24, Current Protocol in Molecular Biology published by John Wiley & Son Inc). Specifically, LC-MS/MS based protein identification methods can be used to associate the MS data of given cell lysate or desired molecular weight enriched samples (excised from SDS-PAGE gel of relevant molecular weight bands to proteins taught herein) with sequence information of the taught proteins and homologs. Any match in peptide sequences indicates the potential of having the homologs in the samples. Additional techniques (protein purification and molecular biology) can be used to isolate the protein and identify the sequences of the homologs.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme cofactor. Probes for hybridization can be made by labeling synthetic oligonucleotides based on the known peptide-encoding nucleic acid sequence disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequence encoding a protein of the disclosure or a fragment or variant thereof. Methods for the preparation of probes for hybridization are generally known in the art and are disclosed in Sambrook and Russell, (2001), supra, herein incorporated by reference.

For example, an entire nucleic acid sequence, encoding an insecticidal protein taught herein, or one or more portions thereof may be used as a probe capable of specifically hybridizing to corresponding nucleic acid sequences encoding like sequences and messenger RNAs. To achieve specific hybridization under a variety of conditions, such probes include sequences that are unique and are preferably at least about 10 nucleotides in length or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook, et al., (1989) Molecular Cloning: A Laboratory Manual (2nd ed., Cold Spring Harbor Laboratory Press, Cold Spring Harbor, N.Y.).

Hybridization of such sequences may be carried out under stringent conditions. "Stringent conditions" or "stringent hybridization conditions" is used herein to refer to conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60°. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl, (1984) Anal. Biochem. 138:267-284: Tm=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology-Hybridization with Nucleic Acid Probes, Part I, Chapter 2 (Elsevier, N.Y.); and Ausubel, et al., eds. (1995) Current Protocols in Molecular Biology, Chapter 2 (Greene Publishing and Wiley-Interscience, New York). See, Sambrook, et al., (1989) Molecular Cloning: A Laboratory Manual (2nd ed., Cold Spring Harbor Laboratory Press, Cold Spring Harbor, N.Y.).

Newly Discovered Insecticidal Proteins, Variants, and Fragments Thereof

Novel insecticidal proteins are disclosed herein, along with variants of said proteins, and fragments thereof. The terms "proteins" and "polypeptides" are in some instances used interchangeably, as it is understood in the art that the separation between the two terms can merely depend upon the number of amino acid sequences. The insecticidal proteins of the disclosure demonstrate insecticidal or pesticidal activity against one or more insects or pests.

In some embodiments, an insecticidal protein is sufficiently homologous to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72. "Sufficiently homologous" is used herein to refer to an amino acid or nucleic acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence homology compared to a reference sequence using one of the alignment programs described herein, or known to one of skill in the art, using standard parameters.

In some embodiments, an insecticidal protein has sufficient sequence identity to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72. "Sufficient sequence identity" is used herein to refer to an amino acid or nucleic acid sequence that has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity compared to a reference sequence using one of the alignment programs described herein, or known to one of skill in the art, using standard parameters.

In some embodiments, the disclosure provides for an amino acid sequence of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, which are encoded by a nucleic acid sequence of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71.

As used herein, the terms "protein," "peptide" or "polypeptide" includes any molecule that comprises five or more amino acids. It is well known in the art that protein, peptide, or polypeptide molecules may undergo modification, including post-translational modifications, such as, but not limited to, disulfide bond formation, glycosylation, phosphorylation or oligomerization. Thus, as used herein, the terms "protein," "peptide molecule" or "polypeptide" includes any protein that is modified by any biological or non-biological process.

A "recombinant protein" is used herein to refer to a protein that is no longer in its natural environment, for example in vitro or in a recombinant bacterial or plant host cell. An insecticidal protein that is substantially free of cellular material includes preparations of protein having less than about 30%, 20%, 10% or 5% (by dry weight) of non-pesticidal protein (also referred to herein as a "contaminating protein").

"Fragments" or "biologically active portions" include protein fragments comprising amino acid sequences sufficiently identical to a protein taught herein and that exhibit insecticidal activity.

Thus, the disclosure contemplates fragments of the amino acid sequences set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

In some embodiments, the protein fragment is an N-terminal and/or a C-terminal truncation of at least about 1, 2, 3, 4, 5, 6, 7, 8, 9, 10, 11, 12, 13, 14 or more amino acids from the N-terminus and/or C-terminus relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO:

24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, e.g., by proteolysis, by insertion of a start codon, by deletion of the codons encoding the deleted amino acids and concomitant insertion of a start codon, and/or insertion of a stop codon.

"Variants" as used herein refers to proteins or polypeptides having an amino acid sequence that is at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the parental amino acid sequence.

The term "about" as used herein with respect to % sequence identity of a nucleic acid or amino acid means up to and including ±1.0% in 0.1% increments. For example "about 90%" sequence identity includes 89.0%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, and 91%. If not used in the context of % sequence identity, then "about" means ±10%.

In some embodiments, an insecticidal protein has at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity across the entire length of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

In some embodiments, the insecticidal proteins have a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to: net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to: solubility, folding, stability, and digestibility. In some embodiments, the taught insecticidal protein has increased digestibility of proteolytic fragments in an insect gut. Models for digestion by simulated gastric fluids are known to one skilled in the art (Fuchs, R. L. and J. D. Astwood. Food Technology 50: 83-88, 1996; Astwood, J. D., et al Nature Biotechnology 14: 1269-1273, 1996; Fu T J et al J. Agric. Food Chem. 50: 7154-7160, 2002).

In some embodiments, variants include polypeptides that differ in amino acid sequence due to mutagenesis. Variant proteins encompassed by the disclosure are biologically active, that is they continue to possess the desired biological activity (i.e. pesticidal activity) of the native protein. In some embodiments, the variant will have at least about 10%, 20%, 30%, 40%, 50%, 60%, 70%, 80%, 90%, or more of insecticidal activity of the native protein. In some embodiments, the variants may have improved activity over the native protein.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present disclosure and may be used in the methods of the present disclosure. It will be understood that, when expressed in plants, it will be necessary to alter the alternate start codon to ATG for proper translation.

In another aspect, the insecticidal protein may be expressed as a precursor protein with an intervening sequence that catalyzes multistep, post translational protein splicing. Protein splicing involves the excision of an intervening sequence from a polypeptide with the concomitant joining of the flanking sequences to yield a new polypeptide (Chong, et al., (1996) J. Biol. Chem., 271:22159-22168). This intervening sequence or protein splicing element, referred to as inteins, which catalyze their own excision through three coordinated reactions at the N-terminal and C-terminal splice junctions: an acyl rearrangement of the N-terminal cysteine or serine; a transesterification reaction between the two termini to form a branched ester or thioester intermediate and peptide bond cleavage coupled to cyclization of the intein C-terminal asparagine to free the intein (Evans, et al., (2000) J. Biol. Chem., 275:9091-9094. The elucidation of the mechanism of protein splicing has led to a number of intein-based applications (Comb, et al., U.S. Pat. No. 5,496,714; Comb, et al., U.S. Pat. No. 5,834,247; Camarero and Muir, (1999) J. Amer. Chem. Soc. 121:5597-5598; Chong, et al., (1997) Gene 192:271-281, Chong, et al., (1998) Nucleic Acids Res. 26:5109-5115; Chong, et al., (1998) J. Biol. Chem. 273:10567-10577; Cotton, et al., (1999) J. Am. Chem. Soc. 121:1100-1101; Evans, et al., (1999) J. Biol. Chem. 274:18359-18363; Evans, et al., (1999) J. Biol. Chem. 274:3923-3926; Evans, et al., (1998) Protein Sci. 7:2256-2264; Evans, et al., (2000) J. Biol. Chem. 275:9091-9094; Iwai and Pluckthun, (1999) FEBS Lett. 459:166-172; Mathys, et al., (1999) Gene 231:1-13; Mills, et al., (1998) Proc. Natl. Acad. Sci. USA 95:3543-3548; Muir, et al., (1998) Proc. Natl. Acad. Sci. USA 95:6705-6710; Otomo, et al., (1999) Biochemistry 38:16040-16044; Otomo, et al., (1999) J. Biolmol. NMR 14:105-114; Scott, et al., (1999) Proc. Natl. Acad. Sci. USA 96: 13638-13643; Severinov and Muir, (1998) J. Biol.

Chem. 273:16205-16209; Shingledecker, et al., (1998) Gene 207: 187-195; Southworth, et al., (1998) EMBO J. 17:918-926; Southworth, et al., (1999) Biotechniques 27: 110-120; Wood, et al., (1999) Nat. Biotechnol. 17:889-892; Wu, et al., (1998a) Proc. Natl. Acad. Sci. USA 95:9226-9231; Wu, et al., (1998b) Biochim. Biophys. Acta 1387:422-432; Xu, et al., (1999) Proc. Natl. Acad. Sci. USA 96:388-393; Yamazaki, et al., (1998) J. Am. Chem. Soc., 120:5591-5592). For the application of inteins in plant transgenes, see, Yang, et al., (Transgene Res. 15:583-593 (2006)) and Evans, et al., (Annu. Rev. Plant Biol. 56:375-392 (2005)).

In another aspect, the insecticidal protein may be encoded by two separate genes where the intein of the precursor protein comes from the two genes, referred to as a split intein, and the two portions of the precursor are joined by a peptide bond formation. This peptide bond formation is accomplished by intein-mediated trans-splicing. For this purpose, a first and a second expression cassette comprising the two separate genes further code for inteins capable of mediating protein trans-splicing. By trans-splicing, the proteins and polypeptides encoded by the first and second fragments may be linked by peptide bond formation. Trans-splicing inteins may be selected from the nucleolar and organelle genomes of different organisms including eukaryotes, archaebacteria and eubacteria. Inteins that may be used are listed at neb.com/neb/inteins.html, which can be accessed on the worldwide web using the "www" prefix. The nucleotide sequence coding for an intein may be split into a 5' and a 3' part that code for the 5' and the 3' part of the intein, respectively. Sequence portions not necessary for intein splicing (e.g. homing endonuclease domain) may be deleted. The intein coding sequence is split such that the 5' and the 3' parts are capable of trans-splicing. For selecting a suitable splitting site of the intein coding sequence, the considerations published by Southworth, et al., (1998) EMBO J. 17:918-926 may be followed. In constructing the first and the second expression cassette, the 5' intein coding sequence is linked to the 3' end of the first fragment coding for the N-terminal part of polypeptide and the 3' intein coding sequence is linked to the 5' end of the second fragment coding for the C-terminal part of the polypeptide.

In general, the trans-splicing partners can be designed using any split intein, including any naturally occurring or artificially split intein. Several naturally occurring split inteins are known, for example: the split intein of the DnaE gene of *Synechocystis* sp. PCC6803 (see, Wu, et al., (1998) Proc. Natl. Acad. Sci. USA. 95(16):9226-31 and Evans, et al., (2000) J. Biol. Chem. 275(13):9091-4 and of the DnaE gene from *Nostoc punctiforme* (see, Iwai, et al., (2006) FEBS Lett. 580(7): 1853-8). Non-split inteins have been artificially split in the laboratory to create new split inteins, for example: the artificially split Ssp DnaB intein (see, Wu, et al., (1998) Biochim. Biophys. Acta. 1387:422-32) and split See VMA intein (see, Brenzel, et al., (2006) Biochemistry 45(6):1571-8) and an artificially split fungal mini-intein (see, Elleuche, et al., (2007) Biochem. Biophys. Res. Commun. 355(3):830-4). Naturally occurring non-split inteins may have endonuclease or other enzymatic activities that can typically be removed when designing an artificially-split split intein. Such mini-inteins or minimized split inteins are well known in the art and are typically less than 200 amino acid residues long (see, Wu, et al., (1998) Biochim. Biophys. Acta. 1387: 422-32). Suitable split inteins may have other purification enabling polypeptide elements added to their structure, provided that such elements do not inhibit the splicing of the split intein or are added in a manner that allows them to be removed prior to splicing. Protein splicing has been reported using proteins that comprise bacterial intein-like (BIL) domains (see, Amitai, et al., (2003) Mol. Microbiol. 47:61-73) and hedgehog (Hog) auto-processing domains (the latter is combined with inteins when referred to as the Hog/intein superfamily or HINT family (see, Dassa, et al., (2004) J. Biol. Chem. 279:32001-7) and domains such as these may also be used to prepare artificially-split inteins. In particular, non-splicing members of such families may be modified by molecular biology methodologies to introduce or restore splicing activity in such related species.

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., (1979) Proc. Natl. Acad. Sci. U.S.A. 76:3218-3222; Teather and Erfle, (1990) J. Bacteriol. 172:3837-3841; Schimming, et al., (1992) Eur. J. Biochem. 204:13-19; Yamiuchi and Minamikawa, (1991) FEBS Lett. 260:127-130; MacGregor, et al., (1996) FEBS Lett. 378:263-266). The first in vitro application of this type of rearrangement to proteins was described by Goldenberg and Creighton (J. Mol. Biol. 165:407-413, 1983). In creating a circular permuted variant, a new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus and the new sequence continues with the same sequence as the original until it reaches a point that is at or near the amino acid that was N-terminal to the breakpoint site of the original sequence, this residue forming the new C-terminus of the chain. The length of the amino acid sequence of the linker can be selected empirically or with guidance from structural information or by using a combination of the two approaches. When no structural information is available, a small series of linkers can be prepared for testing using a design whose length is varied in order to span a range from 0 to 50 Å and whose sequence is chosen in order to be consistent with surface exposure (hydrophilicity, Hopp and Woods, (1983) Mol. Immunol. 20:483-489; Kyte and Doolittle, (1982) J. Mol. Biol. 157: 105-132; solvent exposed surface area, Lee and Richards, (1971) J. Mol. Biol. 55:379-400) and the ability to adopt the necessary conformation without deranging the configuration of the pesticidal polypeptide (conformationally flexible; Karplus and Schulz, (1985) Naturwissenschaften 72:212-213). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, (1992) Critical Rev. Biotech. 12:437-462); if they are too long, entropy effects will likely destabilize the three-dimensional fold, and may also make folding kinetically impractical, and if they are too short, they will likely destabilize the molecule because of torsional or steric strain. Those skilled in the analysis of protein structural information will recognize that using the distance between the chain ends, defined as the distance between the c-alpha carbons, can be used to define the length of the sequence to be used or at least to limit the number of possibilities that must be tested in an empirical selection of linkers. They will also recognize that it is sometimes the case that the positions of the ends of the polypeptide chain are ill defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used. Sequences of pesticidal polypeptides capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence.

It is a central tenet of molecular biology that the primary amino acid sequence of a protein dictates folding to the three-dimensional structure necessary for expression of its biological function. Methods are known to those skilled in the art to obtain and interpret three dimensional structural information using x-ray diffraction of single protein Crystals or nuclear magnetic resonance spectroscopy of protein solutions. Examples of structural information that are relevant to the identification of breakpoint regions include the location and type of protein secondary structure (alpha and 3-10 helices, parallel and anti-parallel beta sheets, chain reversals and turns, and loops; Kabsch and Sander, (1983) Biopolymers 22:2577-2637; the degree of solvent exposure of amino acid residues, the extent and type of interactions of residues with one another (Chothia, (1984) Ann. Rev. Biochem. 53:537-572) and the static and dynamic distribution of conformations along the polypeptide chain (Alber and Mathews, (1987) Methods Enzymol. 154:511-533). In some cases additional information is known about solvent exposure of residues; one example is a site of posttranslational attachment of carbohydrate that is necessarily on the surface of the protein. When experimental structural information is not available or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile and Salvatore, (1993) Eur. J. Biochem. 218:603-621). Thus using either the experimentally derived structural information or predictive methods (e.g., Srinivisan and Rose, (1995) Proteins: Struct., Funct. & Genetics 22:81-99) the parental amino acid sequence is inspected to classify regions according to whether or not they are integral to the maintenance of secondary and tertiary structure. The occurrence of sequences within regions that are known to be involved in periodic secondary structure (alpha and 3-10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region. Polynucleotides encoding circular permuted polypeptides with new N-terminus/C-terminus which contain a linker region separating the original C-terminus and N-terminus can be made essentially following the method described in Mullins, et al., (1994) J. Am. Chem. Soc. 116:5529-5533. Multiple steps of polymerase chain reaction (PCR) amplifications are used to rearrange the DNA sequence encoding the primary amino acid sequence of the protein. Polynucleotides encoding circular permuted polypeptides with new N-terminus/C-terminus which contain a linker region separating the original C-terminus and N-terminus can be made based on the tandem duplication method described in Horlick, et al., (1992) Protein Eng. 5:427-431. Polymerase chain reaction (PCR) amplification of the new N-terminus/C-terminus genes is performed using a tandemly duplicated template DNA.

Fusion Proteins Comprising the Novel Insecticidal Proteins

In another aspect, fusion proteins are provided that include within its amino acid sequence a sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, and active fragments thereof.

Methods for design and construction of fusion proteins (and polynucleotides encoding same) are known to those of skill in the art. Polynucleotides encoding an insecticidal protein may be fused to signal sequences which will direct the localization of the polypeptide to particular compartments of a prokaryotic or eukaryotic cell and/or direct the secretion of the polypeptide from a prokaryotic or eukaryotic cell. For example, in *E. coli*, one may wish to direct the expression of the protein to the periplasmic space.

Examples of signal sequences or proteins (or fragments thereof) to which the insecticidal polypeptide may be fused, in order to direct the expression of the polypeptide to the periplasmic space of bacteria include, but are not limited to: the pelB signal sequence, the maltose binding protein (MBP) signal sequence, MBP, the ompA signal sequence, the signal sequence of the periplasmic *E. coli* heat labile enterotoxin B-subunit, and the signal sequence of alkaline phosphatase.

Several vectors are commercially available for the construction of fusion proteins, which will direct the localization of a protein, such as the pMAL series of vectors (pMAL-p series) available from New England Biolabs® (240 County Road, Ipswich, Mass. 01938-2723). In a specific embodiment, the polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat. No. 7,193,133). Apoplast transit peptides such as rice or barley alpha-amylase secretion signal are also well known in the art. The plastid transit peptide is generally fused N-terminal to the polypeptide to be targeted (e.g., the fusion partner). However, additional amino acid residues may be N-terminal to the plastid transit peptide providing that the fusion protein is at least partially targeted to a plastid. In a specific embodiment, the plastid transit peptide is in the N-terminal half, N-terminal third, or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) Gene 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) J. Biol. Chem. 263(29):15104-9.

In some embodiments, fusion proteins are provided comprising an insecticidal polypeptide as taught herein, and another insecticidal polypeptide joined by an amino acid linker. In some embodiments, fusion proteins are provided represented by a formula selected from the group consisting of: $R^1$-L-$R^2$, $R^2$-L-$R^1$, $R^1$-$R^2$ or $R^2$-$R^1$, wherein $R^1$ is a polypeptide selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, and $R^2$ is another insecticidal polypeptide. The $R^1$ polypeptide is fused either directly or through a linker (L) segment to the R2 polypeptide. The term "directly" defines fusions in which the polypeptides are joined without a peptide linker. Thus "L" represents a chemical bound or polypeptide segment to which both $R^1$ and $R^2$ are fused in frame, most commonly L is a linear peptide to which $R^1$ and $R^2$ are bound by amide bonds linking the carboxy terminus of $R^1$ to the amino terminus of L and carboxy terminus of L to the amino terminus of $R^2$. By "fused in frame" is meant that there is no translation termination or disruption between the reading frames of $R^1$ and $R^2$. The linking group (L) is generally a polypeptide of between 1 and 500 amino acids in length. The linkers joining the two molecules are preferably designed to: (1) allow the two molecules to fold and act independently of each other, (2) not have a propensity for developing an ordered secondary structure which could interfere with the functional domains of the two proteins, (3) have minimal hydrophobic or charged characteristic which could interact with the functional protein domains, and (4) provide steric separation of $R^1$ and $R^2$ such that $R^1$ and $R^2$ could interact simultaneously with their corresponding receptors on a single cell. Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In some embodiments, the linkers comprise sequences selected from the group of formulas: $(Gly_3Ser)_n$, $(Gly_4Ser)_n$, $(Gly_5Ser)_n$, $(Gly_nSer)_n$ or $(AlaGlySer)_n$ where n is an integer. One example of a highly-flexible linker is the (GlySer)-rich spacer region present within the pill protein of the filamentous bacteriophages, e.g. bacteriophages M13 or fd (Schaller, et al., 1975). This region provides a long, flexible spacer region between two domains of the pill surface protein. Also included are linkers in which an endopeptidase recognition sequence is included. Such a cleavage site may be valuable to separate the individual components of the fusion to determine if they are properly folded and active in vitro. Examples of various endopeptidases include, but are not limited to: Plasmin, Enterokinase, Kallikerin, Urokinase, Tissue Plasminogen activator, clostripain, Chymosin, Collagenase, Russell's Viper Venom Protease, Postproline cleavage enzyme, VS protease, Thrombin and factor Xa. In other embodiments, peptide linker segments from the hinge region of heavy chain immunoglobulins IgG, IgA, IgM, IgD or IgE provide an angular relationship between the attached polypeptides. The fusion proteins are not limited by the form, size or number of linker sequences employed and the only requirement of the linker is that functionally it does not interfere adversely with the folding and function of the individual molecules of the fusion.

In another aspect, chimeric proteins are provided that are created through joining two or more portions of the taught insecticidal protein genes, which originally encoded separate insecticidal proteins to create a chimeric gene. The translation of the chimeric gene results in a single chimeric protein with regions, motifs, or domains derived from each of the original proteins. In certain embodiments, the chimeric protein comprises portions, motifs, or domains of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, in any combination.

It is recognized that DNA sequences may be altered by various methods, and that these alterations may result in DNA sequences encoding proteins with amino acid sequences different than that encoded by the wild-type (or native) pesticidal protein. In some embodiments, an insecticidal protein taught herein may be altered in various ways including amino acid substitutions, deletions, truncations, and insertions of one or more amino acids, including up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acid substitutions, deletions and/or insertions or combinations thereof compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

Methods for such manipulations are generally known in the art. For example, amino acid sequence variants of a polypeptide can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a taught polypeptide to confer pesticidal activity may be improved by the use of such techniques upon the compositions of this disclosure.

For example, conservative amino acid substitutions may be made at one or more, predicted, nonessential amino acid residues. A "nonessential" amino acid residue is a residue that can be altered from the wild-type sequence of a taught polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, praline, glycine); nonpolar side chains (e.g., alanine, valine, leucine, isoleucine, pro line, phenylalanine, methionine, tryptophan); large aliphatic, nonpolar residues (e.g., methionine, leucine, isoleucine, valine, cysteine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in non-conserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologs). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment of the homologs). However, one of skill in the art would understand that functional variants may have minor conserved or non-conserved alterations in the conserved residues. Guidance as to appropriate amino acid substitutions that do not affect biological activity of the protein of interest may be found in the model of Dayhoff, et al., (1978) Atlas of Protein Sequence and Structure (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) J Mol Biol. 157(1):105-132). It is accepted that the relative hydropathic character of the amino acid contributes to the secondary structure of the resultant protein, which in tum defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); praline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); praline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Alternatively, alterations may be made to the protein sequence of many proteins at the amino or carboxy terminus without substantially affecting activity. This can include insertions, deletions or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein coding sequences, such as those used commonly in the art to generate protein fusions. Such fusion proteins are often used to (1) increase expression of a protein of interest (2) introduce a binding domain, enzymatic activity or epitope to facilitate either protein purification, protein detection or other experimental uses known in the art (3) target secretion or translation of a protein to a subcellular organelle, such as the periplasmic space of Gram-negative bacteria, mitochondria or chloroplasts of plants or the endoplasmic reticulum of eukaryotic cells, the latter of which often results in glycosylation of the protein.

Variant nucleotide and amino acid sequences of the disclosure also encompass sequences derived from mutagenic and recombinogenic procedures such as DNA shuffling. With such a procedure, one or more different insecticidal polypeptide coding regions can be used to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) Proc. Natl. Acad. Sci. USA 91:10747-10751; Stemmer, (1994) Nature 370:389-391; Crameri, et al., (1997) Nature Biotech. 15:436-438; Moore, et al., (1997) J. Mol. Biol. 272:336-347; Zhang, et al., (1997) Proc. Natl. Acad. Sci. USA 94:4504-4509; Crameri, et al., (1998) Nature 391:288-291; and U.S. Pat. Nos. 5,605,793 and 5,837,458.

Domain swapping or shuffling is another mechanism for generating altered polypeptides. Domains may be swapped between polypeptides, resulting in hybrid or chimeric toxins with improved insecticidal activity or target spectrum. Methods for generating recombinant proteins and testing them for pesticidal activity are well known in the art (see, for example, Naimov, et al., (2001) Appl. Environ. Microbiol. 67:5328-5330; de Maagd, et al., (1996) Appl. Environ. Microbiol. 62:1537-1543; Ge, et al., (1991) J. Biol. Chem. 266:17954-17958; Schnepf, et al., (1990) J. Biol. Chem. 265:20923-20930; Rang, et al., 91999) Appl. Environ. Microbiol. 65:2918-2925).

Both DNA shuffling and site-directed mutagenesis can be used to define polypeptide sequences that possess pesticidal activity. The person skilled in the art will be able to use comparisons to other proteins or functional assays to further define motifs. High throughput screening can be used to test variations of those motifs to determine the role of specific residues.

Receptor Identification and Isolation

Receptors to the taught insecticidal proteins, or to variants or fragments thereof, are also encompassed. Methods for identifying receptors are well known in the art (see, Hofmann, et. al., (1988) Eur. J. Biochem. 173:85-91; Gill, et al., (1995) J. Biol. Chem. 27277-27282) and can be employed to identify and isolate the receptor that recognizes the taught insecticidal proteins using the brush-border membrane vesicles from susceptible insects. In addition to the radioactive labeling method listed in the cited literature, taught proteins can be labeled with fluorescent dye and other common labels such as streptavidin. Brush-border membrane vesicles (BBMV) of susceptible insects such as soybean looper and stink bugs can be prepared according to the protocols listed in the references and separated on SDS-PAGE gel and blotted on suitable membrane. Labeled proteins can be incubated with blotted membrane of BBMV and identified with the labeled reporters. Identification of protein band(s) that interact with the proteins can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the proteins. Receptor function for insecticidal activity by the taught proteins can be verified by an RNAi type of gene knock out method (Rajagopal, et al., (2002) J. Biol. Chem. 277:46849-46851).

Nucleotide Constructs, Expression Cassettes, and Vectors

The use of the term "nucleotide constructs" herein is not intended to limit the embodiments to nucleotide constructs comprising DNA. Those of ordinary skill in the art will recognize that nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and were necessary to join two protein-coding regions in the same reading frame. The construct may additionally contain at least one additional gene to be co-transformed into the organism. Alternatively, the additional gene(s) can be provided on multiple DNA constructs.

In some embodiments, the DNA construct comprises a polynucleotide encoding an insecticidal protein taught herein, which is operably linked to a heterologous regulatory sequence.

In some embodiments, the DNA construct comprises a polynucleotide encoding an insecticidal protein taught herein, which is operably linked to a heterologous regulatory sequence, said polynucleotide selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and SEQ ID NO: 71, or a sequence corresponding to the aforementioned that has been codon optimized for expression in a host cell of interest, for example a plant cell in some embodiments.

In some embodiments, the DNA construct comprises a polynucleotide encoding an insecticidal protein taught herein, which is operably linked to a heterologous regulatory sequence, said protein selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, or a variant thereof.

Such a DNA construct is provided with a plurality of restriction sites for insertion of the polypeptide gene sequence to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host, e.g. a bacterial cell or plant cell.

The transcriptional initiation region (i.e., the promoter) may be native, analogous, foreign, or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "heterologous" to the sequence of the embodiments, it is intended that the promoter is not the native or naturally occurring promoter for the operably linked sequence of the embodiments (i.e., not the native location). As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments, the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, intrans with gene expression enhancing properties in plants (US Patent Application Publication Number 2009/0144863, the ubiquitin intron (i.e., the maize ubiquitin intron 1 (see, for example, NCBI sequence S94464; Christensen and Quail (1996) Transgenic Res. 5:213-218; Christensen et al. (1992) Plant Molecular Biology 18:675-689)), the omega enhancer or the omega prime enhancer (Gallie, et al., (1989) Molecular Biology of RNA ed. Cech (Liss, New York) 237-256 and Gallie, et al., (1987) Gene 60:217-25), the CaMV 35S enhancer (see, e.g., Benfey, et al., (1990) EMBO J. 9: 1685-96), the maize Adh1 intron (Kyozuka et al. (1991) Mol. Gen. Genet. 228:40-48; Kyozuka et al. (1990) Maydica 35:353-357), the enhancers of U.S. Pat. No. 7,803,992, and the sugarcane bacilliform viral (SCBV) enhancer of WO2013130813 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host, or may be derived from another source (i.e., foreign or heterologous to the promoter, the sequence of interest, the plant host or any combination thereof).

Convenient termination regions are available from the Ti-plasmid of A. tumefaciens, such as the octopine synthase and nopaline synthase termination regions. See also, Guerineau, et al., (1991) Mol. Gen. Genet. 262:141-144; Proudfoot, (1991) Cell 64:671-674; Sanfacon, et al., (1991) Genes Dev. 5:141-149; Magen, et al., (1990) Plant Cell 2:1261-1272; Munroe, et al., (1990) Gene 91:151-158; Ballas, et al., (1989) Nucleic Acids Res. 17:7891-7903 and Joshi, et al., (1987) Nucleic Acid Res. 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) Plant Physiol. 92:1-11 for a discussion of host preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons, as these preferences have been shown to differ (Murray et al. (1989) Nucleic Acids Res. 17:477-498).

Thus, one of skill in the art will understand how to utilize specific plant codon usage tables to derive the optimal sequences to express the insecticidal proteins of the disclosure. See, e.g. US 2016/0366891 (U.S. application Ser. No. 15/022,109), which is hereby incorporated by reference in its entirety.

Additional sequence modifications are known to enhance gene expression in a cellular host. These include elimination of sequences encoding spurious polyadenylation signals, exon-intron splice site signals, transposon like repeats, and other well characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector. Host cells may be prokaryotic cells such as E. coli or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picomavirus leaders, for example, EMCV leader (Encephalomyocarditis 5' noncoding region) (Elroy-Stein, et al., (1989) Proc. Natl. Acad. Sci. USA 86:6126-6130); potyvirus leaders, for example, TEV leader (Tobacco Etch Virus) (Gallie, et al., (1995) Gene 165(2):233-238), MDMV leader (Maize Dwarf Mosaic Virus), human immunoglobulin heavy-chain binding protein (BiP) (Macejak, et al., (1991) Nature 353:90-94); untranslated leader from the coat protein mRNA of alfalfa mosaic virus (AMY RNA 4) (Jobling, et al., (1987) Nature 325:622-625); tobacco mosaic virus leader (TMV) (Gallie, et al., (1989) in Molecular Biology of RNA, ed. Cech (Liss, New York), pp. 237-256) and maize chlorotic mottle virus leader (MCMV) (Lommel, et al., (1991) Virology 81:382-385). See also, Della-Cioppa, et al., (1987) Plant Physiol. 84:965-968.

Such constructs may also contain a "signal sequence" or "leader sequence" to facilitate co-translational or post-translational transport of the peptide to certain intracellular structures such as the chloroplast (or other plastid), endoplasmic reticulum or Golgi apparatus. "Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang, (1987) Methods Enzymol. 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved the identification of numerous nuclear encoded lumen proteins (Kieselbach et al. FEBS Lett. 480:271-276, 2000; Peltier et al. Plant Cell 12:319-341, 2000; Bricker et al. Biochim. Biophys. Acta 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., Photosynthesis Research, 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the published draft version of the rice genome (Goff et al, Science 296:92-100, 2002) is a suitable source for lumen targeting signal peptide which may be used in accordance with the present disclosure.

Suitable chloroplast transit peptides (CTP) are well known to one skilled in the art also include chimeric CTPs comprising but not limited to, an N-terminal domain, a central domain or a C-terminal domain from a CTP from *Oryza sativa*-1-deoxy-D xyulose-5-Phosphate Synthase, *Oryza sativa*-Superoxide dismutase, *Oryza sativa*-soluble starch synthase, *Oryza sativa*-NADP-dependent Malic acid enzyme, *Oryza sativa*-Phospho-2-dehydro-3-deoxyheptonate Aldolase 2, *Oryza sativa*-L-Ascorbate peroxidase 5, *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type (US Patent Application Publication 2012/0304336). Chloroplast transit peptides of US Patent Publications US20130205440A1, US20130205441A1 and US20130210114A. The polypeptide gene to be targeted to the chloroplast may be optimized for expression in the chloroplast to account for differences in codon usage between the plant nucleus and this organelle.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

Promoters

A number of promoters can be used in the practice of the embodiments. The promoters can be selected based on the desired outcome. The nucleic acids can be combined with constitutive, tissue-preferred, inducible, or other promoters for expression in the host organism. Promoters of the present invention include homologues of cis elements known to effect gene regulation that show homology with the promoter sequences of the present invention. These cis elements include, but are not limited to, oxygen responsive cis elements (Cowen et al., J. Biol. Chem. 268(36):26904-26910 (1993)), light regulatory elements (Bruce and Quaill, Plant Cell 2 (11):1081-1089 (1990); Bruce et al., EMBO J. 10:3015-3024 (1991); Rocholl et al., Plant Sci. 97:189-198 (1994); Block et al., Proc. Natl. Acad. Sci. USA 87:5387-5391 (1990); Giuliano et al., Proc. Natl. Acad. Sci. USA 85:7089-7093 (1988); Staiger et al., Proc. Natl. Acad. Sci. USA 86:6930-6934 (1989); Izawa et al., Plant Cell 6:1277-1287 (1994); Menkens et al., Trends in Biochemistry 20:506-510 (1995); Foster et al., FASEB J. 8:192-200 (1994); Plesse et al., Mol. Gen. Gene. 254:258-266 (1997); Green et al., EMBO J. 6:2543-2549 (1987); Kuhlemeier et al., Ann. Rev. Plant Physiol. 38:221-257 (1987); Villain et al., J. Biol. Chem. 271:32593-32598 (1996); Lam et al., Plant Cell 2:857-866 (1990); Gilmartin et al., Plant Cell 2:369-378 (1990); Datta et al., Plant Cell 1:1069-1077 (1989); Gilmartin et al., Plant Cell 2:369-378 (1990); Castresana et al., EMBO J. 7:1929-1936 (1988); Ueda et al., Plant Cell 1:217-227 (1989); Terzaghi et al., Annu. Rev. Plant Physiol. Plant Mol. Biol. 46:445-474 (1995); Green et al., EMBO J. 6:2543-2549 (1987); Villain et al., J. Biol. Chem. 271:32593-32598 (1996); Tjaden et al., Plant Cell 6:107-118 (1994); Tjaden et al., Plant Physiol. 108:1109-1117 (1995); Ngai et al., Plant J. 12:1021-1234 (1997); Bruce et al., EMBO J. 10:3015-3024 (1991); Ngai et al., Plant J. 12:1021-1034 (1997)), elements responsive to gibberellin, (Muller et al., J. Plant Physiol. 145:606-613 (1995); Croissant et al., Plant Science 116:27-35 (1996); Lohmer et al., EMBO J. 10:617-624 (1991); Rogers et al., Plant Cell 4:1443-1451 (1992); Lanahan et al., Plant Cell 4:203-211 (1992); Skriver et al., Proc. Natl. Acad. Sci. USA 88:7266-7270 (1991); Gilmartin et al., Plant Cell 2:369-378 (1990); Huang et al., Plant Mol. Biol. 14:655-668 (1990), Gubler et al., Plant Cell 7:1879-1891 (1995)), elements responsive to abscisic acid, (Busk et al., Plant Cell 9:2261-2270 (1997); Guiltinan et al., Science 250:267-270 (1990); Shen et al., Plant Cell 7:295-307 (1995); Shen et al., Plant Cell 8:1107-1119 (1996); Seo et al., Plant Mol. Biol. 27:1119-1131 (1995); Marcotte et al., Plant Cell 1:969-976 (1989); Shen et al., Plant Cell 7:295-307 (1995); Iwasaki et al., Mol Gen Genet 247:391-398 (1995); Hattori et al., Genes Dev. 6:609-618 (1992); Thomas et al., Plant Cell 5:1401-1410 (1993)), elements similar to abscisic acid responsive elements, (Ellerstrom et al., Plant Mol. Biol. 32:1019-1027 (1996)), auxin responsive elements (Liu et al., Plant Cell 6:645-657 (1994); Liu et al., Plant Physiol. 115:397-407 (1997); Kosugi et al., Plant J. 7:877-886 (1995); Kosugi et al., Plant Cell 9:1607-1619 (1997); Ballas et al., J. Mol. Biol. 233:580-596 (1993)), a cis element responsive to methyl jasmonate treatment (Beaudoin and Rothstein, Plant Mol. Biol. 33:835-846 (1997)), a cis element responsive to abscisic acid and stress response (Straub et al., Plant Mol. Biol. 26:617-630 (1994)), ethylene responsive cis elements (Itzhaki et al., Proc. Natl. Acad. Sci. USA 91:8925-8929 (1994); Montgomery et al., Proc. Natl. Acad. Sci. USA 90:5939-5943 (1993); Sessa et al., Plant Mol. Biol. 28:145-153 (1995); Shinshi et al., Plant Mol. Biol. 27:923-932 (1995)), salicylic acid cis responsive elements, (Strange et al., Plant J. 11:1315-1324 (1997); Qin et al., Plant Cell 6:863-874 (1994)), a cis element that responds to water stress and abscisic acid (Lam et al., J. Biol. Chem. 266: 17131-17135 (1991); Thomas et al., Plant Cell 5:1401-1410 (1993); Pia et al., Plant Mol Biol. 21:259-266 (1993)), a cis element essential for M phase-specific expression (Ito et al., Plant Cell 10:331-341 (1998)), sucrose responsive elements (Huang et al., Plant Mol. Biol. 14:655-668 (1990); Hwang et al., Plant Mol Biol 36:331-341 (1998); Grierson et al., Plant J. 5:815-826 (1994)), heat shock response elements (Pelham et al., Trends Genet. 1:31-35 (1985)), elements responsive to auxin and/or salicylic acid and also reported for light regulation (Lam et al., Proc. Natl. Acad. Sci. USA 86:7890-7897 (1989); Benfey et al., Science 250:959-966 (1990)), elements responsive to ethylene and salicylic acid (Ohme-Takagi et al., Plant Mol. Biol. 15:941-946 (1990)), elements responsive to wounding and abiotic stress (Laake et al., Proc. Natl. Acad. Sci. USA 89:9230-9234 (1992); Mhiri et al., Plant Mol. Biol. 33:257-266 (1997)), antioxidant response elements (Rushmore et al., J. Biol. Chem. 266: 11632-11639; Dalton et al., Nucleic Acids Res. 22:5016-5023 (1994)), Sph elements (Suznki et al., Plant Cell 9:799-807 1997)), elicitor responsive elements, (Fnkuda et al., Plant Mol. Biol. 34:81-87 (1997); Rushton et al., EMBO J. 15:5690-5700 (1996)), metal responsive elements (Stuart et al., Nature 317:828-831 (1985); Westin et al., EMBO J. 7:3763-3770 (1988); Thiele et al., Nucleic Acids Res. 20:1183-1191 (1992); Faisst et al., Nucleic Acids Res. 20:3-26 (1992)), low temperature responsive elements, (Baker et al., Plant Mol. Biol. 24:701-713 (1994); Jiang et al., Plant Mol. Biol. 30:679-684 (1996); Nordin et al., Plant Mol. Biol. 21:641-653 (1993); Zhou et al., J. Biol. Chem. 267:23515-23519 (1992)), drought responsive elements, (Yamaguchi et al., Plant Cell 6:251-264 (1994); Wang et al., Plant Mol. Biol. 28:605-617 (1995); Bray E A, Trends in Plant Science 2:48-54 (1997)) enhancer elements for glutenin, (Colot et al., EMBO J. 6:3559-3564 (1987); Thomas et al., Plant Cell 2:1171-1180 (1990); Kreis et al., Philos. Trans. R. Soc. Lond., B314:355-365 (1986)), light-independent regulatory elements, (Lagrange et al., Plant Cell 9:1469-1479 (1997); Villain et al., J. Biol. Chem. 271: 32593-32598 (1996)), OCS enhancer elements, (Bouchez et al., EMBO J. 8:4197-4204 (1989); Foley et al., Plant J. 3:669-679 (1993)), ACGT elements, (Foster et al., FASEB J. 8:192-200 (1994); Izawa et al., Plant Cell 6:1277-1287 (1994); Izawa et al., J. Mol. Biol. 230:1131-1144 (1993)), negative cis elements in plastid related genes, (Zhou et al., J. Biol. Chem. 267:23515-23519 (1992); Lagrange et al., Mol. Cell Biol. 13:2614-2622 (1993); Lagrange et al., Plant Cell 9:1469-1479 (1997); Zhou et al., J. Biol. Chem. 267: 23515-23519 (1992)), prolamin box elements, (Forde et al., Nucleic Acids Res. 13:7327-7339 (1985); Colot et al., EMBO J. 6:3559-3564 (1987); Thomas et al., Plant Cell 2:1171-1180 (1990); Thompson et al., Plant Mol. Biol. 15:755-764 (1990); Vicente et al., Proc. Natl. Acad. Sci. USA 94:7685-7690 (1997)), elements in enhancers from the IgM heavy chain gene (Gillies et al., Cell 33:717-728 (1983); Whittier et al., Nucleic Acids Res. 15:2515-2535 (1987)).

Examples of promoters include those described in: U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter, P-Zm.L3), U.S. Pat. No. 6,429,357 (rice actin 2 promoter as well as a rice actin 2 intron), U.S. Pat. No. 5,837,848 (root specific promoter), U.S. Pat. No.

6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gama-coixin promoter, P-CI.Gcx), U.S. patent application Ser. No. 09/757,089 (maize chloroplast aldolase promoter), and U.S. Pat. No. 8,772,466 (maize transcription factor Nuclear Factor B (NFB2)).

Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) Nature 313:810-812); rice actin (McElroy, et al., (1990) Plant Cell 2:163-171); ubiquitin (Christensen, et al., (1989) Plant Mol. Biol. 12:619-632 and Christensen, et al., (1992) Plant Mol. Biol. 18:675-689); pEMU (Last, et al., (1991) Theor. Appl. Genet. 81:581-588); MAS (Velten, et al., (1984) EMBO J. 3:2723-2730); ALS promoter (U.S. Pat. No. 5,659,026) and the like.

Other constitutive promoters include, for example, those discussed in: U.S. Pat. Nos. 5,608,149; 5,608,144; 5,604,121; 5,569,597; 5,466,785; 5,399,680; 5,268,463; 5,608,142 and 6,177,611.

Suitable constitutive promoters also include promoters that have strong expression in nearly all tissues but have low expression in pollen, including but not limited to: Banana Streak Virus (*Acuminata* Yunnan) promoters (BSV(AY)) disclosed in U.S. Pat. No. 8,338,662; Banana Streak Virus (*Acuminata* Vietnam) promoters (BSV (AV)) disclosed in U.S. Pat. No. 8,350,121; and Banana Streak Virus (Mysore) promoters (BSV(M YS)) disclosed in U.S. Pat. No. 8,395,022.

Depending on the desired outcome, it may be beneficial to express the gene from an inducible promoter. Of particular interest for regulating the expression of the nucleotide sequences of the embodiments in plants are wound inducible promoters. Such wound inducible promoters, may respond to damage caused by insect feeding, and include potato proteinase inhibitor (pin II) gene (Ryan, (1990) Ann. Rev. Phytopath. 28:425-449; Duan, et al., (1996) Nature Biotechnology 14:494-498); wun1 and wun2, U.S. Pat. No. 5,428,148; win1 and win2 (Stanford, et al., (1989) Mol. Gen. Genet. 215:200-208); systemin (McGurl, et al., (1992) Science 225:1570-1573); WIP (Rohmeier, et al., (1993) Plant Mol. Biol. 22:783-792; Eckelkamp, et al., (1993) FEBS Letters 323:73-76); MPI gene (Corderok, et al., (1994) Plant J. 6(2):141-150) and the like, herein incorporated by reference.

Additionally, pathogen inducible promoters may be employed in the methods and nucleotide constructs of the embodiments. Such pathogen inducible promoters include those from pathogenesis related proteins (PR proteins), which are induced following infection by a pathogen; e.g., PR proteins, SAR proteins, beta-1,3-glucanase, chitinase, etc. See, for example, Redolfi, et al., (1983) Neth. J. Plant Pathol. 89:245-254; Uknes, et al., (1992) Plant Cell 4:645-656 and Van Loon, (1985) Plant Mol. Biol. 4:111-116. See also, WO 1999/43819, herein incorporated by reference.

Of interest are promoters that are expressed locally at or near the site of pathogen infection. See, for example, Marineau, et al., (1987) Plant Mol. Biol. 9:335-342; Matton, et al., (1989) Molecular Plant-Microbe Interactions 2:325-331; Somsisch, et al., (1986) Proc. Natl. Acad. Sci. USA 83:2427-2430; Somsisch, et al., (1988) Mol. Gen. Genet. 2:93-98 and Yang, (1996) Proc. Natl. Acad. Sci. USA 93:14972-14977. See also, Chen, et al., (1996) Plant J. 10:955-966; Zhang, et al., (1994) Proc. Natl. A cad. Sci. USA 91:2507-2511; Warner, et al., (1993) Plant J. 3:191-201; Siebertz, et al., (1989) Plant Cell 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) Physiol. Mol. Plant Path. 41:189-200).

Chemical regulated promoters can be used to modulate the expression of a gene in a plant through the application of an exogenous chemical regulator. Depending upon the objective, the promoter may be a chemical inducible promoter, where application of the chemical induces gene expression or a chemical repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical regulated promoters of interest include steroid responsive promoters (see, for example, the glucocorticoid-inducible promoter in Schena, et al., (1991) Proc. Natl. Acad. Sci. USA 88:10421-10425 and McNellis, et al., (1998) Plant J. 14(2):247-257) and tetracycline-inducible and tetracycline-repressible promoters (see, for example, Gatz, et al., (1991) Mol. Gen. Genet. 227:229-237 and U.S. Pat. Nos. 5,814,618 and 5,789,156), herein incorporated by reference.

Tissue preferred promoters can be utilized to target enhanced polypeptide expression within a particular plant tissue. Tissue preferred promoters include those discussed in Yamamoto, et al., (1997) Plant J. 12(2)255-265; Kawamata, et al., (1997) Plant Cell Physiol. 38(7):792-803; Hansen, et al., (1997) Mol. Gen Genet. 254(3):337-343; Russell, et al., (1997) Transgenic Res. 6(2):157-168; Rinehart, et al., (1996) Plant Physiol. 112(3):1331-1341; Van Camp, et al., (1996) Plant Physiol. 112(2):525-535; Canevascini, et al., (1996) Plant Physiol. 112(2):513-524; Yamamoto, et al., (1994) Plant Cell Physiol. 35(5):773-778; Lam, (1994) Results Probl. Cell Differ. 20: 181-196; Orozco, et al., (1993) Plant Mol Biol. 23(6): 1129-1138; Matsuoka, et al., (1993) Proc Natl. Acad. Sci. USA 90(20):9586-9590 and Guevara-Garcia, et al., (1993) Plant J. 4(3):495-505. Such promoters can be modified, if necessary, for weak expression if desired.

Leaf preferred promoters are known in the art. See, for example, Yamamoto, et al., (1997) Plant J. 12(2):255-265; Kwon, et al., (1994) Plant Physiol. 105:357-67; Yamamoto, et al., (1994) Plant Cell Physiol. 35(5):773-778; Gator, et al., (1993) Plant J. 3:509-18; Orozco, et al., (1993) Plant Mol. Biol. 23(6):1129-1138 and Matsuoka, et al., (1993) Proc. Natl. Acad. Sci. USA 90(20):9586-9590.

Root preferred or root specific promoters are known and can be selected from the many available from the literature or isolated de novo from various compatible species. See, for example, Hire, et al., (1992) Plant Mol. Biol. 20(2):207-218 (soybean root specific glutamine synthetase gene); Keller and Baumgartner, (1991) Plant Cell 3(10):1051-1061 (root specific control element in the GRP 1.8 gene of French bean); Sanger, et al., (1990) Plant Mol. Biol. 14(3):433-443 (root specific promoter of the mannopine synthase (MAS) gene of *Agrobacterium tumefaciens*) and Miao et al., (1991) Plant Cell 3(1):11-22 (full length cDNA clone encoding cytosolic glutamine synthetase (GS), which is expressed in roots and root nodules of soybean). See also, Bogusz, et al., (1990) Plant Cell 2(7): 633-641, where two root specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root specific promoter activity was preserved. Leach and Aoyagi, (1991) describe their analysis of the promoters of the highly expressed rolC and rolD root inducing genes of *Agrobacterium rhizogenes* (see, Plant Science (Limerick) 79(1):69-76). They concluded that enhancer and tissue-preferred DNA determinants are dissociated in those promoters. Teeri, et al., (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, EMBO J. 8(2): 343-350). The TRI' gene fused to nptII (neomycin phosphotransferase II) showed similar characteristics. Additional root preferred promoters include the VfENOD-GRP3 gene promoter (Kuster, et al., (1995) Plant Mol. Biol. 29(4):759-772) and rolB promoter (Capana, et al., (1994) Plant Mol. Biol. 25(4):681-691. See also, U.S. Pat. Nos. 5,837,876; 5,750,386; 5,633,363; 5,459,252; 5,401,836; 5,110,732 and 5,023,179. *Arabidopsis thaliana* root preferred regulatory sequences are disclosed in US Patent Application US20130117883. Root preferred sorghum (*Sorghum bicolor*) RCc3 promoters are disclosed in US Patent Application US2012/0210463. The root preferred maize promoters of US Patent Application Publication 2003/0131377, U.S. Pat. Nos. 7,645,919, and 8,735,655. The root cap specific 1 (ZmRCP1) maize promoters of US Patent Application Publication 2013/0025000. The root preferred maize promoters of US Patent Application Publication 2013/0312136.

"Seed preferred"" promoters include both "seed-specific" promoters (those promoters active during seed development such as promoters of seed storage proteins) as well as "seed-germinating" promoters (those promoters active during seed germination). See, Thompson, et al., (1989) BioEssays 10:108, herein incorporated by reference. Such seed preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed specific promoters include, but are not limited to, Kunitz trypsin inhibitor 3 (KTi3) (Jofuku and Goldberg, (1989) Plant Cell 1:1079-1093), bean β-phaseolin, napin, β-conglycinin, glycinin 1, soybean lectin, cruciferin, and the like. For monocots, seed specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed preferred promoters from end1 and end2 genes are disclosed; herein incorporated by reference. In dicots, seed specific promoters include, but are not limited to, seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels. Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) EMBO J. 2:987-992); methotrexate (Herrera Estrella, et al., (1983) Nature 303:209-213 and Meijer, et al., (1991) Plant Mol. Biol. 16:807-820); streptomycin (Jones, et al., (1987) Mol. Gen. Genet. 210:86-91); spectinomycin (Bretagne-Sagnard, et al., (1996) Transgenic Res. 5:131-137); bleomycin (Hille, et al., (1990) Plant Mol. Biol. 7:171-176); sulfonamide (Guerineau, et al., (1990) Plant Mol. Biol. 15:127-136); bromoxynil (Stalker, et al., (1988) Science 242:419-423); glyphosate (Shaw, et al., (1986) Science 233:478-481 and U.S. patent application Ser. Nos. 10/004,357 and 10/427,692); phosphinothricin (DeBlock, et al., (1987) EMBO J. 6:2513-2518). See generally, Yarranton, (1992) Curr. Opin. Biotech. 3:506-511; Christopherson, et al., (1992) Proc. Natl. Acad. Sci. USA 89:6314-6318; Yao, et al., (1992) Cell 71:63-72; Reznikoff, (1992) Mol. Microbiol. 6:2419-2422; Barkley, et al., (1980) in The Operon, pp. 177-220; Hu, et al., (1987) Cell 48:555-566; Brown, et al., (1987) Cell 49:603-612; Figge, et al., (1988) Cell 52:713-722; Deuschle, et al., (1989) Proc. Natl. Acad. Sci. USA 86:5400-5404; Fuerst, et al., (1989) Proc. Natl. Acad. Sci. USA 86:2549-2553; Deuschle, et al., (1990) Science 248:480-483; Gossen, (1993) Ph.D. Thesis, University of Heidelberg; Reines, et al., (1993) Proc. Natl. Acad. Sci. USA 90:1917-1921; Labow, et al., (1990) Mol. Cell. Biol. 10:3343-3356; Zambretti, et al., (1992) Proc. Natl. Acad. Sci. USA 89:3952-3956; Baim, et al., (1991) Proc. Natl. Acad. Sci. USA 88:5072-5076; Wyborski, et al., (1991) Nucleic Acids Res. 19:4647-4653; Hillenand-Wissman, (1989) Topics Mol. Struc. Biol. 10:143-162; Degenkolb, et al., (1991) Antimicrob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-

919; Hlavka, et al., (1985) Handbook of Experimental Pharmacology, Vol. 78 (Springer-Verlag, Berlin) and Gill, et al., (1988) Nature 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) Biotechniques 4:320-334), electroporation (Riggs, et al., (1986) Proc. Natl. Acad. Sci. USA 83:5602-5606), *Agrobacterium*-mediated transformation (U.S. Pat. Nos. 5,563,055 and 5,981,840), direct gene transfer (Paszkowski, et al., (1984) EMBO J. 3:2717-2722) and ballistic particle acceleration (see, for example, U.S. Pat. Nos. 4,945,050; 5,879,918; 5,886,244 and 5,932,782; Tomes, et al., (1995) in Plant Cell, Tissue, and Organ Culture: Fundamental Methods, ed. Gamborg and Phillips (Springer-Verlag, Berlin) and McCabe, et al., (1988) Biotechnology 6:923-926) and Led transformation (WO 00/28058). For potato transformation see, Tu, et al., (1998) Plant Molecular Biology 37:829-838 and Chong, et al., (2000) Transgenic Research 9:71-78. Additional transformation procedures can be found in Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) Biotechnology 6:923-926 (soybean); Finer and McMullen, (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783 and 5,324,646; Klein, et al., (1988) Plant Physiol. 91:440-444 (maize); Fromm, et al., (1990) Biotechnology 8:833-839 (maize); Hooykaas Van Slogteren, et al., (1984) Nature (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford, (1995) Annals of Botany 75:407-413 (rice); Osjoda, et al., (1996) Nature Biotechnology 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the polypeptide or variants and fragments thereof directly into the plant or the introduction of the polypeptide transcript into the plant. Such methods include, for example, microinjection or particle bombardment. See, for example, Crossway, et al., (1986) Mol Gen. Genet. 202:179-185; Nomura, et al., (1986) Plant Sci. 44:53-58; Hepler, et al., (1994) Proc. Natl. Acad. Sci. USA 91:2176-2180 and Hush, et al., (1994) The Journal of Cell Science 107:775-784, all of which are herein incorporated by reference.

Alternatively, the polypeptide polynucleotide can be transiently transformed into the plant using techniques known in the art. Such techniques include viral vector system and the precipitation of the polynucleotide in a manner that precludes subsequent release of the DNA. Thus, transcription from the particle bound DNA can occur, but the frequency with which it is released to become integrated into the genome is greatly reduced. Such methods include the use of particles coated with polyethylenimine (PEI; Sigma #P3143).

Methods are known in the art for the targeted insertion of a polynucleotide at a specific location in the plant genome. In one embodiment, the insertion of the polynucleotide at a desired genomic location is achieved using a site specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) Trends in Plant Science 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) The Plant Journal 6:271-282; Ishida, et al., (1996) Nature Biotechnology 14:745-750). Explants are typically transferred to a fresh supply of the same medium and cultured routinely. A general description of the techniques and methods for generating transgenic plants are found in Ayres and Park, (1994) Critical Reviews in Plant Science 13:219-239 and Bommineni and Jauhar, (1997) Maydica 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) Plant Cell Reports 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired polypeptide. It is also recognized that such a viral polyprotein, comprising at least a portion of the amino acid sequence of a polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367 and 5,316,931; herein incorporated by reference.

Methods for transformation of chloroplasts are known in the art. See, for example, Svab, et al., (1990) Proc. Natl. Acad. Sci. USA 87:8526-8530; Svab and Maliga, (1993) Proc. Natl. Acad. Sci. USA 90:913-917; Svab and Maliga, (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear encoded and plastid directed RNA polymerase. Such a system has been reported in McBride, et al., (1994) Proc. Natl. Acad. Sci. USA 91:7301-7305.

The embodiments further relate to plant propagating material of a transformed plant of the embodiments including, but not limited to, seeds, tubers, corms, bulbs, leaves and cuttings of roots and shoots.

Plant Species Capable of being Transformed and Expressing an Insecticidal Protein The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliottii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristadtum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Paa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithi*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus aifinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include cereals, grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Transformation

Following introduction of heterologous foreign DNA into plant cells, the transformation or integration of a heterologous gene into the plant genome is confirmed by various methods such as analysis of nucleic acids, proteins and metabolites associated with the integrated gene.

PCR analysis is a rapid method to screen transformed cells, tissue or shoots for the presence of an incorporated gene at the earlier stage before transplanting into the soil (Sambrook and Russell, (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of an introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the taught insecticidal proteins.

Stacking of Transgenic Traits in a Plant

Transgenic plants may comprise a stack of one or more insecticidal polynucleotides disclosed herein with one or more additional polynucleotides resulting in the production or suppression of multiple polypeptide sequences.

Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell.

As used herein, the term "stacked" includes having the multiple traits present in the same plant (i.e., both traits are incorporated into the nuclear genome, one trait is incorporated into the nuclear genome and one trait is incorporated into the genome of a plastid, or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, the polynucleotides encoding the pesticidal proteins disclosed herein, alone or stacked with one or more additional insect resistance traits, can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include other pesticidal proteins, such as: Monalysin, PIP, Cry, Cyt, Vip, TC, and any combination thereof. These pesticidal proteins have been set forth in great detail in earlier sections of the specification.

Other transgenes useful for stacking with the taught pesticidal proteins include genes encoding for: plant disease resistance, insect specific hormones or pheromones, antifungal activity, and nematicidal activity.

Transgenes that confer resistance to an herbicide can also be stacked with the taught pesticidal proteins, including (non-limiting class of 9 herbicidal classes below):

(1) A polynucleotide encoding resistance to an herbicide that inhibits the growing point or meristem, such as an imidazolinone or a sulfonylurea. Exemplary genes in this category code for mutant ALS and AHAS enzyme as described, for example, by Lee, et al., (1988) EMBO J. 7:1241 and Miki, et al., (1990) Theor. Appl. Genet. 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(2) A polynucleotide encoding a protein for resistance to Glyphosate (resistance imparted by mutant 5-enolpyruvl-3-phosphikimate synthase (EPSPS) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; U.S. Pat. Nos. 6,040,497; 5,804,425; 5,633,435; 5,145,783; 4,971,908; 5,312,910; 5,188,642; 5,094,945, 4,940, 835; 5,866,775; 6,225,114 B1; U.S. Pat. Nos. 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al., De Greef, et al., (1989) Biol Technology 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1 and 5,879, 903, which are incorporated herein by reference for this purpose. Exemplary genes conferring resistance to phenoxy propionic acids and cyclohexanes, such as sethoxydim and haloxyfop, are the Accl-S1, Accl-S2 and Accl-S3 genes described by Marshall, et al., (1992) Theor. Appl. Genet. 83:435.

(3) A polynucleotide encoding a protein for resistance to herbicide that inhibits photosynthesis, such as a triazine (psbA and gs+ genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) Biochem. J. 285:173.

(4) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) Mol. Gen. Genet. 246:419). Other genes that confer resistance to herbicides include: a gene encoding a chimeric protein of rat cytochrome P4507A and yeast NADPH-cytochrome P450 oxidoreductase (Shiota, et al., (1994) Plant Physiol. 106:1 7), genes for glutathione reductase and superoxide dismutase (Aono, et al., (1995) Plant Cell Physiol. 36:1687) and genes for various phosphotransferases (Datta, et al., (1992) Plant Mol. Biol. 20:619).

(5) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373 and International Publication WO 2001/12825.

(6) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide-tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(7) A polynucleotide encoding a herbicide resistant dicamba monooxygenase disclosed in US Patent Application Publication 2003/0135879 for imparting dicamba tolerance;

(8) A polynucleotide molecule encoding bromoxynil nitrilase (Bxn) disclosed in U.S. Pat. No. 4,810,648 for imparting bromoxynil tolerance;

(9) A polynucleotide molecule encoding phytoene (crtI) described in Misawa, et al., (1993) Plant J. 4:833-840 and in Misawa, et al., (1994) Plant J. 6:481-489 for norflurazon tolerance.

Transgenes that confer or contribute to an altered grain characteristic can also be stacked with the taught pesticidal proteins, including (non-limiting class below relating to altered fatty acids in grain): (1) Down-regulation of stearoyl-ACP to increase stearic acid content of the plant. See, Knultzon, et al., (1992) Proc. Natl. Acad. Sci. USA 89:2624 and WO 1999/64579 (Genes to Alter Lipid Profiles in Corn). (2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245). (3) Altering conjugated linolenic or linoleic acid content, such as in WO 2001/12800. (4) Altering LEC1, AGP, Dek1, Superall, mil ps, various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825, 397 and US Patent Application Publication Numbers US 2003/0079247, US 2003/0204870 and Rivera-Madrid, et al., (1995) Proc. Natl. Acad. Sci. USA 92:5620-5624. (5) Genes encoding delta-8 desaturase for making long-chain polyunsaturated fatty acids (U.S. Pat. Nos. 8,058,571 and 8,338, 152), delta-9 desaturase for lowering saturated fats (U.S. Pat. No. 8,063,269), *Primula* A6-desaturase for improving omega-3 fatty acid profiles. (6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499). (7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794). (8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904). (9) Nucleic acid molecules encoding wrinkled-like polypeptides for modulating sugar metabolism (U.S. Pat. No. 8,217,223).

Transgenes that confer or contribute to an altered grain characteristic can also be stacked with the taught pesticidal proteins, including (non-limiting class below relating to altered phosphorus content in grain): (1) Introduction of a phytase encoding gene would enhance breakdown of phytate, adding more free phosphate to the transformed plant. For example, see, Van Hartingsveldt, et al., (1993) Gene 127:87, for a disclosure of the nucleotide sequence of an *Aspergillus niger* phytase gene. (2) Modulating a gene that reduces phytate content. In maize, this, for example, could be accomplished, by cloning and then reintroducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197, 561, 6,291,224, 6,391,348, WO 2002/059324, US Patent Application Publication Number 2003/0079247, WO 1998/ 45448, WO 1999/55882, WO 2001/04147.

Transgenes that confer or contribute to an altered grain characteristic can also be stacked with the taught pesticidal proteins, including (non-limiting class below relating to altered carbohydrate content in grain): (1) altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) J. Bacteriol. 170:810 (nucleotide sequence of *Streptococcus* mutant fructosyltransferase gene), Steinmetz, et al., (1985) Mol. Gen. Genet. 200:220 (nucleotide sequence of *Bacillus subtilis* levansucrase gene), Pen, et al., (1992) Biotechnology 10:292 (production of transgenic plants that express *Bacillus licheniformis* alpha-amylase), Elliot, et al., (1993) Plant Molec. Biol. 21:515 (nucleotide sequences of tomato invertase genes), Segaard, et al., (1993) J. Biol. Chem. 268:22480 (site-directed mutagenesis of barley alpha-amylase gene) and Fisher, et al., (1993) Plant Physiol. 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

Transgenes that confer or contribute to an altered grain characteristic can also be stacked with the taught pesticidal proteins, including (non-limiting class below relating to altered antioxidant content in grain): (1) alteration of tocopherol or tocotrienols. For example, see, U.S. Pat. No. 6,787,683, US Patent Application Publication Number 2004/ 0034886 and WO 2000/68393 involving the manipulation of antioxidant levels and WO 2003/082899 through alteration of a homogentisate geranylgeranyl transferase (hggt).

Transgenes that confer or contribute to an altered grain characteristic can also be stacked with the taught pesticidal proteins, including (non-limiting class below relating to altered essential amino acid content in grain): (1) For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/ 20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559, 223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

Transgenes that confer or contribute to male sterility can also be stacked with the taught pesticidal proteins. Transgenes that create a site for site specific DNA integration can also be stacked with the taught pesticidal proteins.

Transgenes that affect abiotic stress resistance of a crop plant can also be stacked with the taught pesticidal proteins, including, but not limited to: flowering, ear and seed development, enhancement of nitrogen utilization efficiency, altered nitrogen responsiveness, drought resistance or tolerance, cold resistance or tolerance and salt resistance or tolerance and increased yield under stress. Further examples of abiotic stress resistance genes that can be stacked with the taught pesticidal proteins, include: (1) WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521. (2) WO 199938977 describing genes, including CBF genes and transcription factors effective in mitigating the negative effects of freezing, high salinity and drought on plants, as well as conferring other positive effects on plant phenotype. (3) US Patent Application Publication Number 2004/0148654 and WO 2001/36596 where abscisic acid is altered in plants resulting in improved plant phenotype such as increased yield and/or increased tolerance to abiotic stress. (4) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also see, WO 2002/02776, WO 2003/052063, JP 2002/281975, U.S. Pat. No. 6,084,153, WO 2001/64898, U.S. Pat. Nos. 6,177,275 and 6,107,547 (enhancement of nitrogen utilization and altered nitrogen responsiveness). (5) For ethylene alteration, see, US Patent Application Publication Number 2004/0128719, US Patent Application Publication Number 2003/0166197 and WO 2000/32761. (6) For plant transcription factors or transcriptional regulators of abiotic stress, see, e.g., US Patent Application Publication Number 2004/0098764 or US Patent Application Publication Number 2004/0078852. (7) Genes that increase expression of vacuolar pyrophosphatase such as AVP1 (U.S. Pat. No. 8,058,515) for increased yield; nucleic acid encoding a HSF A4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox I-like (WOX1-like) polypeptide (U. Patent Application Publication Number US 2011/0283420). (8) Down regulation of polynucleotides encoding poly (ADP-ribose) polymerase (PARP) proteins to modulate programmed cell death (U.S. Pat. No. 8,058,510) for increased vigor. (9) Polynucleotide encoding DTP21 polypeptides for conferring drought resistance (US Patent Application Publication Number US 2011/0277181). (10) Nucleotide sequences encoding ACC Synthase 3 (ACS3) proteins for modulating development, modulating response to stress, and modulating stress tolerance (US Patent Application Publication Number US 2010/0287669). (11) Polynucleotides that encode proteins that confer a drought tolerance phenotype (DTP) for conferring drought resistance (WO 2012/058528). (12) Tocopherol cyclase (TC) genes for conferring drought and salt tolerance (US Patent Application Publication Number 2012/0272352). (13) CAAX amino terminal family proteins for stress tolerance (U.S. Pat. No. 8,338,661). (14) Mutations in the SAL1 encoding gene have increased stress tolerance, including increased drought resistant (US Patent Application Publication Number 2010/0257633). (15) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133). (16) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067). (17) Expression of a nucleic acid sequence encoding a Drought Tolerant Phenotype (DTP6) polypeptide, specifically AT-DTP6 of US Patent Application Publication Number 2014/0223595.

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FRI), WO 1997/29123, U.S. Pat. Nos. 6,794,560, 6,307,126 (GAI), WO 1999/09174 (D8 and Rht) and WO 2004/076638 and WO 2004/031349 (transcription factors).

Transgenes that confer increased yield to a crop plant can also be stacked with the taught pesticidal proteins, for example: (1) a transgenic crop plant transformed by a 1-AminoCyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769). (2) overexpression of maize zinc finger protein gene (Zm-ZFP1) using a seed preferred promoter has been shown to enhance plant growth, increase kernel number and total kernel weight per plant (US Patent Application Publication Number 2012/0079623). (3) Constitutive overexpression of maize lateral organ boundaries (LOB) domain protein (Zm-LOBDP1) has been shown to increase kernel number and total kernel weight per plant (US Patent Application Publication Number 2012/0079622). (4) Enhancing yield-related traits in plants by modulating expression in a plant of a nucleic acid encoding a VIM1 (Variant in Methylation 1)-like polypeptide or a VTC2-like (GDP-L-galactose phosphorylase) polypeptide or a DUF1685 polypeptide or an ARF6-like (Auxin Responsive Factor) polypeptide (WO 2012/038893). (5) Modulating expression in a plant of a nucleic acid encoding a Ste20-like polypeptide or a homologue thereof gives plants having increased yield relative to control plants (EP 2431472). (6) Genes encoding nucleoside diphosphatase kinase (NDK) polypeptides and homologs thereof for modifying the plant's root architecture (US Patent Application Publication Number 2009/0064373).

In some aspects, the pesticidal proteins can be stacked with any genetic trait that has received regulatory approval. A non-exhaustive list of such traits can be found in Table 4A-4F of US 2016/0366891 A1, which is incorporated herein by reference. Furthermore, the taught novel insecticidal proteins taught herein can be stacked or combined with any genetic trait from the following Tables B-G listed below.

TABLE B

Rice Traits That Can Be Combined With the Insecticidal Proteins
*Oryza sativa* Rice

| Event | Company | Description |
|---|---|---|
| CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). |
| IMINTA-1, IMINTA-4 | BASF Inc. | Tolerance to imidazolinone herbicides induced by chemical mutagenesis of the acetolactate synthase (ALS) enzyme using sodium azide. |
| LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). |
| LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). |
| PWC16 | BASF Inc. | Tolerance to the imidazolinone herbicide, imazethapyr, induced by chemical mutagenesis of the acetolactate synthase (ALS) enzyme using ethyl methanesulfonate (EMS). |

TABLE C

Alfalfa Traits That Can Be Combined With the Insecticidal Proteins
*Medicago sativa* Alfalfa

| Event | Company | Description |
|---|---|---|
| J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. |

TABLE D

Wheat Traits That Can Be Combined With the Insecticidal Proteins
Triticum aestivum Wheat

| Event | Company | Description |
|---|---|---|
| AP205CL | BASF Inc. | Selection for a mutagenized version of the enzyme acetohydroxyacid synthase (AHAS), also known as acetolactate synthase (ALS) or acetolactate pyruvate-lyase. |
| AP602CL | BASF Inc. | Selection for a mutagenized version of the enzyme acetohydroxyacid synthase (AHAS), also known as acetolactate synthase (ALS) or acetolactate pyruvate-lyase. |
| BW255-2, BW238-3 | BASF Inc. | Selection for a mutagenized version of the enzyme acetohydroxyacid synthase (AHAS), also known as acetolactate synthase (ALS) or acetolactate pyruvate-lyase. |

TABLE D-continued

Wheat Traits That Can Be Combined With the Insecticidal Proteins
Triticum aestivum Wheat

| Event | Company | Description |
|---|---|---|
| BW7 | BASF Inc. | Tolerance to imidazolinone herbicides induced by chemical mutagenesis of the acetohydroxyacid synthase (AHAS) gene using sodium azide. |
| MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. |
| SWP965001 | Cyanamid Crop Protection | Selection for a mutagenized version of the enzyme acetohydroxyacid synthase (AHAS), also known as acetolactate synthase (ALS) or acetolactate pyruvate-lyase. |
| Teal 11A | BASF Inc. | Selection for a mutagenized version of the enzyme acetohydroxyacid synthase (AHAS), also known as acetolactate synthase (ALS) or acetolactate pyruvate-lyase. |

TABLE E

Sunflower Traits That Can Be Combined With the Insecticidal Proteins
Helianthus annuus Sunflower

| Event | Company | Description |
|---|---|---|
| X81359 | BASF Inc. | Tolerance to imidazolinone herbicides by selection of a naturally occurring mutant. |

TABLE F

Soybean Traits That Can Be Combined With the Insecticidal Proteins
Glycine max L. Soybean

| Event | Company | Description |
|---|---|---|
| A2704-12, A2704-21, A5547-35 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| A5547-127 | Bayer CropScience (Aventis CropScience (AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| BPS-CV127-9 | BASF Inc. | The introduced csr1-2 gene from *Arabidopsis thaliana* encodes an acetohydroxyacid synthase protein that confers tolerance to imidazolinone herbicides due to a point mutation that results in a single amino acid substitution in which the serine residue at position 653 is replaced by asparagine (S653N). |

TABLE F-continued

Soybean Traits That Can Be Combined With the Insecticidal Proteins
*Glycine max* L. Soybean

| Event | Company | Description |
| --- | --- | --- |
| DP-305423 | Pioneer Hi-Bred International Inc. | High oleic acid soybean produced by inserting additional copies of a portion of the omega 6 desaturase encoding gene, gm-fad2-1 resulting in silencing of the endogenous omega-6 desaturase gene (FAD2-1). |
| DP356043 | Pioneer Hi-Bred International Inc. | Soybean event with two herbicide tolerance genes: glyphosate N-acetlytransferase, which detoxifies glyphosate, and a modified acetolactate synthase (ALS) gene which is tolerant to ALS-inhibiting herbicides. |
| G94-1, G94-19, G168 | DuPont Canada Agricultural Products | High oleic acid soybean produced by inserting a second copy of the fatty acid desaturase (Gm Fad2-1) encoding gene from soybean, which resulted in "silencing" of the endogenous host gene. |
| GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens.* |
| GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes.* |
| MON87701 | Monsanto Company | Resistance to Lepidopteran pests of soybean including velvetbean caterpillar (*Anticarsia gemmatalis*) and soybean looper (*Pseudoplusia includens*). |
| MON87701 × MON89788 | Monsanto Company | Glyphosate herbicide tolerance through expression of the EPSPS encoding gene from *A. tumefaciens* strain CP4, and resistance to Lepidopteran pests of soybean including velvetbean caterpillar (*Anticarsia gemmatalis*) and soybean looper (*Pseudoplusia includens*) via expression of the Cry1Ac encoding gene from *B. thuringiensis.* |
| MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4. |
| OT96-15 | Agriculture & Agri-Food Canada | Low linolenic acid soybean produced through traditional cross-breeding to incorporate the novel trait from a naturally occurring fan1 gene mutant that was selected for low linolenic acid. |
| W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus.* |

TABLE G

Corn Traits That Can Be Combined With the Insecticidal Proteins
*Zea mays* L. Maize

| Event | Company | Description |
|---|---|---|
| 176 | Syngenta Seeds, Inc. | Insect-resistant maize produced by inserting the Cry1Ab gene from *Bacillus thuringiensis* subsp. *kurstaki*. The genetic modification affords resistance to attack by the European corn borer (ECB). |
| 3751 IR 676, 678, 680 | Pioneer Hi-Bred International Inc. Pioneer Hi-Bred International Inc. | Selection of somaclonal variants by culture of embryos on imidazolinone containing media. Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. |
| B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. |
| BT11 (X4334CBR, X4734CBR) | Syngenta Seeds, Inc. | Insect-resistant and herbicide tolerant maize produced by inserting the Cry1Ab gene from *Bacillus thuringiensis* subsp. *kurstaki*, and the phosphinothricin N-acetyltransferase (PAT) encoding gene from *S. viridochromogenes*. |
| BT11 × GA21 | Syngenta Seeds, Inc. | Stacked insect resistant and herbicide tolerant maize produced by conventional cross breeding of parental lines BT11 (OECD unique identifier: SYN-BTO11-1) and GA21 (OECD unique identifier: MON-OOO21-9). |
| BT11 × MIR162 × MIR604 × GA21 | Syngenta Seeds, Inc. | Resistance to Coleopteran pests, particularly corn rootworm pests (*Diabrotica* spp.) and several Lepidopteran pests of corn, including European corn borer (ECB, *Ostrinia nubilalils*), corn earworm (CEW, *Helicoverpa zea*), fall army worm (FAW, *Spodoptera frupperda*), and black cutworm (BCW, *Agrotis ipsilon*); tolerance to glyphosate and glufosinate-ammonium containing herbicides. |
| BT11 × MIR162 | Syngenta Seeds, Inc. | Stacked insect resistant and herbicide tolerant maize produced by conventional cross breeding of parental lines BT11 (OECD unique identifier: SYN-BTO11-1) and MIR162 (OECD unique identifier: SYN-1R162-4). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Resistance to other Lepidopteran pests, including *H. zea, S. frupperda, A. ipsilon,* and *S. albicosta*, is derived from MIR162, which contains the vip3Aa gene from *Bacillus thuringiensis* strain AB88. |
| BT11 × MIR162 × MIR604 | Syngenta Seeds, Inc. | *Bacillus thuringiensis* Cry1Ab delta-endotoxin protein and the genetic material necessary for its production (via elements of vector pZO1502) in |

TABLE G-continued

Corn Traits That Can Be Combined With the Insecticidal Proteins
*Zea mays* L. Maize

| Event | Company | Description |
|---|---|---|
| | | Event Bt11 corn (OECD Unique Identifier: SYNBTO11-1) × *Bacillus thuringiensis* Vip3Aa20 insecticidal protein and the genetic material necessary for its production (via elements of vector pNOV1300) in Event MIR162 maize (OECD Unique Identifier: SYN-IR162-4) × modified Cry3A protein and the genetic material necessary for its production (via elements of vector pZM26) in Event MIR604 corn (OECD Unique Identifier: SYN-1R604-5). |
| CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. |
| DAS-06275-8 | DOW AgroSciences LLC | Lepidopteran insect resistant and glufosinate ammonium herbicide-tolerant maize variety produced by inserting the Cry1F gene from *Bacillus thuringiensis* var *aizawai* and the phosphinothricin acetyltransferase (PAT) from *Streptomyces hygroscopicus*. |
| BT11 × MIR604 | Syngenta Seeds, Inc. | Stacked insect resistant and herbicide tolerant maize produced by conventional cross breeding of parental lines BT11 (OECD unique identifier: SYN-BTO11-1) and MIR604 (OECD unique identifier: SYN-1R6O5-5). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. |
| BT11 × MIR604 × GA21 | Syngenta Seeds, Inc. | Stacked insect resistant and herbicide tolerant maize produced by conventional cross breeding of parental lines BT11 (OECD unique identifier: SYN-BTO11-1), MIR604 (OECD unique identifier: SYN-1R6O5-5) and GA21 (OECD unique identifier: MON-OOO21-9). Resistance to the European Corn Borer and tolerance to the herbicide glufosinate ammonium (Liberty) is derived from BT11, which contains the Cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mCry3A gene from *Bacillus thuringiensis*. Tolerance to glyphosate herbicide is derived from GA21 which contains a a modified EPSPS gene from maize. |

TABLE G-continued

Corn Traits That Can Be Combined With the Insecticidal Proteins
*Zea mays* L. Maize

| Event | Company | Description |
| --- | --- | --- |
| DAS-59122-7 | DOW AgroSciences LLC and Pioneer Hi-Bred International Inc. | Corn rootworm-resistant maize produced by inserting the Cry34Ab1 and Cry35Ab1 genes from *Bacillus thuringiensis* strain PS149B1. The PAT encoding gene from *Streptomyces viridochromogenes* was introduced as a selectable marker. |
| DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-01507-1) with NK603 (OECD unique identifier: MON-00603-6). Corn rootworm-resistance is derived from DAS-59122-7 which contains the Cry34Ab1 and Cry35Ab1 genes from *Bacillus thuringiensis* strain P5149B1. Lepidopteran resistance and tolerance to glufosinate ammonium herbicide is derived from TC1507. Tolerance to glyphosate herbicide is derived from NK603. |
| DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus*. |
| MIR604 × GA21 | Syngenta Seeds, Inc. | Stacked insect resistant and herbicide tolerant maize produced by conventional cross breeding of parental lines MIR604 (OECD unique identifier: SYN-1R605-5) and GA21 (OECD unique identifier: MON-00021-9). Com rootworm-resi stance is derived from MIR604 which contains the mCry3A gene from *Bacillus thuringiensis*. Tolerance to glyphosate herbicide is derived from GA21. |
| MON80100 | Monsanto Company | Insect-resistant maize produced by inserting the Cry1Ab gene from *Bacillus thuringiensis* subsp. *kurstaki*. The genetic modification affords resistance to attack by the European corn borer (ECB). |
| MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. |
| MON809 | Pioneer Hi-Bred International Inc. | Resistance to European corn borer (*Ostrinia nubilalis*) by introduction of a synthetic Cry1Ab gene. Glyphosate resistance via introduction of the bacterial version of a plant enzyme, 5-enolpynivyl shikimate-3-phosphate synthase (EPSPS). |
| MON810 | Monsanto Company | Insect-resistant maize produced by inserting a truncated form of the Cry1Ab gene from *Bacillus thuringiensis* subsp. *kurstaki* HD-1. |

TABLE G-continued

Corn Traits That Can Be Combined With the Insecticidal Proteins
*Zea mays* L. Maize

| Event | Company | Description |
|---|---|---|
| MON810 × LY038 | Monsanto Company | The genetic modification affords resistance to attack by the European corn borer (ECB). Stacked insect resistant and enhanced lysine content maize derived from conventional crossbreeding of the parental lines MON810 (OECD identifier: MON-OO81O-6) and LY038 (OECD identifier: REN-OOO38-3). |
| MON810 × MON88017 | Monsanto Company | Stacked insect resistant and glyphosate tolerant maize derived from conventional cross-breeding of the parental lines MON810 (OECD identifier: MON-OO81O-6) and MON88017 (OECD identifier: MON-88017-3). European corn borer (ECB) resistance is derived from a truncated form of the Cry1Ab gene from *Bacillus thuringiensis* subsp. *kurstaki* HD-1 present in MON810. Corn rootworm resistance is derived from the Cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. |
| MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. |
| MON863 | Monsanto Company | Corn rootworm resistant maize produced by inserting the Cry3Bb1 gene from *Bacillus thuringiensis* subsp. *kumamotoensis*. |
| MON863 × MON810 | Monsanto Company | Stacked insect resistant corn hybrid derived from conventional cross-breeding of the parental lines MON863 (OECD identifier: MON-00863-5) and MON810 (OECD identifier: MON-00810-6) |
| MON863 × MON810 × Monsanto NK603 | Monsanto Company | Stacked insect resistant and herbicide tolerant corn hybrid derived from conventional crossbreeding of the stacked hybrid MON-00863-5 × MON-00810-6 and NK603 (OECD identifier: MON-00603-6). |
| MON863 × NK603 | Monsanto Company | Stacked insect resistant and herbicide tolerant corn hybrid derived from conventional crossbreeding of the parental lines MON863 (OECD identifier: MON-OO863-5) and NK603 (OECD identifier: MON-OO6O3-6). |
| MON87460 | Monsanto Company | MON 87460 was developed to provide reduced yield loss under water-limited conditions compared to conventional maize. Efficacy in MON 87460 is derived by expression of the inserted *Bacillus subtilis* cold shock protein B (CspB). |

TABLE G-continued

Corn Traits That Can Be Combined With the Insecticidal Proteins
*Zea mays* L. Maize

| Event | Company | Description |
|---|---|---|
| MON88017 | Monsanto Company | Corn rootworm-resistant maize produced by inserting the Cry3Bbl gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4. |
| MON89034 | Monsanto Company | Maize event expressing two different insecticidal proteins from *Bacillus thuringiensis* providing resistance to number of Lepidopteran pests. |
| MON89034 × MON88017 | Monsanto Company | Stacked insect resistant and glyphosate tolerant maize derived from conventional cross-breeding of the parental lines MON89034 (OECD identifier: MON-89O34-3) and MON88017 (OECD identifier: MON-88O17-3). Resistance to Lepidopteran insects is derived from two Cry genes present in MON89043. Corn rootworm resistance is derived from a single Cry genes and glyphosate tolerance is derived from the 5-enolpyruvylshikimate-3-phosphate synthase (EPSPS) encoding gene from *Agrobacterium tumefaciens* present in MON88017. |
| MON89034 × NK603 | Monsanto Company | Stacked insect resistant and herbicide tolerant maize produced by conventional cross breeding of parental lines MON89034 (OECD identifier: MON-89034-3) with NK603 (OECD unique identifier: MON-00603-6). Resistance to Lepidopteran insects is derived from two Cry genes present in MON89043. Tolerance to glyphosate herbicide is derived from NK603. |
| NK603 × MON810 | Monsanto Company | Stacked insect resistant and herbicide tolerant corn hybrid derived from conventional crossbreeding of the parental lines NK603 (OECD identifier: MON-00603-6) and MON810 (OECD identifier: MON-00810-6). |
| MON89034 × TC1507 × MON88017 × DAS-59122-7 | Monsanto Company and Mycogen Seeds c/o Dow AgroSciences LLC | Stacked insect resistant and herbicide tolerant maize produced by conventional cross breeding of parental lines: MON89034, TC1507, MON88017, and DAS-59 122. Resistance to the above-ground and below-ground insect pests and tolerance to glyphosate and glufosinate-ammonium containing herbicides. |
| M53 | Bayer CropScience (Aventis CropScience(AgrEvo)) | Male sterility caused by expression of the barnase ribonuclease gene from *Bacillus amyloliquefaciens;* PPT resistance was via PPT-acetyltransferase (PAT). |
| M56 | Bayer CropScience (Aventis CropScience(AgrEvo)) | Male sterility caused by expression of the barnase ribonuclease gene from *Bacillus amyloliquefaciens;* PPT resistance was via PPT-acetyltransferase (PAT). |
| NK603 | Monsanto Company | Introduction, by particle bombardment, of a modified 5-enolpyruvyl shikimate-3-phosphate synthase (EPSPS), an enzyme |

TABLE G-continued

Corn Traits That Can Be Combined With the Insecticidal Proteins
Zea mays L. Maize

| Event | Company | Description |
|---|---|---|
| | | involved in the shikimate biochemical pathway for the production of the aromatic amino acids. |
| NK603 × T25 | Monsanto Company | Stacked glufosinate ammonium and glyphosate herbicide tolerant maize hybrid derived from conventional cross-breeding of the parental lines NK603 (OECD identifier: MON-00603-6) and T25 (OECD identifier: ACS-ZM003-2). |
| T25 × MON810 | Bayer CropScience (Aventis CropScience(AgrEvo)) | Stacked insect resistant and herbicide tolerant corn hybrid derived from conventional crossbreeding of the parental lines T25 (OECD identifier: ACS-ZMOO3-2) and MON810 (OECD identifier: MON-OO81O-6). |
| TC1507 | Mycogen (c/o Dow AgroSciences); Pioneer (c/o DuPont) | Insect-resistant and glufosinate ammonium herbicide tolerant maize produced by inserting the Cry1F gene from *Bacillus thuringiensis* var. *aizawai* and the phosphinothricin N-acetyltransferase encoding gene from *Streptomyces viridochromogenes*. |
| TC1507 × NK603 | DOW AgroSciences LLC | Stacked insect resistant and herbicide tolerant corn hybrid derived from conventional crossbreeding of the parental lines 1507 (OECD identifier: DAS-O15O7-1) and NK603 (OECD identifier: MON-OO6O3-6). |
| TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-O15O7-1) with DAS-59122-7 (OECD unique identifier: DAS-59122-7). Resistance to Lepidopteran insects is derived from TC1507 due the presence of the Cry1F gene from *Bacillus thuringiensis* var. *aizawai*. Corn rootworm-resistance is derived from DAS-59122-7 which contains the Cry34Ab1 and Cry35Ab1 genes from *Bacillus thuringiensis* strain P5149B1. Tolerance to glufosinate ammonium herbicide is derived from TC1507 from the phosphinothricin N-acetyltransferase encoding gene from *Streptomyces viridochromogenes*. |

Utilization of Microbes to Express the Insecticidal Proteins

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance, and expression of the gene expressing the pesticidal proteins taught herein, and provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Kebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas jluorescens, Pseudomonas chlororaphis, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii,*

*Saccharomyces rosei, S. pretoriensis, S. cerevzszae, Sporobolomyces roseus, S. odorus, Kluyveromyces veronae,* and *Aureobasidium pollulans*. Of particular interest are the pigmented microorganisms. Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa, P. jluorescens, P. chlororaphis*), *Erwinia* spp., and *Flavobacterium* spp., and other such organisms, including *Agrobacterium tumefaciens, E. coli, Bacillus subtilis, Bacillus cereus* and the like.

Genes encoding the taught pesticidal proteins can be introduced into microorganisms that multiply on plants (epiphytes). Epiphytes can be gram positive or gram negative bacteria. Root colonizing bacteria can be isolated from the plant of interest by methods known in the art. Genes encoding the taught pesticidal proteins can be introduced, for example, into the root colonizing or epiphytic bacteria by means of electro transformation. Genes can be cloned into a shuttle vector, for example, pHT3101 (Lerecius, et al., (1989) FEMS Microbiol. Lett. 60:211-218. The shuttle vector pHT3101 containing the coding sequence for the particular polypeptide gene can, for example, be transformed into the bacteria by means of electroporation (Lerecius, et al., (1989) FEMS Microbiol. Lett. 60:211-218). Expression systems can be designed so that the taught pesticidal proteins are secreted outside the cytoplasm of gram negative bacteria, such as *E. coli*, for example.

Pesticidal proteins taught herein may be fermented in a bacterial host and the resulting bacteria processed and used as a microbial spray in the same manner that Bt strains have been used as insecticidal sprays. In the case of a pesticidal protein that is secreted from *Bacillus*, the secretion signal is removed or mutated using procedures known in the art. Such mutations and/or deletions prevent secretion of the protein into the growth medium during the fermentation process. The pesticidal proteins are retained within the cell and the cells are then processed to yield the encapsulated proteins. Any suitable microorganism can be used for this purpose. *Pseudomonas* has been used to express Bt toxins as encapsulated proteins and the resulting cells processed and sprayed as an insecticide (Gaertner, et al., (1993), in: Advanced Engineered Pesticides, ed. Kim).

Alternatively, the taught pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated proteins may then be formulated in accordance with conventional techniques for application to the environment hosting a target pest, e.g., soil, water, and foliage of plants. See, for example EPA 0192319, and the references cited therein.

Pesticidal Compositions

In some embodiments the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time release or biodegradable carrier formulations that permit long term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application promoting adjuvants customarily employed in the art of formulation. Suitable carriers (i.e. agriculturally acceptable carriers) and adjuvants can be solid or liquid and correspond to the substances ordinarily employed in formulation technology, e.g. natural or regenerated mineral substances, solvents, dispersants, wetting agents, sticking agents, tackifiers, binders or fertilizers. Likewise the formulations may be prepared into edible baits or fashioned into pest traps to permit feeding or ingestion by a target pest of the pesticidal formulation.

Methods of applying an active ingredient or an agrochemical composition that contains at least one of the taught insecticidal proteins produced by the bacterial strains include leaf application, seed coating, and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenization, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopterans, Dipterans, Hemipterans, Heteropterans, Nematodes, or Coleopterans may be killed or reduced in numbers in a given area by the methods of the disclosure or may be prophylactically applied to an environmental area to prevent infestation by a susceptible pest. Preferably the pest ingests or is contacted with, a pesticidally effective amount of the disclosed insecticidal protein. A "Pesticidally effective amount" refers to an amount of the pesticide that is able to bring about death to at least one pest or to noticeably reduce pest growth, feeding, or normal physiological development. This amount will vary depending on such factors as, for example: the specific target pests to be controlled, the specific environment, location, plant, crop or agricultural site to be treated, the environmental conditions and the method, rate, concentration, stability, and quantity of application of the pesticidally effective protein composition. The formulations may also vary with respect to climatic conditions, environmental considerations, and/or frequency of application and/or severity of pest infestation.

The pesticide compositions described may be made by formulating either the bacterial cell, Crystal and/or spore suspension, or isolated protein component with the desired agriculturally acceptable carrier.

The compositions may be formulated prior to administration in an appropriate means such as lyophilized, freeze dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid and are well known in the art. The term "agriculturally acceptable carrier" covers all adjuvants, inert components, dispersants, surfactants, stickers, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides.

Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, Bacillus thuringiensis, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinetoram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinetoram, Thiodicarb, Flonicamid, Methiocarb, Emamectin benzoate, Indoxacarb, Forthiazate, Fenamiphos, Cadusaphos, Pyriproxifen, Fenbutatin oxide, Hexthiazox, Methomyl, 4-[[(6-Chlorpyridin-3-yl)methyl](2,2-difluorethyl)amino]furan-2(5H)-on; Fruits Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalothrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon methyl, Pirimicarb, Methiocarb; Maize Herbicides: Atrazine, Alachlor, Bromoxynil, Acetochlor, Dicamba, Clopyralid, S-Dimethenamid, Glufosinate, Glyphosate, Isoxaflutole, S-Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinetoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinetoram, gamma Cyhalothrin, 4-[[(6-Chlorpyridin-3-yl) methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinetoram, Emamectin-Benzoate, Fipronil, Ethiprole, Deltamethrin, β-Cyfluthrin, gamma and lambda Cyhalothrin, 4-[[(6-Chlorpyridin-3-yl)methyl] (2,2-difluorethyl)amino]furan-2 (5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, O-Cyfluthrin, gamma and lambda Cyhalothrin, tau-Fluvaleriate, Ethiprole, Spinosad, Spinetoram, Flubendiamide, Rynaxypyr, Cyazypyr, 4-[[(6-Chlorpyridin-3-yl)methyl] (2,2-difluorethyl)amino] furan-2(5H)-on.

Pests

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* J E Smith (fall armyworm); *S. exigua* Hubner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hubner (cotton leaf worm); *Trichoplusia ni* Hubner (cabbage looper); *Pseudoplusia includens* Walker (soybean looper); *Anticarsia gemmatalis* Hubner (velvet bean caterpillar); *Hypena scabra* Fabricius (green clover worm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hubner (American bollworm); *H. zea* Boddie (corn earworm or cotton bollworm); *Melanchra picta* Harris (zebra caterpillar); *Egira* (Xylomyges) *curialis* Grote (citrus cutworm); borers, case bearers, webworms, coneworms, and skeletonizers from the family Pyralidae *Ostrinia nubilalis* Hubner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hubner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hubner (Indian meal moth); *Scirpophaga incertulas* Walker (yellow stem borer); *Udea rubigalis* Guenee (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rosslerstamm (summer fruit *tortrix* moth); *Cochylis hospes* Walsingham (banded sunflower moth); *Cydia latiferreana* Walsingham (filbertworm); *C. pomonella* Linnaeus (colding moth); *Platynota flavedana* Clemens (variegated leafroller); *P. stultana* Walsingham (omnivorous leafroller); *Lobesia botrana* Denis & Schiffermuller (European grape vine moth); *Spilonota ocellana* Denis & Schiffermuller (eyespotted bud moth); *Endopiza viteana* Clemens (grape berry moth); *Eupoecilia ambiguella* Hubner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guerin-Meneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Euproctis chrysorrhoea* Linnaeus (browntail moth); *Harrisina americana* Guerin-Meneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phrganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenee (onmivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothes moth); *Tuta absoluta* Meyrick (tomato leafminer); *Yponomeuta padella* Linnaeus (ermine moth); *Heliothis subflexa* Guenee; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Gehin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/ Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Melanaphis sacchari* (sugarcane aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stal (brown planthopper); *Peregrinus maidis* Ashmead (corn planthopper); *Sogatella furcifera* Horvath (white backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schaffer (cotton stainer); *Euschistus servus* Say (brown stink bug); *E. variolarius* Palisot de Beauvais (one spotted stink bug); *Graptostethus* spp. (complex of seed bugs); *Leptoglossus corculus* Say (leaf footed pine seed bug);

*Lygus lineolaris* Palisot de Beauvais (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton flea hopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola alii* Knight (onion plant bug); *Pseudatomoscelis seriatus* Reuter (cotton fleahopper); *Adelphocoris rapidus* Say (rapid plant bug); *Poecilocapsus lineatus* Fabricius (four lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Muller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pests of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*-Bean plataspid) and the family Cydnidae (*Scaptocoris castanea*-Root stink bug) and Lepidoptera species including but not limited to: diamondback moth, e.g., *Helicoverpa zea* Boddie; soybean looper, e.g., *Pseudoplusia includens* Walker and velvet bean caterpillar e.g., *Anticarsia gemmatalis* Hubner.

Methods for measuring pesticidal activity are well known in the art. See, for example, Czapla and Lang, (1990) J. Econ. Entomol. 83:2480-2485; Andrews, et al., (1988) Biochem. J. 252:199-206; Marrone, et al., (1985) J. of Economic Entomology 78:290-293 and U.S. Pat. No. 5,743,477, all of which are herein incorporated by reference in their entirety. Generally, the protein is mixed and used in feeding assays. See, for example Marrone, et al., (1985) J. of Economic Entomology 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

In some aspects, the taught insecticidal proteins are active against an insect that is resistant to a Cry protein. For example, the taught insecticidal proteins may be active against an insect that is resistant to mCry3A, Cry3Bb1, eCry3.1Ab, and the binary protein complex Cry34Ab1/Cry35Ab1. In aspects, the taught insecticidal proteins are active against a western corn rootworm (WCR, *Diabrotica virgifera virgifera* LeConte) that is resistant to a Cry protein (e.g. Cry3Bb1 protein expressed by MON88017). In aspects, the taught insecticidal proteins are active against a western corn rootworm (WCR, *Diabrotica virgifera virgifera* LeConte) that is resistant to a Cry protein (e.g. mCry3A). In aspects, the taught insecticidal proteins can be toxic to the corn rootworms of *Diabrotica barberi* and *Diabrotica undecimpunctata howardi* and other beetle species such as *Diabrotica speciosa* and *Phyllotreta cruciferae*. In aspects, the taught insecticidal proteins are not toxic to spotted lady beetle (*Coleomegilla maculata*) or certain Lepidopterans or certain Hemipterans. See, U. Schellenberger et al., "A selective insecticidal protein from *Pseudomonas* for controlling corn rootworms," Science, 2016 Nov. 4; 354(6312): 634-637 (providing IPD072Aa, an 86 AA protein, GenBank Accession No. KT795291) incorporated by reference herein; and Jun-Zhi Wei et al., "A selective insecticidal protein from *Pseudomonas mosselii* for corn rootworm control," Plant Biotechnology Journal, 2018, Vol. 16, pgs. 649-659 (providing PIP-47aa) incorporated by reference herein.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, and/or molluscicides.

These compounds are typically formulated together with further carriers, surfactants or application promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such seed varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments, methods are provided for killing an insect pest, comprising contacting the insect pest with an insecticidally effective amount of a recombinant protein as taught herein. In some embodiments, methods are provided for killing an insect pest, comprising contacting the insect pest with an insecticidally effective amount of a pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, or a variant thereof.

In some embodiments, methods are provided for controlling an insect pest population, comprising contacting the insect pest population with an insecticidally effective amount of a recombinant protein as taught herein. In some embodiments, methods are provided for controlling an insect pest population, comprising contacting the insect pest population with an insecticidally effective amount of a pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, or a variant thereof.

As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments, methods are provided for controlling an insect pest population resistant to a pesticidal protein, comprising contacting the insect pest population with an insecticidally effective amount of a recombinant protein as taught herein. In some embodiments, methods are provided for controlling an insect pest population resistant to a pesticidal protein, comprising contacting the insect pest population with an insecticidally effective amount of a recombinant pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, or a variant thereof.

In some embodiments, methods are provided for protecting a plant from an insect pest, comprising expressing in the plant or cell thereof a recombinant polynucleotide encoding a pesticidal protein as taught herein. In some embodiments, methods are provided for protecting a plant from an insect pest, comprising expressing in the plant or cell thereof a recombinant polynucleotide encoding a pesticidal protein of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72, or a variant thereof.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing an insecticidal protein disclosed herein.

Hidden Markov Model

A hidden Markov model (HMM) is a statistical model that can be used to describe the evolution of observable events that depend on internal factors, which are not directly observable. The observed event is called a "symbol" and the invisible factor underlying the observation a "state". An HMM consists of two stochastic processes, namely, an invisible process of hidden states and a visible process of observable symbols. The hidden states form a Markov chain, and the probability distribution of the observed symbol depends on the underlying state. For this reason, an HMM is also called a doubly-embedded stochastic process. Modeling observations in these two layers, one visible and the other invisible, is very useful, since many real world problems deal with classifying raw observations into a number of categories, or class labels, which are more meaningful. This approach is useful in modeling biological sequences, such as proteins and DNA sequences. Typically, a biological sequence consists of smaller substructures with different functions, and different functional regions often display distinct statistical properties. For example, it is well known that proteins generally consist of multiple domains. Given a new protein, HMMs can be used to predict the constituting domains (corresponding to one or more states in an HMM) and their locations in the amino acid sequence (observations). Furthermore, we may also want to find the protein family to which this new protein sequence belongs. In fact, HMMs have been shown to be very effective in representing biological sequences. As a result, HMMs have become increasingly popular in computational molecular biology, bioinformatics, and many state-of-the-art sequence analysis algorithms have been built on HMMs. See, Byung-Jun Yoon, "Hidden Markov Models and Their Applications in Biological Sequence Analysis," *Current Genomics*, 2009, Vol. 10, pgs. 402-415, for a comprehensive review, said article is incorporated herein by reference.

Thus, it is understood that a Markov model is a system that produces a Markov chain, and a hidden Markov model is one where the rules for producing the chain are unknown or "hidden." The rules include two probabilities: (i) that there will be a certain observation and (ii) that there will be a certain state transition, given the state of the model at a certain time. The Hidden Markov Model (HMM) method is a mathematical approach to solving certain types of problems: (i) given the model, find the probability of the observations; (ii) given the model and the observations, find the most likely state transition trajectory; and (iii) maximize either i or ii by adjusting the model's parameters. For each of these problems, algorithms have been developed, for example: (i) Forward-Backward, (ii) Viterbi, and (iii) Baum-Welch (and the Segmental K-means alternative), among others HMMER Software HMMER is a HMM software package that is used to search sequence databases for homologs of protein or DNA sequences, and to make sequence alignments. HMMER can be used to search sequence databases with single query sequences, but it becomes particularly powerful when the query is an alignment of multiple instances of a sequence family. HMMER makes a profile of the query that assigns a position-specific scoring system for substitutions, insertions, and deletions. HMMER profiles are probabilistic models called "profile hidden Markov models" (profile HMMs) (Krogh et al., 1994; Eddy, 1998; Durbin et al., 1998). Compared to BLAST, FASTA, and other sequence alignment and database search tools based on older scoring methodology, HMMER aims to be significantly more accurate and more able to detect remote homologs, because of the strength of its underlying probability models.

Profile HMMs are statistical models of multiple sequence alignments, or even of single sequences. They capture position-specific information about how conserved each column of the alignment is, and which residues are likely. Anders Krogh, David Haussler, and co-workers at UC Santa Cruz introduced profile HMMs to computational biology (Krogh et al., 1994), adopting HMM techniques which have been used for years in speech recognition. HMMs had been used in biology before the Krogh/Haussler work, notably by Gary Churchill (Churchill, 1989), but the Krogh paper had a dramatic impact because HMM technology was so well-suited to the popular "profile" methods for searching databases using multiple sequence alignments instead of single query sequences. "Profiles" had been introduced by Gribskov and colleagues (Gribskov et al., 1987, 1990), and several other groups introduced similar approaches at about the same time, such as "flexible patterns" (Barton, 1990), and "templates" (Bashford et al., 1987; Taylor, 1986). The term "profile" has stuck. All profile methods (including PSI-BLAST (Altschul et al., 1997)) are more or less statistical descriptions of the consensus of a multiple sequence alignment. They use position-specific scores for amino acids or nucleotides (residues) and position specific penalties for opening and extending an insertion or deletion. Traditional pairwise alignment (for example, BLAST (Altschul et al., 1990), FASTA (Pearson and Lipman, 1988), or the Smith/Waterman algorithm (Smith and Waterman, 1981)) uses position-independent scoring parameters. This property of profiles captures important information about the degree of conservation at various positions in the multiple alignment, and the varying degree to which gaps and insertions are permitted.

The advantage of using HMMs is that HMMs have a formal probabilistic basis. They use probability theory to guide how all the scoring parameters should be set. For example, HMMs have a consistent theory for setting position-specific gap and insertion scores. The methods are consistent and therefore highly automatable, allowing one to make libraries of hundreds of profile HMMs and apply them on a very large scale to whole genome analysis. One such database of protein domain models is Pfam (Sonnhammer et al., 1997; Finn et al., 2010), which is a significant part of the Interpro protein domain annotation system (Mulder et al., 2003). The construction and use of Pfam is tightly tied to the HMMER software package.

Insecticidal Protein Discovery Platform (IPDP)

The disclosure presents a platform for discovering novel insecticidal proteins from highly heterogeneous environmental sources. The methodology utilizes metagenomic enrichment procedures and genetic amplification techniques, which enables access to a broad class of unknown microbial diversity and their resultant proteome.

FIG. 1 provides an overall workflow illustrating the IPDP, which will be discussed in detail below.

Collect Soil Samples 1-10 grams of material is collected from an environmental sample that contains rich microbial diversity.

Resuspend in Buffered Solution

Environmental material is resuspended and stirred continuously in 10-100 mLs of PBS (phosphate buffered solution) for 15 minutes. Large particulates are then allowed to settle.

Dilution and Planting on Solid Nutrient Limiting Agar Media

A series of dilutions of the supernatant is plated on nutrient limiting agar containing cyclohexamide to reduce fungal growth.

Various media recipes have been described in the literature to favor growth of particular families of microbes.

The current IPDP utilizes a proprietary media, and media growth procedure, in order to enrich for microbes of a particular Genus (e.g. *Pseudomonas* in certain embodiments).

Collect Bacterial Growth from Plates—Isolate all Genomic DNA from Enriched Sample as a Mixture Via Lysis and Precipitation All bacterial growth on plates is collected by washing with water, cells are pelleted by centrifugation, and the supernatant is discarded.

Genomic DNA was isolated from the pelleted metagenomics sample using standard bacterial genomic DNA isolation techniques.

Genes Encoding Proteins from the Monalysin Class are Further Enriched Using Degenerate PCR and Cloned into Plasmid Vectors for Recovery and Sequencing Proprietary degenerate primers were utilized to amplify genes encoding proteins from the monalysin class from the metagenomic DNA sample.

A "monalysin class" of protein can be a protein that has a degree of similarity to, e.g. SEQ ID NO: 87, from Table 1. The present IPDP has a substantial library of proprietary degenerate primers, which can be utilized to search for proteins in this class.

Amplified DNA of ~800 bp in size were separated by gel electrophoresis and recovered utilizing standard techniques.

The degenerate primers include tails compatible for cloning into a DNA plasmid. The PCR-amplified DNA were cloned and sequenced to identify full-length genes encoding proteins with similarity to the published monalysin sequence from Opota et al.

The combination of: 1) an initial enrichment of certain microbial populations on nutrient limited agar, followed by 2) amplification of genes encoding monalysin-class proteins, using degenerate PCR from the genomic DNA isolated from the enriched population, are both preferred steps in some embodiments, to recover genes encoding monalysin-like proteins.

"Monalysin-like" proteins can be defined as proteins that have some degree of similarity to the monalysin protein described in Opota, et al., See Opota, et al., "Monalysin, a Novel ß-Pore-Forming Toxin from the *Drosophila* Pathogen *Pseudomonas entomophila*, Contributes to Host Intestinal Damage and Lethality," PLoS Pathogens, September 2011, Vol. 7, Issue 9 (incorporated herein by reference). The terms "monalysin-like" and "monalysin class" of protein are used interchangeably. Furthermore, as aforementioned, the current application provides the sequence for the monalysin described in Opota in Table 1, and SEQ ID NO: 87.

Genomic DNA collected from bacteria isolated on rich media from the original environmental sample did not yield any amplified product using degenerate PCR. Thus, the nutrient limited agar (developed to enrich for microbes of a particular Genus) step was successful in allowing the IPDP to access microbial organisms that are often not available to current methods in the art. Furthermore, sequencing of the enriched genomic DNA did not yield the number of sequences that were eventually obtained utilizing the above described combined approach (i.e. enrichment and degenerate PCR amplification), suggesting the discovered insecticidal protein sequences are quite rare, even in the enriched populations, and the amplification step following enrichment is preferred in some aspects.

Identification of Novel Insecticidal Proteins Utilizing Homology and Profile/HMM Methods The IPDP can optionally involve the use of an HMM to identify insecticidal proteins. An HMM profile built based on known insecticidal proteins (e.g., an HMM built based on known monalysins) can be used to scan the enriched DNA library for genes which encode proteins with amino acid sequences which score highly when analyzed using the HMM profile. Additionally or alternatively, new insecticidal proteins can be identified by comparing sequences in the enriched DNA library to sequences encoding known insecticidal proteins in genomic databases, e.g., using sequence analysis tools like BLAST and searching for mutual best hit sequences against sequences in GENBANK.

An example of the HMM process is described in Example 5 and an example HMM built using insecticidal proteins identified using methods described herein is provided in Table 6. The HMM was built using eight insecticidal proteins discovered via the IPDP and found in Table 3. These proteins have the amino acid sequences shown in: a) SEQ ID NO: 2 that is ZIP1, b) SEQ ID NO: 4 that is ZIP2, c) SEQ ID NO: 12 that is ZIP6, d) SEQ ID NO: 14 that is ZIP8, e) SEQ ID NO: 16 that is ZIP9, f) SEQ ID NO: 18 that is ZIP10, g) SEQ ID NO: 20 that is ZIP11, and h) SEQ ID NO: 22 that is ZIP12. To discover new insecticidal proteins, an enriched genomic DNA library built using the methods disclosed herein can be searched using the HMM provided in Table 6. Sequences which receive a high score based on that comparison can be identified as new insecticidal proteins. In certain embodiments, sequences receiving a high score are those sequences which score at or above a bit score of 521.5 and/or sequences which match with an E-value of less than or equal to 7.9e-161 when scored using the HMM in Table 6.

Thus, in certain embodiments, the disclosure provides novel insecticidal proteins, the proteins having an amino acid sequence which score at or above a bit score of 521.5 and/or sequences which match at an E-value of less than or equal to 7.9e-161 when scored using the HMM in Table 6. These proteins can be provided in any form (e.g., as isolated or recombinant proteins) or as part of any of the compositions (e.g., plants or agricultural compositions) disclosed herein.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents is provided below solely for the purpose of assisting the reader. Nothing in this table of contents is meant to limit the scope of the examples or disclosure of the application.

TABLE 2

| Table of Contents For Example Section | | |
|---|---|---|
| Example | Title | Brief Description |
| 1 | Insecticidal Protein Discovery Platform (IPDP) | Describes implementation of the novel insecticidal protein discovery platform. |
| 2 | Novel Insecticidal Proteins Discovered with the IPDP | Describes a select set of novel insecticidal proteins identified via the IPDP. |
| 3 | Insecticidal Proteins-Lysate Insect Feeding Assays | Describes a lysate feeding assay that contains an insecticidal protein discovered via the IPDP, which shows 100% mortality against an insect pest from the Pentatomidae family (i.e. *Halyomorpha halys* Stål, 1855). |
| 4 | Insecticidal Proteins-Purified Protein Insect Feeding Assays | Describes experiments conducted with a range of assays demonstrating that a purified insecticidal protein, as taught herein, has activity against a host of insect species. |
| 5 | IPDP-HMM Construction | Describes implementation of the IPDP's Hidden Markov Model feature to predict undiscovered insecticidal proteins. |
| 6 | Transformed Plants | Describes experiments conducted demonstrating plants transformed to express the insecticidal proteins. |

Example 1: Insecticidal Protein Discovery Platform (IPDP)

This example describes an implementation of the IPDP. Further details regarding the IPDP can be found in the aforementioned IPDP section, which immediately precedes the Example section.

First, 5 grams of material from an environmental sample rich in microbial diversity was collected and stored.

This material was resuspended in 50 mL of PBS and stirred continuously for 15 minutes. After 15 minutes, large particulates were allowed to settle and serial dilutions of the supernatant were plated on a proprietary nutrient limiting agar media containing cyclohexamide to reduce fungal growth. Plates were grown at 18° C. for 10-14 days.

Bacteria growth on these plates was collected by repeated washing with 4 mLs of water and collected in a 15 mL conical tube. Microbial cells were pelleted by centrifugation and the supernatant was discarded.

Genomic DNA was isolated from cell pellets using the Wizard Genomic DNA Purification Kit from Promega.

Proprietary degenerate primers were used to amplify DNA via PCR. Amplicons of ~800 bp were gel purified and cloned into a DNA plasmid vector.

Cloned amplicons were sequenced using Sanger sequencing and encoded proteins were compared to the published monalysin sequence (i.e. as described in Opota et al. and found in Table 1, and SEQ ID NO: 87).

Example 2: Novel Insecticidal Proteins Discovered with the IPDP

The aforementioned IPDP from Example 1 was able to identify at least 36 novel insecticidal proteins, which are represented in the below Table 3.

From these 36 novel insecticidal proteins, homology based analysis has revealed that at least 32 of these proteins have at least a 20% sequence identity difference from the known sequence identity of any insecticidal protein in this class. This is a significant finding, as it demonstrates the power of the taught IPDP, in finding insecticidal proteins that are novel over those found in the art.

Of the 32 sequences having at least a 20% sequence identity difference, eight insecticidal proteins that have at least a 20% sequence identity difference from any known protein in this class were selected for further analysis and include: (1) ZIP1, (2) ZIP2, (3) ZIP6, (4) ZIP8, (5) ZIP9, (6) ZIP10, (7) ZIP11, and (8) ZIP12. These proteins share significant homology amongst one another and therefore point to conserved insecticidal domains that could be shared among this novel group of insecticidal proteins. The multiple sequence alignment for these eight proteins can be found in FIG. 3 with a corresponding phylogenetic tree found in FIG. 5.

TABLE 3

| Novel Insecticidal Proteins Identified via the IPDP | | |
|---|---|---|
| Identifier | Nucleotide | Amino Acid |
| ZIP1 | SEQ ID NO: 1 | SEQ ID NO: 2 |
| | ATGACGATCAAGGAAGAGCTGAGCCAACCCCAAAGCCATTCG | MTIKEELSQPQSHSVELDQ |
| | GTCGAGCTCGACCAGTTGCAAGTCGGGGAAGTCTCTGCACGC | LQVGEVSAREALTSNFAGS |
| | GAAGCGTTGACCTCCAACTTCGCCGGCAGTTTCGATCAGTTCCC | FDQFPTKSGSFEIDKYLLNY |
| | GACCAAAAGCGGCAGCTTCGAGATCGACAAATACCTGCTCAAC | ADPKKGCWLDGVTVYGDI |
| | TACGCGGATCCGAAAAAAGGCTGCTGGCTGGACGGCGTCACC | YIGKQNWGTYTRPVFAYLQ |
| | GTCTACGGTGACATCTACATCGGCAAGCAGAACTGGGGCACCT | HTDTISIPQQVTQTKSYQLS |
| | ACACGCGCCCGGTGTTCGCCTACCTGCAGCACACCGACACCAT | KGHTQSFTKSVSAKYSVGG |
| | CTCGATTCCGCAGCAGGTGACGCAGACCAAGAGCTACCAGTTG | SIDIVNISSDITVGFSSTEAW |
| | AGCAAAGGCCACACCCAGTCGTTCACCAAGTCGGTCAGCGCCA | STNQTFTQSTELAGPGTFF |

TABLE 3-continued

Novel Insecticidal Proteins Identified via the IPDP

| Identifier | Nucleotide | Amino Acid |
|---|---|---|
| | AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP2 | SEQ ID NO: 3<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACACGATCCTCATCGCCGTTATTGAA<br>CTGAGATCCGGCTGC | SEQ ID NO: 4<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYTILIA<br>VIELRSGC |
| ZIP3 | SEQ ID NO: 5<br>ATGACGATCAAGGAAGAGCTGAGCCAACCCCAAAGCCATTCG<br>GTCGAGCTCGACCAGTTGCAAGTCGGGGAAGTCCCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTTGTTCTTGTTTATGCGCACAACGCCA<br>CTTCGGCGGGCAGGCAGAATGGTAATGCCTTCGCCTATAACAA<br>GACCCAGCAGGTGGGCTCGCGCCTGGACCTGTACTACCTGTCG<br>GCCATCACTCAGAACAGAACGGTCATTGTCGAGTCCAGCAAGG<br>CCATCGACCCGCTGGATTGGGATACGGTGCAACGCAACGTGCT<br>GATGGAAAACTACAACCCAGCCAGTAACAGCGGACACTTCAGC<br>TTCGACTGGAGTGCCTACAACGATCCTCATCGCCGTTAT | SEQ ID NO: 6<br>MTIKEELSQPQSHSVELDQ<br>LQVGEVPAREALTSNFAGS<br>FDQFPTKSGSFEIDKYLLNY<br>ADPKKGCWLDGVTVYGDI<br>YIGKQNWGTYTRPVFAYLQ<br>HTDTISIPQQETQTKSYQLS<br>KGHTQSFTKSVSAKYGVGG<br>SIDIVNISSDITVGFSSTEAW<br>STNQTFTQSTELAGPGTFF<br>VYQVVLVYAHNATSAGRQ<br>NGNAFAYNKTQQVGSRLD<br>LYYLSAITQNRTVIVESSKAI<br>DPLDWDTVQRNVLMENY<br>NPASNSGHFSFDWSAYND<br>PHRRY |
| ZIP4 | SEQ ID NO: 7<br>ATGACGATCAAGGAAGAACTGAGCAATCCTCAAAGCCATTCGG<br>TCGAGCTCGACCAGTTGCAAGTCGGGGAAGTCTCTGCACGCGA<br>AGCGTTGACCGCCAACTTCGCCGGCAGTTTCGATCAGTTCCCG<br>ACCAAAAGCGGCAGCTTCGAGATCGACAAATACCTGCTCAACT<br>ACGCAGACCCGAAACAAGGCTGCTGGCTGGACGGCGTCACCG<br>TCTACGGTGACATCTACATCGGCAAGCAGAACTGGGGCACCTA<br>CACGCGCCCGGTGTTCGCCTACCTGCAGCACACGGACACCATC<br>TCGATTCCGCAGCAGGTGACGCAGACCAAGAGCTACCAGTTGA<br>GCAAAGGCCACACCCAGTCGTTCACCAAGTCGGTCAGCGCCAA<br>GTACAGCGTTGGCGGCAGTATCGACATCGTCAACGTCAGCTCG<br>GATATCACCGTTGGTTTCAGCAGCACCGAGGCCTGGTCGACGA<br>CCCAGACCTTCACCCAGAGCACCGAGCTGGCCGGCCCTGGCAC<br>CTTCTTTGTCTATCAGGTGGTGTTTGTCTACGCGCACAACGCCA<br>CCTCGGCCGGCCAGAATGGCAATGCCTTTGCCTATAGCAA<br>GACCCAGCAGGTGGATTCGCGGCTCGATCTCTACTATCTGTCG<br>GCGATCACCCAGGACCGTACGGTCATCGTCGAGTCCAGCAAGG<br>CAATCAACCCGCTGGACTGGGATACCGTGCAGCGCAACGTGCT<br>GATCGAGAACTACAACCCGGCCTCCAACAGTGGGCACTTCCGC<br>TTCGACTGGAGCGCCTACAACGATCCTCATCGTCGTTAC | SEQ ID NO: 8<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>YVETISIPQNVTTTLSYQLTK<br>GHTRSFETSVNAKYSVGAN<br>IDIVNVGSEISTGFTRSESW<br>STTQSFTDTTEMKGPGTFV<br>IYQVVLVYAHNATSAGRQN<br>ANAFAYSKTQAVGSRVDLY<br>YLSAITQRKRVIVPSSNAVT<br>PLDWDTVQRNVLMENYN<br>PXSNSGHFSFDWSAYNDP<br>HRRY |

TABLE 3-continued

Novel Insecticidal Proteins Identified via the IPDP

| Identifier | Nucleotide | Amino Acid |
|---|---|---|
| ZIP5 | SEQ ID NO: 9<br>ATGACGATCAAGGAAGAGCTGAGCAATCCTCAAAGCCATTCGG<br>TCGAGCTCGACCAGTTGCAAGTCGGGGAAGTCTCTGCACGCGA<br>AGCGTTGACCGCCAACTTCGCCGGCAGTTTCGATCAGTTCCCG<br>ACCAAAAGCGGCAGCTTCGAGATCGACAAATACCTGCTCAACT<br>ACGCAGACCCGAAACAAGGCTGCTGGCTGGACGGCGTCACCG<br>TCTACGGTGACATCTACATCGGCAAGCAGAACTGGGGCACCTA<br>CACGCGCCCGGTGTTCGCCTACCTGCAACACACGGACACCATC<br>TCGATTCCGCAGCAGGTGACGCAGACCAAGAGCTACCAGTTGA<br>GCAAAGGCCACACCCAGTCGTTCACCAAGTCGGTCAGCGCCAA<br>GTACAACGTTGGCGGCAGTATCGACATCGTCAACGTCAGCTCG<br>GATATCACTGTCGGTTTCAGCAGCACCGAGGCCTGGTCGACGA<br>CCCAGACCTTCACCCAGAGCACCGAGCTGGCCGGCCCTGGCAC<br>CTTCTTTGTCTATCAGGTGGTGTTTGTCTACGCGCACAACGCCA<br>CCTCGGCGGGCCGGCAGAATGGCAATGCCTTTGCCTATAGCAA<br>GACCCAGCAGGTGGATTCGCGGCTCGATCTCTACTACCTGTCG<br>GCCATCACCCAGGACCGTACGGTCATCGTCGAGTCCAGCAAGG<br>CAATCAACCCGCTGGACCGGGATACCGTGCAGCGCAACGTGCT<br>GATCGAGAACTACAACCCGGCCTCCAACAGTGGGCACTTCCGC<br>TTCGACTGGAGCGCCTACAACGATCCTCATCGCCGTTAT | SEQ ID NO: 10<br>MTIKEELSNPQSHSVELDQ<br>LQVGEVSAREALTANFAGS<br>FDQFPTKSGSFEIDKYLLNY<br>ADPKQGCWLDGVTVYGDI<br>YIGKQNWGTYTRPVFAYLQ<br>HTDTISIPQQVTQTKSYQLS<br>KGHTQSFTKSVSAKYNVGG<br>SIDIVNVSSDITVGFSSTEA<br>WSTTQTFTQSTELAGPGTF<br>FVYQVVFVYAHNATSAGR<br>QNGNAFAYSKTQQVDSRL<br>DLYYLSAITQDRTVIVESSKA<br>INPLDRDTVQRNVLIENYN<br>PASNSGHFRFDWSAYNDP<br>HRRY |
| ZIP6 | SEQ ID NO: 11<br>ATGACGATCAAGGAAGAGCTGGGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCC<br>CGACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTCCGCCTACCTGCAGCACACGGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTACGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAG<br>GCCATCGCGCCGCTGGATTGGGATACTGTCCAGCGCAATGTAC<br>TGATGGAGAACTACAACCAGAGCAGCAATAGCGGGCACTTCA<br>GTTTCGACTGGAGCGCCTACAACGATCCTCATCGCCGTTAT | SEQ ID NO: 12<br>MTIKEELGQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVSAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESKAI<br>APLDWDTVQRNVLMENY<br>NQSSNSGHFSFDWSAYND<br>PHRRY |
| ZIP8 | SEQ ID NO: 13<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCC<br>CGACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACGGACACCAT<br>CTTGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCCGGCA<br>CCTTCTTTGTCTATCAGGTGGTGTTTGTCTACGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 14<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTILIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP9 | SEQ ID NO: 15<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCC<br>CGACCAAAAGCGGCGGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACGGACACCAT<br>CTCGATTCCGCAGCAGGTGACGCAGACCAAGAGCTACCAGTTG<br>AGCAAAGGCCACACCCAGCCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA | SEQ ID NO: 16<br>MTIKEELSQPQSHSVELDQ<br>LQVGEVSAREALTSNFAGS<br>FDQFPTKSGGFEIDKYLLNY<br>ADPKKGCWLDGVTVYGDI<br>YIGKQNWGTYTRPVFAYLQ<br>HTDTISIPQQVTQTKSYQLS<br>KGHTQPFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI |

TABLE 3-continued

Novel Insecticidal Proteins Identified via the IPDP

| Identifier | Nucleotide | Amino Acid |
|---|---|---|
|  | CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | DPLDWDTVQRNVLIQNYN<br>PASNSGHFSFDWSAYNDP<br>HRRY |
| ZIP10 | SEQ ID NO: 17<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AGTACAGCGTTGGCGGCAGTATCGACATCGTCAACGTCAGCTC<br>GGATATCACTGTCGGTTTCAGCAGCACCGAGGCCTGGTCGACG<br>ACCCAGACCTTCACCCAAAGCACCGAGCTGGCCGGTCCGGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGACCGTACGGTCATCGTCGAGTCCAGCAAT<br>GCAATCGACCCGCTGGACCGGGATACCGTGCAGCGCAACGTG<br>CTGATCCAGAACTACAACCCGGCCAGCAACAGCGGGCACTTCT<br>CGTTCGACTGGAGCGCCTACACGATCCTCATCGCCGTTATTGAA<br>CTGAGATCCGGCTGC | SEQ ID NO: 18<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNVSSDITVGFSSTEA<br>WSTTQTFTQSTELAGPGTF<br>FVYQVVFVYAHNATSAGG<br>QNGNAFAYSKTQQVNSRL<br>DLYYLSAITXDRTVIVESSNA<br>IDPLDRDTVQRNVLIQNYN<br>PASNSGHFSFDWSAYTILIA<br>VIELRSGC |
| ZIP11 | SEQ ID NO: 19<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACGACACCAT<br>CTTGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCCGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 20<br>MTIKEELSNPQSHSVELDQ<br>LQVGEVSAREALTANFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP12 | SEQ ID NO: 21<br>ATGACGATCAAGGAAGAGCTGGGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCCGGCTGGACGGCGTCACC<br>GTCTACGGTGACATCTACATCGGCAAGCAGAACTGGGGCACCT<br>ACACGCGCCCGGTGTTCGCCTACCTGCAGCACACGACACCAT<br>CTCGATTCCGCAGCAGGTGACACAGACTCGCAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 22<br>MTIKEELGQPQSHSVELDQ<br>LQVGEVSAREALTSNFAGS<br>FDQFPTKSGSFEIDKYLLNY<br>ADPKKGCRLDGVTVYGDIYI<br>GKQNWGTYTRPVFAYLQH<br>TDTISIPQQVTQTRSYQLSK<br>GHTQSFTKSVSAKYSVGGSI<br>DIVNISSDITVGFSSTEAWS<br>TNQTFTQSTELAGPGTFFV<br>YQVVFVYAHNATSAGGQN<br>GNAFAYSKTQQVNSRLDLY<br>YLSAITQDRTVIVESSNAIDP<br>LDWDTVQRNVLIQNYNPA<br>SNSGHFSFDWSAYNDPHR<br>RY |
| ZIP13 | SEQ ID NO: 23<br>ATGACGATCAAGGAAGAGCTGGGCCAACCCCAAAGCCGTTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC | SEQ ID NO: 24<br>MTIKEELGQPQSRSVELDQ<br>LQVGEVSAREALTSNFAGS<br>FDQFPTKSGSFEIDKYLLNY |

TABLE 3-continued

Novel Insecticidal Proteins Identified via the IPDP

| Identifier | Nucleotide | Amino Acid |
|---|---|---|
| | GACCAAAAGCGGCAGCTTCGAGATCGACAAATACCTGCTCAAC<br>TACGCGGATCCGAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGACCACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACCTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP16 | SEQ ID NO: 25<br>ATGACGATCAAGGAAGAGCTGGGCCAGCCTCAAAGCCATTCG<br>ATCGAACTGGACGAGGTGAGCAAGGAGGCCGCAAGTACGCG<br>GGCCGCGTTGACTTCCAACCTGTCTGGCCGCTTCGACCAGTACC<br>CGACCAAGAAGGGCGACTTTGCGATCGATGGTTATTTGCTGGA<br>CTACAGCTCACCCAAGCAAGGTTGCTGGGTGGACGGTATCACT<br>GTCTATGGCGATATCTACATCGGCAAGCAGAACTGGGGCACTT<br>ATACCCGCCCGGTGTTTGCCTACCTACAGTATGTGGAAACCATC<br>TCCATTCCACAGAATGTGACGACCACCCTCAGCTATCAGCTGAC<br>CAAGGGGCATACCCGTTCCTTCGAGACCAGTGTCAACGCCAAG<br>TACAGCGTTGGCGCCAACATAGATATCGTCAACGTGGGTTCGG<br>AGATTTCCACCGGGTTTACCCGCAGGTCCTGGTCCACCAC<br>GCAGTCGTTCACCGATACCACCGAGATGAAGGGGCCAGGGAC<br>GTTCGTCATTTACCAGGTCGTGCTGGTGTATGCGCACAACGCC<br>ACCTCGGCAGGGCGGCAGAATGCCAATGCCTTCGCCTACAGCA<br>AAACCCAGGCAGTGGGCTCGCGGGTGGACTTGTACTACTTGTC<br>GGCCATTACCCAGCGCAAGCGGGTCATCGTTCCGTCGAGCAAT<br>GCCGTCACGCCGCTGGACTGGGATACGGTGCAACGCAACGTG<br>CTGATGGAAAACTACAACCCAGGCAGTAACAGCGGGCACTTCG<br>GCTTCGACTGGAGTGCCTACAACGATCCTCATCGCCGTTAT | SEQ ID NO: 26<br>MTIKEELGQPQSHSIELDEV<br>SKEAASTRAALTSNLSGRFD<br>QYPTKKGDFAIDGYLLDYS<br>PKQGCWVDGITVYGDIYIG<br>KQNWGTYTRPVFAYLQYV<br>ETISIPQNVTTTLSYQLTKG<br>HTRSFETSVNAKYSVGANI<br>DIVNVGSEISTGFTRSESWS<br>TTQSFTDTTEMKGPGTFVI<br>YQVVLVYAHNATSAGRQN<br>ANAFAYSKTQAVGSRVDLY<br>YLSAITQRKRVIVPSSNAVT<br>PLDWDTVQRNVLMENYN<br>PGSNSGHFGFDWSAYNDP<br>HRRY |
| ZIP17 | SEQ ID NO: 27<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGGATCAGTTCCC<br>GACCAAAGGCGGCAGCTTCGAGATCGACAAATACCTGCTCAAC<br>TACGCGGATCCGAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGACCACCGACACCAT<br>CTCGATTCCGCAGCAGGTGACGCAGACCAAGAGCTACCAGTTG<br>AGCAAAGGCCACACCCAGTCGTTCACCAAGCCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 28<br>MTIKEELSQPQSHSVELDQ<br>LQVGEVSAREALTSNFAGS<br>FDQFPTKGGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKPVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP18 | SEQ ID NO: 29<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGGATCAGTTCCC<br>GACCAAAGCGGCAGCTTCGAGATCGACAAATACCTGCTCAAC<br>TACGCGGATCCGAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGACCACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTCTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT | SEQ ID NO: 30<br>MTIKEELSQPQSHSVELDQ<br>LQVGEVSAREALTSNFAGS<br>FDQFPTKSGSFEIDKYLLNY<br>ADPKKGCWLDGVTVYGD1<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVSVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |

TABLE 3-continued

Novel Insecticidal Proteins Identified via the IPDP

| Identifier | Nucleotide | Amino Acid |
|---|---|---|
| | GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | |
| ZIP19 | SEQ ID NO: 31<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCGGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTGCCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 32<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>GIDIVNISSDITVGFSSTEA<br>WSTNQTFTQSTELAGPGTF<br>FVYQVVFVYAHNATSAGG<br>QNGNAFAYSKTQQVNSRL<br>DLYCLSAITQDRTVIVESSN<br>AIDPLDWDTVQRNVLIQNY<br>NPASNSGHFSFDWSAYND<br>PHRRY |
| ZIP20 | SEQ ID NO: 33<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCCGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 34<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPPDWDTVQRNVLIQNYN<br>PASNSGHFSFDWSAYNDP<br>HRRY |
| ZIP21 | SEQ ID NO: 35<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATGCA<br>AGACCCAGCAGGTGAACTCGCGGCTCGACCTTTACTACCTGTC<br>GGCCATCACCCAGGACCGTACGGTCATCGTCGAGTCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 36<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYGKTQQVNSRLD<br>LYYLSAITQDRTVIVESSNAI<br>DPLDWDTVQRNVLIQNYN<br>PASNSGHFSFDWSAYNDP<br>HRRY |
| ZIP22 | SEQ ID NO: 37<br>ATGACGATCAAGGAAGAGCTGGGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG | SEQ ID NO: 38<br>MTIKEELGQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW |

TABLE 3-continued

Novel Insecticidal Proteins Identified via the IPDP

| Identifier | Nucleotide | Amino Acid |
|---|---|---|
| | AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP23 | SEQ ID NO: 39<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTCG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 40<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQSS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP24 | SEQ ID NO: 41<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGCCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 42<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVEPSNAI<br>DPLDWDTVQRNVLIQNYN<br>PASNSGHFSFDWSAYNDP<br>HRRY |
| ZIP25 | SEQ ID NO: 43<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCCACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 44<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSHQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |

TABLE 3-continued

Novel Insecticidal Proteins Identified via the IPDP

| Identifier | Nucleotide | Amino Acid |
|---|---|---|
| ZIP26 | SEQ ID NO: 45<br>ATGACGATCAAGGAAGAGCTGAACCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 46<br>MTIKEELNQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP27 | SEQ ID NO: 47<br>ATGACGATCAAGGAAGAGCTGAGCCAACCCCAAAGCCATTTG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 48<br>MTIKEELSQPQSHLVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP28 | SEQ ID NO: 49<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCAAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 50<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP29 | SEQ ID NO: 51<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCGAAGCACCGAGCTGGCCGGCCCTGGCA | SEQ ID NO: 52<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTRSTELAGPGTFFV<br>YQVVFVYAHNATSAGGQN<br>GNAFAYSKTQQVNSRLDLY<br>YLSAITQDRTVIVESSNAIDP |

TABLE 3-continued

Novel Insecticidal Proteins Identified via the IPDP

| Identifier | Nucleotide | Amino Acid |
|---|---|---|
| | CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | LDWDTVQRNVLIQNYNPA<br>SNSGHFSFDWSAYNDPHR<br>RY |
| ZIP30 | SEQ ID NO: 53<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAGC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAGCTCGCGGCTCGACCTTTACTACCTGTC<br>GGCCATCACCCAGGACCGTACGGTCATCGTCGAGTCCAGCAGT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 54<br>MTIKEELSQPQSHSVELDQ<br>LQVGEVSAREALTSNFAGS<br>FDQFPTKSGSFEIDKYLLSYA<br>DPKKGCWLDGVTVYGDIYI<br>GKQNWGTYTRPVFAYLQH<br>TDTISIPQQVTQTKSYQLSK<br>GHTQSFTKSVSAKYSVGGSI<br>DIVNISSDITVGFSSTEAWS<br>TNQTFTQSTELAGPGTFFV<br>YQVVFVYAHNATSAGGQN<br>GNAFAYSKTQQVSSRLDLY<br>YLSAITQDRTVIVESSSAIDP<br>LDWDTVQRNVLIQNYNPA<br>SNSGHFSFDWSAYNDPHR<br>RY |
| ZIP31 | SEQ ID NO: 55<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCGGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 56<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQRVNSRLDL<br>YYLSAITQDRTVIVESSNAID<br>PLDWDTVQRNVLIQNYNP<br>ASNSGHFSFDWSAYNDPH<br>RRY |
| ZIP32 | SEQ ID NO: 57<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACGCCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 58<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHAQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP33 | SEQ ID NO: 59<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAACTTCGAGATCGACAAATACCTGCTCAAC | SEQ ID NO: 60<br>MTIKEELSQPQSHSVELDQ<br>LQVGEVSAREALTSNFAGS<br>FDQFPTKSGNFEIDKYLLNY<br>ADPKKGCWLDGVTVYGDI |

TABLE 3-continued

Novel Insecticidal Proteins Identified via the IPDP

| Identifier | Nucleotide | Amino Acid |
|---|---|---|
| | TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP34 | SEQ ID NO: 61<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGATCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 62<br>MTIKEELSQPQSHSVELDQ<br>LQVGEVSAREALTSNFAGS<br>FDQFPTKSGSFEIDKYLINY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP35 | SEQ ID NO: 63<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGACACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGGGCGCCTACAACGATCCTCATCGCCGTTAT | SEQ ID NO: 64<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTDTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWGAYNDP<br>HRRY |
| ZIP36 | SEQ ID NO: 65<br>ATGACGATCAAGGAAGAGCTGGGCCAGCCTCAAAGCCATTCG<br>ATCGAACTGGACGAGGTGAGCAAGGAGGCCGCAAGTACGCG<br>GGCCGCGTTGACTTCCAACCTGTCTGGCCGCTTCGACCAGTACC<br>CGACCAAGAAGGGCGACTTTGCGATCGATGGTTATTTGCTGGA<br>CTACAGCTCACCCAAGCAAGGTTGCTGGGTGGACGGTATCACT<br>GTCTATGGCGATATCTACATCGGCAAGCAGAACTGGGGCACTT<br>ATACCCGCCCGGTGTTTGCCTACCTACAGTATGTGGAAACCATC<br>TCCATTCCACAGAATGTGACGACCACCCTCAGCTATCAGCTGAC<br>CAAGGGGCATACCCGTTCCTTCGAGACCAGTGTCAACGCCAAG<br>TACAGCGTTGGCGCCAACATAGATATCGTCAACGTGGGTTCGG<br>AGATTTCCACCGGGTTTACCCGCAGCGAGTCCTGGTCCACCAC<br>GCAGTCGTTCACCGATACCACCGAGATGAAGGGGCCAGGGAC<br>GTTCGTCATTTACCAGGTCGTGCTGGTGTATGCGCACAACGCC<br>ACCTCGGCAGGGCGGCAGAATGCCAATGCCTTCGCCTACAGCA<br>AAACCCAGGCAGTGGGCTCGCGGGTGGACTTGTACTACTTGTC<br>GGCCATTACCCAGCGCAAGCGGGTCATCGTTCCGTCGAGCAAT<br>GCCGTCACGCCGCTGGACTGGGATACCGTGCAACGCAACGTG | SEQ ID NO: 66<br>MTIKEELGQPQSHSIELDEV<br>SKEAASTRAALTSNLSGRFD<br>QYPTKKGDFAIDGYLLDYSS<br>PKQGCWVDGITVYGDIYIG<br>KQNWGTYTRPVFAYLQYV<br>ETISIPQNVTTTLSYQLTKG<br>HTRSFETSVNAKYSVGANI<br>DIVNVGSEISTGFTRSESWS<br>TTQSFTDTTEMKGPGTFVI<br>YQVVLVYAHNATSAGRQN<br>ANAFAYSKTQAVGSRVDLY<br>YLSAITQRKRVIVPSSNAVT<br>PLDWDTVQRNVLMENYN<br>PGSNSGHFSFDWSAYNDP<br>HRRY |

TABLE 3-continued

Novel Insecticidal Proteins Identified via the IPDP

| Identifier | Nucleotide | Amino Acid |
|---|---|---|
| | CTGATGGAAAACTACAACCCAGGCAGTAACAGCGGACACTTCA<br>GCTTCGACTGGAGTGCCTACAACGATCCTCATCGCCGTTAT | |
| ZIP37 | SEQ ID NO: 67<br>ATGACGATCAAGGAAGAGCTGGGCCAGCCTCAAAGCCATTCG<br>ATCGAACTGGACGAGGTGAGCAAGGAGGCCGCAAGTACGCG<br>GGCCGCGTTGACTTCCAACCTGTCTGGCCGCTTCGACCAGTACC<br>CGACCAAGAAGGGCGACTTTGCGATCGATGGTTATTTGCTGGA<br>CTACAGCTCACCCAAGCAAGGTTGCTGGGTGGACGGTATCACT<br>GTCTATGGCGATATCTACATCGGCAAGCAGAACTGGGGCACTT<br>ATACCCGCCCGGTGTTTGCCTACCTACAGTATGTGGAAACCATC<br>TCCATTCCACAGAATGTGACGACCACCCTCAGCTATCAGCTGAC<br>CAAGGGGCATACCCGTTCCTTCGAGACCAGTGTCAACGCCAAG<br>TACAGCGTTGGCGCCAACATAGATATCGTCAACGTGGGTTCGG<br>AGATTTCCACCGGGTTTACCCGCAGCGAGTCCTGGTCCACCAC<br>GCAGTCGTTCACCGATACCACCGAGATGAAGGGGCCAGGGAC<br>GTTCGTCATTTACCAGGTCGTGCTGGTGTATGCGCACAACGCC<br>ACCTCGGCAGGGCGGCAGAATGCCAATGCCTTCGCCTACAGCA<br>AAACCCAGGCAGTGGGCTCGCGGGTGGACTTGTACTACTTGTC<br>GGCCATTACCCAGCGCAAGCGGGTCATCGTTCCGTCGAGCAAT<br>GCCGTCACGCCGCTGGACTGGGATACGGTGCAACGCAACGTG<br>CTGATGGAAAACTACAACCCAGGCAGTAACAGCGGACACTTCC<br>GCTCCGACTGGAGCGCCTACAACGATCCTCATCGCCGTTAT | SEQ ID NO: 68<br>MTIKEELGQPQSHSIELDEV<br>SKEAASTRAALTSNLSGRFD<br>QYPTKKGDFAIDGYLLDYSS<br>PKQGCWVDGITVYGDIYIG<br>KQNWGTYTRPVFAYLQYV<br>ETISIPQNVTTTLSYQLTKG<br>HTRSFETSVNAKYSVGANI<br>DIVNVGSEISTGFTRSESWS<br>TTQSFTDTTEMKGPGTFVI<br>YQVVLVYAHNATSAGRQN<br>ANAFAYSKTQAVGSRVDLY<br>YLSAITQRKRVIVPSSNAVT<br>PLDWDTVQRNVLMENYN<br>PGSNSGHFRSDWSAYNDP<br>HRRY |
| ZIP38 | SEQ ID NO: 69<br>ATGACGATCAAGGAAGAGCTGAGCCAACCCCAAAGCCATTCG<br>GTCGAGCTCGACCAGTTGCAAGTCGGGGAAGTCTCTGCACGC<br>GAAGCGTTGACCTCCAACTTCGCCGGCAGTTTCGATCAGTTCCC<br>GACCAAAAGCGGCAGCTTCGAGATCGACAAATACCTGCTCAAC<br>TACGCGGATCCGAAAAAAGGCTGCTGGCTGGACGGCGTCACC<br>GTCTACGGTGACATCTACATCGGCAAGCAGAACTGGGGCACCT<br>ACACGCGCCCGGTGTTCGCCTACCTGCAGCACACCGGCACCAT<br>CTCGATTCCGCAGCAGGTGACGCAGACCAAGAGCTACCAGTTG<br>AGCAAAGGCCACACCCAGTCGTTCACCAAGTCGGTCAGCGCCA<br>AATACAGCGTTGGCGGCAGTATCGACATCGTCAACATCAGCTC<br>GGATATCACCGTTGGTTTCAGCAGCACCGAGGCCTGGTCGACG<br>AACCAGACCTTCACCCAAAGCACCGAGCTGGCCGGCCCTGGCA<br>CCTTCTTTGTCTATCAGGTGGTGTTTGTCTATGCGCACAACGCC<br>ACTTCGGCCGGTGGGCAGAATGGCAATGCCTTTGCCTATAGCA<br>AGACCCAGCAGGTGAACTCGCGGCTCGACCTTTACTACCTGTC<br>GGCCATCACCCAGGACCGTACGGTCATCGTCGAGTCCAGCAAT<br>GCAATCGACCCGCTGGACTGGGATACCGTGCAGCGCAACGTG<br>CTGATCCAGAACTACAACCCGGCCAGCAACAGCGGGCACTTCT<br>CGTTCGACTGGAGCGCCTACAACGATCCTCATCGCCGTTAT | SEQ ID NO: 70<br>MTIKEELSQPQSHSVELDQ<br>LQVGEVSAREALTSNFAGS<br>FDQFPTKSGSFEIDKYLLNY<br>ADPKKGCWLDGVTVYGDI<br>YIGKQNWGTYTRPVFAYLQ<br>HTGTISIPQQVTQTKSYQLS<br>KGHTQSFTKSVSAKYSVGG<br>SIDIVNISSDITVGFSSTEAW<br>STNQTFTQSTELAGPGTFF<br>VYQVVFVYAHNATSAGGQ<br>NGNAFAYSKTQQVNSRLD<br>LYYLSAITQDRTVIVESSNAI<br>DPLDWDTVQRNVLIQNYN<br>PASNSGHFSFDWSAYNDP<br>HRRY |
| ZIP39 | SEQ ID NO: 71<br>ATGACGATCAAGGAAGAGCTGAGCAATCCTCAAAGCCATTCGG<br>TCGAGCTCGACCAGTTGCAAGTCGGGGAAGTCTCTGCACGCGA<br>AGCGTTGACCGCCAACTTCGCCGGCAGTTTCGATCAGTTCCCG<br>ACCAAAAGCGGCAGCTTCGAGATCGACAAATACCTGCTCAACT<br>ACGCAGACCCGAAACAAGGCTGCTGGCTGGACGGCGTCACCG<br>TCTACGGTGACATCTACATCGGCAAGCAGAACTGGGGCACCTA<br>CACGCGCCCGGTGTTCGCCTACCTGCAGCACACGGACACCATC<br>TCGATTCCGCAGCAGGTGACGCAGACCAAGAGCTACCAGCTGA<br>GCAAAGGCCACACCCAGTCGTTCACCAAGTCGGTCAGCGCCAA<br>GTACAGCGTTGGCGGCAGTATCGACATCGTCAACGTCAGCTCG<br>GATATCACTGTCGGTTTCAGCAGCACCGAGGCCTGGTCGACGA<br>CCCAGACCTTCACCCAAAGCACCGAGCTGGCCGGTCCGGGCAC<br>CTTCTTTGTCTATCAGGTGGTGTTTGTCTACGCGCACAACGCCA<br>CCTCGGCGGGCCGGCAGAATGGCAATGCCTTTGCCTATAGCAA<br>GACCCAGCAGGTGGATTCGCGGCTCGATCTCTACTACCTGTCG<br>GCCATCACCCAGGACCGTACGGTCATCGTCGAGTCCAGCAAGG<br>CAATCAACCCGCTGGACTGGGATACCGTGCAGCGCAACGTGCT<br>GATCGAGAACTACAACCCGGCCTCCAACAGTGGGCACTTCCGC<br>TTCGACTGGAGCGCCTACAACGATCCTCATCGTCGTTAC | SEQ ID NO: 72<br>MTIKEELSNPQSHSVELDQ<br>LQVGEVSAREALTANFAGS<br>FDQFPTKSGSFEIDKYLLNY<br>ADPKQGCWLDGVTVYGDI<br>YIGKQNWGTYTRPVFAYLQ<br>HTDTISIPQQVTQTKSYQLS<br>KGHTQSFTKSVSAKYSVGG<br>SIDIVNVSSDITVGFSSTEA<br>WSTTQTFTQSTELAGPGTF<br>FVYQVVFVYAHNATSAGR<br>QNGNAFAYSKTQQVDSRL<br>DLYYLSAITQDRTVIVESSKA<br>INPLDWDTVQRNVLIENYN<br>PASNSGHFRFDWSAYNDP<br>HRRY |

Figure 6:
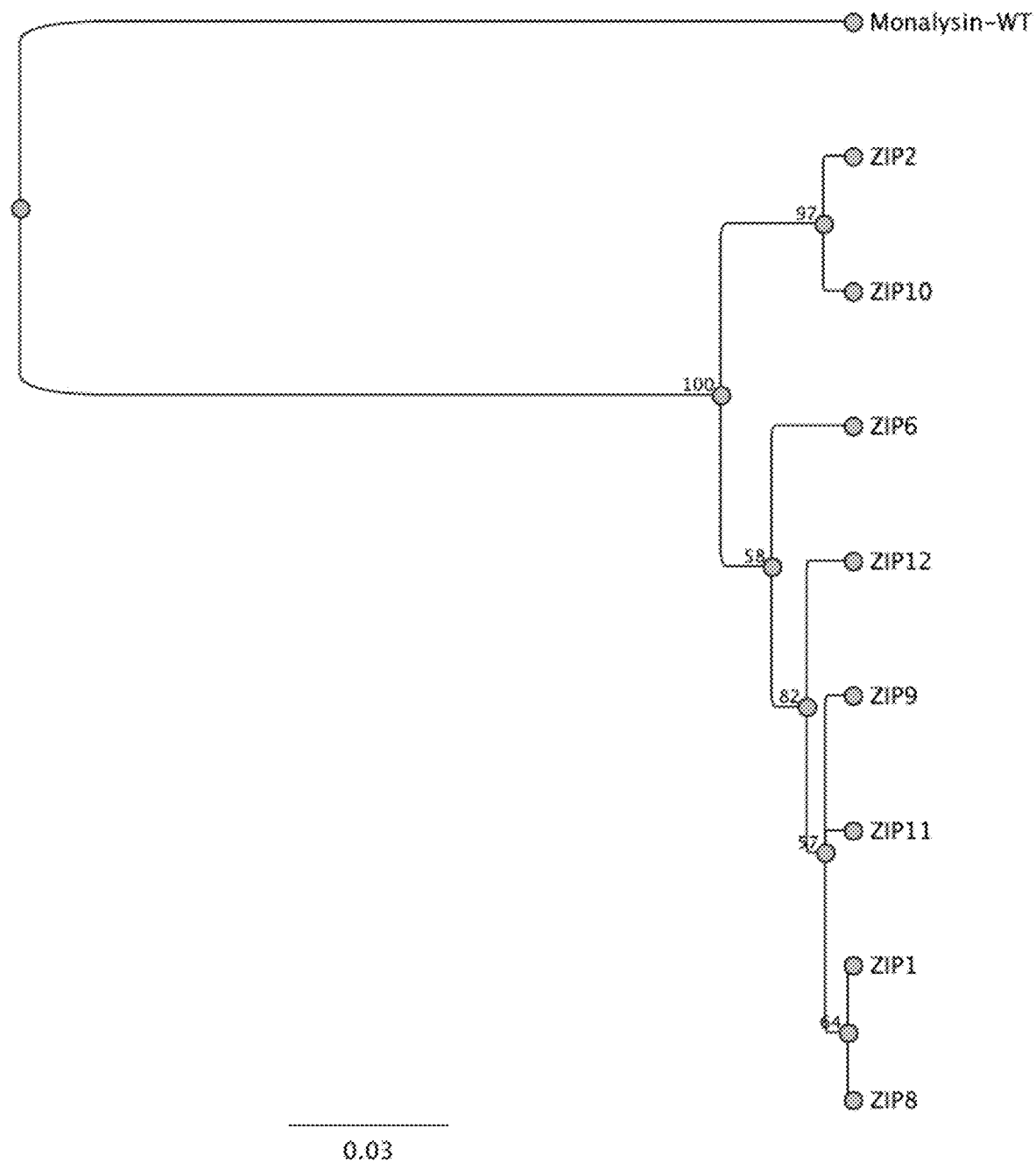
FIG. 6 illustrates a phylogenetic tree of eight novel insecticidal proteins found in Table 3 and FIG. 4, which were discovered utilizing the IPDP, as compared to monalysin.

Further, reference can be had to FIG. 4, which illustrates a multiple sequence alignment comparing eight of the discovered insecticidal proteins (i.e., ZIP1, ZIP2, ZIP6, ZIP8, ZIP9, ZIP10, ZIP11, and ZIP12) to that of Monalysin, with a corresponding phylogenetic tree found in FIG. 6.

The below Table 4 is an identity matrix, which illustrates the percent identity amongst the 32 aforementioned proteins having at least 20% sequence identity difference from any known protein in this class.

Furthermore, Table 5 compares the identity from these newly discovered 32 proteins to that of Monalysin, which was the first protein discovered in this class. As can be seen from Table 5, the taught insecticidal proteins are sufficiently different from Monalysin at the amino acid level.

This result further illustrates the power of the taught IPDP to discover novel proteins.

TABLE 4

Sequence Identity Matrix of 32 Novel Insecticidal Proteins From Table 3 Identified via the IPDP

| | ZIP1 | ZIP2 | ZIP3 | ZIP5 | ZIP6 | ZIP8 | ZIP9 | ZIP10 | ZIP11 | ZIP12 | ZIP13 |
|---|---|---|---|---|---|---|---|---|---|---|---|
| ZIP1 | | 97.42 | 95.94 | 95.20 | 97.05 | 99.65 | 99.25 | 95.96 | 99.26 | 98.89 | 99.26 |
| ZIP2 | 97.42 | | 93.36 | 92.62 | 94.47 | 97.05 | 96.68 | 98.57 | 96.68 | 96.31 | 96.68 |
| ZIP3 | 95.94 | 93.36 | | 94.10 | 95.20 | 95.57 | 95.20 | 91.90 | 95.2o | 94.83 | 95.20 |
| ZIP5 | 95.20 | 92.62 | 94.10 | | 94.10 | 94.83 | 94.47 | 93.38 | 95.94 | 94.10 | 94.47 |
| ZIP6 | 97.05 | 94.47 | 95.20 | 94.10 | | 96.58 | 96.31 | 93.01 | 96.31 | 96.68 | 97.05 |
| ZIP8 | 99.53 | 97.05 | 95.57 | 94.83 | 96.68 | | 98.89 | 95.59 | 98.89 | 98.52 | 98.89 |
| ZIP9 | 99.26 | 96.68 | 95.20 | 94.47 | 96.31 | 98.89 | | 95.22 | 98.52 | 98.16 | 98.52 |
| ZIP10 | 95.96 | 98.57 | 91.90 | 93.38 | 93.01 | 95.59 | 95.22 | | 95.22 | 94.85 | 95.22 |
| ZIP11 | 99.26 | 96.68 | 95.20 | 95.94 | 96.31 | 98.89 | 98.52 | 95.22 | | 98.16 | 98.52 |
| ZIP12 | 98.89 | 96.31 | 94.83 | 94.10 | 96.68 | 98.52 | 98.16 | 94.85 | 98.16 | | 98.89 |
| ZIP13 | 99.26 | 96.68 | 95.20 | 94.47 | 97.05 | 98.89 | 98.52 | 95.22 | 98.52 | 98.89 | |
| ZIP17 | 99.26 | 96.68 | 95.20 | 94.47 | 96.31 | 98.89 | 98.52 | 95.22 | 98.52 | 98.16 | 98.52 |
| ZIP18 | 99.63 | 97.05 | 95.94 | 94.83 | 96.68 | 99.26 | 98.89 | 95.59 | 98.89 | 98.52 | 98.89 |
| ZIP19 | 99.26 | 96.68 | 95.20 | 94.47 | 96.31 | 98.89 | 98.52 | 95.22 | 98.52 | 98.16 | 98.52 |
| ZIP20 | 99.63 | 97.05 | 95.57 | 94.83 | 96.68 | 99.26 | 98.89 | 95.59 | 98.89 | 98.52 | 98.89 |
| ZIP21 | 99.63 | 97.05 | 95.94 | 94.83 | 95.68 | 99.26 | 98.89 | 95.59 | 98.89 | 98.52 | 98.89 |
| ZIP22 | 99.63 | 97.05 | 95.57 | 94.83 | 97.42 | 99.26 | 98.89 | 95.59 | 98.89 | 99.26 | 99.63 |
| ZIP23 | 99.63 | 97.05 | 95.57 | 94.83 | 96.68 | 99.26 | 98.89 | 95.59 | 98.83 | 98.52 | 98.89 |
| ZIP24 | 99.63 | 97.05 | 95.57 | 94.83 | 96.68 | 99.26 | 98.89 | 95.59 | 98.89 | 98.52 | 98.89 |
| ZIP25 | 99.63 | 97.05 | 95.57 | 94.83 | 96.68 | 99.26 | 98.89 | 95.59 | 98.89 | 98.52 | 98.89 |
| ZIP26 | 99.63 | 97.05 | 95.57 | 94.83 | 97.05 | 99.26 | 98.89 | 95.59 | 98.89 | 98.89 | 99.26 |
| ZIP27 | 99.63 | 97.05 | 95.57 | 94.83 | 96.68 | 99.26 | 98.89 | 95.59 | 98.89 | 98.52 | 98.89 |
| ZIP28 | 99.63 | 97.05 | 95.57 | 94.83 | 96.68 | 99.26 | 98.89 | 95.59 | 98.89 | 98.52 | 98.89 |
| ZIP29 | 99.63 | 97.05 | 95.57 | 94.83 | 96.68 | 99.26 | 98.89 | 95.59 | 98.89 | 98.52 | 98.89 |
| ZIP30 | 98.89 | 96.31 | 95.57 | 94.83 | 96.31 | 98.52 | 98.16 | 94.85 | 98.16 | 97.79 | 98.16 |
| ZIP31 | 99.63 | 97.05 | 95.57 | 94.83 | 96.68 | 99.26 | 98.89 | 95.59 | 98.89 | 98.52 | 98.89 |
| ZIP32 | 99.63 | 97.05 | 95.57 | 94.83 | 96.68 | 99.26 | 98.89 | 95.59 | 98.89 | 98.52 | 98.89 |
| ZIP33 | 99.63 | 97.05 | 95.57 | 94.83 | 96.68 | 99.26 | 99.26 | 95.59 | 98.89 | 98.52 | 98.89 |
| ZIP34 | 99.63 | 97.05 | 95.57 | 94.83 | 96.68 | 99.26 | 98.89 | 95.59 | 98.89 | 98.52 | 98.89 |
| ZIP35 | 99.63 | 97.05 | 95.57 | 94.83 | 96.68 | 99.26 | 98.89 | 95.59 | 98.89 | 98.52 | 98.89 |
| ZIP38 | 99.63 | 97.05 | 95.57 | 94.83 | 96.68 | 99.26 | 98.89 | 95.59 | 98.89 | 98.52 | 98.89 |
| ZIP39 | 95.94 | 93.35 | 94.47 | 99.26 | 94.83 | 95.57 | 95.20 | 93.38 | 96.68 | 94.83 | 95.20 |

| | ZIP17 | ZIP18 | ZIP19 | ZIP20 | ZIP21 | ZIP22 | ZIP23 | ZIP24 | ZIP25 | ZIP26 | ZIP27 |
|---|---|---|---|---|---|---|---|---|---|---|---|
| ZIP1 | 99.26 | 99.63 | 99.26 | 99.63 | 99.63 | 99.63 | 99.63 | 99.63 | 99.63 | 99.63 | 99.63 |
| ZIP2 | 96.68 | 97.05 | 96.68 | 97.05 | 97.05 | 97.05 | 97.05 | 97.05 | 97.05 | 97.05 | 97.05 |
| ZIP3 | 95.20 | 95.94 | 95.20 | 95.57 | 95.94 | 95.57 | 95.57 | 95.57 | 95.57 | 95.57 | 95.57 |
| ZIP5 | 94.47 | 94.83 | 94.47 | 94.83 | 94.83 | 94.83 | 94.83 | 94.83 | 94.83 | 94.83 | 94.83 |
| ZIP6 | 96.31 | 96.68 | 96.51 | 96.68 | 96.68 | 97.42 | 96.68 | 96.68 | 96.68 | 97.05 | 96.68 |
| ZIP8 | 98.89 | 99.26 | 98.89 | 99.26 | 99.26 | 99.26 | 99.26 | 99.26 | 99.26 | 99.26 | 99.26 |
| ZIP9 | 98.52 | 98.89 | 98.52 | 98.89 | 98.89 | 98.89 | 98.83 | 98.89 | 98.89 | 98.89 | 98.89 |
| ZIP10 | 95.22 | 95.59 | 95.22 | 95.59 | 95.59 | 95.59 | 95.59 | 95.59 | 95.59 | 95.59 | 95.59 |
| ZIP11 | 98.52 | 98.89 | 98.52 | 98.89 | 98.89 | 98.89 | 98.89 | 98.89 | 98.89 | 98.89 | 98.89 |
| ZIP12 | 98.16 | 98.52 | 98.16 | 98.52 | 98.52 | 99.26 | 98.52 | 98.52 | 98.52 | 98.89 | 98.52 |
| ZIP13 | 98.52 | 98.89 | 98.52 | 98.89 | 98.89 | 99.63 | 98.89 | 98.89 | 98.89 | 99.26 | 98.89 |
| ZIP17 | | 98.89 | 98.52 | 98.89 | 98.89 | 98.89 | 98.89 | 98.89 | 98.89 | 98.89 | 98.89 |
| ZIP18 | 98.89 | | 98.89 | 99.26 | 99.26 | 99.26 | 99.26 | 99.26 | 99.26 | 99.26 | 99.26 |
| ZIP19 | 98.52 | 98.89 | | 98.89 | 98.89 | 98.89 | 98.89 | 98.89 | 98.89 | 98.89 | 98.89 |
| ZIP20 | 98.89 | 99.26 | 98.89 | | 99.26 | 99.26 | 99.26 | 99.26 | 99.26 | 99.26 | 99.26 |
| ZIP21 | 98.89 | 99.26 | 98.89 | 99.26 | | 99.26 | 99.26 | 99.26 | 99.26 | 99.26 | 99.26 |
| ZIP22 | 98.89 | 99.26 | 98.89 | 99.26 | 99.26 | | 99.26 | 99.26 | 99.26 | 99.63 | 99.26 |
| ZIP23 | 98.89 | 99.26 | 98.89 | 99.26 | 99.26 | 99.26 | | 99.26 | 99.26 | 99.26 | 99.26 |
| ZIP24 | 98.89 | 99.26 | 98.89 | 99.26 | 99.26 | 99.26 | 99.26 | | 99.26 | 99.26 | 99.26 |
| ZIP25 | 98.89 | 99.26 | 98.89 | 99.26 | 99.26 | 99.26 | 99.26 | 99.26 | | 99.26 | 99.26 |
| ZIP26 | 98.89 | 99.26 | 98.89 | 99.26 | 99.26 | 99.63 | 99.26 | 99.26 | 99.26 | | 99.26 |
| ZIP27 | 98.89 | 99.26 | 98.89 | 99.26 | 99.26 | 99.26 | 99.26 | 99.26 | 99.26 | 99.26 | |
| ZIP28 | 98.89 | 99.26 | 98.89 | 99.26 | 99.26 | 99.26 | 99.26 | 99.26 | 99.26 | 99.26 | 99.26 |
| ZIP29 | 98.89 | 99.26 | 98.89 | 99.26 | 99.26 | 99.26 | 99.26 | 99.26 | 99.26 | 99.26 | 99.26 |
| ZIP30 | 98.16 | 98.52 | 98.16 | 98.52 | 98.52 | 98.52 | 98.52 | 98.52 | 98.52 | 98.52 | 98.52 |
| ZIP31 | 98.89 | 99.26 | 98.89 | 99.26 | 99.26 | 99.26 | 99.26 | 99.26 | 99.26 | 99.26 | 99.26 |
| ZIP32 | 98.89 | 99.26 | 98.89 | 99.26 | 99.26 | 99.26 | 99.26 | 99.26 | 99.26 | 99.26 | 99.26 |
| ZIP33 | 98.89 | 99.26 | 98.89 | 99.26 | 99.26 | 99.26 | 99.26 | 99.26 | 99.26 | 99.26 | 99.26 |
| ZIP34 | 98.89 | 99.26 | 98.89 | 99.26 | 99.26 | 99.26 | 99.26 | 99.26 | 99.26 | 99.26 | 99.26 |

TABLE 4-continued

Sequence Identity Matrix of 32 Novel Insecticidal Proteins From Table 3 Identified via the IPDP

| | | | | | | | | | | |
|---|---|---|---|---|---|---|---|---|---|---|
| ZIP35 | 98.89 | 99.26 | 98.89 | 99.26 | 99.26 | 99.26 | 99.26 | 99.26 | 99.26 | 99.26 | 99.26 |
| ZIP38 | 98.89 | 99.26 | 98.89 | 99.26 | 99.26 | 99.26 | 99.26 | 99.26 | 99.26 | 99.26 | 99.26 |
| ZIP39 | 95.20 | 95.57 | 95.20 | 95.57 | 95.57 | 95.57 | 95.57 | 95.57 | 95.57 | 95.57 | 95.57 |

| | ZIP28 | ZIP29 | ZIP30 | ZIP31 | ZIP32 | ZIP33 | ZIP34 | ZIP35 | ZIP38 | ZIP39 |
|---|---|---|---|---|---|---|---|---|---|---|
| ZIP1 | 99.63 | 99.63 | 98.89 | 99.63 | 99.63 | 99.63 | 99.63 | 99.63 | 99.63 | 95.94 |
| ZIP2 | 97.05 | 97.05 | 96.31 | 97.05 | 97.05 | 97.05 | 97.05 | 97.05 | 97.05 | 93.36 |
| ZIP3 | 95.57 | 95.57 | 95.57 | 95.57 | 95.57 | 95.57 | 95.57 | 95.57 | 95.57 | 94.47 |
| ZIP5 | 94.83 | 94.83 | 94.83 | 94.83 | 94.83 | 94.83 | 94.83 | 94.83 | 94.83 | 99.25 |
| ZIP6 | 96.68 | 96.68 | 96.31 | 96.68 | 96.68 | 96.68 | 96.68 | 96.68 | 96.68 | 94.83 |
| ZIP8 | 99.26 | 99.26 | 98.52 | 99.26 | 99.26 | 99.26 | 99.26 | 99.26 | 99.26 | 95.57 |
| ZIP9 | 98.89 | 98.89 | 98.16 | 98.89 | 98.89 | 99.26 | 98.89 | 98.89 | 98.89 | 95.20 |
| ZIP10 | 95.59 | 95.59 | 94.85 | 95.59 | 95.59 | 95.59 | 95.59 | 95.59 | 95.59 | 93.38 |
| ZIP11 | 98.89 | 98.89 | 98.16 | 98.89 | 98.89 | 98.89 | 98.89 | 98.89 | 98.89 | 96.63 |
| ZIP12 | 98.52 | 98.52 | 97.79 | 98.52 | 98.52 | 98.52 | 98.52 | 98.52 | 98.52 | 94.83 |
| ZIP13 | 98.89 | 98.89 | 98.16 | 98.89 | 98.89 | 98.89 | 98.89 | 98.89 | 98.89 | 95.20 |
| ZIP17 | 98.89 | 98.89 | 98.16 | 98.89 | 98.89 | 98.89 | 98.89 | 98.89 | 98.89 | 95.20 |
| ZIP18 | 99.26 | 99.26 | 98.52 | 99.26 | 99.26 | 99.26 | 99.26 | 99.26 | 99.26 | 95.57 |
| ZIP19 | 98.89 | 98.89 | 98.16 | 98.89 | 98.89 | 98.89 | 98.89 | 98.89 | 98.89 | 95.20 |
| ZIP20 | 99.26 | 99.26 | 98.52 | 99.26 | 99.26 | 99.26 | 99.26 | 99.26 | 99.26 | 95.57 |
| ZIP21 | 99.26 | 99.26 | 98.52 | 99.26 | 99.26 | 99.26 | 99.26 | 99.26 | 99.26 | 95.57 |
| ZIP22 | 99.26 | 99.26 | 98.52 | 99.26 | 99.26 | 99.26 | 99.26 | 99.26 | 99.26 | 95.57 |
| ZIP23 | 99.26 | 99.26 | 98.52 | 99.26 | 99.26 | 99.26 | 99.26 | 99.26 | 99.26 | 95.57 |
| ZIP24 | 99.26 | 99.26 | 98.52 | 99.26 | 99.26 | 99.26 | 99.26 | 99.26 | 99.26 | 95.57 |
| ZIP25 | 99.26 | 99.26 | 98.52 | 99.26 | 99.26 | 99.26 | 99.26 | 99.26 | 99.26 | 95.57 |
| ZIP26 | 99.26 | 99.26 | 98.52 | 99.26 | 99.26 | 99.26 | 99.26 | 99.26 | 99.26 | 95.57 |
| ZIP27 | 99.26 | 99.26 | 98.52 | 99.26 | 99.26 | 99.26 | 99.26 | 99.26 | 99.26 | 95.57 |
| ZIP28 |  | 99.26 | 98.52 | 99.26 | 99.26 | 99.26 | 99.26 | 99.25 | 99.26 | 95.57 |
| ZIP29 | 99.26 |  | 98.52 | 99.26 | 99.26 | 99.26 | 99.26 | 99.26 | 99.26 | 95.57 |
| ZIP30 | 98.52 | 98.52 |  | 98.52 | 98.52 | 98.52 | 98.52 | 98.52 | 98.52 | 95.57 |
| ZIP31 | 99.26 | 99.26 | 98.52 |  | 99.26 | 99.26 | 99.26 | 99.26 | 99.26 | 95.57 |
| ZIP32 | 99.26 | 99.26 | 98.52 | 99.26 |  | 99.26 | 99.26 | 99.26 | 99.26 | 95.57 |
| ZIP33 | 99.26 | 99.26 | 98.52 | 99.26 | 99.26 |  | 99.26 | 99.26 | 99.26 | 95.57 |
| ZIP34 | 99.26 | 99.26 | 98.52 | 99.26 | 99.26 | 99.26 |  | 99.26 | 99.26 | 95.57 |
| ZIP35 | 99.26 | 99.26 | 98.52 | 99.26 | 99.26 | 99.26 | 99.26 |  | 99.26 | 95.57 |
| ZIP38 | 99.26 | 99.26 | 98.52 | 99.26 | 99.26 | 99.26 | 99.26 | 99.26 |  | 95.57 |
| ZIP39 | 95.57 | 95.57 | 95.57 | 95.57 | 95.57 | 95.57 | 95.57 | 95.57 | 95.57 |  |

TABLE 5

Sequence Identity Matrix of 32 Novel Insecticidal Proteins From Table 3 Identified via the IPDP and Monalysin

| | Monalysin | ZIP1 | ZIP2 | ZIP3 | ZIP5 | ZIP6 | ZIP8 | ZIP9 | ZIP10 | ZIP11 | ZIP12 | ZIP13 |
|---|---|---|---|---|---|---|---|---|---|---|---|---|
| Monalysin |  | 74.17 | 71.59 | 74.17 | 73.80 | 74.17 | 73.80 | 73.80 | 71.60 | 73.43 | 74.17 | 74.17 |
| ZIP1 | 74.17 |  | 97.42 | 95.94 | 95.20 | 97.05 | 99.63 | 99.26 | 95.96 | 99.26 | 98.89 | 99.26 |
| ZIP2 | 71.59 | 97.42 |  | 93.36 | 92.62 | 94.47 | 97.05 | 96.68 | 98.57 | 96.68 | 96.31 | 96.68 |
| ZIP3 | 74.17 | 95.94 | 93.36 |  | 94.10 | 95.20 | 95.57 | 95.20 | 91.90 | 95.20 | 94.83 | 95.20 |
| ZIP5 | 73.80 | 95.20 | 92.62 | 94.10 |  | 94.10 | 94.83 | 94.47 | 93.38 | 95.94 | 94.10 | 94.47 |
| ZIP6 | 74.17 | 97.05 | 94.47 | 95.20 | 94.10 |  | 96.68 | 96.31 | 93.01 | 96.31 | 96.68 | 97.05 |
| ZIP8 | 73.80 | 99.63 | 97.05 | 95.57 | 94.83 | 96.68 |  | 98.89 | 95.59 | 98.89 | 95.82 | 98.89 |
| ZIP9 | 73.80 | 99.26 | 96.68 | 95.20 | 94.47 | 96.31 | 98.89 |  | 95.22 | 98.52 | 98.16 | 98.52 |
| ZIP10 | 71.60 | 95.96 | 98.57 | 91.90 | 93.38 | 93.01 | 95.59 | 95.22 |  | 95.22 | 94.85 | 95.22 |
| ZIP11 | 73.43 | 99.26 | 99.68 | 95.20 | 95.94 | 96.31 | 98.89 | 98.52 | 95.22 |  | 98.16 | 98.52 |
| ZIP12 | 74.17 | 98.89 | 96.31 | 94.83 | 94.10 | 96.68 | 98.52 | 96.16 | 94.85 | 98.16 |  | 98.89 |
| ZIP13 | 74.17 | 99.26 | 96.68 | 95.20 | 94.47 | 97.05 | 98.89 | 98.52 | 95.22 | 98.52 | 98.89 |  |
| ZIP17 | 73.80 | 99.26 | 96.58 | 95.20 | 94.47 | 96.31 | 98.89 | 98.52 | 95.22 | 98.52 | 98.16 | 98.52 |
| ZIP18 | 74.17 | 99.63 | 97.05 | 95.94 | 94.83 | 96.68 | 99.26 | 98.89 | 95.59 | 98.89 | 98.52 | 98.89 |
| ZIP19 | 73.80 | 99.26 | 96.68 | 95.20 | 94.47 | 96.31 | 98.89 | 98.52 | 95.22 | 98.52 | 98.16 | 98.52 |
| ZIP20 | 73.80 | 99.63 | 97.05 | 95.57 | 94.83 | 96.68 | 99.26 | 98.89 | 95.59 | 98.89 | 98.52 | 98.89 |
| ZIP21 | 73.80 | 99.63 | 97.05 | 95.94 | 94.83 | 96.68 | 99.26 | 98.89 | 95.59 | 98.89 | 98.52 | 98.89 |
| ZIP22 | 74.54 | 99.63 | 97.05 | 95.57 | 94.83 | 97.42 | 99.26 | 98.89 | 95.59 | 98.89 | 99.26 | 99.63 |
| ZIP23 | 73.80 | 99.63 | 97.05 | 95.57 | 94.83 | 96.68 | 99.26 | 98.89 | 95.59 | 98.89 | 98.52 | 98.89 |
| ZIP24 | 73.80 | 99.63 | 97.05 | 95.57 | 94.83 | 96.68 | 99.26 | 98.89 | 95.59 | 98.59 | 98.52 | 98.89 |
| ZIP25 | 73.80 | 99.63 | 97.05 | 95.57 | 94.83 | 96.68 | 99.26 | 98.89 | 95.59 | 98.89 | 98.52 | 98.89 |
| ZIP26 | 74.17 | 99.63 | 97.05 | 95.57 | 94.83 | 97.05 | 99.26 | 98.89 | 95.59 | 98.89 | 98.89 | 99.26 |
| ZIP27 | 73.80 | 99.63 | 97.05 | 95.57 | 94.83 | 96.68 | 99.26 | 98.89 | 95.59 | 98.89 | 98.52 | 98.89 |
| ZIP28 | 74.17 | 99.63 | 97.05 | 95.57 | 94.83 | 96.68 | 99.26 | 98.89 | 95.59 | 98.89 | 98.52 | 98.89 |
| ZIP29 | 74.17 | 99.63 | 97.05 | 95.57 | 94.83 | 96.68 | 99.26 | 98.89 | 95.59 | 98.89 | 98.52 | 98.89 |
| ZIP30 | 73.80 | 98.89 | 96.31 | 95.57 | 94.83 | 96.31 | 98.52 | 98.16 | 94.85 | 98.16 | 97.79 | 98.16 |
| ZIP31 | 74.17 | 99.63 | 97.05 | 95.57 | 94.83 | 96.68 | 99.26 | 98.89 | 95.59 | 98.89 | 98.52 | 98.89 |
| ZIP32 | 73.80 | 99.63 | 97.05 | 95.57 | 94.83 | 96.68 | 99.26 | 98.89 | 95.59 | 98.89 | 98.52 | 98.89 |
| ZIP33 | 74.17 | 99.63 | 97.05 | 95.57 | 94.83 | 96.68 | 99.26 | 99.26 | 95.59 | 98.89 | 98.52 | 98.89 |
| ZIP34 | 73.80 | 99.63 | 97.05 | 95.57 | 94.83 | 96.68 | 99.26 | 96.89 | 95.59 | 98.89 | 98.52 | 96.89 |

TABLE 5-continued

Sequence Identity Matrix of 32 Novel Insecticidal Proteins From Table 3 Identified via the IPDP and Monalysin

| | | | | | | | | | | | |
|---|---|---|---|---|---|---|---|---|---|---|---|
| ZIP35 | 73.80 | 99.63 | 97.05 | 95.57 | 94.83 | 96.68 | 99.26 | 98.89 | 95.59 | 98.89 | 98.52 | 98.89 |
| ZIP38 | 74.17 | 99.63 | 97.05 | 95.57 | 94.83 | 96.68 | 99.26 | 98.89 | 95.59 | 98.89 | 98.52 | 98.89 |
| ZIP39 | 74.54 | 95.94 | 93.36 | 94.47 | 99.26 | 94.83 | 95.57 | 95.20 | 93.38 | 96.68 | 94.83 | 95.20 |

| | Monalysin | ZIP17 | ZIP18 | ZIP19 | ZIP20 | ZIP21 | ZIP22 | ZIP23 | ZIP24 | ZIP25 | ZIP26 | ZIP27 |
|---|---|---|---|---|---|---|---|---|---|---|---|---|
| Monalysin | | 73.80 | 74.17 | 73.80 | 73.80 | 73.80 | 74.54 | 73.80 | 73.80 | 73.80 | 74.17 | 73.80 |
| ZIP1 | 74.17 | 99.26 | 99.63 | 99.26 | 99.63 | 99.63 | 99.63 | 99.63 | 99.63 | 99.63 | 99.63 | 99.63 |
| ZIP2 | 71.59 | 96.68 | 97.05 | 96.68 | 97.05 | 97.05 | 97.05 | 97.05 | 97.05 | 97.05 | 97.05 | 97.05 |
| ZIP3 | 74.17 | 95.20 | 95.94 | 95.20 | 95.57 | 95.94 | 95.57 | 95.57 | 95.57 | 95.57 | 95.57 | 95.57 |
| ZIP5 | 73.80 | 94.47 | 94.83 | 94.47 | 94.83 | 94.83 | 94.83 | 94.83 | 94.83 | 94.83 | 94.83 | 94.83 |
| ZIP6 | 74.17 | 96.31 | 96.68 | 96.31 | 96.65 | 96.68 | 97.42 | 96.68 | 96.65 | 96.68 | 97.05 | 96.68 |
| ZIP8 | 73.80 | 98.89 | 99.26 | 98.89 | 99.26 | 99.26 | 99.26 | 99.26 | 99.26 | 99.26 | 99.26 | 99.26 |
| ZIP9 | 73.80 | 98.52 | 98.89 | 98.52 | 98.89 | 98.89 | 98.89 | 98.89 | 98.89 | 98.89 | 98.89 | 98.89 |
| ZIP10 | 71.60 | 95.22 | 95.59 | 95.22 | 95.59 | 95.59 | 95.59 | 95.59 | 95.59 | 95.59 | 95.59 | 95.59 |
| ZIP11 | 73.43 | 98.52 | 98.89 | 98.52 | 98.89 | 98.89 | 98.89 | 98.89 | 98.89 | 98.89 | 98.89 | 98.89 |
| ZIP12 | 74.17 | 98.16 | 98.52 | 98.16 | 98.52 | 98.52 | 99.26 | 98.52 | 98.52 | 98.52 | 98.89 | 98.52 |
| ZIP13 | 74.17 | 98.52 | 98.89 | 98.52 | 98.89 | 98.89 | 99.63 | 98.89 | 98.89 | 98.89 | 99.26 | 98.89 |
| ZIP17 | 73.80 | | 98.89 | 98.52 | 98.89 | 98.89 | 95.89 | 98.89 | 98.89 | 98.89 | 98.89 | 98.89 |
| ZIP18 | 74.17 | 98.89 | | 98.89 | 99.26 | 99.26 | 99.26 | 99.26 | 99.26 | 99.26 | 99.26 | 99.26 |
| ZIP19 | 73.80 | 98.52 | 98.89 | | 98.89 | 98.89 | 98.89 | 98.89 | 98.89 | 98.89 | 98.89 | 98.89 |
| ZIP20 | 73.80 | 98.89 | 99.26 | 98.89 | | 99.26 | 99.26 | 99.26 | 99.26 | 99.26 | 99.26 | 99.26 |
| ZIP21 | 73.80 | 98.89 | 99.26 | 98.89 | 99.26 | | 99.26 | 99.26 | 99.26 | 99.26 | 99.26 | 99.26 |
| ZIP22 | 74.54 | 98.89 | 99.26 | 98.89 | 99.26 | 99.26 | | 99.26 | 99.26 | 99.26 | 99.63 | 99.26 |
| ZIP23 | 73.80 | 98.89 | 99.26 | 98.89 | 99.26 | 99.26 | 99.26 | | 99.26 | 99.26 | 99.26 | 99.26 |
| ZIP24 | 73.80 | 98.89 | 99.26 | 98.89 | 99.26 | 99.26 | 99.26 | 99.26 | | 99.26 | 99.26 | 99.26 |
| ZIP25 | 73.80 | 98.89 | 99.26 | 98.89 | 99.26 | 99.26 | 99.26 | 99.26 | 99.26 | | 99.26 | 99.26 |
| ZIP26 | 74.17 | 98.89 | 99.26 | 98.89 | 99.26 | 99.26 | 99.63 | 99.26 | 99.26 | 99.26 | | 99.26 |
| ZIP27 | 73.80 | 98.89 | 99.26 | 98.89 | 99.26 | 99.26 | 99.26 | 99.26 | 99.26 | 99.26 | 99.26 | |
| ZIP28 | 74.17 | 98.89 | 99.26 | 98.89 | 99.26 | 99.26 | 99.26 | 99.26 | 99.26 | 99.26 | 99.26 | 99.26 |
| ZIP29 | 74.17 | 98.89 | 99.26 | 98.89 | 99.26 | 99.26 | 99.26 | 99.26 | 99.26 | 99.26 | 99.26 | 99.26 |
| ZIP30 | 73.80 | 98.16 | 98.52 | 98.16 | 98.52 | 98.52 | 98.52 | 98.52 | 98.52 | 98.52 | 98.52 | 98.52 |
| ZIP31 | 74.17 | 98.89 | 99.26 | 98.89 | 99.26 | 99.26 | 99.26 | 99.26 | 99.26 | 99.26 | 99.26 | 99.26 |
| ZIP32 | 73.80 | 98.89 | 99.26 | 98.89 | 99.26 | 99.26 | 99.26 | 99.26 | 99.26 | 99.26 | 99.26 | 99.26 |
| ZIP33 | 74.17 | 98.89 | 99.26 | 98.89 | 99.26 | 99.26 | 99.26 | 99.26 | 99.26 | 99.26 | 99.26 | 99.26 |
| ZIP34 | 73.80 | 98.89 | 99.26 | 98.89 | 99.26 | 99.26 | 99.26 | 99.26 | 99.26 | 99.26 | 99.26 | 99.26 |
| ZIP35 | 73.80 | 98.89 | 99.26 | 98.89 | 99.26 | 99.26 | 99.26 | 99.26 | 99.26 | 99.26 | 99.26 | 99.26 |
| ZIP38 | 74.17 | 98.89 | 99.26 | 98.89 | 99.26 | 99.26 | 99.26 | 99.26 | 99.26 | 99.26 | 99.26 | 99.26 |
| ZIP39 | 74.54 | 95.20 | 95.57 | 95.20 | 95.57 | 95.57 | 95.57 | 95.57 | 95.57 | 95.57 | 95.57 | 95.57 |

| | Monalysin | ZIP28 | ZIP29 | ZIP30 | ZIP31 | ZIP32 | ZIP33 | ZIP34 | ZIP35 | ZIP38 | ZIP39 |
|---|---|---|---|---|---|---|---|---|---|---|---|
| Monalysin | | 74.17 | 74.17 | 73.80 | 74.17 | 73.80 | 74.17 | 73.80 | 73.80 | 74.17 | 74.54 |
| ZIP1 | 74.17 | 99.63 | 99.63 | 98.89 | 99.63 | 99.63 | 99.63 | 99.63 | 99.63 | 99.63 | 95.94 |
| ZIP2 | 71.59 | 97.05 | 97.05 | 96.31 | 97.05 | 97.05 | 97.05 | 97.05 | 97.05 | 97.05 | 93.36 |
| ZIP3 | 74.17 | 95.57 | 95.57 | 95.57 | 95.57 | 95.57 | 95.57 | 95.57 | 95.57 | 95.57 | 94.47 |
| ZIP5 | 73.80 | 94.83 | 94.83 | 94.83 | 94.83 | 94.83 | 94.83 | 94.83 | 94.83 | 94.83 | 99.26 |
| ZIP6 | 74.17 | 96.68 | 96.68 | 96.31 | 96.68 | 96.68 | 96.68 | 96.68 | 96.68 | 96.68 | 94.83 |
| ZIP8 | 73.80 | 99.26 | 99.26 | 98.52 | 99.26 | 99.26 | 99.26 | 99.26 | 99.26 | 99.26 | 95.57 |
| ZIP9 | 73.80 | 98.89 | 98.89 | 98.16 | 98.89 | 98.89 | 98.89 | 98.89 | 98.89 | 98.89 | 95.20 |
| ZIP10 | 71.60 | 95.59 | 95.59 | 94.85 | 95.59 | 95.59 | 95.59 | 95.59 | 95.59 | 95.59 | 93.38 |
| ZIP11 | 73.43 | 98.89 | 98.89 | 98.16 | 98.89 | 98.89 | 98.89 | 98.89 | 98.89 | 98.89 | 96.68 |
| ZIP12 | 74.17 | 98.52 | 98.52 | 97.79 | 98.52 | 98.52 | 98.52 | 98.52 | 98.52 | 98.52 | 94.83 |
| ZIP13 | 74.17 | 98.89 | 98.89 | 98.16 | 98.89 | 98.89 | 98.89 | 98.89 | 98.89 | 98.89 | 95.20 |
| ZIP17 | 73.80 | 98.89 | 98.89 | 98.16 | 98.89 | 98.89 | 98.89 | 98.89 | 98.89 | 98.89 | 95.20 |
| ZIP18 | 74.17 | 99.26 | 99.26 | 98.52 | 99.26 | 99.26 | 99.26 | 99.26 | 99.26 | 99.26 | 95.57 |
| ZIP19 | 73.80 | 98.89 | 98.89 | 98.16 | 98.89 | 98.89 | 98.89 | 98.89 | 98.89 | 98.89 | 95.20 |
| ZIP20 | 73.80 | 99.26 | 99.26 | 98.52 | 99.26 | 99.26 | 99.26 | 99.26 | 99.26 | 99.26 | 95.57 |
| ZIP21 | 73.80 | 99.26 | 99.26 | 98.52 | 99.26 | 99.26 | 99.26 | 99.26 | 99.26 | 99.26 | 95.57 |
| ZIP22 | 74.54 | 99.26 | 99.26 | 98.52 | 99.26 | 99.26 | 99.26 | 99.26 | 99.26 | 99.26 | 95.57 |
| ZIP23 | 73.80 | 99.26 | 99.26 | 98.52 | 99.26 | 99.26 | 99.26 | 99.26 | 99.26 | 99.26 | 95.57 |
| ZIP24 | 73.80 | 99.26 | 99.26 | 98.52 | 99.26 | 99.26 | 99.26 | 99.26 | 99.26 | 99.26 | 95.57 |
| ZIP25 | 73.80 | 99.26 | 99.26 | 98.52 | 99.26 | 99.26 | 99.26 | 99.26 | 99.26 | 99.26 | 95.57 |
| ZIP26 | 74.17 | 99.26 | 99.26 | 98.52 | 99.26 | 99.26 | 99.26 | 99.26 | 99.26 | 99.26 | 95.57 |
| ZIP27 | 73.80 | 99.26 | 99.26 | 98.52 | 99.26 | 99.26 | 99.26 | 99.26 | 99.26 | 99.26 | 95.57 |
| ZIP28 | 74.17 | | 99.26 | 98.52 | 99.26 | 99.26 | 99.26 | 99.26 | 99.26 | 99.26 | 95.57 |
| ZIP29 | 74.17 | 99.26 | | 98.52 | 99.26 | 99.26 | 99.26 | 99.26 | 99.26 | 99.26 | 95.57 |
| ZIP30 | 73.80 | 98.52 | 98.52 | | 98.52 | 98.52 | 98.52 | 98.52 | 98.52 | 98.52 | 95.57 |
| ZIP31 | 74.17 | 99.26 | 99.26 | 98.52 | | 99.26 | 99.26 | 99.26 | 99.26 | 99.26 | 95.57 |
| ZIP32 | 73.80 | 99.26 | 99.26 | 98.52 | 99.26 | | 99.26 | 99.26 | 99.26 | 99.26 | 95.57 |
| ZIP33 | 74.17 | 99.26 | 99.26 | 98.52 | 99.26 | 99.26 | | 99.26 | 99.26 | 99.26 | 95.57 |
| ZIP34 | 73.80 | 99.26 | 99.26 | 98.52 | 99.26 | 99.26 | 99.26 | | 99.26 | 99.26 | 95.57 |
| ZIP35 | 73.80 | 99.26 | 99.26 | 98.52 | 99.26 | 99.26 | 99.26 | 99.26 | | 99.26 | 95.57 |
| ZIP38 | 74.17 | 99.26 | 99.26 | 98.52 | 99.26 | 99.26 | 99.26 | 99.26 | 99.26 | | 95.57 |
| ZIP39 | 74.54 | 95.57 | 95.57 | 95.57 | 95.57 | 95.57 | 95.57 | 95.57 | 95.57 | 95.57 | |

Figure 5:
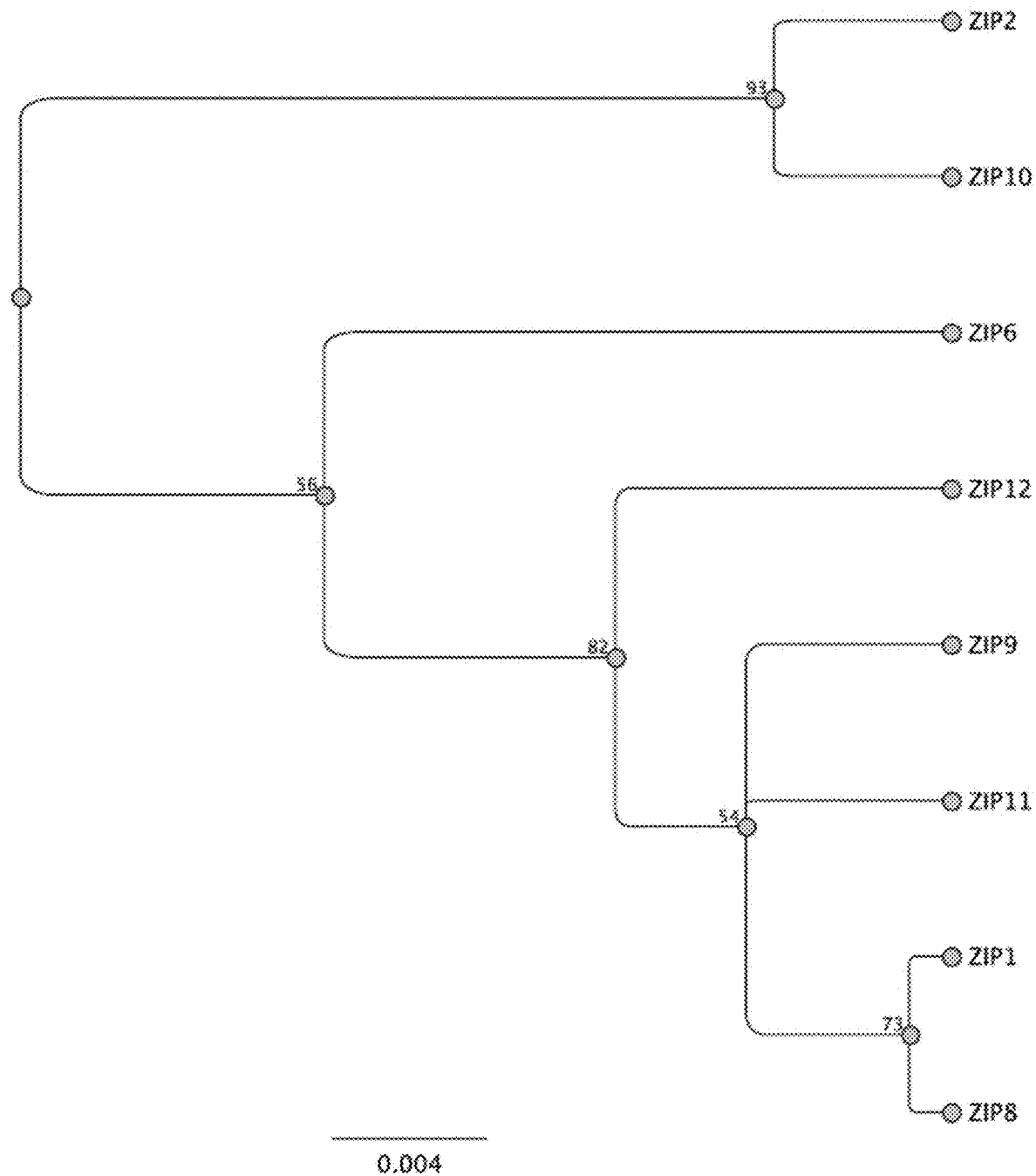
FIG. 5 illustrates a phylogenetic tree of eight novel insecticidal proteins found in Table 3 and FIG. 3, which were discovered utilizing the IPDP.

A multiple sequence alignment for the eight novel insecticidal proteins from Table 3 (i.e., ZIP1, ZIP2, ZIP6, ZIP8, ZIP9, ZIP10, ZIP11, and ZIP12) can be found in FIG. 3, with a corresponding phylogenetic tree found in FIG. 5. A multiple sequence alignment of the eight novel insecticidal proteins from Table 3 (i.e., ZIP1, ZIP2, ZIP6, ZIP8, ZIP9, ZIP10, ZIP11, and ZIP12), plus monalysin, can be found in FIG. 4, with a corresponding phylogenetic tree found in FIG. 6.

Example 3: Insecticidal Proteins—Lysate Insect Feeding Assays

Lysate from bacteria expressing either ZIP1 (SEQ ID NO: 2), or an empty vector control, were compared to water in an insect feeding assay utilizing Brown Marmorated Stinkbugs (*Halyomorpha halys*).

2 cm of a wick was moistened with 0.5 mL of lysate, or water, and placed in a plate with 2 first instar nymphs (one observation). 8 observations per lysate, or water, were tested for a total of 16 insects per sample.

Mortality was measured after 7 days.

Insects allowed to ingest bacterial lysate from cells containing empty vector showed similar levels of mortality, as those ingesting water.

Figure 10:
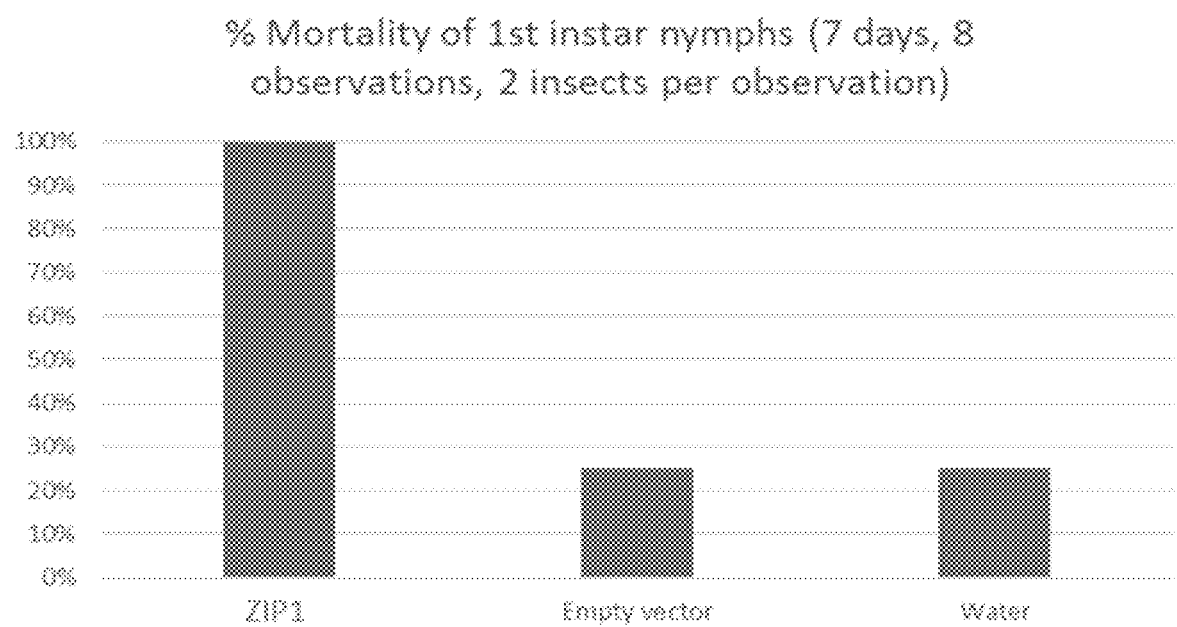
FIG. 10 illustrates the results from an insect lysate experiment. Insects (*Halyomorpha halys*—Brown Marmorated Stink Bug) that ingested bacterial lysate containing an insecticidal protein discovered via the IPDP exhibited a 100% mortality rate.

Insects allowed to ingest bacterial lysate expressing ZIP1 (SEQ ID NO: 2) showed 100% mortality in this assay. These results are illustrated in FIG. 10.

Consequently, an insecticidal protein as taught herein demonstrates significant insecticidal activity against a member of the Order Hemiptera and family Pentatomidae.

Example 4: Insecticidal Proteins—Purified Protein Insect Feeding Assays

From the 36 novel insecticidal proteins represented in Table 3, we engineered 10 protein sequences to be fused with an N-terminal 6xHis protein tag for purification: a) SEQ ID NO: 2 that is ZIP1, b) SEQ ID NO: 4 that is ZIP2, c) SEQ ID NO: 8 that is ZIP4, d) SEQ ID NO: 12 that is ZIP6, e) SEQ ID NO: 14 that is ZIP8, f) SEQ ID NO: 16 that is ZIP9, g) SEQ ID NO: 18 that is ZIP10, h) SEQ ID NO: 20 that is ZIP11, i) SEQ ID NO: 22 that is ZIP12 and i) SEQ ID NO: 26 that is ZIP16. Lysate from bacteria expressing these 10 tagged proteins were incubated with Ni-NTA beads (Qiagen) to specifically bind the proteins. These proteins were eluted from the beads, dialyzed and used for insect feeding assay utilizing Brown Marmorated Stinkbugs (*Halyomorpha halys*).

For Brown Marmorated Stinkbugs, 2 cm of a wick was moistened with 0.5 mL of purified protein, or buffer control or water, and placed in a plate with 2 first instar nymphs (one observation). 8 observations per lysate, or water, were tested for a total of 16 insects per sample.

Mortality was measured after 5 days.

Insects allowed to ingest these 10 purified proteins showed varying degrees of mortality in this assay. These results are illustrated in FIG. 7.

Furthermore, of the ten tested proteins, three purified proteins (ZIP1, ZIP2, and ZIP4) of varying dilutions were used for replicate insect feeding assays with Brown Marmorated Stinkbugs to establish a LC50 value through Probit Analysis. These results are illustrated in FIG. 8.

Consequently, these insecticidal proteins as taught herein demonstrates significant insecticidal activity against a member of the Order Hemiptera and family Pentatomidae.

To determine the effective range of insects for these insecticidal proteins, we performed insect bioassays against members of the two other major Orders of insects—Fall Armyworm (*Spodoptera frugiperda*) from the order Lepidoptera and Southern Corn Rootworm (*Diabrotica undecimpunctata*) from the order Coleoptera. Briefly, for Fall armyworm, warm multispecies insect diet is dispensed into standard 128-well bioassay trays at a rate of 1.0 ml/well which provides a surface area of 1.5 $cm^2$ within each well. Each test well was treated by applying 40 µl of purified protein onto the diet surface. Once the application has dried, one neonate fall armyworm larva is placed into each well. The assay consists of 16 individual wells per treatment. Buffer-only treated wells serve as the negative control. Growth by weight was measured after 7 days.

The methods used for Southern Corn Rootworm were similar to those used for Fall Armyworm except a Southern Corn Rootworm specific diet was used.

Insects allowed to ingest purified protein expressing ZIP1, ZIP2 and ZIP4 showed varying degrees of growth inhibition in this assay. The results for Fall Armyworm are illustrated in FIG. 9A and the results for Southern Corn Rootworm are illustrated in FIG. 9B.

Consequently, these insecticidal proteins as taught herein demonstrates significant growth inhibitory activity against a members of the Order Lepidoptera and family Noctuidae, and the Order Coleoptera and family Chrysomelidae.

Example 5: Identification of Novel Insecticidal Proteins Utilizing Homology and Profile/HMM Methods (IPDP—HMM Construction)

As discussed previously, the IPDP can optionally involve the utilization of a HMM algorithm and modeling procedure. This procedure allows for the development of a HMM profile from the discovered insecticidal protein sequences that identifies genes encoding monalysin-like insecticidal proteins that would not be possible to identify using some methods of the art, e.g. BLAST.

An example of the HMM process is described below and was built using eight insecticidal proteins discovered via the IPDP and found in Table 3 and highlighted in FIG. 4. An example HMM built using eight insecticidal proteins identified using methods described herein is provided in Table 6. These proteins have the amino acid sequences shown in: a) SEQ ID NO: 2 that is ZIP1, b) SEQ ID NO: 4 that is ZIP2, c) SEQ ID NO: 12 that is ZIP6, d) SEQ ID NO: 14 that is ZIP8, e) SEQ ID NO: 16 that is ZIP9, f) SEQ ID NO: 18 that is ZIP10, g) SEQ ID NO: 20 that is ZIP11 and h) SEQ ID NO: 22 that is ZIP12.

The model was constructed using the HMMER software (Version 3.1b2; February 2015) and the output model can be found in Table 6. The HMM utilized the aforementioned eight sequences to create a model of what a "monalysin-like" sequence (based on the eight utilized sequences) would entail. Now, based on the HMM, it is possible to analyze future putative insecticidal proteins discovered with the IPDP to determine the likelihood that the newly discovered sequences are a "monalysin-like" sequence.

Example 6: Transformed Plants

Experiments were conducted to transform a plant of interest (e.g., maize and soybean) for stable expression of insecticidal proteins disclosed herein. Three ZIP proteins, ZIP1, ZIP2 and ZIP4, demonstrated to kill insects in in vitro bioassays (see, e.g., Example 4) were selected to be transformed into two crop plants of interest—soybean and maize. These sequences were codon optimized for optimal expression in the plants of interest and synthesized and cloned into specific expression vectors for both soybean and maize.

Soybean

Soybean seeds are surface sanitized in 20% Clorox, rinsed with sterile water, then primed by allowing them to sit for 2 hours at room temperature. Seeds are then imbibed in Germination Medium overnight. Meristem explants are prepared the next day by removing seed coats and cotyledons from the seed. Meristem explants are then either dried under a variety of conditions, or used fresh. For biolistic DNA delivery, vectors are coated onto gold particles (0.6 μm) for particle bombardment via the Bio-Rad PDS-1000 Helium gun according to standard protocol. For particle bombardment, explants are pre-cultured overnight, bombarded, allowed to rest, then transferred to selection. Shoots from spectinomycin resistant plantlets are harvested and rooted on rooting media containing IAA and spectinomycin. Rooted plants are transplanted to soil and grown in the greenhouse to produce T1 seed.

Maize

Immature embryos (1.5-2.0 mm) from greenhouse or field grown Hi-II maize are dissected out in a sterile hood. Embryos are co-cultured for 1-2 days at 23° C. in the dark with *Agrobacterium* strain AGL-1 at a final OD660 of ~0.4 axis side down on solid co-cultivation medium. Embryos are then transferred to solid induction media, axis side down, and incubated at 28° C. for 5 days in the dark. Embryos are then transferred to solid selection 1 medium (bialaphos) and incubated at 28° C. for two weeks in the dark. Embryos are transferred to solid selection medium 2 (bialaphos) and incubated at 28° C. in the dark. Resistant callus forming embryos are transferred every two weeks until diameter is about 1.5-2 cm. Transfer resistant calli to solid regeneration medium 1 at 28° C. for 2 weeks. Transfer calli to regeneration medium 2 at 28° C. under 16 hour photoperiod until shoots and roots develop. Transfer plantlets to soil and grow to maturity.

Figure 11:
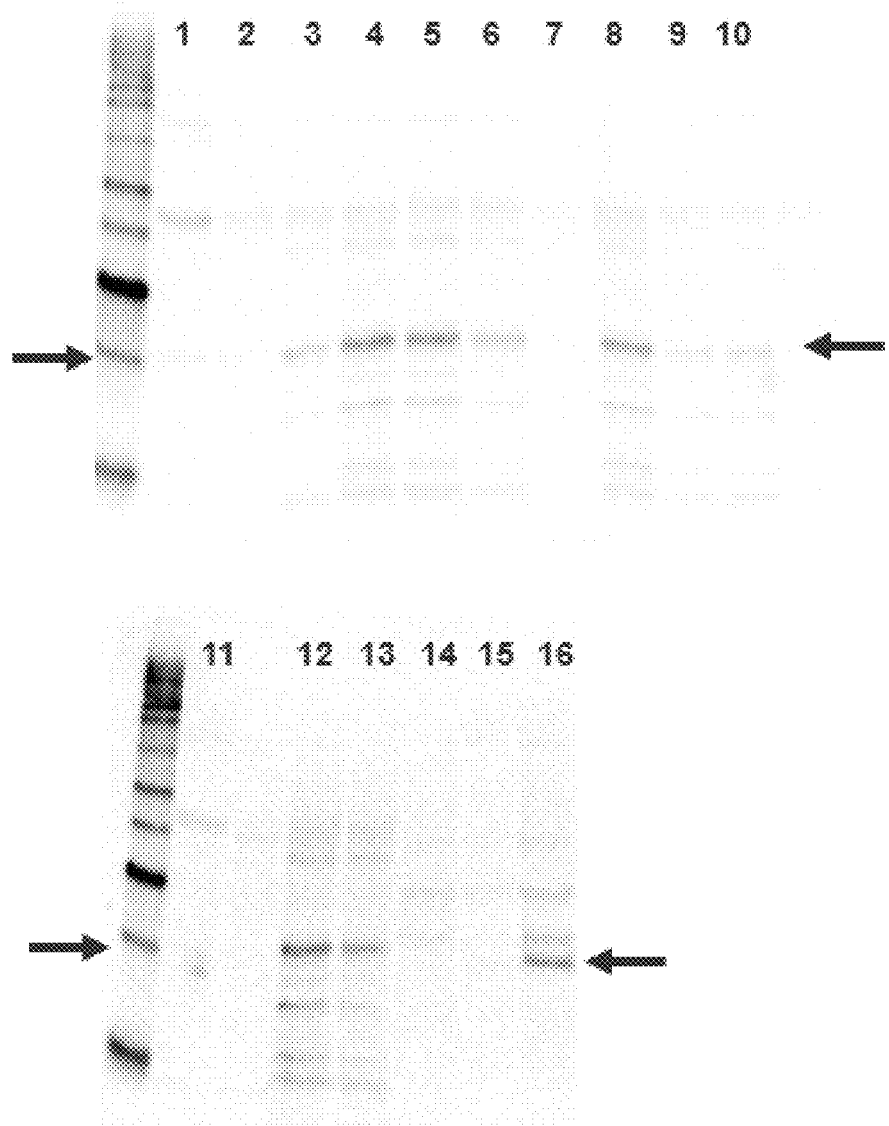
FIG. 11 illustrates the western blot results from Example 6, which shows expression of ZIP proteins from soybean and corn leaves. Lanes 1 and 11: Negative Control (untransformed soybean leaves); Lanes 2 and 3: ZIP1 Transformed soybean leaves; Lanes 4-10: ZIP2 Transformed soybean leaves; Lanes 12 and 13: ZIP4 Transformed soybean leaves; Lane 14: Negative Control (untransformed maize leaves); Lanes 15 and 16: ZIP2 Transformed maize leaves.

To select plants expressing insecticidal proteins taught in this disclosure, antibiotic selection media was used for further growth of regenerated shoots from the calli, and the regenerated plants were tested for the expression of insecticidal proteins disclosed herein. As shown in FIG. 11, expression of ZIP1, ZIP2 and ZIP4 proteins was detected by Western Blotting with a ZIP-specific antibody from leaves of the transformed soybean plants (Lanes 2-10 and 12-13 of FIG. 11). Also, ZIP2 protein expression was confirmed in leaves of maize plants transformed with expression vector specific for ZIP2 (Lanes 15 and 16 of FIG. 11). Other transgenic soybean and maize plants expressing insecticidal proteins found in Table 3 are being tested for expression of the proteins of interest.

Furthermore, insect feeding assays are being carried out with a part (e.g. leaves, stems, roots, flowers, fruits, seeds, or seedlings) of the transformed plants stably expressing the insecticidal proteins of interest, including ZIP1, ZIP2, and ZIP4 shown in Example 6 as well as other ZIP proteins found in Table 3.

TABLE 6

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD  -5.1315   0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| COMPO | 2.49688 | 4.38085 | 2.89420 | 2.83896 | 3.17739 | 2.74693 | 3.76314 | 2.84203 | 2.81709 | 2.55776 | 3.86213 | 3.04964 | 3.45042 | 3.03015 | 3.10670 | 2.49841 | 2.71919 | 2.59721 | 4.46810 | 3.23303 | |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.00000 | * | | | | | | | | | | | | | | |
| 1 | 2.92069 | 4.48020 | 3.98129 | 3.57113 | 3.18275 | 3.78627 | 4.32118 | 2.35208 | 3.34223 | 1.78828 | 1.50662 | 3.85616 | 4.24761 | 3.72903 | 3.55483 | 3.26253 | 3.22531 | 2.35043 | 5.01429 | 3.76968 | 1 m - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 2 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 2 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 3 | 2.98131 | 4.41980 | 4.24162 | 3.85620 | 3.33257 | 3.94480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 3 i - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 4 | 2.91557 | 4.87384 | 3.08714 | 2.72252 | 4.24557 | 3.41039 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.13178 | 4 k - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 5 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.05993 | 3.09149 | 2.88987 | 3.20420 | 3.46469 | 5.51627 | 4.24017 | 5 e - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 6 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.05993 | 3.09149 | 2.88987 | 3.20420 | 3.46469 | 5.51622 | 4.24017 | 6 e - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 7 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 7 l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 8 | 2.19939 | 4.16075 | 3.07524 | 2.86856 | 4.19842 | 2.26559 | 4.04696 | 3.66282 | 3.00754 | 3.34450 | 4.18714 | 3.11776 | 3.61262 | 3.31263 | 3.33572 | 1.44764 | 2.67538 | 3.13195 | 5.52641 | 4.27542 | 8 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 9 | 2.73569 | 4.88388 | 2.64985 | 2.40631 | 4.13527 | 3.28203 | 3.66153 | 3.71230 | 2.33599 | 3.27126 | 4.16322 | 2.63239 | 3.81944 | 1.71852 | 2.66538 | 2.74932 | 3.01644 | 3.37216 | 5.36856 | 4.00601 | 9 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

| HMMER3/f [3.1b2] | February 2015 | | | | | | | | | | | | | | | | | | | | | |
|---|---|---|---|---|---|---|---|---|---|---|---|---|---|---|---|---|---|---|---|---|---|---|
| NAME | zips | | | | | | | | | | | | | | | | | | | | | |
| LENG | 272 | | | | | | | | | | | | | | | | | | | | | |
| ALPH | amino | | | | | | | | | | | | | | | | | | | | | |
| RF | no | | | | | | | | | | | | | | | | | | | | | |
| MM | no | | | | | | | | | | | | | | | | | | | | | |
| CONS | yes | | | | | | | | | | | | | | | | | | | | | |
| CS | no | | | | | | | | | | | | | | | | | | | | | |
| MAP | yes | | | | | | | | | | | | | | | | | | | | | |
| DATE | Thu Feb 21 21:13:29 2019 | | | | | | | | | | | | | | | | | | | | | |
| NSEQ | 8 | | | | | | | | | | | | | | | | | | | | | |
| EFFN | 0.417969 | | | | | | | | | | | | | | | | | | | | | |
| CKSUM | 1653877865 | | | | | | | | | | | | | | | | | | | | | |
| STATS | LOCAL MSV | −11.4830 | 0.70210 | | | | | | | | | | | | | | | | | | | |
| STATS | LOCAL VITERBI | −11.8487 | 0.70210 | | | | | | | | | | | | | | | | | | | |
| STATS | LOCAL FORWARD | −5.1315 | 0.70210 | | | | | | | | | | | | | | | | | | | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m → m | m → i | m → d | i → m | i → i | d → m | d → d | | | | | | | | | | | | | | |
| 10 | 2.67118 | 4.43758 | 3.27171 | 3.10268 | 4.10073 | 3.12878 | 4.18431 | 3.63096 | 3.15473 | 3.26429 | 4.31243 | 3.41512 | 0.95588 | 3.54553 | 3.40634 | 2.83701 | 3.10805 | 3.28352 | 5.30361 | 4.22102 | 10 p - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 11 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 11 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 12 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 12 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 13 | 2.92923 | 4.75570 | 3.06737 | 2.82225 | 3.24301 | 3.39609 | 1.28522 | 3.62204 | 2.66722 | 3.12353 | 4.16260 | 3.23362 | 3.94584 | 3.18806 | 2.93608 | 3.00091 | 3.23101 | 3.35853 | 4.70870 | 3.19598 | 13 h - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 14 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 14 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 15 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 15 v - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 16 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.05593 | 3.09149 | 2.88987 | 3.20420 | 3.46469 | 5.51622 | 4.24017 | 16 e - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 17 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 17 l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 18 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 18 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 19 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 19 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 20 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 20 l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| 21 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 21 q |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 22 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 22 v |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 23 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 23 g |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 24 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.03593 | 3.09149 | 2.88987 | 3.20420 | 3.46469 | 5.51622 | 4.24017 | 24 e |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 25 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 25 v |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 26 | 2.28599 | 4.20474 | 3.15513 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 26 s |
| | 2.68618 | 4.42225 | 2.77519 | 2.73123 | 3.46354 | 2.40513 | 3.72494 | 3.24354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 27 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 27 a |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 28 | 2.93567 | 4.77649 | 3.42005 | 2.94650 | 4.11486 | 3.43409 | 3.78227 | 3.65333 | 2.21804 | 3.18106 | 4.18431 | 3.31043 | 3.94105 | 3.60701 | 1.08112 | 3.02376 | 3.20684 | 3.38040 | 5.22475 | 4.05755 | 28 r |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 29 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.03593 | 3.09149 | 2.88987 | 3.20420 | 3.46469 | 5.51622 | 4.24017 | 29 e |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 30 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 30 a |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 31 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 31 l |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

| HMMER3/f [3.1b2] \| February 2015 | | | | | | | | | | | | | | | | | | | | | | |
|---|---|---|---|---|---|---|---|---|---|---|---|---|---|---|---|---|---|---|---|---|---|---|
| NAME | zips | | | | | | | | | | | | | | | | | | | | | | |
| LENG | 272 | | | | | | | | | | | | | | | | | | | | | | |
| ALPH | amino | | | | | | | | | | | | | | | | | | | | | | |
| RF | no | | | | | | | | | | | | | | | | | | | | | | |
| MM | no | | | | | | | | | | | | | | | | | | | | | | |
| CONS | yes | | | | | | | | | | | | | | | | | | | | | | |
| CS | no | | | | | | | | | | | | | | | | | | | | | | |
| MAP | yes | | | | | | | | | | | | | | | | | | | | | | |
| DATE | Thu Feb 21 21:13:29 2019 | | | | | | | | | | | | | | | | | | | | | | |
| NSEQ | 8 | | | | | | | | | | | | | | | | | | | | | | |
| EFFN | 0.417969 | | | | | | | | | | | | | | | | | | | | | | |
| CKSUM | 165377865 | | | | | | | | | | | | | | | | | | | | | | |
| STATS | LOCAL MSV | −11.4830 | 0.70210 | | | | | | | | | | | | | | | | | | | | |
| STATS | LOCAL VITERBI | −11.8487 | 0.70210 | | | | | | | | | | | | | | | | | | | | |
| STATS | LOCAL FORWARD | −5.1315 | 0.70210 | | | | | | | | | | | | | | | | | | | | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| 32 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 32 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 33 | 2.00874 | 4.12949 | 3.18245 | 2.95794 | 4.11369 | 2.88690 | 4.07663 | 3.47283 | 3.02570 | 3.23256 | 4.11484 | 3.16284 | 3.62621 | 3.35625 | 3.32901 | 1.36684 | 2.66847 | 3.00171 | 5.49017 | 4.22951 | 33 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 34 | 2.67266 | 4.66469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 34 n - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 35 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 4.21744 | 35 f - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 36 | 1.11031 | 4.16266 | 3.39952 | 3.18951 | 3.99036 | 2.98856 | 4.21886 | 3.10649 | 3.20414 | 2.94084 | 4.03105 | 3.35470 | 3.72187 | 3.55158 | 3.45819 | 2.51417 | 2.78716 | 2.77211 | 5.42402 | 4.21744 | 36 a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 37 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 37 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 38 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32278 | 1.19199 | 2.76159 | 3.07699 | 5.39114 | 4.09669 | 38 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 39 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 39 f - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 40 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 40 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 41 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.84411 | 3.13068 | 3.32998 | 5.25766 | 3.94763 | 41 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 42 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 42 f - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| 43 | 2.67118 | 4.43758 | 3.27171 | 3.10268 | 4.10073 | 3.12878 | 4.18431 | 3.63096 | 3.15473 | 3.26429 | 4.31243 | 3.41512 | 0.95588 | 3.54553 | 3.40634 | 2.83701 | 3.10805 | 3.28352 | 5.30361 | 4.22102 | 43 p |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 44 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 44 t |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 45 | 2.91557 | 4.87384 | 3.08714 | 2.72252 | 4.24557 | 3.41039 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.13178 | 45 k |
| | 2.68618 | 4.42225 | 2.77519 | 2.73123 | 3.46354 | 2.40513 | 3.72494 | 3.29354 | 2.67741 | 2.69355 | 4.24690 | 2.40347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 46 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 46 s |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 47 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 47 g |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.63351 | 3.80839 | 4.53074 | 0.61958 | 0.77255 | 0.48576 | 0.95510 | | | | | | | | | | | | | | |
| 48 | 2.20984 | 4.16363 | 3.08719 | 2.88717 | 4.17468 | 2.53250 | 4.05422 | 3.64534 | 3.01073 | 3.33804 | 4.19084 | 3.13103 | 3.62005 | 3.32767 | 3.32855 | 1.33690 | 2.68690 | 3.12426 | 5.50843 | 4.25298 | 48 s |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 49 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 49 f |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 50 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.03593 | 3.09149 | 2.88987 | 3.20420 | 3.46469 | 5.51622 | 4.24017 | 50 e |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 51 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 51 i |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 52 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 52 d |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 53 | 2.91557 | 4.87384 | 3.08714 | 2.72252 | 4.24557 | 3.41039 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.13178 | 53 k |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 163877865
STATS LOCAL MSV       -11.4830  0.70210
STATS LOCAL VITERBI   -11.8487  0.70210
STATS LOCAL FORWARD    -5.1315  0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 54 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07444 | 54 y |
|    | 2.68618 | 4.42225 | 2.77519 | 2.73123 | 3.46354 | 2.40513 | 3.72494 | 3.29354 | 2.67741 | 2.69355 | 4.24640 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 55 | 3.08469 | 4.56681 | 4.08883 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 55 l |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 56 | 3.08469 | 4.56681 | 4.08883 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 56 l |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 57 | 2.67266 | 4.66469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 57 n |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 58 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07444 | 58 y |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 59 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 59 a |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 60 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 60 d |
|    | 2.68618 | 4.42225 | 2.77519 | 2.73123 | 3.46354 | 2.40513 | 3.72494 | 3.29354 | 2.67741 | 2.69355 | 4.24690 | 2.94347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 61 | 2.67118 | 4.43758 | 3.27171 | 3.10268 | 4.10073 | 3.12878 | 4.18431 | 3.63096 | 3.15473 | 3.26429 | 4.31243 | 3.41512 | 0.95588 | 3.54553 | 3.40634 | 2.83701 | 3.10805 | 3.28352 | 5.30361 | 4.22102 | 61 p |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 62 | 2.91557 | 4.87384 | 3.08714 | 2.72252 | 4.24557 | 3.41039 | 3.72746 | 3.67115 | 1.12970 | 3.25103 | 4.21733 | 3.14973 | 3.91643 | 2.92363 | 2.42483 | 2.96260 | 3.17436 | 3.38305 | 5.32773 | 4.13178 | 62 k |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 63 | 2.91557 | 4.87384 | 3.08714 | 2.72252 | 4.24557 | 3.41039 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.13178 | 63 k |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |
| 64 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 64 g |
|    | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|    | 0.03351 | 3.80839 | 4.53074 | 0.61958 | 0.77255 | 0.48576 | 0.95510 | | | | | | | | | | | | | | |

TABLE 6-continued

| HMMER3/f [3.1b2] | February 2015 | | | | | | | | | | | | | | | | | | | | | | |
|---|---|---|---|---|---|---|---|---|---|---|---|---|---|---|---|---|---|---|---|---|---|---|---|
| NAME | zips | | | | | | | | | | | | | | | | | | | | | | |
| LENG | 272 | | | | | | | | | | | | | | | | | | | | | | |
| ALPH | amino | | | | | | | | | | | | | | | | | | | | | | |
| RF | no | | | | | | | | | | | | | | | | | | | | | | |
| MM | no | | | | | | | | | | | | | | | | | | | | | | |
| CONS | yes | | | | | | | | | | | | | | | | | | | | | | |
| CS | no | | | | | | | | | | | | | | | | | | | | | | |
| MAP | yes | | | | | | | | | | | | | | | | | | | | | | |
| DATE | Thu Feb 21 21:13:29 2019 | | | | | | | | | | | | | | | | | | | | | | |
| NSEQ | 8 | | | | | | | | | | | | | | | | | | | | | | |
| EFFN | 0.417969 | | | | | | | | | | | | | | | | | | | | | | |
| CKSUM | 163377865 | | | | | | | | | | | | | | | | | | | | | | |
| STATS | LOCAL MSV | −11.4830 | 0.70210 | | | | | | | | | | | | | | | | | | | | |
| STATS | LOCAL VITERBI | −11.8487 | 0.70210 | | | | | | | | | | | | | | | | | | | | |
| STATS | LOCAL FORWARD | −5.1315 | 0.70210 | | | | | | | | | | | | | | | | | | | | |

| HMM | A | C | D | E | F | G | H | I | K | L | M | N | P | Q | R | S | T | V | W | Y | |
| --- | --- | --- | --- | --- | --- | --- | --- | --- | --- | --- | --- | --- | --- | --- | --- | --- | --- | --- | --- | --- |
| | m→m | m→i | m→d | i→m | i→i | d→m | d→d | | | | | | | | | | | | | | |
| 65 | 2.51796 | 1.08037 | 4.02002 | 3.74616 | 3.75363 | 3.15316 | 4.40750 | 2.88810 | 3.57311 | 2.80586 | 3.92566 | 3.75027 | 3.85502 | 3.92202 | 3.70837 | 2.78924 | 2.97954 | 2.63671 | 5.18182 | 4.04137 | 65 c - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 66 | 2.86633 | 4.50319 | 3.67292 | 3.18234 | 2.80653 | 3.61109 | 3.68768 | 3.06521 | 2.75280 | 2.59879 | 3.66030 | 3.46849 | 4.05108 | 3.28633 | 2.60423 | 3.05056 | 3.12115 | 2.88599 | 1.73785 | 2.82731 | 66 w - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 67 | 3.08469 | 4.56681 | 4.08883 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 67 l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 68 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 68 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 69 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 69 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 70 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 70 v - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 71 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 71 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 72 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 72 v - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 73 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 73 y - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 74 | 2.58929 | 4.36940 | 3.24976 | 3.14188 | 4.28221 | 0.63523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 74 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 75 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 75 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | | |
|---|---|---|---|---|---|---|---|---|---|---|---|---|---|---|---|---|---|---|---|---|---|---|
| | m->m | m->i | m->d | i->m | i->i | d->m | d->d | | | | | | | | | | | | | | | |
| 76 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 76 | l |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 77 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 77 | y |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 78 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 78 | i |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 79 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 79 | g |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 80 | 2.91557 | 4.87384 | 3.08714 | 2.72252 | 4.24557 | 3.41039 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.11178 | 80 | k |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 81 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.84411 | 3.13068 | 3.32998 | 5.25766 | 3.94763 | 81 | q |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 82 | 2.67266 | 4.66469 | 2.67738 | 2.55713 | 4.61837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 82 | n |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 83 | 3.23357 | 4.63032 | 3.99599 | 3.68726 | 2.60690 | 3.66065 | 3.82592 | 3.25571 | 3.41132 | 2.66106 | 3.89235 | 3.84955 | 4.17341 | 3.80241 | 3.55653 | 3.43778 | 3.53106 | 3.14428 | 1.02517 | 2.61260 | 83 | w |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 84 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 84 | g |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 85 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 85 | t |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 86 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 86 | y |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 1653877865
STATS LOCAL MSV       -11.4830  0.70210
STATS LOCAL VITERBI   -11.8487  0.70210
STATS LOCAL FORWARD    -5.1315  0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 87 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 87 t - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 88 | 2.93567 | 4.77649 | 3.42005 | 2.94650 | 4.11486 | 3.43409 | 3.78227 | 3.65333 | 2.21804 | 3.18106 | 4.18431 | 3.31043 | 3.94105 | 3.00701 | 1.08112 | 3.02376 | 3.20684 | 3.38040 | 5.22475 | 4.05755 | 88 r - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 89 | 2.67118 | 4.43758 | 3.27171 | 3.10268 | 4.10073 | 3.12878 | 4.18431 | 3.63096 | 3.15473 | 3.26429 | 4.31243 | 3.41512 | 0.95588 | 3.54553 | 3.40634 | 2.83701 | 3.10805 | 3.28352 | 5.30361 | 4.22162 | 89 p - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 90 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 90 v - - - |
|  | 2.68618 | 4.42225 | 2.77519 | 2.73123 | 3.46354 | 2.40513 | 3.72494 | 3.24354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 91 | 2.73092 | 4.35800 | 3.73706 | 3.36576 | 1.56351 | 3.56518 | 3.77172 | 2.75896 | 3.29904 | 2.36459 | 3.51384 | 3.56082 | 4.07743 | 3.56463 | 3.53311 | 2.63475 | 3.05442 | 2.60563 | 4.26403 | 2.67171 | 91 f - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.63351 | 3.80839 | 4.53074 | 0.61958 | 0.77255 | 0.48576 | 0.95510 | | | | | | | | | | | | | | |
| 92 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 92 a - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 93 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 93 y - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 94 | 3.08469 | 4.56681 | 4.08583 | 3.72691 | 3.11381 | 3.89935 | 4.40279 | 2.31622 | 3.49521 | 0.95845 | 3.15956 | 4.00841 | 4.34677 | 3.87896 | 3.68117 | 3.46490 | 3.38246 | 2.33662 | 4.96833 | 3.67637 | 94 l - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 95 | 2.83288 | 4.61384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 95 q - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 96 | 2.92923 | 4.75570 | 3.06737 | 2.82225 | 3.24301 | 3.39609 | 1.28522 | 3.62204 | 2.66722 | 3.12353 | 4.16260 | 3.23362 | 3.94584 | 3.18806 | 2.93608 | 3.00091 | 3.23101 | 3.35853 | 4.70870 | 3.19598 | 96 h - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |
| 97 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 97 t - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
|  | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 98 | 2.92310 2.68618 0.03351 | 5.03735 4.42225 3.80839 | 1.01454 2.77519 4.53074 | 2.30009 2.73123 0.61958 | 4.40640 3.46354 0.77255 | 3.16420 2.40513 0.48576 | 3.87837 3.72494 0.95510 | 3.98050 3.29354 | 2.95099 2.67741 | 3.60099 2.69355 | 4.57912 4.24690 | 2.85261 2.90347 | 3.81266 2.73739 | 3.11848 3.18146 | 3.45728 2.89801 | 2.89377 2.37887 | 3.26085 2.77519 | 3.62704 2.98518 | 5.58736 4.58477 | 4.29177 3.61503 | 98 d - - - |
| 99 | 2.38088 2.68618 0.03351 | 4.22532 4.42225 3.80839 | 3.37373 2.77519 4.53074 | 3.12452 2.73123 0.61958 | 3.91469 3.46354 0.77255 | 3.06626 2.40513 0.48576 | 4.14640 3.72494 0.95510 | 3.03411 3.29354 | 3.06620 2.67741 | 2.89981 2.69355 | 3.95571 4.24690 | 3.34319 2.90347 | 3.76550 2.73739 | 3.46463 3.18146 | 3.32709 2.89801 | 2.58160 2.37887 | 1.28546 2.77519 | 2.73596 2.98518 | 5.35824 4.58477 | 4.13176 3.61503 | 99 t - - - |
| 100 | 2.98131 2.68618 0.03351 | 4.41980 4.42225 3.80839 | 4.24162 2.77519 4.53074 | 3.85620 2.73123 0.61958 | 3.33257 3.46354 0.77255 | 3.99480 2.40513 0.48576 | 4.59720 3.72494 0.95510 | 1.16111 3.29354 | 3.68296 2.67741 | 1.93351 2.69355 | 3.27971 4.24690 | 4.11059 2.90347 | 4.43351 2.73739 | 4.03877 3.18146 | 3.88695 2.89801 | 3.48513 2.37887 | 3.28221 2.77519 | 1.84862 2.98518 | 5.20905 4.58477 | 3.94078 3.61503 | 100 i - - - |
| 101 | 2.36588 2.68618 0.03351 | 4.26905 4.42225 3.80839 | 3.21789 2.77519 4.53074 | 2.89869 2.73123 0.61958 | 3.73913 3.46354 0.77255 | 3.09456 2.40513 0.48576 | 3.93689 3.72494 0.95510 | 3.15907 3.29354 | 2.84145 2.67741 | 2.61114 2.69355 | 3.88420 4.24690 | 3.19454 2.90347 | 3.74532 2.73739 | 3.23703 3.18146 | 3.14944 2.89801 | 1.51879 2.37887 | 2.77535 2.77519 | 2.83604 2.98518 | 5.19347 4.58477 | 3.84812 3.61503 | 101 s - - - |
| 102 | 2.98131 2.68618 0.03351 | 4.41980 4.42225 3.80839 | 4.24162 2.77519 4.53074 | 3.85620 2.73123 0.61958 | 3.33257 3.46354 0.77255 | 3.99480 2.40513 0.48576 | 4.59720 3.72494 0.95510 | 1.16111 3.29354 | 3.68296 2.67741 | 1.93351 2.69355 | 3.27971 4.24690 | 4.11059 2.90347 | 4.43351 2.73739 | 4.03877 3.18146 | 3.88695 2.89801 | 3.48513 2.37887 | 3.28221 2.77519 | 1.84862 2.98518 | 5.20905 4.58477 | 3.94078 3.61503 | 102 i - - - |
| 103 | 2.67118 2.68618 0.03351 | 4.43758 4.42225 3.80839 | 3.27171 2.77519 4.53074 | 3.10268 2.73123 0.61958 | 4.10073 3.46354 0.77255 | 3.12878 2.40513 0.48576 | 4.18431 3.72494 0.95510 | 3.63096 3.29354 | 3.15473 2.67741 | 3.26429 2.69355 | 4.31243 4.24690 | 3.41512 2.90347 | 0.95588 2.73739 | 3.54553 3.18146 | 3.40634 2.89801 | 2.83701 2.37887 | 3.10805 2.77519 | 3.28352 2.98518 | 5.30361 4.58477 | 4.22102 3.61503 | 103 p - - - |
| 104 | 2.83288 2.68618 0.03351 | 4.81384 4.42225 3.80839 | 2.86375 2.77519 4.53074 | 2.61915 2.73123 0.61958 | 3.97341 3.46354 0.77255 | 3.32530 2.40513 0.48576 | 3.77632 3.72494 0.95510 | 3.59581 3.29354 | 2.44483 2.67741 | 3.10440 2.69355 | 4.13570 4.24690 | 3.07769 2.90347 | 3.87889 2.73739 | 1.35270 3.18146 | 2.72959 2.89801 | 2.84411 2.37887 | 3.13068 2.77519 | 3.32998 2.98518 | 5.25766 4.58477 | 3.94763 3.61503 | 104 q - - - |
| 105 | 2.83288 2.68618 0.03351 | 4.81384 4.42225 3.80839 | 2.86375 2.77519 4.53074 | 2.61915 2.73123 0.61958 | 3.97341 3.46354 0.77255 | 3.32530 2.40513 0.48576 | 3.77632 3.72494 0.95510 | 3.59581 3.29354 | 2.44483 2.67741 | 3.10440 2.69355 | 4.13570 4.24690 | 3.07769 2.90347 | 3.87889 2.73739 | 1.35270 3.18146 | 2.72959 2.89801 | 2.84411 2.37887 | 3.13068 2.77519 | 3.32998 2.98518 | 5.25766 4.58477 | 3.94763 3.61503 | 105 q - - - |
| 106 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.18146 | 3.78921 2.89801 | 3.15664 2.37887 | 3.12163 2.77519 | 1.11004 2.98518 | 5.27795 4.58477 | 4.00490 3.61503 | 106 v - - - |
| 107 | 2.38088 2.68618 0.03351 | 4.22532 4.42225 3.80839 | 3.37373 2.77519 4.53074 | 3.12452 2.73123 0.61958 | 3.91469 3.46354 0.77255 | 3.06626 2.40513 0.48576 | 4.14640 3.72494 0.95510 | 3.03411 3.29354 | 3.06620 2.67741 | 2.89981 2.69355 | 3.95571 4.24690 | 3.34319 2.90347 | 3.76550 2.73739 | 3.46463 3.18146 | 3.32709 2.89801 | 2.58160 2.37887 | 1.28546 2.77519 | 2.73596 2.98518 | 5.35824 4.58477 | 4.13176 3.61503 | 107 t - - - |
| 108 | 2.83288 2.68618 0.03351 | 4.81384 4.42225 3.80839 | 2.86375 2.77519 4.53074 | 2.61915 2.73123 0.61958 | 3.97341 3.46354 0.77255 | 3.32530 2.40513 0.48576 | 3.77632 3.72494 0.95510 | 3.59561 3.29354 | 2.44483 2.67741 | 3.10440 2.69355 | 4.13570 4.24690 | 3.07769 2.90347 | 3.87889 2.73739 | 1.35270 3.16146 | 2.72959 2.89801 | 2.84411 2.37887 | 3.13068 2.77519 | 3.32998 2.98518 | 5.25766 4.58477 | 3.94763 3.61503 | 108 q - - - |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 163377865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| 109 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 109 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 110 | 2.89232 | 4.96281 | 3.17183 | 2.66167 | 4.34568 | 3.49482 | 3.58934 | 3.73478 | 1.33144 | 3.24825 | 4.14154 | 3.08520 | 3.92108 | 2.74582 | 2.04245 | 2.91186 | 3.10000 | 3.42808 | 5.34210 | 4.13228 | 110 k - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 111 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 111 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 112 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 112 y - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 113 | 2.83288 | 4.81384 | 2.86375 | 2.61958 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 113 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80639 | 4.53074 | 0.61958 | 0.77255 | 0.48576 | 0.95510 | | | | | | | | | | | | | | |
| 114 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 114 l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 115 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 115 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 116 | 2.91557 | 4.87384 | 3.08714 | 2.72252 | 4.24557 | 3.41049 | 3.72746 | 3.67115 | 1.12970 | 3.25103 | 4.21733 | 3.14931 | 3.91643 | 2.92363 | 2.42483 | 2.96260 | 3.17436 | 3.38305 | 5.32773 | 4.13178 | 116 k - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.16146 | 2.89601 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 117 | 2.58929 | 4.36940 | 3.24976 | 3.14188 | 4.28221 | 0.83522 | 4.26473 | 3.86748 | 3.31425 | 3.52541 | 4.50578 | 3.41443 | 3.75846 | 3.64375 | 3.55601 | 2.75963 | 3.06560 | 3.40832 | 5.39294 | 4.38245 | 117 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 118 | 2.92923 | 4.75570 | 3.06737 | 2.82225 | 3.24301 | 3.39609 | 1.28522 | 3.62204 | 2.66722 | 3.12353 | 4.16260 | 3.23362 | 3.94584 | 3.16806 | 2.93608 | 3.00091 | 3.23101 | 3.35853 | 4.70870 | 3.19598 | 118 h - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 119 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 119 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD  -5.1315   0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 120 | 2.83288 2.68618 0.03351 | 4.81384 4.42225 3.80839 | 2.86675 2.77519 4.53074 | 2.61915 2.73123 0.61958 | 3.97341 3.46354 0.77255 | 3.32530 2.40513 0.48576 | 3.77632 3.72494 0.95510 | 3.59581 3.29354 | 2.44483 2.67741 | 3.10440 2.69355 | 4.13570 4.24690 | 3.07769 2.90347 | 3.87889 2.73739 | 1.35270 3.18146 | 2.72959 2.89801 | 2.88411 2.37887 | 3.13068 2.77519 | 3.32998 2.98518 | 5.25766 4.58477 | 3.94763 3.61503 | 120 q - - - |
| 121 | 2.24451 2.68618 0.03351 | 4.20330 4.42225 3.80839 | 3.08217 2.77519 4.53074 | 2.84301 2.73123 0.61958 | 4.11231 3.46354 0.77255 | 2.92809 2.40513 0.48576 | 3.99936 3.72494 0.95510 | 3.56680 3.29354 | 2.92262 2.67741 | 3.25198 2.69355 | 4.11942 4.24690 | 3.11757 2.90347 | 3.03611 2.73739 | 3.26149 3.18146 | 3.24979 2.89801 | 1.39331 2.37887 | 2.70133 2.77519 | 3.08921 2.98518 | 5.45557 4.58477 | 4.18647 3.61503 | 121 s - - - |
| 122 | 3.17889 2.68618 0.03351 | 4.60008 4.42225 3.80839 | 4.15032 2.77519 4.53074 | 3.85387 2.73123 0.61958 | 1.12282 3.46354 0.77255 | 3.88119 2.40513 0.48576 | 3.85245 3.72494 0.95510 | 2.71188 3.29354 | 3.76280 2.67741 | 2.09750 2.69355 | 3.45251 4.24690 | 3.94779 2.90347 | 4.34224 2.73739 | 3.94887 3.18146 | 3.89833 2.89801 | 3.45132 2.37887 | 3.48052 2.77519 | 2.69761 2.98518 | 4.12292 4.58477 | 2.49894 3.61503 | 122 f - - - |
| 123 | 2.38088 2.68618 0.03351 | 4.22532 4.42225 3.80839 | 3.37373 2.77519 4.53074 | 3.12452 2.73123 0.61958 | 3.91469 3.46354 0.77255 | 3.06626 2.40513 0.48576 | 4.14640 3.72494 0.95510 | 3.03411 3.24354 | 3.06620 2.67741 | 2.89981 2.69355 | 3.95571 4.24690 | 3.34319 2.90347 | 3.76550 2.73739 | 3.46463 3.18146 | 3.32709 2.89801 | 2.58160 2.37887 | 1.28546 2.77519 | 2.73596 2.98518 | 5.35824 4.58477 | 4.13176 3.61503 | 123 t - - - |
| 124 | 2.91557 2.68618 0.03351 | 4.87384 4.42225 3.80839 | 3.08714 2.77519 4.53074 | 2.72252 2.73123 0.61958 | 4.24557 3.46354 0.77255 | 3.41039 2.40513 0.48576 | 3.72746 3.72494 0.95510 | 3.67115 3.29354 | 1.12970 2.67741 | 3.25103 2.69355 | 4.21733 4.24690 | 3.14931 2.90347 | 3.91643 2.73739 | 2.92363 3.18146 | 2.42483 2.89801 | 2.96260 2.37887 | 3.17436 2.77519 | 3.38305 2.98518 | 5.32773 4.58477 | 4.13178 3.61503 | 124 k - - - |
| 125 | 2.28599 2.68618 0.03351 | 4.20474 4.42225 3.80839 | 3.15313 2.77519 4.53074 | 2.96740 2.73123 0.61958 | 4.01316 3.46354 0.77255 | 2.93592 2.40513 0.48576 | 4.07832 3.72494 0.95510 | 3.52777 3.29354 | 3.03676 2.67741 | 3.25353 2.69355 | 4.18606 4.24690 | 3.20153 2.90347 | 3.66974 2.73739 | 3.39147 3.18146 | 3.32378 2.89801 | 1.19199 2.37887 | 2.76159 2.77519 | 3.07699 2.98518 | 5.39114 4.58477 | 4.09669 3.61503 | 125 s - - - |
| 126 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.18146 | 3.78302 2.89801 | 3.15664 2.37887 | 3.12163 2.77519 | 1.11004 2.98518 | 5.27795 4.58477 | 4.00490 3.61503 | 126 v - - - |
| 127 | 2.28599 2.68618 0.03351 | 4.20474 4.42225 3.80839 | 3.15313 2.77519 4.53074 | 2.96740 2.73123 0.61958 | 4.01316 3.46354 0.77255 | 2.93592 2.40513 0.48576 | 4.07832 3.72494 0.95510 | 3.52777 3.29354 | 3.03676 2.67741 | 3.25353 2.69355 | 4.18606 4.24690 | 3.20153 2.90347 | 3.66974 2.73739 | 3.39147 3.18146 | 3.32378 2.89801 | 1.19199 2.37887 | 2.76159 2.77519 | 3.07699 2.98518 | 5.39114 4.58477 | 4.09669 3.61503 | 127 s - - - |
| 128 | 1.11031 2.68618 0.03351 | 4.16266 4.42225 3.80839 | 3.39952 2.77519 4.53074 | 3.18951 2.73123 0.61958 | 3.90036 3.46354 0.77255 | 2.98856 2.40513 0.48576 | 4.21886 3.72494 0.95510 | 3.10649 3.29354 | 3.20414 2.67741 | 2.99084 2.69355 | 4.03105 4.24690 | 3.35470 2.90347 | 3.72187 2.73739 | 3.55158 3.18146 | 3.45819 2.89801 | 2.51417 2.37887 | 2.78716 2.77519 | 2.77211 2.98518 | 5.42402 4.58477 | 4.21744 3.61503 | 128 a - - - |
| 129 | 2.91557 2.68618 0.03351 | 4.87384 4.42225 3.80839 | 3.08714 2.77519 4.53074 | 2.72252 2.73123 0.61958 | 4.24557 3.46354 0.77255 | 3.41039 2.40513 0.48576 | 3.72746 3.72494 0.95510 | 3.67115 3.29354 | 1.12970 2.67741 | 3.25103 2.69355 | 4.21733 4.24690 | 3.14931 2.90347 | 3.91643 2.73739 | 2.92363 3.18146 | 2.42483 2.89801 | 2.96260 2.37887 | 3.17436 2.77519 | 3.38305 2.98518 | 5.32773 4.58477 | 4.13178 3.61503 | 129 k - - - |
| 130 | 3.15726 2.68618 0.03351 | 4.67219 4.42225 3.80839 | 3.74475 2.77519 4.53074 | 3.46341 2.73123 0.61958 | 2.29976 3.46354 0.77255 | 3.75634 2.40513 0.48576 | 3.59289 3.72494 0.95510 | 3.17566 3.29354 | 3.32278 2.67741 | 2.64581 2.69355 | 3.85778 4.24690 | 3.64645 2.90347 | 4.23235 2.73739 | 3.64422 3.18146 | 3.51908 2.89801 | 3.29987 2.37887 | 3.44402 2.77519 | 3.04338 2.98518 | 3.94061 4.58477 | 1.07944 3.61503 | 130 y - - - |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD   -5.1315  0.70210
```

| HMM | A | C | D | E | F | G | H | I | K | L | M | N | P | Q | R | S | T | V | W | Y | | |
|---|---|---|---|---|---|---|---|---|---|---|---|---|---|---|---|---|---|---|---|---|---|---|
| | m→m | m→i | m→d | i→m | i→i | d→m | d→d | | | | | | | | | | | | | | | |
| 131 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 131 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 132 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 132 v - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89601 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 133 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 133 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 134 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 134 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 135 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 135 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 136 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 136 i - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 137 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 137 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 138 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 138 i - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 139 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 139 v - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 140 | 2.67266 | 4.66469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.31189 | 3.97225 | 140 n - - - |
| | 2.68618 | 4.42225 | 2.77519 | 2.73123 | 3.46354 | 2.40513 | 3.72494 | 3.24354 | 2.67741 | 2.69355 | 4.24690 | 2.90147 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 141 | 2.96177 | 4.37429 | 4.41281 | 3.94113 | 3.36272 | 4.13652 | 4.69082 | 1.27201 | 3.78761 | 1.89165 | 3.22369 | 4.19385 | 4.51411 | 4.09740 | 4.00776 | 3.53044 | 3.24517 | 1.61177 | 5.29720 | 4.06537 | 141 i - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD   -5.1315   0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
|  | m->m | m->i | m->d | i->m | i->i | d->m | d->d |  |  |  |  |  |  |  |  |  |  |  |  |  |  |
| 142 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5%39114 | 4.09669 | 142 s - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 143 | 2.28599 | 4.20474 | 3.15313 | 2.96740 | 4.61316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 143 s - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 144 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 144 d - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 145 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 145 i - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 146 | 2.38088 | 4.22532 | 3.37873 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 146 t - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 147 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 147 v - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 148 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 148 g - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 149 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 149 f - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 150 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 150 s - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 151 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 151 s - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 152 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 152 t - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |

TABLE 6-continued

| HMMER3/f [3.1b2] \| February 2015 | | | | | | | | | | | | | | | | | | | | | | |
|---|---|---|---|---|---|---|---|---|---|---|---|---|---|---|---|---|---|---|---|---|---|---|
| NAME zips | | | | | | | | | | | | | | | | | | | | | | |
| LENG 272 | | | | | | | | | | | | | | | | | | | | | | |
| ALPH amino | | | | | | | | | | | | | | | | | | | | | | |
| RF no | | | | | | | | | | | | | | | | | | | | | | |
| MM no | | | | | | | | | | | | | | | | | | | | | | |
| CONS yes | | | | | | | | | | | | | | | | | | | | | | |
| CS no | | | | | | | | | | | | | | | | | | | | | | |
| MAP yes | | | | | | | | | | | | | | | | | | | | | | |
| DATE Thu Feb 21 21:13:29 2019 | | | | | | | | | | | | | | | | | | | | | | |
| NSEQ 8 | | | | | | | | | | | | | | | | | | | | | | |
| EFFN 0.417969 | | | | | | | | | | | | | | | | | | | | | | |
| CKSUM 165377865 | | | | | | | | | | | | | | | | | | | | | | |
| STATS LOCAL MSV     -11.4830  0.70210 | | | | | | | | | | | | | | | | | | | | | | |
| STATS LOCAL VITERBI -11.8487  0.70210 | | | | | | | | | | | | | | | | | | | | | | |
| STATS LOCAL FORWARD  -5.1315  0.70210 | | | | | | | | | | | | | | | | | | | | | | |

| HMM | A | C | D | E | F | G | H | I | K | L | M | N | P | Q | R | S | T | V | W | Y | | |
|---|---|---|---|---|---|---|---|---|---|---|---|---|---|---|---|---|---|---|---|---|---|---|
|  | m->m | m->i | m->d | i->m | i->i | d->m | d->d |  |  |  |  |  |  |  |  |  |  |  |  |  |  |  |
| 153 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.03593 | 3.09149 | 2.88487 | 3.20420 | 3.46469 | 5.51622 | 4.24017 | 153 e | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 154 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 154 a | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 155 | 3.23357 | 4.63032 | 3.99599 | 3.68726 | 2.60690 | 3.66065 | 3.82592 | 3.25571 | 3.41132 | 2.66106 | 3.89235 | 3.84955 | 4.17341 | 3.80241 | 3.55053 | 3.43778 | 3.53106 | 3.14428 | 1.02517 | 2.61260 | 155 w | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 156 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 156 s | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 157 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 157 t | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 158 | 2.49754 | 4.54631 | 2.69929 | 2.50989 | 4.12129 | 3.09926 | 3.61647 | 3.55010 | 2.66261 | 3.25288 | 4.14900 | 1.68050 | 3.73627 | 3.03747 | 3.03371 | 2.58350 | 2.55829 | 3.16634 | 5.44237 | 4.09318 | 158 n | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 159 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 159 q | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 160 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 160 t | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 161 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89761 | 3.45132 | 3.48052 | 2.69761 | 4.12292 | 2.49894 | 161 f | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 162 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 162 t | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |
| 163 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 163 q | - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |  |
|  | 0.03351 | 3.80839 | 4.53074 | 0.61958 | 0.77255 | 0.48576 | 0.95510 |  |  |  |  |  |  |  |  |  |  |  |  |  |  |  |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | | |
|---|---|---|---|---|---|---|---|---|---|---|---|---|---|---|---|---|---|---|---|---|---|---|
| | m→m | m→i | m→d | i→m | i→i | d→m | d→d | | | | | | | | | | | | | | | |
| 164 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 164 | s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 165 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 165 | t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 166 | 2.89992 | 4.99376 | 2.46525 | 1.12027 | 4.33240 | 3.23467 | 3.81790 | 3.77361 | 2.69052 | 3.40180 | 4.38024 | 2.90101 | 3.83668 | 3.03593 | 3.09149 | 2.88987 | 3.20420 | 3.46469 | 5.51622 | 4.24017 | 166 | e - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 167 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 167 | l - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 168 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 168 | a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 169 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39244 | 4.38245 | 169 | g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 170 | 2.67118 | 4.43758 | 3.27171 | 3.10268 | 4.10073 | 3.12878 | 4.18431 | 3.63096 | 3.15473 | 3.26429 | 4.31243 | 3.41512 | 0.95588 | 3.54553 | 3.40634 | 2.83701 | 3.10805 | 3.28352 | 5.30361 | 4.22102 | 170 | p - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 171 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 171 | g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 172 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 172 | t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 173 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 173 | f - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |
| 174 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 174 | f - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | |
| | 0.03351 | 3.80839 | 4.53074 | 0.61958 | 0.77255 | 0.48576 | 0.95510 | | | | | | | | | | | | | | | |

TABLE 6-continued

| HMMER3/f [3.1b2] | February 2015 | | | | | | | | | | | | | | | | | | | | |
|---|---|---|---|---|---|---|---|---|---|---|---|---|---|---|---|---|---|---|---|---|---|
| NAME | zips | | | | | | | | | | | | | | | | | | | | |
| LENG | 272 | | | | | | | | | | | | | | | | | | | | |
| ALPH | amino | | | | | | | | | | | | | | | | | | | | |
| RF | no | | | | | | | | | | | | | | | | | | | | |
| MM | no | | | | | | | | | | | | | | | | | | | | |
| CONS | yes | | | | | | | | | | | | | | | | | | | | |
| CS | no | | | | | | | | | | | | | | | | | | | | |
| MAP | yes | | | | | | | | | | | | | | | | | | | | |
| DATE | Thu Feb 21 21:13:29 2019 | | | | | | | | | | | | | | | | | | | | |
| NSEQ | 8 | | | | | | | | | | | | | | | | | | | | |
| EFFN | 0.417969 | | | | | | | | | | | | | | | | | | | | |
| CKSUM | 1653877865 | | | | | | | | | | | | | | | | | | | | |
| STATS | LOCAL MSV | −11.4830 | 0.70210 | | | | | | | | | | | | | | | | | | |
| STATS | LOCAL VITERBI | −11.8487 | 0.70210 | | | | | | | | | | | | | | | | | | |
| STATS | LOCAL FORWARD | −5.1315 | 0.70210 | | | | | | | | | | | | | | | | | | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
|  | m→m | m→i | m→d | i→m | i→i | d→m | d→d |  |  |  |  |  |  |  |  |  |  |  |  |  |  |
| 175 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 175 v - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 176 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 176 y - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 177 | 2.83288 | 4.81384 | 2.86375 | 2.61915 | 3.97341 | 3.32520 | 3.77632 | 3.59581 | 2.44483 | 3.10440 | 4.13570 | 3.07769 | 3.87889 | 1.35270 | 2.72959 | 2.88411 | 3.13068 | 3.32998 | 5.25766 | 3.94763 | 177 q - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 178 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 178 v - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 179 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 179 v - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 180 | 3.17889 | 4.60008 | 4.15032 | 3.85387 | 1.12282 | 3.88119 | 3.85245 | 2.71188 | 3.76280 | 2.09750 | 3.45251 | 3.94779 | 4.34224 | 3.94887 | 3.89833 | 3.45132 | 3.48052 | 2.69761 | 4.12292 | 2.49894 | 180 f - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 181 | 2.75784 | 4.31972 | 4.03530 | 3.69790 | 3.50486 | 3.65597 | 4.51118 | 2.05876 | 3.56463 | 2.20413 | 3.48128 | 3.89758 | 4.22110 | 3.92973 | 3.78302 | 3.15664 | 3.12163 | 1.11004 | 5.27795 | 4.00490 | 181 v - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 182 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 182 y - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 183 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 183 a - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 184 | 2.92923 | 4.75570 | 3.06737 | 2.82225 | 3.24301 | 3.39607 | 1.28522 | 3.62204 | 2.66722 | 3.12353 | 4.16260 | 3.23362 | 3.94584 | 3.18806 | 2.93608 | 3.00091 | 3.23101 | 3.35853 | 4.70870 | 3.19598 | 184 h - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |
| 185 | 2.67266 | 4.64469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 185 n - - - |
|  | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 |  |
|  | 0.03351 | 3.80839 | 4.53074 | 0.61958 | 0.77255 | 0.48576 | 0.95510 |  |  |  |  |  |  |  |  |  |  |  |  |  |  |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD   -5.1315  0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 186 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 186 a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 187 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 187 t - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 188 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 188 s - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 189 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 189 a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 190 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 190 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 191 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 191 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 192 | 2.83288 | 4.81384 | 2.86375 | 2.61915 | 3.97341 | 3.32530 | 3.77632 | 3.59581 | 2.44483 | 3.10440 | 4.13570 | 3.07769 | 3.87889 | 1.35270 | 2.72959 | 2.84411 | 3.13068 | 3.32998 | 5.25766 | 3.94763 | 192 q - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 193 | 2.67266 | 4.66469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 193 n - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 194 | 2.58929 | 4.36940 | 3.24976 | 3.14188 | 4.28221 | 0.83523 | 4.26473 | 3.86748 | 3.31425 | 3.52941 | 4.50578 | 3.41443 | 3.75846 | 3.64375 | 3.55601 | 2.75963 | 3.06560 | 3.40832 | 5.39294 | 4.38245 | 194 g - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 195 | 2.67266 | 4.66469 | 2.67738 | 2.55713 | 4.01837 | 3.14279 | 3.87335 | 3.71632 | 2.77246 | 3.37097 | 4.32772 | 1.27686 | 3.79220 | 3.14721 | 3.12388 | 2.74309 | 3.05315 | 3.34503 | 5.33189 | 3.97225 | 195 n - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 196 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 196 a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A<br>m->m | C<br>m->i | D<br>m->d | E<br>i->m | F<br>i->i | G<br>d->m | H<br>d->d | I | K | L | M | N | P | Q | R | S | T | V | W | Y | |
|---|---|---|---|---|---|---|---|---|---|---|---|---|---|---|---|---|---|---|---|---|---|
| 197 | 3.17889<br>2.68618<br>0.03351 | 4.60008<br>4.42225<br>3.80839 | 4.15032<br>2.77519<br>4.53074 | 3.85387<br>2.73123<br>0.61958 | 1.12282<br>3.46354<br>0.77255 | 3.88119<br>2.40513<br>0.48576 | 3.85245<br>3.72494<br>0.95510 | 2.71188<br>3.29354 | 3.76280<br>2.67741 | 2.09750<br>2.69355 | 3.45251<br>4.24690 | 3.94779<br>2.90347 | 4.34224<br>2.73739 | 3.94887<br>3.18146 | 3.89833<br>2.89801 | 3.45132<br>2.37887 | 3.48052<br>2.77519 | 2.69761<br>2.98518 | 4.12292<br>4.58477 | 2.49894<br>3.61503 | 197 f - - - |
| 198 | 1.11031<br>2.68618<br>0.03351 | 4.16266<br>4.42225<br>3.80839 | 3.39952<br>2.77519<br>4.53074 | 3.18951<br>2.73123<br>0.61958 | 3.99036<br>3.46354<br>0.77255 | 2.98856<br>2.40513<br>0.48576 | 4.21886<br>3.72494<br>0.95510 | 3.10649<br>3.29354 | 3.20414<br>2.67741 | 2.99084<br>2.69355 | 4.03105<br>4.24690 | 3.35470<br>2.90347 | 3.72187<br>2.73739 | 3.55158<br>3.18146 | 3.45819<br>2.89801 | 2.51417<br>2.37887 | 2.78716<br>2.77519 | 2.77211<br>2.98518 | 5.42402<br>4.58477 | 4.21744<br>3.61503 | 198 a - - - |
| 199 | 3.15726<br>2.68618<br>0.03351 | 4.67219<br>4.42225<br>3.80839 | 3.74475<br>2.77519<br>4.53074 | 3.46341<br>2.73123<br>0.61958 | 2.29976<br>3.46354<br>0.77255 | 3.75634<br>2.40513<br>0.48576 | 3.59289<br>3.72494<br>0.95510 | 3.17566<br>3.29354 | 3.32278<br>2.67741 | 2.64581<br>2.69355 | 3.85778<br>4.24690 | 3.64645<br>2.90347 | 4.23235<br>2.73739 | 3.64422<br>3.18146 | 3.51908<br>2.89801 | 3.29987<br>2.37887 | 3.44402<br>2.77519 | 3.04338<br>2.98518 | 3.94061<br>4.58477 | 1.07944<br>3.61503 | 199 y - - - |
| 200 | 2.28599<br>2.68618<br>0.03351 | 4.20474<br>4.42225<br>3.80839 | 3.15313<br>2.77519<br>4.53074 | 2.96740<br>2.73123<br>0.61958 | 4.01316<br>3.46354<br>0.77255 | 2.93592<br>2.40513<br>0.48576 | 4.07832<br>3.72494<br>0.95510 | 3.52777<br>3.29354 | 3.03676<br>2.67741 | 3.25353<br>2.69355 | 4.18606<br>4.24690 | 3.20153<br>2.90347 | 3.66974<br>2.73739 | 3.39147<br>3.18146 | 3.32378<br>2.89801 | 1.19199<br>2.37887 | 2.76159<br>2.77519 | 3.07699<br>2.98518 | 5.39199<br>4.58477 | 4.09669<br>3.61543 | 200 s - - - |
| 201 | 2.91557<br>2.68618<br>0.03351 | 4.87384<br>4.42225<br>3.80839 | 3.08714<br>2.77519<br>4.53074 | 2.72252<br>2.73123<br>0.61958 | 4.24557<br>3.46354<br>0.77255 | 3.41039<br>2.40513<br>0.48576 | 3.72746<br>3.72494<br>0.95510 | 3.67115<br>3.29354 | 1.12970<br>2.67741 | 3.25103<br>2.69355 | 4.21733<br>4.24690 | 3.14931<br>2.90347 | 3.91643<br>2.73739 | 2.92363<br>3.18146 | 2.42483<br>2.89801 | 2.96260<br>2.37887 | 3.17436<br>2.77519 | 3.38305<br>2.98518 | 5.32773<br>4.58477 | 4.13178<br>3.61503 | 201 k - - - |
| 202 | 2.38088<br>2.68618<br>0.03351 | 4.22532<br>4.42225<br>3.80839 | 3.37373<br>2.77519<br>4.53074 | 3.12452<br>2.73123<br>0.61958 | 3.51469<br>3.46354<br>0.77255 | 3.06626<br>2.40513<br>0.48576 | 4.14640<br>3.72494<br>0.95510 | 3.03411<br>3.25354 | 3.06620<br>2.67741 | 2.89981<br>2.69355 | 3.95571<br>4.24690 | 3.34319<br>2.90347 | 3.76550<br>2.73739 | 3.46463<br>3.18146 | 3.32709<br>2.89801 | 2.58160<br>2.37887 | 1.28546<br>2.77519 | 2.73596<br>2.98518 | 5.35824<br>4.58477 | 4.13176<br>3.61503 | 202 t - - - |
| 203 | 2.83288<br>2.68618<br>0.03351 | 4.81384<br>4.42225<br>3.80839 | 2.86375<br>2.77519<br>4.53074 | 2.61915<br>2.73123<br>0.61958 | 3.97341<br>3.46354<br>0.77255 | 3.32530<br>2.40513<br>0.48576 | 3.77632<br>3.72494<br>0.95510 | 3.59581<br>3.29354 | 2.44483<br>2.67741 | 3.10440<br>2.69355 | 4.13570<br>4.24690 | 3.07769<br>2.90347 | 3.87889<br>2.73739 | 1.35270<br>3.18146 | 2.72959<br>2.89801 | 2.84411<br>2.37887 | 3.13068<br>2.77519 | 3.32998<br>2.98518 | 5.25766<br>4.58477 | 3.94763<br>3.61503 | 203 q - - - |
| 204 | 2.83288<br>2.68618<br>0.03351 | 4.81384<br>4.42225<br>3.80839 | 2.86375<br>2.77519<br>4.53074 | 2.61915<br>2.73123<br>0.61958 | 3.97341<br>3.46354<br>0.77255 | 3.32530<br>2.40513<br>0.48576 | 3.77632<br>3.72494<br>0.95510 | 3.59581<br>3.29354 | 2.44483<br>2.67741 | 3.10440<br>2.69355 | 4.13570<br>4.24690 | 3.07769<br>2.90347 | 3.87889<br>2.73739 | 1.35270<br>3.18146 | 2.72959<br>2.89801 | 2.84411<br>2.37887 | 3.13068<br>2.77519 | 3.32998<br>2.98518 | 5.25766<br>4.58477 | 3.94763<br>3.61503 | 204 q - - - |
| 205 | 2.75784<br>2.68618<br>0.03351 | 4.31972<br>4.42225<br>3.80839 | 4.03530<br>2.77519<br>4.53074 | 3.69790<br>2.73123<br>0.61958 | 3.50486<br>3.46354<br>0.77255 | 3.65597<br>2.40513<br>0.48576 | 4.51118<br>3.72494<br>0.95510 | 2.05876<br>3.29354 | 3.56463<br>2.67741 | 2.20413<br>2.69355 | 3.48128<br>4.24690 | 3.89758<br>2.90347 | 4.22110<br>2.73739 | 3.92973<br>3.18146 | 3.78262<br>2.89801 | 3.15664<br>2.37887 | 3.12163<br>2.77519 | 1.11004<br>238518 | 5.27795<br>4.58477 | 4.00490<br>3.61503 | 205 v - - - |
| 206 | 2.67266<br>2.68618<br>0.03351 | 4.66469<br>4.42225<br>3.80839 | 2.67738<br>2.77519<br>4.53074 | 2.55713<br>2.73123<br>0.61958 | 4.01837<br>3.46354<br>0.77255 | 3.14279<br>2.40513<br>0.48576 | 3.87335<br>3.72494<br>0.95510 | 3.71632<br>3.29354 | 2.77246<br>2.67741 | 3.37097<br>2.69355 | 4.32772<br>4.24690 | 1.27686<br>2.90347 | 3.79220<br>2.73739 | 3.14721<br>3.18146 | 3.12388<br>2.89801 | 2.74309<br>2.37887 | 3.05315<br>2.77519 | 3.34503<br>2.98518 | 5.33189<br>4.58477 | 3.97225<br>3.61503 | 206 n - - - |
| 207 | 2.28599<br>2.68618<br>0.03351 | 4.20474<br>4.42225<br>3.80839 | 3.15313<br>2.77519<br>4.53074 | 2.96740<br>2.73123<br>0.61958 | 4.01316<br>3.46354<br>0.77255 | 2.93592<br>2.40513<br>0.48576 | 4.07832<br>3.72494<br>0.95510 | 3.52777<br>3.29354 | 3.03676<br>2.67741 | 3.25353<br>2.69355 | 4.18606<br>4.24690 | 3.20153<br>2.90347 | 3.66974<br>2.73739 | 3.39147<br>3.18146 | 3.32378<br>2.89801 | 1.19199<br>2.37887 | 2.76159<br>2.77519 | 3.07699<br>2.98518 | 5.39114<br>4.58477 | 4.09669<br>3.61503 | 207 s - - - |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 1653877865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | | | |
|---|---|---|---|---|---|---|---|---|---|---|---|---|---|---|---|---|---|---|---|---|---|---|---|
| | m->m | m->i | m->d | i->m | i->i | d->m | d->d | | | | | | | | | | | | | | | | |
| 208 | 2.93567 | 4.77649 | 3.42005 | 2.94650 | 4.11486 | 3.43409 | 3.78227 | 3.65333 | 2.21804 | 3.18106 | 4.18431 | 3.31043 | 3.94105 | 3.00701 | 1.08112 | 3.02376 | 3.20684 | 3.38040 | 5.22475 | 4.05755 | 208 | r | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 209 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 209 | l | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 210 | 2.92310 | 5.03735 | 1.01454 | 2.30009 | 4.40640 | 3.16420 | 3.87837 | 3.98050 | 2.95099 | 3.60099 | 4.57912 | 2.85261 | 3.81266 | 3.11848 | 3.45728 | 2.89377 | 3.26085 | 3.62704 | 5.58736 | 4.29177 | 210 | d | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.63351 | 3.80839 | 4.53074 | 0.61958 | 0.77255 | 0.48576 | 0.95510 | | | | | | | | | | | | | | | | |
| 211 | 3.08469 | 4.56681 | 4.08583 | 3.72691 | 3.11381 | 3.69935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 211 | l | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 212 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 212 | y | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 213 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07544 | 213 | y | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 214 | 3.08469 | 4.56681 | 4.08583 | 3.72691 | 3.11381 | 3.89935 | 4.40279 | 2.31622 | 3.49522 | 0.95845 | 3.15956 | 4.00841 | 4.34677 | 3.87896 | 3.68117 | 3.46490 | 3.38246 | 2.33662 | 4.96833 | 3.67637 | 214 | l | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 215 | 2.28599 | 4.20474 | 3.15313 | 2.96740 | 4.01316 | 2.93592 | 4.07832 | 3.52777 | 3.03676 | 3.25353 | 4.18606 | 3.20153 | 3.66974 | 3.39147 | 3.32378 | 1.19199 | 2.76159 | 3.07699 | 5.39114 | 4.09669 | 215 | s | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 216 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 216 | a | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 217 | 2.98131 | 4.41980 | 4.24162 | 3.85620 | 3.33257 | 3.99480 | 4.59720 | 1.16111 | 3.68296 | 1.93351 | 3.27971 | 4.11059 | 4.43351 | 4.03877 | 3.88695 | 3.48513 | 3.28221 | 1.84862 | 5.20905 | 3.94078 | 217 | i | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |
| 218 | 2.38088 | 4.22532 | 3.37373 | 3.12452 | 3.91469 | 3.06626 | 4.14640 | 3.03411 | 3.06620 | 2.89981 | 3.95571 | 3.34319 | 3.76550 | 3.46463 | 3.32709 | 2.58160 | 1.28546 | 2.73596 | 5.35824 | 4.13176 | 218 | t | - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | | | |
| | 0.03351 | 3.80839 | 4.53074 | 0.61958 | 0.77255 | 0.48576 | 0.95510 | | | | | | | | | | | | | | | | |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 1653877865
STATS LOCAL MSV       -11.4830  0.70210
STATS LOCAL VITERBI   -11.8487  0.70210
STATS LOCAL FORWARD    -5.1315  0.70210
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | | | | | | | | | | | | | | |
| 219 | 2.61338 2.68618 0.03351 | 4.63513 4.42225 3.80839 | 2.98982 2.77519 4.53074 | 2.49568 2.73123 0.61958 | 3.86125 3.46354 0.77255 | 3.37483 2.40513 0.48576 | 3.58066 3.72494 0.95510 | 3.33848 3.29354 | 2.28320 2.67741 | 2.95092 2.69355 | 3.79875 4.24690 | 2.96940 2.90347 | 3.78724 2.73739 | 1.96490 3.18146 | 2.62957 2.89801 | 2.67100 2.37887 | 2.84872 2.77519 | 3.04772 2.98518 | 5.06862 4.58477 | 3.82222 3.61503 | 219 q - - - |
| 220 | 2.92310 2.68618 0.03351 | 5.03735 4.42225 3.80839 | 1.01454 2.77519 4.53074 | 2.30009 2.73123 0.61958 | 4.40640 3.46354 0.77255 | 3.16420 2.40513 0.48576 | 3.87837 3.72494 0.95510 | 3.98050 3.29354 | 2.95099 2.67741 | 3.60099 2.69355 | 4.57912 4.24690 | 2.85261 2.90347 | 3.81266 2.73739 | 3.11848 3.18146 | 3.45726 2.89801 | 2.89377 2.37887 | 3.26085 2.77519 | 3.62704 2.98518 | 5.58736 4.58477 | 4.29177 3.61503 | 220 d - - - |
| 221 | 2.93567 2.68618 0.03351 | 4.77649 4.42225 3.80839 | 3.42005 2.77519 4.53074 | 2.94650 2.73123 0.61958 | 4.11486 3.46354 0.77255 | 3.43409 2.40513 0.48576 | 3.78227 3.72494 0.95510 | 3.65333 3.29354 | 2.21804 2.67741 | 3.18106 2.69355 | 4.18431 4.24690 | 3.31043 2.90347 | 3.94105 2.73739 | 3.00701 3.18146 | 1.08112 2.89801 | 3.02376 2.37887 | 3.20684 2.77519 | 3.38040 2.98518 | 5.22475 4.58477 | 4.05755 3.61503 | 221 r - - - |
| 222 | 2.38088 2.68618 0.03351 | 4.22532 4.42225 3.80839 | 3.37373 2.77519 4.53074 | 3.12452 2.73123 0.61958 | 3.91469 3.46354 0.77255 | 3.06626 2.40513 0.48576 | 4.14640 3.72494 0.95510 | 3.03411 3.29354 | 3.06620 2.67741 | 2.89981 2.69355 | 3.95571 4.24690 | 3.34319 2.90347 | 3.76550 2.73739 | 3.46463 3.18146 | 3.32709 2.89801 | 2.58160 2.37887 | 1.28546 2.77519 | 2.73596 2.98518 | 5.35824 4.58477 | 4.13176 3.61503 | 222 t - - - |
| 223 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.18146 | 3.78302 2.89801 | 3.15664 2.37887 | 3.12163 2.77519 | 1.11004 2.98518 | 5.27795 4.58477 | 4.00490 3.61503 | 223 v - - - |
| 224 | 2.98131 2.68618 0.03351 | 4.41980 4.42225 3.80839 | 4.2416Z 2.77519 4.53074 | 3.85620 2.73123 0.61958 | 3.33257 3.46354 0.77255 | 3.99480 2.40513 0.48576 | 4.59720 3.72494 0.95510 | 1.16111 3.29354 | 3.68296 2.67741 | 1.93351 2.69355 | 3.27971 4.24690 | 4.11059 2.90147 | 4.43351 2.73739 | 4.03877 3.18146 | 3.88695 2.89801 | 3.48513 2.37887 | 3.28221 2.77519 | 1.84862 2.98518 | 5.20905 4.58477 | 3.94078 3.61503 | 224 i - - - |
| 225 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.18146 | 3.78302 2.89801 | 3.15664 2.37887 | 3.12163 2.77519 | 1.11004 2.98518 | 5.27795 4.58477 | 4.00490 3.61503 | 225 v - - - |
| 226 | 2.89992 2.68618 0.03351 | 4.99376 4.42225 3.80839 | 2.46525 2.77519 4.53074 | 1.12027 2.73123 0.61958 | 4.33240 3.46354 0.77255 | 3.23647 2.40513 0.48576 | 3.81790 3.72494 0.95510 | 3.77361 3.29354 | 2.69052 2.67741 | 3.40180 2.69355 | 4.38024 4.24690 | 2.90101 2.90347 | 3.83668 2.73739 | 3.03593 3.18146 | 3.09149 2.89801 | 2.88987 2.37887 | 3.20420 2.77519 | 3.46469 2.98518 | 5.51622 4.58477 | 4.24017 3.61503 | 226 e - - - |
| 227 | 2.28599 2.68618 0.03351 | 4.20474 4.42225 3.80839 | 3.15313 2.77519 4.53074 | 2.96740 2.73123 0.61958 | 4.01316 3.46354 0.77255 | 2.93592 2.40513 0.48576 | 4.07832 3.72494 0.95510 | 3.52777 3.29354 | 3.03676 2.67741 | 3.25353 2.69355 | 4.18606 4.24690 | 3.20153 2.90347 | 3.66974 2.73739 | 3.39147 3.18146 | 3.32378 2.89801 | 1.19199 2.37887 | 2.76159 2.77519 | 3.07699 2.98518 | 5.39114 4.58477 | 4.09669 3.61503 | 227 s - - - |
| 228 | 2.28599 2.68618 0.03351 | 4.20474 4.42225 3.80839 | 3.15313 2.77519 4.53074 | 2.96740 2.73123 0.61958 | 4.01316 3.46354 0.77255 | 2.93592 2.40513 0.48576 | 4.07832 3.72494 0.95510 | 3.52777 3.29354 | 3.03676 2.67741 | 3.25353 2.69355 | 4.18606 4.24690 | 3.20153 2.90347 | 3.66974 2.73739 | 3.39147 3.18146 | 3.32378 2.89801 | 1.19199 2.37887 | 2.76159 2.77519 | 3.07699 2.98518 | 5.39114 4.58477 | 4.09669 3.61503 | 228 s - - - |
| 229 | 2.71151 2.68618 0.03351 | 4.86762 4.42225 3.80839 | 2.55085 2.77519 4.53074 | 2.36054 2.73123 0.61958 | 4.22135 3.46354 0.77255 | 3.22801 2.40513 0.48576 | 3.69454 3.72494 0.95510 | 3.73053 3.29354 | 2.23879 2.67741 | 3.33117 2.69355 | 4.21189 4.24690 | 1.69444 2.90347 | 3.79743 2.73739 | 2.86684 3.18146 | 2.79192 2.89801 | 2.72523 2.37887 | 3.01237 2.77519 | 3.37329 2.98518 | 5.44965 4.58477 | 4.09171 3.61503 | 229 n - - - |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 163377865
STATS LOCAL MSV      -11.4830  0.70210
STATS LOCAL VITERBI  -11.8487  0.70210
STATS LOCAL FORWARD   -5.1315  0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 230 | 1.11031 2.68618 0.03351 | 4.16266 4.42225 3.80839 | 3.39952 2.77519 4.53074 | 3.18951 2.73123 0.61958 | 3.99036 3.46354 0.77255 | 2.98856 2.40513 0.48576 | 4.21886 3.72494 0.95510 | 3.10649 3.29354 | 3.20414 2.67741 | 2.99084 2.69355 | 4.03105 4.24690 | 3.35470 2.90347 | 3.72187 2.73739 | 3.55158 3.18146 | 3.45819 2.89801 | 2.51417 2.37887 | 2.78716 2.77519 | 2.77211 2.98518 | 5.42402 4.58477 | 4.21744 3.61503 | 230 a - - - |
| 231 | 2.98131 2.68618 0.03351 | 4.41980 4.42225 3.80839 | 4.24162 2.77519 4.53074 | 3.85620 2.73123 0.61958 | 3.33257 3.46354 0.77255 | 3.99480 2.40513 0.48576 | 4.59720 3.72494 0.95510 | 1.16111 3.29354 | 3.68296 2.67741 | 1.93351 2.69355 | 3.27971 4.24690 | 4.11059 2.90147 | 4.43351 2.73739 | 4.03877 3.18146 | 3.88695 2.89801 | 3.48513 2.37887 | 3.28221 2.77519 | 1.84862 2.98518 | 5.20905 4.58477 | 3.94078 3.61503 | 231 i - - - |
| 232 | 2.43242 2.68618 0.03351 | 4.94379 4.42225 3.80839 | 1.41602 2.77519 4.53074 | 2.20498 2.73123 0.61958 | 4.38970 3.46354 0.77255 | 3.12406 2.40513 0.48576 | 3.76776 3.72494 0.95510 | 3.77053 3.29354 | 2.76895 2.67741 | 3.45364 2.69355 | 4.36242 4.24690 | 2.74764 2.90347 | 3.75771 2.73739 | 2.96307 3.18146 | 3.29061 2.89801 | 2.69377 2.37887 | 3.04302 2.77519 | 3.40240 2.98518 | 5.67216 4.58477 | 4.25963 3.61503 | 232 d - - - |
| 233 | 2.67118 2.68618 0.03351 | 4.43758 4.42225 3.80839 | 3.27171 2.77519 4.53074 | 3.10268 2.73123 0.61958 | 4.10073 3.46354 0.77255 | 3.12878 2.40513 0.48576 | 4.18431 3.72494 0.95510 | 3.63096 3.29354 | 3.15473 2.67741 | 3.26429 2.69355 | 4.31243 4.24690 | 3.41512 2.90347 | 0.95588 2.73739 | 3.54553 3.18146 | 3.40634 2.89801 | 2.83701 2.37887 | 3.10805 2.77519 | 3.28352 2.98518 | 5.30361 4.58477 | 4.22102 3.61503 | 233 p - - - |
| 234 | 3.08469 2.68618 0.03351 | 4.56681 4.42225 3.80839 | 4.08883 2.77519 4.53074 | 3.72691 2.73123 0.61958 | 3.11381 3.46354 0.77255 | 3.89935 2.40513 0.48576 | 4.40279 3.72494 0.95510 | 2.31622 3.29354 | 3.49522 2.67741 | 0.95845 2.69355 | 3.15956 4.24690 | 4.00841 2.90347 | 4.34677 2.73739 | 3.87896 3.18146 | 3.68117 2.89801 | 3.46490 2.37887 | 3.38246 2.77519 | 2.33662 2.98518 | 4.96833 4.58477 | 3.67637 3.61503 | 234 l - - - |
| 235 | 2.92310 2.68618 0.03351 | 5.03735 4.42225 3.80839 | 1.01454 2.77519 4.53074 | 2.30009 2.73123 0.61958 | 4.40640 3.46354 0.77255 | 3.16420 2.40513 0.48576 | 3.87837 3.72494 0.95510 | 3.98050 3.29354 | 2.95099 2.67741 | 3.60099 2.69355 | 4.57912 4.24690 | 2.85261 2.90347 | 3.81266 2.73739 | 3.11848 3.18146 | 3.45728 2.89801 | 2.89377 2.37887 | 3.26085 2.77519 | 3.62704 2.98518 | 5.58736 4.58477 | 4.29177 3.61503 | 235 d - - - |
| 236 | 2.85644 2.68618 0.03351 | 4.50201 4.42225 3.80839 | 3.66038 2.77519 4.53074 | 3.16223 2.73123 0.61958 | 2.82982 3.46354 0.77255 | 3.60762 2.40513 0.48576 | 3.68523 3.72494 0.95510 | 3.06393 3.29354 | 2.72567 2.67741 | 2.60253 2.69355 | 3.65678 4.24690 | 3.45451 2.90347 | 4.04446 2.73739 | 3.26564 3.18146 | 2.56136 2.89801 | 3.03906 2.37887 | 3.10912 2.77519 | 2.88190 2.98518 | 1.77632 4.58477 | 2.85170 3.61503 | 236 w - - - |
| 237 | 2.92310 2.68618 0.03351 | 5.03735 4.42225 3.80839 | 1.01454 2.77519 4.53074 | 2.30009 2.73123 0.61958 | 4.40640 3.46354 0.77255 | 3.16420 2.40513 0.48576 | 3.87837 3.72494 0.95510 | 3.98050 3.29354 | 2.95099 2.67741 | 3.60099 2.69355 | 4.57912 4.24690 | 2.85261 2.90347 | 3.81266 2.73739 | 3.11848 3.18146 | 3.45728 2.89801 | 2.89377 2.37887 | 3.26085 2.77519 | 3.62704 2.98518 | 5.58736 4.58477 | 4.29177 3.61503 | 237 d - - - |
| 238 | 2.38088 2.68618 0.03351 | 4.22532 4.42225 3.80839 | 3.37373 2.77519 4.53074 | 3.12452 2.73123 0.61958 | 3.91469 3.46354 0.77255 | 3.06626 2.40513 0.48576 | 4.14640 3.72494 0.95510 | 3.03411 3.29354 | 3.06620 2.67741 | 2.89981 2.69355 | 3.95571 4.24690 | 3.34319 2.90347 | 3.76550 2.73739 | 3.46463 3.18146 | 3.32709 2.89801 | 2.58160 2.37887 | 1.28546 2.77519 | 2.73596 2.98518 | 5.35824 4.58477 | 4.13176 3.61503 | 238 t - - - |
| 239 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.16146 | 3.78302 2.89801 | 3.15664 2.37887 | 3.12163 2.77519 | 1.11004 2.98518 | 5.27795 4.58477 | 4.00490 3.61503 | 239 v - - - |
| 240 | 2.83288 2.68618 0.03351 | 4.81384 4.42225 3.80839 | 2.86375 2.77519 4.53074 | 2.61915 2.73123 0.61958 | 3.97341 3.46354 0.77255 | 3.32530 2.40513 0.48576 | 3.77632 3.72494 0.95510 | 3.59581 3.24354 | 2.44483 2.67741 | 3.10440 2.69355 | 4.13570 4.24690 | 3.07769 2.90347 | 3.87889 2.73739 | 1.35270 3.18146 | 2.72959 2.89801 | 2.88411 2.37887 | 3.13068 2.77519 | 3.32998 2.98518 | 5.25766 4.58477 | 3.94763 3.61503 | 240 q - - - |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV       -11.4830  0.70210
STATS LOCAL VITERBI   -11.8487  0.70210
STATS LOCAL FORWARD    -5.1315  0.70210
```

| HMM | A m->m | C m->i | D m->d | E i->m | F i->i | G d->m | H d->d | I | K | L | M | N | P | Q | R | S | T | V | W | Y | |
|---|---|---|---|---|---|---|---|---|---|---|---|---|---|---|---|---|---|---|---|---|---|
| 241 | 2.93567 2.68618 0.03351 | 4.77649 4.42225 3.80839 | 3.42005 2.77519 4.53074 | 2.94650 2.73123 0.61958 | 4.11486 3.46354 0.77255 | 3.43409 2.40513 0.48576 | 3.78227 3.72494 0.95510 | 3.65333 3.29354 | 2.21804 2.67741 | 3.18106 2.69355 | 4.18431 4.24690 | 3.31043 2.90347 | 3.94105 2.73739 | 3.00701 3.18146 | 1.08112 2.89801 | 3.02376 2.37887 | 3.20684 2.77519 | 3.38040 2.98518 | 5.22475 4.58477 | 4.05755 3.61503 | 241 r - - - |
| 242 | 2.67266 2.68618 0.03351 | 4.64469 4.42225 3.80839 | 2.67738 2.77519 4.53074 | 2.55713 2.73123 0.61958 | 4.01837 3.46354 0.77255 | 3.14279 2.40513 0.48576 | 3.87335 3.72494 0.95510 | 3.71632 3.29354 | 2.77246 2.67741 | 3.37097 2.69355 | 4.32772 4.24690 | 1.27686 2.90347 | 3.79220 2.73739 | 3.14721 3.18146 | 3.12388 2.89801 | 2.74309 2.37887 | 3.05315 2.77519 | 3.34503 2.98518 | 5.33189 4.58477 | 3.97225 3.61503 | 242 n - - - |
| 243 | 2.75784 2.68618 0.03351 | 4.31972 4.42225 3.80839 | 4.03530 2.77519 4.53074 | 3.69790 2.73123 0.61958 | 3.50486 3.46354 0.77255 | 3.65597 2.40513 0.48576 | 4.51118 3.72494 0.95510 | 2.05876 3.29354 | 3.56463 2.67741 | 2.20413 2.69355 | 3.48128 4.24690 | 3.89758 2.90347 | 4.22110 2.73739 | 3.92973 3.18146 | 3.78302 2.89801 | 3.15664 2.37887 | 3.12163 2.77519 | 1.11004 2.98518 | 5.27795 4.58477 | 4.00490 3.61503 | 243 v - - - |
| 244 | 3.08469 2.68618 0.03351 | 4.56681 4.42225 3.80839 | 4.08583 2.77519 4.53074 | 3.72691 2.73123 0.61958 | 3.11381 3.46354 0.77255 | 3.89935 2.40513 0.48576 | 4.40279 3.72494 0.95510 | 2.31622 3.29354 | 3.49522 2.67741 | 0.95845 2.69355 | 3.15956 4.24690 | 4.00841 2.90347 | 4.34677 2.73739 | 3.87896 3.18146 | 3.68117 2.89601 | 3.46490 2.37687 | 3.38246 2.77519 | 2.33662 2.98518 | 4.96833 4.58477 | 3.67637 3.61503 | 244 l - - - |
| 245 | 3.01012 2.68618 0.03351 | 4.41428 4.42225 3.80839 | 4.41093 2.77519 4.53074 | 3.89648 2.73123 0.61958 | 3.23739 3.46354 0.77255 | 4.19710 2.40513 0.48576 | 4.60930 3.72494 0.95510 | 1.33047 3.29354 | 3.71957 2.67741 | 1.73611 2.69355 | 2.77119 4.24690 | 4.17860 2.90347 | 4.51388 2.73739 | 4.01448 3.18146 | 3.93268 2.89801 | 3.56091 2.37887 | 3.26688 2.77519 | 1.83382 2.98518 | 5.18268 4.58477 | 3.98317 3.61503 | 245 i - - - |
| 246 | 2.79822 2.68618 0.03351 | 4.99164 4.42225 3.80839 | 2.58917 2.77519 4.53074 | 2.18348 2.73123 0.61958 | 4.25929 3.46354 0.77255 | 3.31397 2.40513 0.48576 | 3.64736 3.72494 0.95510 | 3.71794 3.29354 | 2.30881 2.67741 | 3.26588 2.69355 | 4.16696 4.24690 | 2.86913 2.90347 | 3.83263 2.73739 | 1.72335 3.18146 | 2.64609 2.89801 | 2.78808 2.37887 | 3.05306 2.77519 | 3.39930 2.98518 | 5.44088 4.58477 | 4.11133 3.61503 | 246 q - - - |
| 247 | 2.67266 2.68618 0.03351 | 4.64469 4.42225 3.80839 | 2.67738 2.77519 4.53074 | 2.55713 2.73123 0.61958 | 4.01837 3.46354 0.77255 | 3.14279 2.40513 0.48576 | 3.87335 3.72494 0.95510 | 3.71632 3.29354 | 2.77246 2.67741 | 3.37097 2.69355 | 4.32772 4.24690 | 1.27686 2.90347 | 3.79220 2.73739 | 3.14721 3.18146 | 3.12388 2.89801 | 2.74309 2.37887 | 3.05315 2.77519 | 3.34503 2.98518 | 5.33189 4.58477 | 3.97225 3.61503 | 247 n - - - |
| 248 | 3.15726 2.68618 0.03351 | 4.67219 4.42225 3.80839 | 3.74475 2.77519 4.53074 | 3.46341 2.73123 0.61958 | 2.29976 3.46354 0.77255 | 3.75634 2.40513 0.48576 | 3.59289 3.72494 0.95510 | 3.17566 3.29354 | 3.32278 2.67741 | 2.64581 2.69355 | 3.85778 4.24690 | 3.64645 2.90347 | 4.23235 2.73739 | 3.64422 3.18146 | 3.51908 2.89801 | 3.29987 2.37887 | 3.44402 2.77519 | 3.04338 2.98518 | 3.94061 4.58477 | 1.07944 3.61503 | 248 y - - - |
| 249 | 2.67266 2.68618 0.03351 | 4.64469 4.42225 3.80839 | 2.67738 2.77519 4.53074 | 2.55713 2.73123 0.61958 | 4.01837 3.46354 0.77255 | 3.14279 2.40513 0.48576 | 3.87335 3.72494 0.95510 | 3.71632 3.29354 | 2.77246 2.67741 | 3.37097 2.69355 | 4.32772 4.24690 | 1.27686 2.90347 | 3.79220 2.73739 | 3.14721 3.18146 | 3.12388 2.89801 | 2.74309 2.37887 | 3.05315 2.77519 | 3.34503 2.98518 | 5.33189 4.58477 | 3.97225 3.61503 | 249 n - - - |
| 250 | 2.57439 2.68618 0.03351 | 4.57351 4.42225 3.80839 | 2.83143 2.77519 4.53074 | 2.58496 2.73123 0.61958 | 4.01396 3.46354 0.77255 | 3.18385 2.40513 0.48576 | 3.80153 3.72494 0.95510 | 3.50981 3.29354 | 2.59095 2.67741 | 3.10465 2.69355 | 4.04186 4.24690 | 3.02031 2.90347 | 1.77449 2.73739 | 2.65661 3.18146 | 2.92673 2.89801 | 2.66527 2.37887 | 2.92228 2.77519 | 3.17417 2.98518 | 5.32541 4.58477 | 4.02468 3.61503 | 250 p - - - |
| 251 | 1.29653 2.68618 0.03351 | 4.08489 4.42225 3.80839 | 3.30251 2.77519 4.53074 | 3.06256 2.73123 0.61958 | 4.06991 3.46354 0.77255 | 2.88906 2.40513 0.48576 | 4.12659 3.72494 0.95510 | 3.31602 3.29354 | 3.09903 2.67741 | 3.14997 2.69355 | 4.05671 4.24690 | 3.22665 2.90347 | 3.63269 2.73739 | 3.42360 3.18146 | 3.38369 2.89801 | 2.13641 2.37887 | 2.65470 2.77519 | 2.88235 2.98518 | 5.47235 4.58477 | 4.23432 3.61503 | 251 a - - - |

TABLE 6-continued

```
HMMER3/f [3.1b2] | February 2015
NAME  zips
LENG  272
ALPH  amino
RF    no
MM    | no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD   -5.1315  0.70210
```

| HMM | A<br>m→m | C<br>m→i | D<br>m→d | E<br>i→m | F<br>i→i | G<br>d→m | H<br>d→d | I | K | L | M | N | P | Q | R | S | T | V | W | Y | | |
|---|---|---|---|---|---|---|---|---|---|---|---|---|---|---|---|---|---|---|---|---|---|---|
| 252 | 2.28599<br>2.68618<br>0.03351 | 4.20474<br>4.42225<br>3.80839 | 3.15313<br>2.77519<br>4.53074 | 2.96740<br>2.73123<br>0.61958 | 4.01316<br>3.46354<br>0.77255 | 2.93592<br>2.40513<br>0.48576 | 4.07832<br>3.72494<br>0.95510 | 3.52777<br>3.29354 | 3.03676<br>2.67741 | 3.25353<br>2.69355 | 4.18606<br>4.24690 | 3.20153<br>2.90147 | 3.66974<br>2.73739 | 3.39147<br>3.18146 | 3.32378<br>2.89801 | 1.19199<br>2.37887 | 2.76159<br>2.77519 | 3.07699<br>2.98518 | 5.39114<br>4.58477 | 4.09669<br>3.61503 | 252 | s - - - |
| 253 | 2.67266<br>2.68618<br>0.03351 | 4.64469<br>4.42225<br>3.80839 | 2.67738<br>2.77519<br>4.53074 | 2.55713<br>2.73123<br>0.61958 | 4.01837<br>3.46354<br>0.77255 | 3.14279<br>2.40513<br>0.48576 | 3.87335<br>3.72494<br>0.95510 | 3.71632<br>3.29354 | 2.77246<br>2.67741 | 3.37097<br>2.69355 | 4.32772<br>4.24690 | 1.27686<br>2.90147 | 3.79220<br>2.73739 | 3.14721<br>3.18146 | 3.12388<br>2.89801 | 2.74309<br>2.37887 | 3.05315<br>2.77519 | 3.34503<br>2.98518 | 5.33189<br>4.58477 | 3.97225<br>3.61503 | 253 | n - - - |
| 254 | 2.28599<br>2.68618<br>0.03351 | 4.20474<br>4.42225<br>3.80839 | 3.15313<br>2.77519<br>4.53074 | 2.96740<br>2.73123<br>0.61958 | 4.01316<br>3.46354<br>0.77255 | 2.93592<br>2.40513<br>0.48576 | 4.07832<br>3.72494<br>0.95510 | 3.52777<br>3.29354 | 3.03676<br>2.67741 | 3.25353<br>2.69355 | 4.18606<br>4.24690 | 3.20153<br>2.90347 | 3.66974<br>2.73739 | 3.39147<br>3.18146 | 3.32378<br>2.89801 | 1.19199<br>2.37887 | 2.76159<br>2.77519 | 3.07699<br>2.98518 | 5.39114<br>4.58477 | 4.09669<br>3.61503 | 254 | s - - - |
| 255 | 2.58929<br>2.68618<br>0.03351 | 4.36940<br>4.42225<br>3.80839 | 3.24976<br>2.77519<br>4.53074 | 3.14188<br>2.73123<br>0.61958 | 4.28221<br>3.46354<br>0.77255 | 0.83523<br>2.40513<br>0.48576 | 4.26473<br>3.72494<br>0.95510 | 3.86748<br>3.29354 | 3.31425<br>2.67741 | 3.52941<br>2.69355 | 4.50578<br>4.24690 | 3.41443<br>2.90347 | 3.75846<br>2.73739 | 3.64375<br>3.18146 | 3.55601<br>2.89801 | 2.75463<br>2.37887 | 3.06560<br>2.77519 | 3.40832<br>2.98518 | 5.39294<br>4.58477 | 4.38245<br>3.61503 | 255 | g - - - |
| 256 | 2.92923<br>2.68618<br>0.03351 | 4.75570<br>4.42225<br>3.80839 | 3.06737<br>2.77519<br>4.53074 | 2.82225<br>2.73123<br>0.61958 | 3.24301<br>3.46354<br>0.77255 | 3.39609<br>2.40513<br>0.48576 | 1.28822<br>3.72494<br>0.95510 | 3.62204<br>3.29354 | 2.66722<br>2.67741 | 3.12353<br>2.69355 | 4.16260<br>4.24690 | 3.23362<br>2.90347 | 3.94584<br>2.73739 | 3.18806<br>3.18146 | 2.93608<br>2.89801 | 3.00091<br>2.37887 | 3.23101<br>2.77519 | 3.35853<br>2.98518 | 4.70870<br>4.58477 | 3.19598<br>3.61503 | 256 | h - - - |
| 257 | 3.17889<br>2.68618<br>0.03351 | 4.60008<br>4.42225<br>3.80639 | 4.15032<br>2.77519<br>4.53074 | 3.85387<br>2.73123<br>0.61958 | 1.12282<br>3.46354<br>0.77255 | 3.88119<br>2.40513<br>0.48576 | 3.85245<br>3.72494<br>0.95510 | 2.71188<br>3.29354 | 3.76280<br>2.67741 | 2.09750<br>2.69355 | 3.45251<br>4.24690 | 3.94779<br>2.90347 | 4.34224<br>2.73739 | 3.94887<br>3.18146 | 3.89833<br>2.89801 | 3.45132<br>2.37887 | 3.48052<br>2.77519 | 2.69761<br>2.98518 | 4.12292<br>4.58477 | 2.49894<br>3.61503 | 257 | f - - - |
| 258 | 2.28599<br>2.68618<br>0.03351 | 4.20474<br>4.42225<br>3.80839 | 3.15313<br>2.77519<br>4.53074 | 2.96740<br>2.73123<br>0.61958 | 4.01316<br>3.46354<br>0.77255 | 2.93592<br>2.40513<br>0.48576 | 4.07832<br>3.72494<br>0.95510 | 3.52777<br>3.29354 | 3.03676<br>2.67741 | 3.25353<br>2.69355 | 4.18606<br>4.24690 | 3.20153<br>2.90347 | 3.66974<br>2.73739 | 3.39147<br>3.18146 | 3.32378<br>2.89801 | 1.19199<br>2.37887 | 2.76159<br>2.77519 | 3.07699<br>2.98518 | 5.39114<br>4.58477 | 4.09669<br>3.61503 | 258 | s - - - |
| 259 | 3.17889<br>2.68618<br>0.03351 | 4.60008<br>4.42225<br>3.80839 | 4.15032<br>2.77519<br>4.53074 | 3.85387<br>2.73123<br>0.61958 | 1.12282<br>3.46354<br>0.77255 | 3.88119<br>2.40513<br>0.48576 | 3.85245<br>3.72494<br>0.95510 | 2.71188<br>3.29354 | 3.76280<br>2.67741 | 2.09750<br>2.69355 | 3.45251<br>4.24690 | 3.94779<br>2.90347 | 4.34224<br>2.73739 | 3.94887<br>3.18146 | 3.89833<br>2.89801 | 3.45132<br>2.37887 | 3.48052<br>2.77519 | 2.69761<br>2.98518 | 4.12292<br>4.58477 | 2.49894<br>3.61503 | 259 | f - - - |
| 260 | 2.92310<br>2.68618<br>0.03351 | 5.03735<br>4.42225<br>3.80839 | 1.01454<br>2.77519<br>4.53074 | 2.30009<br>2.73123<br>0.61958 | 4.40640<br>3.46354<br>0.77255 | 3.16420<br>2.40513<br>0.48576 | 3.87837<br>3.72494<br>0.95510 | 3.98050<br>3.29354 | 2.95099<br>2.67741 | 3.60099<br>2.69355 | 4.57912<br>4.24690 | 2.85261<br>2.90147 | 3.81266<br>2.73739 | 3.11848<br>3.18146 | 3.45728<br>2.89801 | 2.89377<br>2.37887 | 3.26085<br>2.77519 | 3.62704<br>2.98518 | 5.58736<br>4.58477 | 4.29177<br>3.61503 | 260 | d - - - |
| 261 | 3.23357<br>2.68618<br>0.03351 | 4.63032<br>4.42225<br>3.80839 | 3.99599<br>2.77519<br>4.53074 | 3.68726<br>2.73123<br>0.61958 | 2.60690<br>3.46354<br>0.77255 | 3.66065<br>2.40513<br>0.48576 | 3.82592<br>3.72494<br>0.95510 | 3.25571<br>3.29354 | 3.41132<br>2.67741 | 2.66106<br>2.69355 | 3.89235<br>4.24690 | 3.84955<br>2.90347 | 4.17141<br>2.73739 | 3.80241<br>3.18146 | 3.55053<br>2.89801 | 3.43778<br>2.37887 | 3.53106<br>2.77519 | 3.14428<br>2.98518 | 1.02517<br>4.58477 | 2.61260<br>3.61503 | 261 | w - - - |
| 262 | 2.43471<br>2.68618<br>0.03351 | 4.33947<br>4.42225<br>3.80839 | 3.10763<br>2.77519<br>4.53074 | 2.65043<br>2.73123<br>0.61958 | 3.72256<br>3.46354<br>0.77255 | 3.22351<br>2.40513<br>0.48576 | 3.70592<br>3.72494<br>0.95510 | 3.17554<br>3.29354 | 2.56941<br>2.67741 | 2.85511<br>2.69355 | 3.70850<br>4.24690 | 3.05491<br>2.90347 | 3.73148<br>2.73739 | 2.95850<br>3.18146 | 2.92934<br>2.89801 | 1.78239<br>2.37887 | 2.74595<br>2.77519 | 2.86658<br>2.98518 | 5.01126<br>4.58477 | 3.78736<br>3.61503 | 262 | s - - - |

TABLE 6-continued

```
HMMER3/f [3.1b2] | February 2015
NAME  zips
LENG  272
ALPH  amino
RF    no
MM    no
CONS  yes
CS    no
MAP   yes
DATE  Thu Feb 21 21:13:29 2019
NSEQ  8
EFFN  0.417969
CKSUM 165377865
STATS LOCAL MSV      -11.4830  0.70210
STATS LOCAL VITERBI  -11.8487  0.70210
STATS LOCAL FORWARD   -5.1315  0.70210
HMM          A        C        D        E        F        G        H        I        K        L        M        N        P        Q        R        S        T        V        W        Y
           m->m     m->i     m->d     i->m     i->i     d->m     d->d
```

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 263 | 1.11031 | 4.16266 | 3.39952 | 3.18951 | 3.99036 | 2.98856 | 4.21886 | 3.10649 | 3.20414 | 2.99084 | 4.03105 | 3.35470 | 3.72187 | 3.55158 | 3.45819 | 2.51417 | 2.78716 | 2.77211 | 5.42402 | 4.21744 | 263 a - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 264 | 3.15726 | 4.67219 | 3.74475 | 3.46341 | 2.29976 | 3.75634 | 3.59289 | 3.17566 | 3.32278 | 2.64581 | 3.85778 | 3.64645 | 4.23235 | 3.64422 | 3.51908 | 3.29987 | 3.44402 | 3.04338 | 3.94061 | 1.07944 | 264 y - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 265 | 2.46429 | 4.50277 | 2.76194 | 2.53711 | 4.10808 | 3.09914 | 3.81452 | 3.50193 | 2.65822 | 3.20971 | 4.09377 | 1.83311 | 3.72764 | 3.03155 | 3.03107 | 2.55947 | 2.32552 | 3.11459 | 5.42657 | 4.09622 | 265 n - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37687 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 266 | 2.66368 | 4.71314 | 1.86174 | 2.43871 | 3.87910 | 3.32864 | 3.75508 | 2.53007 | 2.66567 | 2.87600 | 3.86608 | 2.95100 | 3.84113 | 2.96441 | 3.11604 | 2.73315 | 2.94304 | 2.80811 | 5.30301 | 3.93501 | 266 d - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 267 | 2.57183 | 4.40147 | 3.29756 | 2.92021 | 3.58155 | 3.32013 | 3.92617 | 2.90376 | 2.81038 | 2.11477 | 3.65609 | 3.28096 | 1.96754 | 3.22756 | 3.11759 | 2.75095 | 2.91246 | 2.70333 | 5.09267 | 3.78923 | 267 p - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80639 | 4.53074 | 0.61958 | 0.77255 | 0.48576 | 0.95510 | | | | | | | | | | | | | | |
| 268 | 2.70401 | 4.52485 | 3.27058 | 2.81601 | 3.16826 | 3.51121 | 2.18756 | 2.48108 | 2.61094 | 2.59297 | 3.62015 | 3.22034 | 3.94808 | 3.07183 | 2.91785 | 2.84887 | 2.95894 | 2.75950 | 4.69941 | 3.22516 | 268 h - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 269 | 2.19646 | 4.57897 | 3.20488 | 2.73469 | 4.06159 | 3.30402 | 3.72028 | 3.39767 | 2.27081 | 3.04174 | 3.96013 | 3.11981 | 3.82748 | 2.91470 | 1.70636 | 2.70466 | 2.90940 | 3.08482 | 5.28820 | 4.04460 | 269 r - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 270 | 2.65927 | 4.55369 | 3.36479 | 2.82353 | 3.79413 | 3.43170 | 3.74118 | 3.05153 | 2.32580 | 2.74721 | 3.75184 | 3.20718 | 3.89989 | 2.96147 | 1.78252 | 2.75430 | 2.93484 | 2.37446 | 5.15155 | 3.88489 | 270 r - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 271 | 2.58892 | 4.24418 | 3.49767 | 2.95550 | 3.00683 | 3.53970 | 3.68743 | 2.54874 | 2.83074 | 2.41907 | 3.35230 | 3.30705 | 3.91445 | 3.16371 | 3.13745 | 2.82088 | 2.82225 | 2.51305 | 4.49536 | 2.20914 | 271 y - - - |
| | 2.68618 | 4.42225 | 2.77519 | 2.73123 | 3.46354 | 2.40513 | 3.72494 | 3.29354 | 2.67741 | 2.69355 | 4.24690 | 2.90347 | 2.73739 | 3.18146 | 2.89801 | 2.37887 | 2.77519 | 2.98518 | 4.58477 | 3.61503 | |
| | 0.03351 | 3.80839 | 4.53074 | 0.61958 | 0.77255 | 0.48576 | 0.95510 | | | | | | | | | | | | | | |
| 272 | 2.68027 | 4.58936 | 2.49030 | 1.70991 | 3.90297 | 3.05916 | 3.69222 | 3.28621 | 2.53357 | 2.98575 | 4.02875 | 2.86073 | 3.66258 | 2.95416 | 2.86307 | 2.74011 | 3.00313 | 3.02529 | 5.15154 | 3.92226 | 272 e - - - |
| | 2.68623 | 4.42138 | 2.77525 | 2.73129 | 3.46359 | 2.40506 | 3.72500 | 3.29359 | 2.67746 | 2.69344 | 4.24695 | 2.90352 | 2.73745 | 3.18152 | 2.89786 | 2.37880 | 2.77525 | 2.98524 | 4.58482 | 3.61508 | |
| | 0.11903 | 2.18732 | * | 1.27779 | 0.32663 | 0.00000 | | | | | | | | | | | | | | | |

//

NUMBERED EMBODIMENTS OF THE DISCLOSURE

Notwithstanding the appended claims, the disclosure sets forth the following numbered embodiments:

Isolated Nucleic Acids

1. An isolated nucleic acid molecule encoding an insecticidal protein having at least about 80% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
2. The isolated nucleic acid molecule of embodiment 1, wherein said nucleic acid molecule encodes an insecticidal protein having at least about 90% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
3. The isolated nucleic acid molecule of embodiment 1, wherein said nucleic acid molecule encodes an insecticidal protein having at least about 95% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
4. The isolated nucleic acid molecule of embodiment 1, wherein said nucleic acid molecule encodes an insecticidal protein having at least about 99% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
5. The isolated nucleic acid molecule of embodiment 1, wherein said nucleic acid molecule encodes an insecticidal protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
6. The isolated nucleic acid molecule of embodiment 1, wherein said nucleic acid molecule is codon optimized for expression in a host cell of interest.
7. The isolated nucleic acid molecule of embodiment 1, wherein said nucleic acid molecule is codon optimized for expression in a plant cell.
8. The isolated nucleic acid molecule of embodiment 1, wherein said nucleic acid molecule is selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and SEQ ID NO: 71.
9. An isolated nucleic acid as presented in Table 3.
10. An isolated protein, polypeptide, amino acid sequence, or variant thereof, as presented in Table 3.

Nucleotide Constructs

1. A nucleotide construct, comprising: a nucleic acid molecule encoding an insecticidal protein having at least about 80% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72, said nucleic acid molecule operably linked to a heterologous regulatory element.
2. The nucleotide construct of embodiment 1, wherein said nucleic acid molecule encodes an insecticidal protein having at least about 90% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

3. The nucleotide construct of embodiment 1, wherein said nucleic acid molecule encodes an insecticidal protein having at least about 95% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

4. The nucleotide construct of embodiment 1, wherein said nucleic acid molecule encodes an insecticidal protein having at least about 99% sequence identity to a protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

5. The nucleotide construct of embodiment 1, wherein said nucleic acid molecule encodes an insecticidal protein selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

6. The nucleotide construct of embodiment 1, wherein said heterologous regulatory element is a promoter.

7. The nucleotide construct of embodiment 1, wherein said nucleotide construct is contained in an expression cassette.

8. The nucleotide construct of embodiment 1, wherein said heterologous regulatory element is capable of expressing the encoded protein in a plant.

9. The nucleotide construct of embodiment 1, wherein said nucleic acid molecule is codon optimized for expression in a host cell of interest.

10. The nucleotide construct of embodiment 1, wherein said nucleic acid molecule is codon optimized for expression in a plant cell.

11. The nucleotide construct of embodiment 1, wherein said nucleic acid molecule is selected from the group consisting of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, and SEQ ID NO: 71.

12. An expression vector comprising the nucleotide construct of embodiment 1.

13. A plasmid comprising the nucleotide construct of embodiment 1.

14. A host cell comprising the nucleotide construct of embodiment 1.

15. A method of killing an insect, comprising contacting the insect with a host cell expressing the nucleotide construct of embodiment 1.

16. A prokaryotic host cell comprising the nucleotide construct of embodiment 1.

17. A eukaryotic host cell comprising the nucleotide construct of embodiment 1.

18. A plant cell comprising the nucleotide construct of embodiment 1.

19. A monocot plant cell comprising the nucleotide construct of embodiment 1.

20. A dicot plant cell comprising the nucleotide construct of embodiment 1.

21. A plant stably transformed with the nucleotide construct of embodiment 1.

22. A seed produced by a plant that has been stably transformed with the nucleotide construct of embodiment 1.

Isolated Proteins

1. An isolated insecticidal protein, comprising: an amino acid sequence with at least about 80% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

2. The isolated insecticidal protein of embodiment 1, comprising: an amino acid sequence with at least about 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

3. The isolated insecticidal protein of embodiment 1, comprising: an amino acid sequence with at least about 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

4. The isolated insecticidal protein of embodiment 1, comprising: an amino acid sequence with at least about 99% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

5. The isolated insecticidal protein of embodiment 1, comprising: an amino acid sequence selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

Recombinant Proteins

1. A recombinant insecticidal protein, comprising: an amino acid sequence with at least about 80% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

2. The recombinant insecticidal protein of embodiment 1, comprising: an amino acid sequence with at least about 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

3. The recombinant insecticidal protein of embodiment 1, comprising: an amino acid sequence with at least about 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

4. The recombinant insecticidal protein of embodiment 1, comprising: an amino acid sequence with at least about 99% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

5. The recombinant insecticidal protein of embodiment 1, comprising: an amino acid sequence selected from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

Transgenic Plant Cells

1. A transgenic plant cell, comprising:
    a. a DNA construct, comprising: a polynucleotide encoding a polypeptide having at least about 80%, 81%, 82%, 83%, 84%, 85%, 86%, 87%, 88%, 89%, 90%, 91%, 92%, 93%, 94%, 95%, 96%, 97%, 98%, 99%, or greater, sequence identity to an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72; and
a heterologous regulatory sequence operably linked to the polynucleotide.
2. The transgenic plant cell of embodiment 1, wherein said polynucleotide encodes a polypeptide having an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
3. The transgenic plant cell of embodiment 1, wherein said heterologous regulatory element is a promoter.
4. The transgenic plant cell of embodiment 1, wherein said cell is from a monocot species.
5. The transgenic plant cell of embodiment 1, wherein said cell is from corn, wheat, oat, or rice.
6. The transgenic plant cell of embodiment 1, wherein said cell is from a dicot species.
7. The transgenic plant cell of embodiment 1, wherein said cell is from cotton, potato, or soybean.
8. The transgenic plant cell of embodiment 1, wherein said cell is from an agricultural row crop species.

Transgenic Plant

1. A transgenic plant stably transformed with a DNA construct, comprising:
   a. a polynucleotide encoding a polypeptide having at least about 80%, 81%, 82%, 83%, 84%, 85%, 86%, 87%, 88%, 89%, 90%, 91%, 92%, 93%, 94%, 95%, 96%, 97%, 98%, 99%, or greater, sequence identity to an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72; and
   b. a heterologous regulatory sequence operable linked to the polynucleotide.
2. The transgenic plant of embodiment 1, wherein said polynucleotide encodes a polypeptide having an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
3. The transgenic plant of embodiment 1, wherein said heterologous regulatory element is a promoter.
4. The transgenic plant of embodiment 1, wherein said plant is a monocot species.
5. The transgenic plant of embodiment 1, wherein said plant is corn, wheat, oat, or rice.
6. The transgenic plant of embodiment 1, wherein said plant is a dicot species.
7. The transgenic plant of embodiment 1, wherein said plant is cotton, potato, or soybean.
8. The transgenic plant of embodiment 1, wherein said plant is from an agricultural row crop species.
9. A seed produced by the plant of embodiment 1.
10. A progeny plant produced from the plant of embodiment 1.
11. The transgenic plant of embodiment 1, further comprising: a DNA construct comprising a polynucleotide encoding a Monalysin protein, Pseudomonas insecticidal protein, Cry protein, Cyt protein, vegetative insecticidal protein, toxin complex protein, and any combination thereof.
12. A method of killing a target pest, comprising: providing the transgenic plant of embodiment 1 to an area, wherein said target pest is exposed to the transgenic plant.
13. A method of killing a target pest, comprising: providing the transgenic plant of embodiment 1 to an area, wherein said target pest feeds on the transgenic plant.
14. A method of killing a target pest that is resistant to a pesticidal protein, comprising: providing the transgenic plant of embodiment 1 to an area, wherein said target pest is exposed to the transgenic plant, and wherein the target pest is resistant to at least one of a Monalysin protein, Pseudomonas insecticidal protein, Cry protein, Cyt protein, vegetative insecticidal protein, toxin complex protein, and any combination thereof.
15. A method of killing a target pest that is resistant to a pesticidal protein, comprising: providing the transgenic plant of embodiment 1 to an area, wherein said target pest feeds on the transgenic plant, and wherein the target pest is resistant to at least one of a Monalysin protein, Pseudomonas insecticidal protein, Cry protein, Cyt protein, vegetative insecticidal protein, toxin complex protein, and any combination thereof.
16. A method of killing a target pest, comprising: providing the transgenic plant of embodiment 1 to an area, wherein said target pest is exposed to the transgenic plant and said target pest is a member of the Order Coleoptera, Diptera, Hymenoptera, Lepidoptera, Hemiptera, Orthroptera, Thysanoptera, or Dermaptera.

Agricultural Compositions

1. An insecticidal composition, comprising:
   a. an isolated insecticidal protein having an amino acid sequence with at least about 80%, 81%, 82%, 83%, 84%, 85%, 86%, 87%, 88%, 89%, 90%, 91%, 92%, 93%, 94%, 95%, 96%, 97%, 98%, 99%, or greater, sequence identity to an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72; and b. an agriculturally acceptable carrier.

2. The insecticidal composition of embodiment 1, wherein the isolated insecticidal protein has an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.

3. The insecticidal composition of embodiment 1, wherein said isolated insecticidal protein is present in an insecticidally effective amount.

4. The insecticidal composition of embodiment 1, wherein said agriculturally acceptable carrier is at least one selected from the group consisting of: adjuvants, inert components, dispersants, surfactants, sticking agents, tackifiers, binders, natural or regenerated mineral substances, solvents, wetting agents, fertilizers, and combinations thereof.

5. The insecticidal composition of embodiment 1, formulated as a dry solid.

6. The insecticidal composition of embodiment 1, formulated as a liquid.

7. The insecticidal composition of embodiment 1, formulated for foliar application.

8. The insecticidal composition of embodiment 1, formulated for in-furrow application.

9. The insecticidal composition of embodiment 1, formulated as a seed coating or seed treatment.

10. The insecticidal composition of embodiment 1, further comprising: at least one additional pesticidal compound.

11. The insecticidal composition of embodiment 1, further comprising: at least one additional pesticidal compound selected from the group consisting of: a Monalysin protein, *Pseudomonas* insecticidal protein, Cry protein, Cyt protein, vegetative insecticidal protein, toxin complex protein, and any combination thereof.

12. The insecticidal composition of embodiment 1, further comprising: at least one additional herbicidal compound.

13. A method of killing a target pest, comprising: applying to said target pest the insecticidal composition of embodiment 1.

14. A method of killing a target pest, comprising: applying to a locus the insecticidal composition of embodiment 1, wherein said target pest comes into contact with said locus.

15. A method of killing a target pest, comprising: applying to a crop the insecticidal composition of embodiment 1, wherein said target pest comes into contact with said crop.

16. A method of killing a target pest, comprising: applying to a crop the insecticidal composition of embodiment 1, wherein said target pest comes into contact with said crop, and said target pest is a member of the Order Coleoptera, Diptera, Hymenoptera, Lepidoptera, Hemiptera, Orthroptera, Thysanoptera, or Dermaptera.

Cell Lysate

1. Cell lysate, comprising: an insecticidal protein comprising an amino acid sequence with at least about 80% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

2. The cell lysate of embodiment 1, comprising: an insecticidal protein comprising an amino acid sequence with at least about 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

3. The cell lysate of embodiment 1, comprising: an insecticidal protein comprising an amino acid sequence with at least about 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

4. The cell lysate of embodiment 1, comprising: an insecticidal protein comprising an amino acid sequence with at least about 99% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

5. The cell lysate of embodiment 1, comprising: an insecticidal protein comprising an amino acid sequence selected from SEQ ID NO: 2, SEQ ID NO: 4, SEQ ID NO: 6, SEQ ID NO: 8, SEQ ID NO: 10, SEQ ID NO:

12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, or SEQ ID NO: 72.

6. A method of killing a target pest, comprising: applying to said target pest the cell lysate of embodiment 1.

Methods of Killing Pests with a Natural Microbe Expressing the Insecticidal Protein 1. A method of killing a target pest, comprising: applying to said target pest a host cell that expresses a polynucleotide encoding a polypeptide having at least about 80%, 81%, 82%, 83%, 84%, 85%, 86%, 87%, 88%, 89%, 90%, 91%, 92%, 93%, 94%, 95%, 96%, 97%, 98%, 99%, or greater, sequence identity to an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
2. The method of embodiment 1, wherein the host cell expresses a polynucleotide that encodes a polypeptide having an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, and SEQ ID NO: 72.
3. The method of embodiment 1, wherein the host cell is a Prokaryotic host cell.
4. The method of embodiment 1, wherein the host cell naturally expresses the polynucleotide.
5. The method of embodiment 1, wherein the host cell is from the genus *Pseudomonas*.
6. The method of embodiment 1, wherein said target pest is a member of the Order Coleoptera, Diptera, Hymenoptera, Lepidoptera, Hemiptera, Orthroptera, Thysanoptera, or Dermaptera.

Insecticidal Protein Discovery Platform

1. A method for constructing a genomic library, enriched for DNA from *Pseudomonas* encoding insecticidal proteins, comprising:
    a. providing an initial sample comprising one or more microorganisms;
    b. exposing the initial sample to a solid nutrient limiting media that enriches for growth of species from the genus *Pseudomonas*, which results in a subsequent sample enriched for *Pseudomonas* sp.;
    c. isolating DNA from the subsequent enriched sample;
    d. extracting DNA from the isolated DNA and performing degenerate PCR with primers selected to amplify target insecticidal protein genes;
    e. cloning the PCR-amplified DNA into a plasmid; and
    f. sequencing the cloned DNA from said plasmid.
2. The method of embodiment 1, further comprising: assembling the sequenced DNA into a genomic library.
3. The method of embodiment 1, further comprising: identifying insecticidal protein genes within the sequenced DNA.
4. The method of embodiment 1, further comprising: identifying insecticidal protein genes within the sequenced DNA, wherein said identified insecticidal protein genes are unknown.
5. The method of embodiment 1, further comprising: utilizing a Hidden Markov model to identify insecticidal protein genes within the sequenced DNA.
6. The method of embodiment 1, further comprising: identifying insecticidal protein genes within the sequenced DNA, wherein said identified insecticidal protein genes are selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, and 71.
7. The method of embodiment 1, further comprising: identifying insecticidal protein genes within the sequenced DNA, wherein said identified insecticidal protein genes encode a protein selected from the group consisting of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72.
8. The method of embodiment 1, wherein the primers are selected to amplify target insecticidal protein genes that encode a protein with at least 50% sequence identity to SEQ ID NO: 39.
9. The method of embodiment 1, wherein the initial sample is from soil.
10. An insecticidal genomic library enriched for DNA from *Pseudomonas* encoding insecticidal proteins, as constructed by the method of embodiment 1.

HMM Model Proteins

1. An insecticidal protein, comprising: a) an amino acid sequence that scores at or above a bit score of 521.5; and/or b) an amino acid sequence that matches at an E-value of less than or equal to 7.9e-161, when scored or matched using the HMM in Table 6.

An insecticidal protein encoding nucleic acid, as set forth in Table 3, or an insecticidal protein having an amino acid sequence, as set forth in Table 3, are embodiments of the present disclosure, as well as methods of using the same for the control of insect pests, and methods of discovering same.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A nucleotide construct, comprising: a nucleic acid molecule encoding an insecticidal protein having an amino acid sequence (i) with at least 97% sequence identity to a protein with the amino acid sequence of SEQ ID NO: 20; or (ii) with at least 96% sequence identity to a protein with an amino acid sequence selected from the group consisting of: SEQ ID NO: 2, SEQ ID NO: 4, SEQ ID NO: 12, SEQ ID NO: 14, SEQ ID NO: 16, SEQ ID NO: 18, and SEQ ID NO: 22; or (iii) with at least 94% sequence identity to a protein with the amino acid sequence of SEQ ID NO: 8, said nucleic acid molecule operably linked to a heterologous regulatory element.

2. The nucleotide construct of claim 1, wherein said nucleic acid molecule encodes an insecticidal protein having an amino acid sequence with at least 97% about sequence identity to a protein with an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, and SEQ ID NO: 22.

3. The nucleotide construct of claim 1, wherein said nucleic acid molecule encodes an insecticidal protein having an amino acid sequence with at least about 98% sequence identity to a protein with an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, SEQ ID NO: 20, and SEQ ID NO: 22.

4. The nucleotide construct of claim 1, wherein said nucleic acid molecule encodes an insecticidal protein having an amino acid sequence with at least about 99% sequence identity to a protein with an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, SEQ ID NO: 20, and SEQ ID NO: 22.

5. The nucleotide construct of claim 1, wherein said nucleic acid molecule encodes an insecticidal protein with an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, SEQ ID NO: 20, and SEQ ID NO: 22.

6. The nucleotide construct of claim 1, wherein said heterologous regulatory element is a promoter.

7. The nucleotide construct of claim 1, wherein said nucleotide construct is contained in an expression cassette.

8. The nucleotide construct of claim 1, wherein said heterologous regulatory element is capable of expressing the encoded protein in a plant.

9. The nucleotide construct of claim 1, wherein said nucleic acid molecule is codon optimized for expression in a host cell of interest.

10. The nucleotide construct of claim 9, wherein said host cell of interest is a plant cell.

11. The nucleotide construct of claim 1, wherein said nucleic acid molecule is selected from the group consisting of: SEQ ID NO: 1, SEQ ID NO: 3, SEQ ID NO: 7, SEQ ID NO: 11, SEQ ID NO: 13, SEQ ID NO: 15, SEQ ID NO: 17, SEQ ID NO: 19, and SEQ ID NO: 21.

12. An expression vector comprising the nucleotide construct of claim 1.

13. A plasmid comprising the nucleotide construct of claim 1.

14. A host cell comprising the nucleotide construct of claim 1.

15. A method of killing an insect, comprising contacting the insect with the host cell of claim 14.

16. A prokaryotic host cell comprising the nucleotide construct of claim 1.

17. A eukaryotic host cell comprising the nucleotide construct of claim 1.

18. A plant cell comprising the nucleotide construct of claim 1.

19. A monocot plant cell comprising the nucleotide construct of claim 1.

20. A dicot plant cell comprising the nucleotide construct of claim 1.

21. A plant stably transformed with the nucleotide construct of claim 1.

22. A seed produced by a plant that has been stably transformed with the nucleotide construct of claim 1.

23. A transgenic plant cell, comprising:
   a. a DNA construct, comprising: a polynucleotide encoding a polypeptide having an amino acid sequence (i) with at least 97% sequence identity to the amino acid sequence of SEQ ID NO: 20; or (ii) with at least 96% sequence identity to an amino acid sequence selected from the group consisting of: SEQ ID NO: 2, SEQ ID NO: 4, SEQ ID NO: 12, SEQ ID NO: 14, SEQ ID NO: 16, SEQ ID NO: 18, and SEQ ID NO: 22; or (iii) with at least 94% sequence identity to the amino acid sequence of SEQ ID NO: 8; and a heterologous regulatory sequence operably linked to the polynucleotide.

24. The nucleotide construct of claim 1, wherein said nucleic acid molecule encodes an insecticidal protein having an amino acid sequence with at least about 95% sequence identity to a protein with an amino acid sequence set forth in SEQ ID NO: 8.

25. The nucleotide construct of claim 1, wherein said nucleic acid molecule encodes an insecticidal protein having an amino acid sequence with at least about 96% sequence identity to a protein with an amino acid sequence set forth in SEQ ID NO: 8.

26. The transgenic plant cell of claim 23, wherein said polynucleotide encodes a polypeptide having an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, SEQ ID NO: 20, and SEQ ID NO: 22.

27. The transgenic plant cell of claim 23, wherein said heterologous regulatory element is a promoter.

28. The transgenic plant cell of any claim 23, wherein said plant cell is from a monocot species.

29. The transgenic plant cell of any one of claim 23, wherein said plant cell is from corn, wheat, oat, or rice.

30. The transgenic plant cell of claim 23, wherein said plant cell is from a dicot species.

31. The transgenic plant cell of claim 23, wherein said plant cell is from cotton, potato, or soybean.

32. The transgenic plant cell of claim 23, wherein said plant cell is from an agricultural row crop species.

33. The transgenic plant cell claim 23, further comprising: a DNA construct comprising a polynucleotide encoding a protein selected from the group consisting of: a Monalysin protein, *Pseudomonas* insecticidal protein, Cry protein, Cyt protein, vegetative insecticidal protein, toxin complex protein, and any combination thereof.

34. A method of killing an insect, comprising contacting the insect with the plant cell of claim 23.

35. A transgenic plant stably transformed with a DNA construct, comprising:
   a. a polynucleotide encoding a polypeptide having an amino acid sequence (i) with at least 97% sequence identity to the amino acid sequence of SEQ ID NO: 20; or (ii) with at least 96% sequence identity to an amino acid sequence selected from the group consisting of: SEQ ID NO: 2, SEQ ID NO: 4, SEQ ID NO: 12, SEQ ID NO: 14, SEQ ID NO: 16, SEQ ID NO: 18, and SEQ ID NO: 22; or (iii) with at least 94% sequence identity to the amino acid sequence of SEQ ID NO: 8; and
   b. a heterologous regulatory sequence operable operably linked to the polynucleotide.

36. The transgenic plant of claim 35, wherein said polynucleotide encodes a polypeptide having an amino acid sequence selected from the group consisting of: SEQ ID NO: 2, SEQ ID NO: 4, SEQ ID NO: 8, SEQ ID NO: 12, SEQ ID NO: 14, SEQ ID NO: 16, SEQ ID NO: 18, SEQ ID NO: 20, and SEQ ID NO: 22.

37. The transgenic plant of claim 35, wherein said heterologous regulatory element is a promoter.

38. The transgenic plant of claim 35, wherein said plant is a monocot species.

39. The transgenic plant of claim 35, wherein said plant is corn, wheat, oat, or rice.

40. The transgenic plant of claim 35, wherein said plant is a dicot species.

41. The transgenic plant of claim 35, wherein said plant is cotton, potato, or soybean.

42. The transgenic plant of claim 35, wherein said plant is from an agricultural row crop species.

43. A seed produced by the transgenic plant of claim 35.

44. The transgenic plant of claim 35, further comprising: a DNA construct comprising a polynucleotide encoding a protein selected from the group consisting of: a Monalysin protein, *Pseudomonas* insecticidal protein, Cry protein, Cyt protein, vegetative insecticidal protein, toxin complex protein, and any combination thereof.

45. A method of killing a target pest, comprising: providing the transgenic plant of claim 35 to an area, wherein said target pest is exposed to the transgenic plant.

46. The method of claim 45, wherein said target pest feeds on the transgenic plant.

47. The method of claim 46, wherein said target pest is a member of the Order Coleoptera, Diptera, Hymenoptera, Lepidoptera, Hemiptera, Orthroptera, Thysanoptera, or Dermaptera.

* * * * *